US008053552B2

(12) United States Patent
Von Knebel-Doeberitz et al.

(10) Patent No.: US 8,053,552 B2
(45) Date of Patent: Nov. 8, 2011

(54) NEOPEPTIDES AND METHODS USEFUL FOR DETECTION AND TREATMENT OF CANCER

(75) Inventors: Magnus Von Knebel-Doeberitz, Heidelberg (DE); Johannes Gebert, Heidelberg (DE); Michael Linnebacher, Stennweiler (DE); Stefan Woerner, Heidelberg (DE); Ruediger Ridder, Schriesheim (DE); Peer Bork, Heidelberg (DE); Yan Ping Yuan, Heidelberg (DE)

(73) Assignee: MTM Laboratories, AG, Heidelberg (DE)

( * ) Notice: Subject to any disclaimer, the term of this patent is extended or adjusted under 35 U.S.C. 154(b) by 1034 days.

(21) Appl. No.: 10/511,698

(22) PCT Filed: Apr. 17, 2003

(86) PCT No.: PCT/EP03/04083
§ 371 (c)(1),
(2), (4) Date: Jun. 2, 2005

(87) PCT Pub. No.: WO03/087162
PCT Pub. Date: Oct. 23, 2003

(65) Prior Publication Data
US 2005/0239070 A1    Oct. 27, 2005

(30) Foreign Application Priority Data

Apr. 18, 2002  (EP) .................................... 02008771
Apr. 18, 2002  (EP) .................................... 02008773
Apr. 18, 2002  (EP) .................................... 02008774

(51) Int. Cl.
*A61K 38/00* (2006.01)
*C07K 1/00* (2006.01)
(52) U.S. Cl. ...................................... 530/300; 530/350
(58) Field of Classification Search .................. None
See application file for complete search history.

(56) References Cited

U.S. PATENT DOCUMENTS 5,866,323 A      2/1999  Markowitz et al.
6,277,974 B1 *   8/2001  Lo et al. ....................... 536/23.1

FOREIGN PATENT DOCUMENTS

WO   WO 99/58552      11/1999
WO   WO 02/04664       1/2002
WO   PCT/EP03/04083    8/2003

OTHER PUBLICATIONS

Mori, Yuriko et al. Instabilotyping: Comprehensive identification of frameshift mutations caused by coding region microsatellite instability. 2001. Cancer Research. vol. 61. pp. 6046-6049.*

Yang et al (Molecular and Cellular Biology, Nov. 1996, 16(11):6603-6616).*
Mayer et al (JBC, 1992, 267(29): 20589-20593).*
(XP-002226919) Database EMBL Online.
(XP-002226916) Database EMBL Online.
(XP-002226917) Database EMBL Online.
(XP-002226918) Database EMBL Online.
(XP-002226920) Database EMBL Online.
Michael Linnebacher, et al.; "Frameshift Peptide-derived T-Cell Epitopes: A Source of Novel Tumor-Specific Antigens"; Int. J. Cancer; 93, 6-11 (2001).
Stefan M. Woerner; et al. "Systematic Identification of Genes with Coding Microsatellites Mutated in DNA Mismatch Repair-Deficient Cancer Cells"; Int. J. Cancer 93, 12-19 (2001).
C. Di Pietro; Genomic localization of the human genes TAF1A, TAF1B and TAF1C, encoding $TAF_I48$, $TAF_I63$ and $FAF_I$ 110 subunits of class I general transcription initiation factor SL1'; Cytogenetics and Cell Genetics 89:133-136 (2000).
Ingvil Saeterdal; "Frameshift-mutation-derived peptides as tumor-specific antigens in inherited and spontaneous colorectal cancer"; PNAS; Nov. 6, 2001 vol. 98, No. 23; 13255-13260.
C. Richard Boland; "A National Caner Institute Workshop on Microsatallite Instability for Cancer Dectection and Familial Predisposition: Development of International Criteria for the Determination of Microsatellite Instability in Colorectal Cancer"; Cancer Research 58; 5248-5257; Nov. 15, 1998.
Lucio Comai, et al.; "Reconstitution of Transcription Factor SL1: Exclusive Binding of TBP by SL1 or TFIID Subunits"; Science; vol. 266; Dec. 23, 1994.

* cited by examiner

*Primary Examiner* — Sean Aeder
(74) *Attorney, Agent, or Firm* — Perkins Coie LLP; Viola T. Kung

(57) ABSTRACT

The present invention relates to compounds and methods useful for the detection and treatment of disorders associated with frameshift mutations in coding microsatellite regions. The compounds and methods are applicable in cancers, especially of DNA mismatch repair deficient (MMR) sporadic tumors and HNPCC associated tumors. The compounds disclosed in the invention are useful for detection of disorders and in therapy such as e.g. immuno-therapy. The diagnostic methods relate to diagnosis and prognostic assessment of disorders associated with frameshift polypeptides originating from frameshift mutations in coding microsatellite regions of genes based on the detection of immunological entities directed against said frameshift polypeptides in body fluids. With respect to the treatment of cancer, especially of DNA mismatch repair deficient (MMR) sporadic tumors and HNPCC associated tumors, the invention pertains to methods which use immuno therapy with combinatorial mixtures of tumor specific frameshift peptides to elicit a cytotoxic T-cell response specifically directed against tumor cells for use in prevention as well as in curative treatment of cancers and precancers.

19 Claims, 10 Drawing Sheets

FIG.1
ELISpot analysis of FSP01 to FSP18
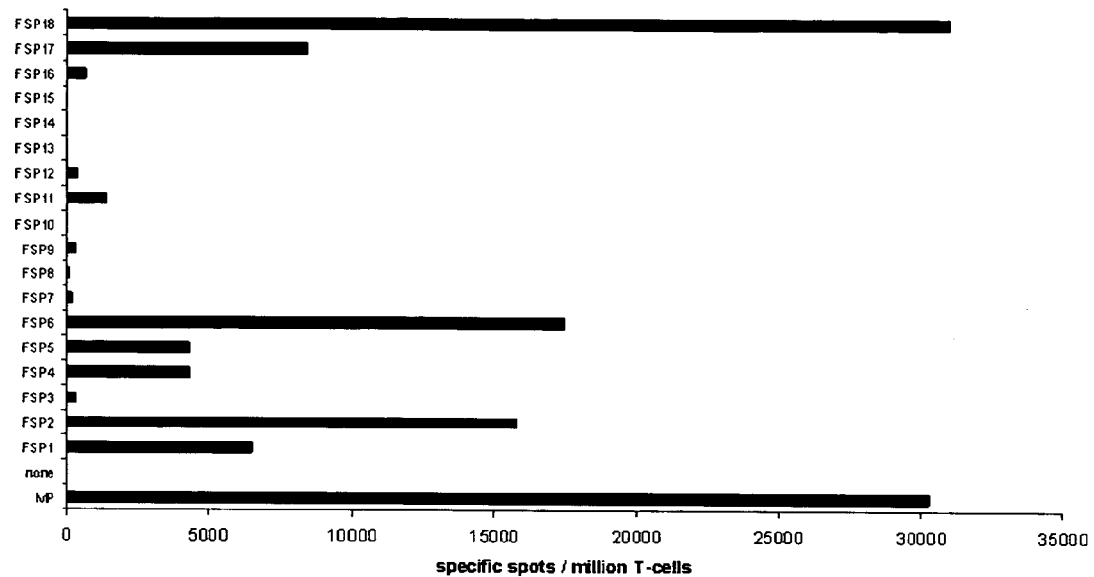
ELISpot analysis of FSP19 to FSP34
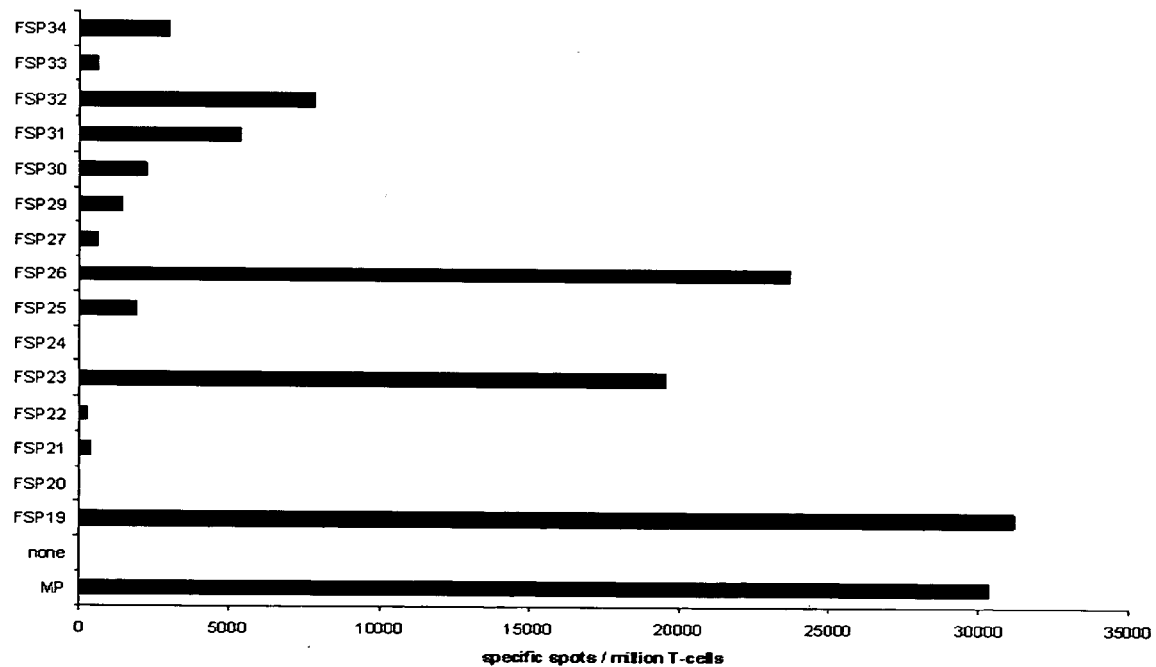

FIG. 2-1

HT001
wt ORF (SEQ ID NO: 1)
MQRPNAHRISQPIRQIIYGLLLNASPHLDKTSWNALPPQPLAFSEVERINKNIRTSIIDAVELAKDHSDLSRLTELSLRRRQMLLLETLKV
KQTILEPIPTSLKLPIAVSCYWLQHTETKAKLHHLQSLLLTMLVGPLIAIINSPGKEELQEDGAKMLYAEFQRVKAQTRLGTRLDLDTAHI
FCQWQSCLQMGMYLNQLLSTPLPEPDLTRLYSGSLVHGLCQQLLASTSVESLLSICPEAKQLYEYLFNATRSYAPAEIFLPKGRSNSK
KKRQKKQNTSCSKNRGRTTAHTKCWYEGNNRFGLLMVENLEEHSEASNIE
(-1) ORF (SEQ ID NO: 2)
MQRPNAHRISQPIRQIIYGLLLNASPHLDKTSWNALPPQPLAFSEVERINKNIRTSIIDAVELAKDHSDLSRLTELSLRRRQMLLLETLKV
KQTILEPIPTSLKLPIAVSCYWLQHTETKAKLHHLQSLLLTMLVGPLIAIINSPGKEELQEDGAKMLYAEFQRVKAQTRLGTRLDLDTAHI
FCQWQSCLQMGMYLNQLLSTPLPEPDLTRLYSGSLVHGLCQQLLASTSVESLLSICPEAKQLYEYLFNATRSYAPAEIFLPKGRSNSK
KK*GRRNRIPAVLRTEGEPLHTPSVGMRETTGLGC*
(+1)/(-2) ORF (SEQ ID NO: 3/118)
MQRPNAHRISQPIRQIIYGLLLNASPHLDKTSWNALPPQPLAFSEVERINKNIRTSIIDAVELAKDHSDLSRLTELSLRRRQMLLLETLKV
KQTILEPIPTSLKLPIAVSCYWLQHTETKAKLHHLQSLLLTMLVGPLIAIINSPGKEELQEDGAKMLYAEFQRVKAQTRLGTRLDLDTAHI
FCQWQSCLQMGMYLNQLLSTPLPEPDLTRLYSGSLVHGLCQQLLASTSVESLLSICPEAKQLYEYLFNATRSYAPAEIFLPKGRSNSK
KK*(K)AEETEYQLF*

U79260
wt ORF (SEQ ID NO: 4)
MGHPRAIQPSVFFSPYDVHFLLYPIRCPYLKIGRFHIKLKGLHFLFSFLFFFFETQSHSVTRLECSGTISAHCNLCLPGSSNSPASASRV
AGTAGTCRRAQLIFVFLAEMGFHHVGRDGLDLNLVIHPPRSPKALGLQA
(-1)ORF (SEQ ID NO: 5)
MGHPRAIQPSVFFSPYDVHFLLYPIRCPYLKIGRFHIKLKGLHFLFSFLFFF*LRHSLTLSPGWSAVARSRLTATSASQVQVILLPQPPEW
LGLQARAAAPS*
(+1)/(-2)ORF (SEQ ID NO: 6)
MGHPRAIQPSVFFSPYDVHFLLYPIRCPYLKIGRFHIKLKGLHFLFSFLFFF(F)

PTHL3
(wt)ORF (SEQ ID NO: 7)
MQRRLVQQWSVAVFLLSYAVPSCGRSVEGLSRRLKRAVSEHQLLHDKGKSIQDLRRRFFLHHLIAEIHTAEIRATSEVSPNSKPSPNT
KNHPVRFGSDDEGRYLTQETNKVETYKEQPLKTPGKKKKGKPGKRKEQEKKKRRTRSAWLDSGVTGSGLEGDHLSDTSTTSLELD
SRTALLWGLKKKKENNRRTHHMQLMISLFKSPLLLL
(-1)ORF (SEQ ID NO: 8)
MQRRLVQQWSVAVFLLSYAVPSCGRSVEGLSRRLKRAVSEHQLLHDKGKSIQDLRRRFFLHHLIAEIHTAEIRATSEVSPNSKPSPNT
KNHPVRFGSDDEGRYLTQETNKVETYKEQPLKTPGKKKKGKPGKRKEQEKKKRRTRSAWLDSGVTGSGLEGDHLSDTSTTSLELD
SRTALLWGLKKK*RKTTEEHIICN*
(+1)/(-2)ORF (SEQ ID NO: 9)
MQRRLVQQWSVAVFLLSYAVPSCGRSVEGLSRRLKRAVSEHQLLHDKGKSIQDLRRRFFLHHLIAEIHTAEIRATSEVSPNSKPSPNT
KNHPVRFGSDDEGRYLTQETNKVETYKEQPLKTPGKKKKGKPGKRKEQEKKKRRTRSAWLDSGVTGSGLEGDHLSDTSTTSLELD
SRTALLWGLKKK(K)*GKQQKNTSYATNDLII*

TGFbRII
(wt) (SEQ ID NO: 10)
MGRGLLRGLWPLHIVLWTRIASTIPPHVQKSVNNDMIVTDNNGAVKFPQLCKFCDVRFSTCDNQKSCMSNCSITSICEKPQEVCVAV
WRKNDENITLETVCHDPKLPYHDFILEDAASPKCIMKEKKKPGETFFMCSCSSDECNDNIIFSEEYNTSNPDLLLVIFQVTGISLLPPLG
VAISVIIIFYCYRVNRQQKLSSTWETGKTRKLMEFSEHCAIILEDDRSDISSTCANNINHNTELLPIELDTLVGKGRFAEVYKAKLKQNTS
EQFETVAVKIFPYEEYASWKTEKDIFSDINLKHENILQFLTAEERKTELGKQYWLITAFHAKGNLQEYLTRHVISWEDLRKLGSSLARGI
AHLHSDHTPCGRPKMPIVHRDLNSSNILVKNDLTCCLCDFGLSLRLDPTLSVDDLANSGQVGTARYMAPEVLESRMNLENAESFKQT
DVYSMALVLWEMTSRCNAVGEVKDYEPPFGSKVREHPCVESMKDNVLRDRGRPEIPSFWLNHQGIQMVCETLTECWDHDPEARLT
AQCVAERFSELEHLDRLSGRSCSEEKIPEDGSLNTTK
(-1)ORF (SEQ ID NO: 11)
MGRGLLRGLWPLHIVLWTRIASTIPPHVQKSVNNDMIVTDNNGAVKFPQLCKFCDVRFSTCDNQKSCMSNCSITSICEKPQEVCVAV
WRKNDENITLETVCHDPKLPYHDFILEDAASPKCIMKEKK*SLVRLSSCVPVALMSAMTTSSSQKNITPAILTCC*
(+1)/(-2)ORF (SEQ ID NO: 12/119)
MGRGLLRGLWPLHIVLWTRIASTIPPHVQKSVNNDMIVTDNNGAVKFPQLCKFCDVRFSTCDNQKSCMSNCSITSICEKPQEVCVAV
WRKNDENITLETVCHDPKLPYHDFILEDAASPKCIMKEKK(K)*AW*

MACS
(wt)ORF (SEQ ID NO: 13)
MGAQFSKTAAKGEAAAERPGEAAVASSPSKANGQENGHVKVNGDASPAAAESGAKEELQANGSAPAADKEEPAAAGSGAASPSS
AEKGEPAAAAAPEAGASPVEKEAPAEGEAAEPGSATAAEGEAASAASSTSSPKAEDGATPSPSNETPKKKKKRFSFKKSFKLSGFS
FKKNKKEAGEGGEAEAPAAEGGKDEAAGGAAAAAAEAGAASGEQAAAPGEEAAAGEEGAAGGDPQEAKPQEAAVAPEKPPASDE
TKAAEEPSKVEEKKAEEAGASAAACEAPSAAGPGAPPEQEAAPAEEPAAAAASSACAAPSQEAQPECSPEAPPAEAAE
(-1)ORF (SEQ ID NO: 14)
MGAQFSKTAAKGEAAAERPGEAAVASSPSKANGQENGHVKVNGDASPAAAESGAKEELQANGSAPAADKEEPAAAGSGAASPSS
AEKGEPAAAAAPEAGASPVEKEAPAEGEAAEPGSATAAEGEAASAASSTSSPKAEDGATPSPSNETPKKK*RSAFPSRSLSS*
(+1)/(-2)ORF (SEQ ID NO: 15)

FIG. 2-2

MGAQFSKTAAKGEAAAERPGEAAVASSPSKANGQENGHVKVNGDASPAAAESGAKEELQANGSAPAADKEEPAAAGSGAASPSS
AEKGEPAAAAAPEAGASPVEKEAPAEGEAAEPGSATAAEGEAASAASSTSSPKAEDGATPSPSNETPKKK(K)*EALFLQEVFQAERL*
*LLQEEQEGGWRRR*

TCF-4
(wt)ORF (SEQ ID NO: 16)
MPQLNGGGGDDLGANDELISFKDEGEQEEKSSENSSAERDLADVKSSLVNESETNQNSSSDSEAERRPPPRSESFRDKSRESLEEA
AKRQDGGLFKGPPYPGYPFIMIPDLTSPYLPNGSLSPTARTYLQMKWPLLDVQAGSLQSRQALKDARSPSPAHIVSNKVPVVQHPHH
VHPLTPLITYSNEHFTPGNPPPHLPADVDPKTGIPRPPHPPDISPYYPLSPGTVGQIPHPLGWLVPQQGQPVYPITTGGFRHPYPTALT
VNASVSRFPPHMVPPHHTLHTTGIPHPAIVTPTVKQESSQSDVGSLHSSKHQDSKKEEEKKKPHIKKPLNAFMLYMKEMRAKVVAEC
TLKESAAINQILGRRWHALSREEQAKYYELARKERQLHMQLYPGWSARDNYGKKKKRKRDKQPGETNEHSECFLNPCLSLPPITDLS
APKKCRARFGLDQQNNWCGPCRRKKKCVRYIQGEGSCLSPPSSDGSLLDSPPPSPNLLGSPPRDAKSQTEQTQPLSLSLKPDPLAH
LSMMPPPPALLLAEATHKASALCPNGALDLPPAALQPAAPSSSIAQPSTSWLHSHSSLAGTQPQPLSLVTKSLE
(-1)ORF (SEQ ID NO: 17)
MPQLNGGGGDDLGANDELISFKDEGEQEEKSSENSSAERDLADVKSSLVNESETNQNSSSDSEAERRPPPRSESFRDKSRESLEEA
AKRQDGGLFKGPPYPGYPFIMIPDLTSPYLPNGSLSPTARTYLQMKWPLLDVQAGSLQSRQALKDARSPSPAHIVSNKVPVVQHPHH
VHPLTPLITYSNEHFTPGNPPPHLPADVDPKTGIPRPPHPPDISPYYPLSPGTVGQIPHPLGWLVPQQGQPVYPITTGGFRHPYPTALT
VNASVSRFPPHMVPPHHTLHTTGIPHPAIVTPTVKQESSQSDVGSLHSSKHQDSKKEEEKKKPHIKKPLNAFMLYMKEMRAKVVAEC
TLKESAAINQILGRRWHALSREEQAKYYELARKERQLHMQLYPGWSARDNYGKKKKRKRDKQPGETNEHSECFLNPCLSLPPITDLS
APKKCRARFGLDQQNNWCGPCRRKK*SAFATYKVKAAASAHPLQMEAY*
(+1)/(-2)ORF (SEQ ID NO: 18)
MPQLNGGGGDDLGANDELISFKDEGEQEEKSSENSSAERDLADVKSSLVNESETNQNSSSDSEAERRPPPRSESFRDKSRESLEEA
AKRQDGGLFKGPPYPGYPFIMIPDLTSPYLPNGSLSPTARTYLQMKWPLLDVQAGSLQSRQALKDARSPSPAHIVSNKVPVVQHPHH
VHPLTPLITYSNEHFTPGNPPPHLPADVDPKTGIPRPPHPPDISPYYPLSPGTVGQIPHPLGWLVPQQGQPVYPITTGGFRHPYPTALT
VNASVSRFPPHMVPPHHTLHTTGIPHPAIVTPTVKQESSQSDVGSLHSSKHQDSKKEEEKKKPHIKKPLNAFMLYMKEMRAKVVAEC
TLKESAAINQILGRRWHALSREEQAKYYELARKERQLHMQLYPGWSARDNYGKKKKRKRDKQPGETNEHSECFLNPCLSLPPITDLS
APKKCRARFGLDQQNNWCGPCRRKK(K)*VRSLHTR*

TAF1b
(wt)ORF (SEQ ID NO: 19)
IPAFPAGTVLQPFPEAALATRVTVPAVEAPAAPRLDLEESEEFKERCTQCAAVSWGLTDEGKYYCTSCHNVTERYQEVTNTDLIPNT
QIKALNRGLKKKNNTEKGWDWYVCEGFQYILYQQAEALKNLGVGPELKNDVLHNFWKRYLQKSKQAYCKNPVYTTGRKPTVLEDNL
SHSDWASEPELLSDVSCPPFLESGAESQSDIHTRKPFPVSKASQSETSVCSGSLDGVEYSQRKEKGIVKMTMPQTLAFCYLSLLWQ
REAITLSDLLRFVEEDHIPYINAFQHFPEQMKLYGRDRGIFGIESWPDYEDIYKKTIEVGTFLDLPRFPDITEDCYLHPNILCMKYLMEVN
LPDEMHSLTCHVVKMTGMGEVDFLTFDPIAKMAKAVKYDVQAVAIIVVVLKLLFLMDDSFEWSLSNLAEKHNEKNKKDKPWFDFRKW
YQIMKKAFDEKKQKWEEARAKYLWKSEKPLYYSFVDKPVAYKKREMVVNLQKQFSTLVDSTATAGKKSPSSFQFNWTEEDTDRTC
FHGHSLQGVLKEKGQSLLTKNSLYWLSTQKFCRW
(-1)ORF (SEQ ID NO: 20)
IPAFPAGTVLQPFPEAALATRVTVPAVEAPAAPRLDLEESEEFKERCTQCAAVSWGLTDEGKYYCTSCHNVTERYQEVTNTDLIPNT
QIKALNRGLKKK*TILKKAGIGMCVKVSSIFFINKQKP*
(+1)/(-2)ORF (SEQ ID NO: 21/120)
IPAFPAGTVLQPFPEAALATRVTVPAVEAPAAPRLDLEESEEFKERCTQCAAVSWGLTDEGKYYCTSCHNVTERYQEVTNTDLIPNT
QIKALNRGLKKK*(K)QY*

AC-1
(wt)ORF (SEQ ID NO: 22)
MDTQKQIHKTHNSKNQFFTIFFFLSVEFGKEGTRKNFYLLLSIGHYGRKSRRADLGTADTADKTEPECFAASWTFDPNPSVTVSGAHS
TAVHQ
(-1)ORF (SEQ ID NO: 23)
MDTQKQIHKTHNSKNQFFTIFF*SCQLNLGRKEHAKIFTFFFQLDTMDGNPGELTLELQTLQIKQSQNALLPAGPLTQTPV*
(+1)/(-2)ORF (SEQ ID NO: 24)
MDTQKQIHKTHNSKNQFFTIFF(F)*PVS*

Sec63
(wt)ORF (SEQ ID NO: 25)
MAGQQFQYDDSGNTFFYFLTSFVGLIVIPATYYLWPRDQNAEQIRLKNIRKVYGRCMWYRLRLLKPQPNIIPTVKKIVLLAGWALFLFL
AYKVSKTDREYQEYNPYEVLNLDPGATVAEIKKQYRLLSLKYHPDKGGDEVMFMRIAKAYAALTDEESRKNWEEFGNPDGPQATSF
GIALPAWIVDQKNSILVLLVYGLAFMVILPVVVGSWWYRSIRYSGDQILIRTTQIYTYFVYKTRNMDMKRLIMVLAGASEFDPQYNKDAT
SRPTDNILIPQLIREIGSINLKKNEPPLTCPYSLKARVLLLSHLARMKIPETLEEDQQFMLKKCPALLQEMVNVICQLIVMARNREEREFR
APTLASLENCMKLSQMAVQGLQQFKSPLLQLPHIEEDNLRRVSNHKKYKIKTIQDLVSLKESDRHTLLHFLEDEKYEEVMAVLGSFPY
VTMDIKSQVLDDEDSNNITVGSLVTVLVKLTRQTMAEVFEKEQSICAAEEQPAEDGQGETNKNRTKGGWQQKSKGPKKTAKSKKKK
PLKKKPTPVLLPQSKQQKQKQANGVVGNEAAVKEDEEEVSDKGSDSEEEETNRDSQSEKDDGSDRDSDREQDEKQNKDDEAEW
QELQQSIQRKERALLETKSKITHPVYSLYFPEEKQEWWWLYIADRKEQTLISMPYHVCTLKDTEEVELKFPAPGKPGNYQYTVFLRSD
SYMGLDQIKPLKLEVHEAKPVPENHPQWDTAIEGDEDQEDSEGFEDSFEEEEEEEEDDD
(-1) 9er A-Repeat (SEQ ID NO: 26)
MAGQQFQYDDSGNTFFYFLTSFVGLIVIPATYYLWPRDQNAEQIRLKNIRKVYGRCMWYRLRLLKPQPNIIPTVKKIVLLAGWALFLFL
AYKVSKTDREYQEYNPYEVLNLDPGATVAEIKKQYRLLSLKYHPDKGGDEVMFMRIAKAYAALTDEESRKNWEEFGNPDGPQATSF
GIALPAWIVDQKNSILVLLVYGLAFMVILPVVVGSWWYRSIRYSGDQILIRTTQIYTYFVYKTRNMDMKRLIMVLAGASEFDPQYNKDAT
SRPTDNILIPQLIREIGSINLKKNEPPLTCPYSLKARVLLLSHLARMKIPETLEEDQQFMLKKCPALLQEMVNVICQLIVMARNREEREFR
APTLASLENCMKLSQMAVQGLQQFKSPLLQLPHIEEDNLRRVSNHKKYKIKTIQDLVSLKESDRHTLLHFLEDEKYEEVMAVLGSFPY
VTMDIKSQVLDDEDSNNITVGSLVTVLVKLTRQTMAEVFEKEQSICAAEEQPAEDGQGETNKNRTKGGWQQKSKGPKKTAKSKK*RN*
*L*

FIG. 2-3

(+1)/(-2) 9er A-Repeat (SEQ ID NO: 27)
MAGGQQFQYDDSGNTFFYFLTSFVGLIVIPATYYLWPRDQNAEQIRLKNIRKVYGRCMWYRLRLLKPQPNIIPTVKKIVLLAGWALFLFL
AYKVSKTDREYQEYNPYEVLNLDPGATVAEIKKQYRLLSLKYHPDKGGDEVMFMRIAKAYAALTDEESRKNWEEFGNPDGPQATSF
GIALPAWIVDQKNSILVLLVYGLAFMVILPVVVGSWWYRSIRYSGDQILIRTTQIYTYFVYKTRNMDMKRLIMVLAGASEFDPQYNKDAT
SRPTDNILIPQLIREIGSINLKKNEPPLTCPYSLKARVLLLSHLARMKIPETLEEDQQFMLKKCPALLQEMVNVICQLIVMARNREEREFR
APTLASLENCMKLSQMAVQGLQQFKSPLLQLPHIEEDNLRRVSNHKKYKIKTIQDLVSLKESDRHTLLHFLEDEKYEEVMAVLGSFPY
VTMDIKSQVLDDEDSNNITVGSLVTVLVKLTRQTMAEVFEKEQSICAAEEQPAEDGQGETNKNRTKGGWQQ
KSKGPKKTAKSKK(K)*ETFKKKTYTCAITTVKATETKAGKWSRWE*

(-1) 10er A-Repeat (SEQ ID NO: 28)
MAGGQQFQYDDSGNTFFYFLTSFVGLIVIPATYYLWPRDQNAEQIRLKNIRKVYGRCMWYRLRLLKPQPNIIPTVKKIVLLAGWALFLFL
AYKVSKTDREYQEYNPYEVLNLDPGATVAEIKKQYRLLSLKYHPDKGGDEVMFMRIAKAYAALTDEESRKNWEEFGNPDGPQATSF
GIALPAWIVDQKNSILVLLVYGLAFMVILPVVVGSWWYRSIRYSGDQILIRTTQIYTYFVYKTRNMDMKRLIMVLAGASEFDPQYNKDAT
SRPTDNILIPQLIREIGSINLKKNEPPLTCPYSLKARVLLLSHLARMKIPETLEEDQQFMLKKCPALLQEMVNVICQLIVMARNREEREFR
APTLASLENCMKLSQMAVQGLQQFKSPLLQLPHIEEDNLRRVSNHKKYKIKTIQDLVSLKESDRHTLLHFLEDEKYEEVMAVLGSFPY
VTMDIKSQVLDDEDSNNITVGSLVTVLVKLTRQTMAEVFEKEQSICAAEEQPAEDGQGETNKNRTKGGWQQ
KSKGPKKTAKSKKKKPLKK*NLHLCYYHSQSNRNKSRQMESLGMKLQ*

(+1)/(-2) 10er A-Repeat (SEQ ID NO: 29)
MAGGQQFQYDDSGNTFFYFLTSFVGLIVIPATYYLWPRDQNAEQIRLKNIRKVYGRCMWYRLRLLKPQPNIIPTVKKIVLLAGWALFLFL
AYKVSKTDREYQEYNPYEVLNLDPGATVAEIKKQYRLLSLKYHPDKGGDEVMFMRIAKAYAALTDEESRKNWEEFGNPDGPQATSF
GIALPAWIVDQKNSILVLLVYGLAFMVILPVVVGSWWYRSIRYSGDQILIRTTQIYTYFVYKTRNMDMKRLIMVLAGASEFDPQYNKDAT
SRPTDNILIPQLIREIGSINLKKNEPPLTCPYSLKARVLLLSHLARMKIPETLEEDQQFMLKKCPALLQEMVNVICQLIVMARNREEREFR
APTLASLENCMKLSQMAVQGLQQFKSPLLQLPHIEEDNLRRVSNHKKYKIKTIQDLVSLKESDRHTLLHFLEDEKYEEVMAVLGSFPY
VTMDIKSQVLDDEDSNNITVGSLVTVLVKLTRQTMAEVFEKEQSICAAEEQPAEDGQGETNKNRTKGGWQQ
KSKGPKKTAKSKKKKPLKK(K)*TYTCAITTVKATETKAGKWSRWE*

Caspase 5

(wt)ORF (SEQ ID NO: 30)
MFKGILQSGLDNFVINHMLKNNVAGQTSIQTLVPNTDQKSTSVKKDNHKKKTVKMLEYLGKDVLHGVFNYLAKHDVLTLKEEEKKKYY
DAKIEDKALILVDSLRKNRVAHQMFTQTLLNMDQKITSVKPLLQIEAGPPESAESTNILKLCPREEFLRLCKKNHDEIYPIKKREDRRRLA
LIICNTKFDHLPARNGAHYDIVGMKRLLQGLGYTVVDEKNLTARDMESVLRAFAARPEHKSSDSTFLVLMSHGILEGICGTAHKKKKPD
VLLYDTIFQIFNNRNCLSLKDKPKVIIVQACRGEKHGELWVRDSPASLAVISSQSSENLEADSVCKIHEEKDFIAFCSSTPHNVSWRDR
TRGSIFITELITCFQKYSCCCHLMEIFRKVQKSFEVPQAKAQMPTIERATLTRDFYLFPGN

(-1)ORF (SEQ ID NO: 31)
MFKGILQSGLDNFVINHMLKNNVAGQTSIQTLVPNTDQKSTSVKKDNHKKK*QLRCWNTWAKMFFMVFLIIWQNTMF*

(+1)/(-2)ORF (SEQ ID NO: 32)
MFKGILQSGLDNFVINHMLKNNVAGQTSIQTLVPNTDQKSTSVKKDNHKK(K)*NS*

AIM2

(wt)ORF (SEQ ID NO: 33)
MESKYKEILLLTGLDNITDEELDRFKFFLSDEFNIATGKLHTANRIQVATLMIQNAGAVSAVMKTIRIFQKLNYMLLAKRLQEEKEKVDKQ
YKSVTKPKPLSQAEMSPAASAAIRNDVAKQRAAPKVSPHVKPEQKQMVAQQESIREGFQKRCLPVMVLKAKKPFTFETQEGKQEMF
HATVATEKEFFFVKVFNTLLKDKFIPKRIIIARYYRHSGFLEVNSASRVLDAESDQKVNVPLNIIRKAGETPKINTLQTQPLGTIVNGLFV
VQKVTEKKKNILFDLSDNTGKMEVLGVRNEDTMKCKEGDKVRLTFFTLSKNGEKLQLTSGVHSTIKVIKAKKKT

(-1)ORF (SEQ ID NO: 34)
MESKYKEILLLTGLDNITDEELDRFKFFLSDEFNIATGKLHTANRIQVATLMIQNAGAVSAVMKTIRIFQKLNYMLLAKRLQEEKEKVDKQ
YKSVTKPKPLSQAEMSPAASAAIRNDVAKQRAAPKVSPHVKPEQKQMVAQQESIREGFQKRCLPVMVLKAKKPFTFETQEGKQEMF
HATVATEKEFFFVKVFNTLLKDKFIPKRIIIARYYRHSGFLEVNSASRVLDAESDQKVNVPLNIIRKAGETPKINTLQTQPLGTIVNGLFV
VQKVTEKKKNILFDLSDNTGKMEVLGVRNEDTMKCKEGDKVRLTFFTLSKNGEKLQLTSGVHSTIKVIKAKKKK*HREVKRTNSSQLV*

(+1)/(-2)ORF (SEQ ID NO: 35)
MESKYKEILLLTGLDNITDEELDRFKFFLSDEFNIATGKLHTANRIQVATLMIQNAGAVSAVMKTIRIFQKLNYMLLAKRLQEEKEKVDKQ
YKSVTKPKPLSQAEMSPAASAAIRNDVAKQRAAPKVSPHVKPEQKQMVAQQESIREGFQKRCLPVMVLKAKKPFTFETQEGKQEMF
HATVATEKEFFFVKVFNTLLKDKFIPKRIIIARYYRHSGFLEVNSASRVLDAESDQKVNVPLNIIRKAGETPKINTLQTQPLGTIVNGLFV
VQKVTEKKKNILFDLSDNTGKMEVLGVRNEDTMKCKEGDKVRLTFFTLSKNGEKLQLTSGVHSTIKVIKAKK(K)*NIEK*

SLC23A1

(wt)ORF (SEQ ID NO: 36)
MMGIGKNTTSKSMEAGSSTEGKYEDEAKHPAFFTLPVVINGGATSSGEQDNEDTELMAIYTTENGIAEKSSLAETLDSTGSLDPQRS
DMIYTIEDVPPWYLCIFLGLQHYLTCFSGTIAVPFLLADAMCVGYDQWATSQLIGTIFFCVGITTLLQTTFGCRLPLFQTSAFAFLAPARA
ILSLDKWKCNTTDVSVANGTAELLHTEHIWYPRIREIQGAIIMSSLIEVVIGLLGLPGALLKYIGPLTITPTVALIGLSGFQAAGERAGKHW
GIAMLTIFLVLLFSQYARNVKFPLPIYKSKKGWTAYKLQLFKMFPIILAILVSWLLCFIFTVTDVFPPDSTKYGFYARTDARQGVLLVAPW
FKVPYPFQWGLPTVSAAGVIGMLSAVVASIIESIGDYYACARLSCAPPPPIHAINRGIFVEGLSCVLDGIFGTGNGSTSSSPNIGVLGITK
VGSRRVIQCGAALMLALGMIGKFSALFASLPDPVLGALFCTLFGMITAVGLSNLQFIDLNSSRNLFVLGFSIFFGLVLPSYLRQNPLVTGI
TGIDQVLNVLLTTAMFVGGCVAFILDNTIPGTPEERGIRKWKKGVGKGNKSLDGMESYNLPFGMNIIKKYRCFSYLPISPTFVGYTWK
GLRKSDNSRSSDEDSQATG

(-1)ORF (SEQ ID NO: 37)
MMGIGKNTTSKSMEAGSSTEGKYEDEAKHPAFFTLPVVINGGATSSGEQDNEDTELMAIYTTENGIAEKSSLAETLDSTGSLDPQRS
DMIYTIEDVPPWYLCIFLGLQHYLTCFSGTIAVPFLLADAMCVGYDQWATSQLIGTIFFCVGITTLLQTTFGCRLPLFQTSAFAFLAPARA
ILSLDKWKCNTTDVSVANGTAELLHTEHIWYPRIREIQGAIIMSSLIEVVIGLLGLPGALLKYIGPLTITPTVALIGLSGFQAAGERAGKHW
GIAMLTIFLVLLFSQYARNVKFPLPIYKSKKGWTAYKLQLFKMFPIILAILVSWLLCFIFTVTDVFPPDSTKYGFYARTDARQGVLLVAPW
FKVPYPFQWGLPTVSAAGVIGMLSAVVASIIESIGDYYACARLSCAPPPP*STQ*

(+1)/(-2)ORF (SEQ ID NO: 38)

FIG. 2-4

MMGIGKNTTSKSMEAGSSTEGKYEDEAKHPAFFTLPVVINGGATSSGEQDNEDTELMAIYTTENGIAEKSSLAETLDSTGSLDPQRS
DMIYTIEDVPPWYLCIFLGLQHYLTCFSGTIAVPFLLADAMCVGYDQWATSQLIGTIFFCVGITTLLQTTFGCRLPLFQTSAFAFLAPARA
ILSLDKWKCNTTDVSVANGTAELLHTEHIWYPRIREIQGAIIMSSLIEVVIGLLGLPGALLKYIGPLTITPTVALIGLSGFQAAGERAGKHW
GIAMLTIFLVLLFSQYARNVKFPLPIYKSKKGWTAYKLQLFKMFPIILAILVSWLLCFIFTVTDVFPPDSTKYGFYARTDARQGVLLVAPW
FKVPYPFQWGLPTVSAAGVIGMLSAVVASIIESIGDYYACARLSCAPPP
(P)*HPRNKQGNFRGRPLLCS*

ABCF1
(wt)ORF (SEQ ID NO: 39)
MPKAPKQQPPEPEWIGDGESTSPSDKVVKKGKKDKKIKKTFFEELAVEDKQAGEEEKVLKEKEQQQQQQQQQKKKRDTRKGRR
KKDVDDDGEEKELMERLKKLSVPTSDEEDEVPAPKPRGGKKTKGGNVFAALIQDQSEEEEEEEKHPPKPAKPEKNRINKAVSEEQQ
PALKGKKGKEEKSKGKAKPQNKFAALDNEEEDKEEEIIKEKEPPKQGKEKAKKAEQMEYERQVASLKAANAAENDFSVSQAEMSSR
QAMLENASDIKLEKFSISAHGKELFVNADLYIVAGRRYGLVGPNGKGKTTLLKHIANRALSIPPNIDVLLCEQEVVADETPAVQAVLRAD
TKRLKLLEEERRLQGGQLEQGDDTAAERLEKVYEELRATGAAAAEAKARRILAGLGFDPEMQNRPTQKFSGGWRMRVSLARALFMEP
TLLMLDEPTNHLDLNAVIWLNNYLQGWRKTLLIVSHDQGFLDDVCTDIIHLDAQRLHYYRGNYMTFKKMYQQKQKELLKQYEKQEKKL
KELKAGGKSTKQAEKQTKEALTRKQQKCRRKNQDEESQEAPELLKRPKEYTVRFTFPDPPPLSPPVLGLHGVTFGYQGQKPLFKNL
DFGIDMDSRICIVGPNGVGKSTLLLLLTGKLTPTHGEMRKNHRLKIGFFNQQYAEQLRMEETPTEYLQRGFNLPYQDARKCLGRFGLE
SHAHTIQICKLSGGQKARVVFAELACREPDVLILDEPTNNLDIESIDALGEAINEYKGAVIVVSHDARLITETNCQLWVVEEQSVSQIDG
DFEDYKREVLEALGEVMVSRPRE

(-1)ORF (SEQ ID NO: 40)
MPKAPKQQPPEPEWIGDGESTSPSDKVVKKGKKDKKIKKTFFEELAVEDKQAGEEEKVLKEKEQQQQQQQQQKK*SEIPEKAGGR
RMWMMMEKRKSSWSVLRSSQCQPVMRRMKYPPQNPAEGRKPRVVMFLQP*

(+1)/(-2)ORF (SEQ ID NO: 41)
MPKAPKQQPPEPEWIGDGESTSPSDKVVKKGKKDKKIKKTFFEELAVEDKQAGEEEKVLKEKEQQQQQQQQQKK(K)*ARYPKRQA
EEGCG*

HSPC259
(wt)ORF (SEQ ID NO: 42)
SPDYFPQISSQFGTVEK ???-
MEKIFISSSTKAEGKGISPFEAPINTQAPPEKGKEAVVQEPERSWFQTKEERKKEKIAKALQEFDLALRGKKKRKKFMKDAKKKGEMT
AEERSQFEILKAQMFAERLAKRNRRAKRARAMPEEEPVRGPAKKQKQGKKSVFDEELTNTSKKALKQYRAGPSFEERKQLGLPHQR
RGGNFKSNPDTRGGSSCRGLKKFMGAALKSLPCGKSSWLVCLFSICLKKKQKQKTTLWCGGMVRSYFPKHVCQSPFLLISFHMTIL
NGSIFGKRE

(-1)ORF (SEQ ID NO: 43)
MEKIFISSSTKAEGKGISPFEAPINTQAPPEKGKEAVVQEPERSWFQTKEERKKEKIAKALQEFDLALRGKKKRKKFMKDAKKKGEMT
AEERSQFEILKAQMFAERLAKRNRRAKRARAMPEEEPVRGPAKKQKQGKKSVFDEELTNTSKKALKQYRAGPSFEERKQLGLPHQR
RGGNFKSNPDTRGGSSCRGLKKFMGAALKSLPCGKSSWLVCLFSICLKK*NKNKKQHFGVVVWYVAIFLSMSVNLPSC*

(+1)/(-2)ORF (SEQ ID NO: 44)
MEKIFISSSTKAEGKGISPFEAPINTQAPPEKGKEAVVQEPERSWFQTKEERKKEKIAKALQEFDLALRGKKKRKKFMKDAKKKGEMT
AEERSQFEILKAQMFAERLAKRNRRAKRARAMPEEEPVRGPAKKQKQGKKSVFDEELTNTSKKALKQYRAGPSFEERKQLGLPHQR
RGGNFKSNPDTRGGSSCRGLKKFMGAALKSLPCGKSSWLVCLFSICLKK(K)*TKTKNNTLVWWYGT*

Bax
(wt)ORF (SEQ ID NO: 45)
MDGSGEQPRGGGPTSSEQIMKTGALLLQGFIQDRAGRMGGEAPELALDPVPQDASTKKLSECLKRIGDELDSNMELQRMIAAVDTD
SPREVFFRVAADMFSDGNFNWGRVVALFYFASKLVLKALCTKVPELIRTIMGWTLDFLRERLLGWIQDQGGWDGLLSYFGTPTWQT
VTIFVAGVLTASLTIWKKMG

(-1)ORF (SEQ ID NO: 46)
MDGSGEQPRGGGPTSSEQIMKTGALLLQGFIQDRAGRMGG*RHPSWPWTRCLRMRPPRS*

(+1)/(-2)ORF (SEQ ID NO: 47)
MDGSGEQPRGGGPTSSEQIMKTGALLLQGFIQDRAGRMGG*(G)GTRAGPGPGASGCVHQEAERVSQAHRGRTGQ*

TCF6L1
(wt)ORF (SEQ ID NO: 48)
MAFLRSMWGVLSALGRSGAELCTGCGSRLRSPFSFVYLPRWFSSVLASCPKKPVSSYLRFSKEQLPIFKAQNPDAKTTELIRRIAQR
WRELPDSKKKIYQDAYRAEWQVYKEEISRFKEQLTPSQIMSLEKEIMDKHLRKAMTKKKELTLLGKPKRPRSAYNVYVAERFQEAK
GDSPQEKLKTVKENWKNLSDSEKELYIQHAKEDETRYHNEMKSWEEQMIEVGRKDLLRRTIKKQRKYGAEEC

(-1)ORF (SEQ ID NO: 49)
MAFLRSMWGVLSALGRSGAELCTGCGSRLRSPFSFVYLPRWFSSVLASCPKKPVSSYLRFSKEQLPIFKAQNPDAKTTELIRRIAQR
WRELPDSKKKIYQDAYRAEWQVYKEEISRFKEQLTPSQIMSLEKEIMDKHLRKAMTKKK*S*

(+1)/(-2)ORF (SEQ ID NO: 50)
MAFLRSMWGVLSALGRSGAELCTGCGSRLRSPFSFVYLPRWFSSVLASCPKKPVSSYLRFSKEQLPIFKAQNPDAKTTELIRRIAQR
WRELPDSKKKIYQDAYRAEWQVYKEEISRFKEQLTPSQIMSLEKEIMDKHLRKAMTKK(K)*RVNTAWKTKKTSFSL*

FTL3L
(wt)ORF (SEQ ID NO: 51)
MTVLAPAWSPTTYLLLLLLLSSGLSGTQDCSFQHSPISSDFAVKIRELSDYLLQDYPVTVASNLQDEELCGGLWRLVLAQRWMERLKT
VAGSKMQGLLERVNTEIHFVTKCAFQPPPSCLRFVQTNISRLLQETSEQLVALKPWITRQNFSRCLELQCQPDSSTLPPPWSPRPLE
ATAPTAPQPPLLLLLLPVGLLLLAAAWCLHWQRTRRRTPRPGEQVPPVPSPQDLLLVEH

(-1)ORF (SEQ ID NO: 52)
MTVLAPAWSPTTYLLLLLLLSSGLSGTQDCSFQHSPISSDFAVKIRELSDYLLQDYPVTVASNLQDEELCGGLWRLVLAQRWMERLKT
VAGSKMQGLLERVNTEIHFVTKCAFQ
PPP*AVFASSRPTSPASCRRPPSSWWR*

FIG. 2-5

(+1)/(-2)ORF (SEQ ID NO: 53)
MTVLAPAWSPTTYLLLLLLLSSGLSGTQDCSFQHSPISSDFAVKIRELSDYLLQDYPVTVASNLQDEELCGGLWRLVLAQRWMERLKT
VAGSKMQGLLERVNTEIHFVTKCAFQ
PP(P)*QLSSLRPDQHLPPPAGDLRAAGGAEALDHSPELLPVPGAAVSAR*

OGT

(wt)ORF (SEQ ID NO: 54)
MLQGHFWLVREGIMISPSSPPPPNLFFFPLQIFPFPFTSFPSHLLSLTPPKACYLKAIETQPNFAVAWSNLGCVFNAQGEIWLAIHHFE
KAVTLDPNFLDAYINLGNVLKEARIFDRAVAAYLRALSLSPNHAVVHGNLACVYYEQGLIDLAIDTYRRAIELQPHFPDAYCNLANALKE
KGSVAEAEDCYNTALRLCPTHADSLNNLANIKREQGNIEEAVRLYRKALEVFPEFAAAHSNLASVLQQQGKLQEALMHYKEAIRISPTF
ADAYSNMGNTLKEMQDVQGALQCYTRAIQINPAFADAHSNLASIHKDSGNIPEAIASYRTALKLKPDFPDAYCNLAHCLQIVCDWTDY
DERMKKLVSIVADQLEKNRLPSVHPHHSMLYPLSHGFRKAIAERHGNLCLDKINVLHKPPYEHPKDLKLSDGRLRVGYVSSDFGNHPT
SHLMQSIPGMHNPDKFEVFCYALSPDDGTNFRVKVMAEANHFIDLSQIPCNGKAADRIHQDGIHILVNMNGYTKGARNELFALRPAPI
QAMWLGYPGTSGALFMDYIITDQETSPAEVAEQYSEKLAYMPHTFFIGDHANMFPHLKKKAVIDFKSNGHIYDNRIVLNGIDLKAFLDS
LPDVKIVKMKCPDGGDNADSSNTALNMPVIPMNTIAEAVIEMINRGQIQITINGFSISNGLATTQINNKAATGEEVPRTIIVTTRSQYGLP
EDAIVYCNFNQLYKIDPSTLQMWANILKRVPNSVLWLLRFPAVGEPNIQQYAQNMGLPQNRIIFSPVAPKEEHVRRGQLADVCLDTPL
CNGHTTGMDVLWAGTPMVTMPGETLASRVAASQLTCLGCLELIAKNRQEYEDIAVKLGTDLEYLKKVRGKVWKQRISSPLFNTKQYT
MELERLYLQMWEHYAAGNKPDHMIKPVEVTESA

(-1)ORF (SEQ ID NO: 55)
MLQGHFWLVREGIMISPSSPPPPNLFF*SLYKFSPFPLPPFPPIFFH*

(+1)/(-2)ORF (SEQ ID NO: 56)
MLQGHFWLVREGIMISPSSPPPPNLFF(F)*PFTNFPLSLYLLSLPSSFINPS*

ELAVL3

(wt)ORF (SEQ ID NO: 57)
MESQVGGGPAGRPAQRPLLGTNGATDDSKTNLIVNYLPQNMTQDEFKSLFGSIGDIESCKLVRDKITGQSLGYGFVNYSDPNDADKA
INTLNGLKLQTKTIKVSYARPSSASIRDANLYVSGLPKTMSQKEMEQLFSQYGRIITSRILVDQVTGVSRGVGFIRFDKRIEAEEAIKGLN
GQKPLGAREPITVKFANNPSQKTGQALLTHLYQSSARRYAGPLHHQTQRFRLDNLLNMAYAVKRFSPIAIDGMSGLAGVGLSGGAAG
GWCIFVYNLSPEPDQSVLWQLFGPFGAVTNVKVIRDFTTNKCKGFGFMTMTNYDEAAMAIASLNGYRLGQRVLQVSFKTSKQHKA

(-1)ORF (SEQ ID NO: 58)
MESQVGG*ARPAGLPNGHSLVQMEPLTTARPTSSSTTCPRT*

(+1)/(-2)ORF (SEQ ID NO: 59)
MESQVGG(G)*PGRPACPTATPWYKWSH*

MAC30X

(wt)ORF (SEQ ID NO: 60)
LFSHQRVQAQPTDYGGSFTRRCVEWLLGLYFLSHIPITLFMDLQAVVPRELYPVEFRNLLKWYAKEFKDPLLQEPPAWFKSFLFCELV
FQLPFFPIATYAFLKGSCKWIRTPAIIYSVHTMTTLILILSTFLFEDFSKASGFKGQRPETLHERLTLVSVYAPYLLIPFILLIFMLRSPYYKY
EEKRKKK

(-1)ORF (SEQ ID NO: 61)
LFSHQRVQAQPTDYGGSFTRRCVEWLLGLYFLSHIPITLFMDLQAVVPRELYPVEFRNLLKWYAKEFKDPLLQEPPAWFKSFLFCELV
FQLPFFPIATYAFLKGSCKWIRTPAIIYSVHTMTTLILILSTFLFEDFSKASGFKGQRPETLHERLTLVSVYAPYLLIPFILLIFMLRSPYYKY
EEKRKKK*NEGNNHWPRVEMPTGWLLVGYIQEHCSEPTSSAAFETLAAMHKSKMVSGTMSNPHLLPFFFFF*

(+1)/(-2)ORF (SEQ ID NO: 62)
LFSHQRVQAQPTDYGGSFTRRCVEWLLGLYFLSHIPITLFMDLQAVVPRELYPVEFRNLLKWYAKEFKDPLLQEPPAWFKSFLFCELV
FQLPFFPIATYAFLKGSCKWIRTPAIIYSVHTMTTLILILSTFLFEDFSKASGFKGQRPETLHERLTLVSVYAPYLLIPFILLIFMLRSPYYKY
EEKRKKK(K)*MKETTTGPG*

SLC4A3

(wt)ORF (SEQ ID NO: 63)
MANGVIPPPGGASPLPQVRVPLEEPPLSPDVEEEDDDLGKTLAVSRFGDLISKPPAWDPEKPSRSYSERDFEFHRHTSHHTHHPLSA
RLPPPHKLRRLPPTSARHTRRKRKKEKTSAPPSEGTPPIQEEGGAGVDEEEEEEEEEEGESEAEPVEPPPSGTPQKAKFSIGSDEDD
SPGLPGRAAVTKPLPSVGPHTDKSPQHSSSSPSPRARASRLAGEKSRPWSPSASYDLRERLCPGSALGNPGGPEQQVPTDEAEAQ
MLGSADLDDMKSHRLEDNPVGVRRHLVKKPSRTQGGRGSPSGLAPILRRKKKKKKKLDRRPHEVFVELNELMLDRSQEPHWRETARW
IKFEEDVEEETERWGKPHVASLSFRSLLELRRTIAHGAALLDLEQTTLPGIAHLVVETMIVSDQIRPEDRASVLRTLLLKHSHPNDDKDS
GFFPRNPSSSSMNSVLGNHHPTPSHGPDGAVPTMADDLGEPAPLWPHDPDAKEKPLHMPGGDGHRGKSLKLLEKIPEDAEATVVL
VGCVPFLEQPAAAFVRLNEAVLLESVLEVPVPVRFLFVMLGPSHTSTDYHELGRSIATLMSDKLFHEAAYQADDRQDLLSAISEFLDG
SIVIPPSEVEGRDLLRSVAAFQRELLRKRREREQTKVEMTTRGGYTAPGKELSLELGGSEATPEDDPLLRTGSVFGGLVRDVRRRYP
HYPSDLRDALHSQCVAAVLFIYFAALSPAITFGGLLGEKTEGLMGVSELIVSTAVLGVLFSLLGAQPLLVVGFSGPLLVFEEAFFKFCRA
QDLEYLTGRVWVGLWLVVFVLALVAAEGSFLVRYISPFTQEIFAFLISLIFIYETFYKLYKVFTEHPLLPFYPPEGALEGSLAAGLEPNGS
ALPPTEGPPSPRNQPNTALLSLILMLGTFFFIAFFLRKFRNSRFLGGKARRIIGDFGIPISILVMVLVDYSITDTYTQKLTVPTGLSVTSPDK
RSWFIPPLGSARPFPPWMMVAAAVPALLVLILFMETQITALIVSQKARRLLKGSGFHLDLLLIGSLGLQCGLFGLPWLTAATVRSVTHV
NALTVMRTAIAPGDKPQIQEVREQRVTGVLIASLVGLSIVMGAVLRRIPLAVLFGIFLYMGVTSLSGIQLSQRLLLILMPAKHHPEQPYVT
KVKTWRMHLFTCIQLGCIALLWVVKSTAASLAFPFLLLLTVPLRHCLLPRLFQDRELQALDSEDAEPNFDEDGQDEYNELHMPV

(-1)ORF (SEQ ID NO: 64)
MANGVIPPPGGASPLPQVRVPLEEPPLSPDVEEEDDDLGKTLAVSRFGDLISKPPAWDPEKPSRSYSERDFEFHRHTSHHTHHPLSA
RLPPPHKLRRLPPTSARHTRRKRKKEKTSAPPSEGTPPIQEEGGAGVDEEEEEEEEEEGESEAEPVEPPP*QGPHRRQSSPLEVTRM
TVQASLGGLLSPSPCPRWAHTLTRAPSTPAAPPAPGPGPPDSLGRKAGPGAHRPVMTCGSDCAQAVPWATQVVQSSRCPQMRRR
PRCWVLQTWTT*

(+1)/(-2)ORF (SEQ ID NO: 65)
MANGVIPPPGGASPLPQVRVPLEEPPLSPDVEEEDDDLGKTLAVSRFGDLISKPPAWDPEKPSRSYSERDFEFHRHTSHHTHHPLSA
RLPPPHKLRRLPPTSARHTRRKRKKEKTSAPPSEGTPPIQEEGGAGVDEEEEEEEEEEGESEAEPVEPP(P)*LRDPTEGKVLHWK*

FIG. 2-6

PRKDC

(wt)ORF (SEQ ID NO: 66)
MAGSGAGVRCSLLRLQETLSAADRCGAALAGHQLIRGLGQECVLSSSPAVLALQTSLVFSRDFGLLVFVRKSLNSIEFRECREEILKFL
CIFLEKMGQKIAPYSVEIKNTCTSVYTKDRAAKCKIPALDLLIKLLQTFRSSRLMDEFKIGELFSKFYGELALKKKIPDTVLEKVYELLGLL
GEVHPSEMINNAENLFRAFLGELKTQMTSAVREPKLPVLAGCLKGLSSLLCNFTKSMEEDPQTSREIFNFVLKAIRPQIDLKRYAVPSA
GLRLFALHASQFSTCLLDNYVSLFEVLLKWCAHTNVELKKAALSALESFLKQVSNMVAKNAEMHKNKLQYFMEQFYGIIRNVDSNNKE
LSIAIRGYGLFAGPCKVINAKDVDFMYVELIQRCKQMFLTQTDTGDDRVYQMPSFLQSVASVLLYLDTVPEVYTPVLEHLVVMQIDSFP
QYSPKMQLVCCRAIVKVFLALAAKGPVLRNCISTVVHQGLIRICSKPVVLPKGPESESEDHRASGEVRTGKWKVPTYKDYVDLFRHLL
SSDQMMDSILADEAFFSVNSSSESLNHLLYDEFVKSVLKIVEKLDLTLEIQTVGEQENGDEAPGVWMIPTSDPAANLHPAKPKDFSAFI
NLVEFCREILPEKQAEFFEPWVYSFSYELILQSTRLPLISGFYKLLSITVRNAKKIKYFEGS
(-1)ORF (SEQ ID NO: 67)
MAGSGAGVRCSLLRLQETLSAADRCGAALAGHQLIRGLGQECVLSSSPAVLALQTSLVFSRDFGLLVFVRKSLNSIEFRECREEILKFL
CIFLEKMGQKIAPYSVEIKNTCTSVYTKDRAAKCKIPALDLLIKLLQTFRSSRLMDEFKIGELFSKFYGELALKKK*YQIQF*
(+1)/(-2)ORF (SEQ ID NO: 68)
MAGSGAGVRCSLLRLQETLSAADRCGAALAGHQLIRGLGQECVLSSSPAVLALQTSLVFSRDFGLLVFVRKSLNSIEFRECREEILKFL
CIFLEKMGQKIAPYSVEIKNTCTSVYTKDRAAKCKIPALDLLIKLLQTFRSSRLMDEFKIGELFSKFYGELALKK(K)*NTRYSFRKSI*

UVRAG

(wt)ORF) (SEQ ID NO: 69)
MSASASVGGPVPQPPPGPAAALPPGSAARALHVELPSQQRRLRHLRNIAARNIVNRNGHQLLDTYFTLHLCSTEKIYKEFYRSEVIKN
SLNPTWRSLDFGIMPDRLDTSVSCFVVKIWGGKENIYQLLIEWKVCLDGLKYLGQQIHARNQNEIIFGLNDGYYGAPFEHKGYSNAQK
TILLQVDQNCVRNSYDVFSLLRLHRAQCAIKQTQVTVQKIGKEIEEKLRLTSTSNELKKKSECLQLKILVLQNELERQKKALGREVALLH
KQQIALQDKGSAFSAEHLKLQLQKESLNELRKECTAKRELFLKTNAQLTIRCRQLLSELSYIYPIDLNEHKDYFVCGVKLPNSEDFQAK
DDGSIAVALGYTAHLVSMISFFLQVPLRYPIIHKGSRSTIKDNINDKLTEKEREFPLYPKGGEKLQFDYGVYLLNKNIAQLRYQHGLGTP
DLRQTLPNLKNFMEHGLMVRCDRHHTSSAIPVPKRQSSIFGGADVGFSGGIPSPDKGHRKRASSENERLQYKTPPPSYNSALAQPVT
TVPSMGETERKITSLSSSLDTSLDFSKENKKKGEDLVGSLNGGHANVHPSQEQGEALSGHRATVNGTLLPSEQAGSASVQLPGEFH
PVSEAELCCTVEQAEEIIGLEAQVSPQVIS
(-1)ORF (SEQ ID NO: 70)
MSASASVGGPVPQPPPGPAAALPPGSAARALHVELPSQQRRLRHLRNIAARNIVNRNGHQLLDTYFTLHLCSTEKIYKEFYRSEVIKN
SLNPTWRSLDFGIMPDRLDTSVSCFVVKIWGGKENIYQLLIEWKVCLDGLKYLGQQIHARNQNEIIFGLNDGYYGAPFEHKGYSNAQK
TILLQVDQNCVRNSYDVFSLLRLHRAQCAIKQTQVTVQKIGKEIEEKLRLTSTSNELKKK*VNACS*
(+1)/(-2)ORF (SEQ ID NO: 71)
MSASASVGGPVPQPPPGPAAALPPGSAARALHVELPSQQRRLRHLRNIAARNIVNRNGHQLLDTYFTLHLCSTEKIYKEFYRSEVIKN
SLNPTWRSLDFGIMPDRLDTSVSCFVVKIWGGKENIYQLLIEWKVCLDGLKYLGQQIHARNQNEIIFGLNDGYYGAPFEHKGYSNAQK
TILLQVDQNCVRNSYDVFSLLRLHRAQCAIKQTQVTVQKIGKEIEEKLRLTSTSNELKKK*(K)*

MSH3

(wt)ORF (SEQ ID NO: 72)
MSRRKPASGGLAASSSAPARQAVLSRFFQSTGSLKSTSSSTGAADQVDPGAAAAAAAAAAAAPPAPPAPAFPPQLPPHVATEIDRR
KKRPLENDGPVKKKVKKVQQKEGGSDLGMSGNSEPKKCLRTRNVSKSLEKLKEFCCDSALPQSRVQTESLQERFAVLPKCTDFDDI
SLLHAKNAVSSEDSKRQINQKDTTLFDLSQFGSSNTSHENLQKTASKSANKRSKSIYTPLELQYIEMKQQHKDAVLCVECGYKYRFFG
EDAEIAARELNIYCHLDHNFMTASIPTHRLFVHVRRLVAKGYKVGVVKQTETAALKAIGDNRSSLFSRKLTALYTKSTLIGEDVNPLIKLD
DAVNVDEIMTDTSTSYLLCISENKENVRDKKKGNIFIGIVGVQPATGEVVFDSFQDSASRSELETRMSSLQPVELLLPSALSEQTEALIH
RATSVSVQDDRIRVERMDNIYFEYSHAFQAVTEFYAKDTVDIKGSQIISGIVNLEKPVICSLAAIIKYLKEFNLEKMLSKPENFKQLSSKM
EFMTINGTTLRNLEILQNQTDMKTKGSLLWVLDHTKTSFGRRKLKKWVTQPLLKLREINARLDAVSEVLHSESSVFGQIENHLRKLPDI
GRGLCSIYHKKCSTQEFFLIVKTLYHLKSEFQAIIPAVNSHIQSDLLRTVILEIPELLSPVEHYLKILNEQAAKVGDKTELFKDLSDFPLIKK
RKDEIQGVIDEIRMHLQEIRKILKNPSAQYVTVSGQEFMIEIKNSAVSCIPTDWVKVGSTKAVSRFHSPFIVENYRHLNQLREQLVLDCS
AEWLDFLEKFSEHYHSLCKAVHHLATVDCIFSLAKVAKQGDYCRPTVQEERKIVIKNGRHPVIDVLLGEQDQYVPNNTDLSEDSERVM
IITGPNMGGKSSYIKQVALITIMAQIGSYVPAEEATIGIVDGIFTRMGAADNIYKGRSTFMEELTDTAEIIRKATSQSLVILDELGRGTSTH
DGIAIAYATLEYFIRDVKSLTLFVTHYPPVCELEKNYSHQVGNYHMGFLVSEDESKLDPGTAEQVPDFVTFLYQITRGIAARSYGLNVA
KLADVPGEILKKAAHKSKELEGLINTKRKRLKYFAKLWTMHNAQDLQKWTEEFNMEETQTSLLH
(-1)ORF (SEQ ID NO: 73)
MSRRKPASGGLAASSSAPARQAVLSRFFQSTGSLKSTSSSTGAADQVDPGAAAAAAAAAAAAPPAPPAPAFPPQLPPHVATEIDRR
KKRPLENDGPVKKKVKKVQQKEGGSDLGMSGNSEPKKCLRTRNVSKSLEKLKEFCCDSALPQSRVQTESLQERFAVLPKCTDFDDI
SLLHAKNAVSSEDSKRQINQKDTTLFDLSQFGSSNTSHENLQKTASKSANKRSKSIYTPLELQYIEMKQQHKDAVLCVECGYKYRFFG
EDAEIAARELNIYCHLDHNFMTASIPTHRLFVHVRRLVAKGYKVGVVKQTETAALKAIGDNRSSLFSRKLTALYTKSTLIGEDVNPLIKLD
DAVNVDEIMTDTSTSYLLCISENKENVRDKK*RATFLLALWECSLPQARLCLIVSRTLLLVQS*
(+1)/(-2)ORF (SEQ ID NO: 74)
MSRRKPASGGLAASSSAPARQAVLSRFFQSTGSLKSTSSSTGAADQVDPGAAAAAAAAAAAAPPAPPAPAFPPQLPPHVATEIDRR
KKRPLENDGPVKKKVKKVQQKEGGSDLGMSGNSEPKKCLRTRNVSKSLEKLKEFCCDSALPQSRVQTESLQERFAVLPKCTDFDDI
SLLHAKNAVSSEDSKRQINQKDTTLFDLSQFGSSNTSHENLQKTASKSANKRSKSIYTPLELQYIEMKQQHKDAVLCVECGYKYRFFG
EDAEIAARELNIYCHLDHNFMTASIPTHRLFVHVRRLVAKGYKVGVVKQTETAALKAIGDNRSSLFSRKLTALYTKSTLIGEDVNPLIKLD
DAVNVDEIMTDTSTSYLLCISENKENVRDKK(K)*GQHFYWHCGSAACHRRGCV*

ACVR2,

(wt) ORF (SEQ ID NO: 107)
MGAAAKLAFA VFLISCSSGA ILGRSETQEC LFFNANWEKD RTNQTGVEPC YGDKDKRRHC FATWKNISGS IEIVKQGCWL
DDINCYDRTD CVEKKDSPEV YFCCCEGNMC NEKFSYFPEM EVTQPTSNPV TPKPPYYNIL LYSLVPLMLI AGIVICAFWV

FIG. 2-7

YRHHKMAYPP VLVPTQDPGP PPPSPLLGLK PLQLLEVKAR GRFGCVWKAQ LLNEYVAVKI FPIQDKQSWQ NEYEVYSLPG
MKHENILQFI GAEKRGTSVD VDLWLITAFH EKGSLSDFLK ANVVSWNELC HIAETMARGL AYLHEDIPGL KDGHKPAISH
RDIKSKNVLL KNNLTACIAD FGLALKFEAG KSAGDTHGQV GTRRYMAPEV LEGAINFQRD AFLRIDMYAM GLVLWELASR
CTAADGPVDE YMLPFEEEIG QHPSLEDMQE VVVHKKKRPV LRDYWQKHAG MAMLCETIEE CWDHDAEARL SAGCVGERIT
QMQRLTNIIT TEDIVTVVTM VTNVDFPPKE SSL*

A8, Pos. 451: -1 ORF (Mut.rate 16.3%) (SEQ ID NO: 108)

MGAAAKLAFA VFLISCSSGA ILGRSETQEC LFFNANWEKD RTNQTGVEPC YGDKDKRRHC FATWKNISGS IEIVKQGCWL
DDINCYDRTD CVEK*KTALKY IFVAVRAICV MKSFLIFRRW KSHSPLQIQL HLSHPITTSC SIPWCHLC**

A8 Pos. 1476: -1 (Mut.rate 81.6%) (SEQ ID NO: 109)

MGAAAKLAFA VFLISCSSGA ILGRSETQEC LFFNANWEKD RTNQTGVEPC YGDKDKRRHC FATWKNISGS IEIVKQGCWL
DDINCYDRTD CVEKKDSPEV YFCCCEGNMC NEKFSYFPEM EVTQPTSNPV TPKPPYYNIL LYSLVPLMLI AGIVICAFWV
YRHHKMAYPP VLVPTQDPGP PPPSPLLGLK PLQLLEVKAR GRFGCVWKAQ LLNEYVAVKI FPIQDKQSWQ NEYEVYSLPG
MKHENILQFI GAEKRGTSVD VDLWLITAFH EKGSLSDFLK ANVVSWNELC HIAETMARGL AYLHEDIPGL KDGHKPAISH
RDIKSKNVLL KNNLTACIAD FGLALKFEAG KSAGDTHGQV GTRRYMAPEV LEGAINFQRD AFLRIDMYAM GLVLWELASR
CTAADGPVDE YMLPFEEEIG QHPSLEDMQE VVVHKK*RGLF**

FLJ11053, A11 Pos. 1695, Mut.rate 52.2% wt ORF (SEQ ID NO: 110)

MVLRKLSKKD VTTKLKAMQE FGTMCTERDT ETVKGVLPYW PRIFCKISLD HDRRVREATQ QAFEKLTLKV KKQLAPYLKS
LMGYWLMAQC DTYTPAAFAA KDAFEAAFPP SKQPEAIAFC KDEITSVLQD HLIKETPDTL SDPQTVPEEE REAKFYRVVT
CSLLALKRLL CLLPDNELDS LEEKFKSLLS QNKFWKYGKH SVPQIRSAYF ELVSALCQRI PQLMKEEASK VSPSVLLSID
DSDPIVCPAL WEAVLYTLTT IEDCWLHVNA KKSVFPKLST VIREGGRGLA TVIYPYLLPF ISKLPHSITN PKLDFFKNFL
TSLVAGLSTE RTKTSSSESS AVISAFYECL RFIMQQNLGE EEIEQMLVND QLIPFIDAVL KDPGLQHGQL FNHLAETLSS
WEAKADTEKD EKTAHNLENV LIHFWERLSE ICVAKISEPE ADVESVLGVS NLLQVLQKPK SSLKSSKKKN GKVRFADEIL
ESNKENEKCV SSEGEKIEGW ELTTEPSLTH NSSGLLSPLR KKPLEDLVCK LADISINYVN ERKSEQHLRF LSTLLDSFSS
SRVFKMLLGD EKQSIVQAKP LEIAKLVQKN PAVQFLYQKL IGWLNEDQRK DFGFLVDILY SALRCCDNDM

-1 ORF (SEQ ID NO: 111)

MVLRKLSKKD VTTKLKAMQE FGTMCTERDT ETVKGVLPYW PRIFCKISLD HDRRVREATQ QAFEKLTLKV KKQLAPYLKS
LMGYWLMAQC DTYTPAAFAA KDAFEAAFPP SKQPEAIAFC KDEITSVLQD HLIKETPDTL SDPQTVPEEE REAKFYRVVT
CSLLALKRLL CLLPDNELDS LEEKFKSLLS QNKFWKYGKH SVPQIRSAYF ELVSALCQRI PQLMKEEASK VSPSVLLSID
DSDPIVCPAL WEAVLYTLTT IEDCWLHVNA KKSVFPKLST VIREGGRGLA TVIYPYLLPF ISKLPHSITN PKLDFFKNFL
TSLVAGLSTE RTKTSSSESS AVISAFYECL RFIMQQNLGE EEIEQMLVND QLIPFIDAVL KDPGLQHGQL FNHLAETLSS
WEAKADTEKD EKTAHNLENV LIHFWERLSE ICVAKISEPE ADVESVLGVS NLLQVLQKPK SSLKSSKKK*M VRLDLLMRYL
KAIKRMKNVY LQKERRLKAG N**

-2 ORF (SEQ ID NO: 112)

MVLRKLSKKD VTTKLKAMQE FGTMCTERDT ETVKGVLPYW PRIFCKISLD HDRRVREATQ QAFEKLTLKV KKQLAPYLKS
LMGYWLMAQC DTYTPAAFAA KDAFEAAFPP SKQPEAIAFC KDEITSVLQD HLIKETPDTL SDPQTVPEEE REAKFYRVVT
CSLLALKRLL CLLPDNELDS LEEKFKSLLS QNKFWKYGKH SVPQIRSAYF ELVSALCQRI PQLMKEEASK VSPSVLLSID
DSDPIVCPAL WEAVLYTLTT IEDCWLHVNA KKSVFPKLST VIREGGRGLA TVIYPYLLPF ISKLPHSITN PKLDFFKNFL
TSLVAGLSTE RTKTSSSESS AVISAFYECL RFIMQQNLGE EEIEQMLVND QLIPFIDAVL KDPGLQHGQL FNHLAETLSS
WEAKADTEKD EKTAHNLENV LIHFWERLSE ICVAKISEPE ADVESVLGVS NLLQVLQKPK SSLKSSKKK*W**

+1 ORF (SEQ ID NO: 113)

MVLRKLSKKD VTTKLKAMQE FGTMCTERDT ETVKGVLPYW PRIFCKISLD HDRRVREATQ QAFEKLTLKV KKQLAPYLKS
LMGYWLMAQC DTYTPAAFAA KDAFEAAFPP SKQPEAIAFC KDEITSVLQD HLIKETPDTL SDPQTVPEEE REAKFYRVVT
CSLLALKRLL CLLPDNELDS LEEKFKSLLS QNKFWKYGKH SVPQIRSAYF ELVSALCQRI PQLMKEEASK VSPSVLLSID
DSDPIVCPAL WEAVLYTLTT IEDCWLHVNA KKSVFPKLST VIREGGRGLA TVIYPYLLPF ISKLPHSITN PKLDFFKNFL
TSLVAGLSTE RTKTSSSESS AVISAFYECL RFIMQQNLGE EEIEQMLVND QLIPFIDAVL KDPGLQHGQL FNHLAETLSS
WEAKADTEKD EKTAHNLENV LIHFWERLSE ICVAKISEPE ADVESVLGVS NLLQVLQKPK SSLKSSKKK*K W**

KIAA1052, A11 Pos. 689, Mut.rate 42.2%

Wt ORF (SEQ ID NO: 114)

MAGRPLRIGD QLVLEEDYDE TYIPSEQEIL EFAREIGIDP IKEPELMWLA REGIVAPLPG EWKPCQDITG DIYYFNFANG
QSMWDHPCDE HYRSLVIQER AKLSTSGAIK KKKKKKEKKD KKDRDPPKSS LALGSSLAPV HVPLGGLAPL RGLVDTPPSA
LRGSQSVSLG SSVESGRQLG ELMLPSQGLK TSAYTKGLLG SIYEDKTALS LLGLGEETNE EDEEESDNQS VHSSSEPLRN
LHLDIGALGG DFEYEESLRT SQPEEKKDVS LDSDAAGPPT PCKPSSPGAD SSLSSAVGKG RQGSGARPGL PEKEENEKSE
PKICRNLVTP KADPTGSEPA KASEKEAPED TVDAGEEGSR REEAAKEPKK KASALEEGSS DASQELEISE HMKEPQLSDS
IASDPKSFHG LDFGFRSRIS EHLLDVDVLS PVLGGACRQA QQPLGIEDKD DSQSSQDELQ SKQSKGLEER YHRLSPPLPH
EERAQSPPRS LATEEEPPQG PEGQPEWKEA EELGEDSAAS LSLQLSLQRE QAPSPPAACE KGKEQHSQAE ELGPGQEEAE
DPEEKVAVSP TPPVSPEVRS TEPVAPPEQL SEAALKAMEE AVAQVLEQDQ RHLLESKQEK MQQLREKLCQ EEEEEILRLH
QQKEQSLSSL RERLQKAIEE EEARMREEES QRLSWLRAQV QSSTQADEDQ IRAEQEASLQ KLREELESQQ KAERASLEQK

FIG. 2-8

NRQMLEQLKE EIEASEKSEQ AALNAAKEKA LQQLREQLEG ERKEAVATLE KEHSAELERL CSSLEAKHRE VVSSLQKKIQ
EAQQKEEAQL QKCLGQVEHR VHQKSYHVAG YEHELSSLLR EKRQEVEGEH ERRLDKMKEE HQQVMAKARE QYEAEERKQR
AELLGHLTGE LERLQRAHER ELETVRQEQH KRLEDLRRRH REQERKLQDL ELDLETRAKD VKARLALLEV QEETARREKQ
QLLDVQRQVA LKSEEATATH QQLEEAQKEH THLLQSNQQL REILDELQAR KLKLESQVDL LQAQSQQLQK HFSSLEAEAQ
KKQHLLREVT VEENNASPHF EPDLHIEDLR KSLGTNQTKE VSSSLSQSKE DLYLDSLSSH NVWHLLSAEG VALRSAKEFL
VQQTRSMRRR QTALKAAQQH WRHELASAQE VAKDPPGIKA LEDMRKNLEK ETRHLDEMKS AMRKGHNLLK KKEEKLNQLE
SSLWEEASDE GTLGGSPTKK AVTFDLSDMD SLSSESSESF SPPHLDSTPS LTSRKIHGLS HSLRQISSQL SSVLSILDSL
NPQSPPPLLA SMPAQLPPRD PKSTPTPTYY GSLARFSALS SATPTSTQWA WDSGQGPRLP SSVAQTVDDF LLEKWRKYFP
SGIPLLSNSP TPLESRLGYM SASEQLRLLQ HSHSQVPEAG STTFQGIIEA NRRWLERVKN DPRLPLFSST PKPKATLSLL
QLGLDEHNRV KVYRF*

- 1 ORF (SEQ ID NO: 115)

MAGRPLRIGD QLVLEEDYDE TYIPSEQEIL EFAREIGIDP IKEPELMWLA REGIVAPLPG EWKPCQDITG DIYYFNFANG
QSMWDHPCDE HYRSLVIQER AKLSTSGAIK KKKKK*RKRKT RRTETPPKVR WPWVPH**

- 2ORF (SEQ ID NO: 116)

MAGRPLRIGD QLVLEEDYDE TYIPSEQEIL EFAREIGIDP IKEPELMWLA REGIVAPLPG EWKPCQDITG DIYYFNFANG
QSMWDHPCDE HYRSLVIQER AKLSTSGAIK KKKKK*GKERQ EGQRPPQKFA GLGFLISPSS CSSWGPGSFT RSCGYPTLCS
SWISKREPGE LSGVWTSAWR THAAFTGSQD LCLYKGSLGLHI**

+ 1 ORF (SEQ ID NO: 117)

MAGRPLRIGD QLVLEEDYDE TYIPSEQEIL EFAREIGIDP IKEPELMWLA REGIVAPLPG EWKPCQDITG DIYYFNFANG
QSMWDHPCDE HYRSLVIQER AKLSTSGAIK KKKKKK*GKER QEGQRPPQKF AGLGFLISPS SCSSWGPGSF TRSCGYPTLC
SSWISKREPG ELSGVWTSAW RTHAAFTGSQ DLCLYKGSLG LHI**

FSP02

FSP06

SEQUENCE LISTING

```
<160> NUMBER OF SEQ ID NOS: 124

<210> SEQ ID NO 1
<211> LENGTH: 320
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 1

Met Gln Arg Pro Asn Ala His Arg Ile Ser Gln Pro Ile Arg Gln Ile
 1               5                  10                  15

Ile Tyr Gly Leu Leu Leu Asn Ala Ser Pro His Leu Asp Lys Thr Ser
            20                  25                  30

Trp Asn Ala Leu Pro Pro Gln Pro Leu Ala Phe Ser Glu Val Glu Arg
        35                  40                  45

Ile Asn Lys Asn Ile Arg Thr Ser Ile Ile Asp Ala Val Glu Leu Ala
    50                  55                  60

Lys Asp His Ser Asp Leu Ser Arg Leu Thr Glu Leu Ser Leu Arg Arg
```

```
              65                  70                  75                  80
Arg Gln Met Leu Leu Leu Glu Thr Leu Lys Val Lys Gln Thr Ile Leu
                    85                  90                  95

Glu Pro Ile Pro Thr Ser Leu Lys Leu Pro Ile Ala Val Ser Cys Tyr
                100                 105                 110

Trp Leu Gln His Thr Glu Thr Lys Ala Lys Leu His His Leu Gln Ser
                115                 120                 125

Leu Leu Leu Thr Met Leu Val Gly Pro Leu Ile Ala Ile Asn Ser
            130                 135                 140

Pro Gly Lys Glu Glu Leu Gln Glu Asp Gly Ala Lys Met Leu Tyr Ala
145                 150                 155                 160

Glu Phe Gln Arg Val Lys Ala Gln Thr Arg Leu Gly Thr Arg Leu Asp
                165                 170                 175

Leu Asp Thr Ala His Ile Phe Cys Gln Trp Gln Ser Cys Leu Gln Met
                180                 185                 190

Gly Met Tyr Leu Asn Gln Leu Leu Ser Thr Pro Leu Pro Glu Pro Asp
                195                 200                 205

Leu Thr Arg Leu Tyr Ser Gly Ser Leu Val His Gly Leu Cys Gln Gln
                210                 215                 220

Leu Leu Ala Ser Thr Ser Val Glu Ser Leu Leu Ser Ile Cys Pro Glu
225                 230                 235                 240

Ala Lys Gln Leu Tyr Glu Tyr Leu Phe Asn Ala Thr Arg Ser Tyr Ala
                245                 250                 255

Pro Ala Glu Ile Phe Leu Pro Lys Gly Arg Ser Asn Ser Lys Lys Lys
                260                 265                 270

Arg Gln Lys Lys Gln Asn Thr Ser Cys Ser Lys Asn Arg Gly Arg Thr
                275                 280                 285

Thr Ala His Thr Lys Cys Trp Tyr Glu Gly Asn Asn Arg Phe Gly Leu
                290                 295                 300

Leu Met Val Glu Asn Leu Glu Glu His Ser Glu Ala Ser Asn Ile Glu
305                 310                 315                 320

<210> SEQ ID NO 2
<211> LENGTH: 304
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 2

Met Gln Arg Pro Asn Ala His Arg Ile Ser Gln Pro Ile Arg Gln Ile
1               5                   10                  15

Ile Tyr Gly Leu Leu Asn Ala Ser Pro His Leu Asp Lys Thr Ser
            20                  25                  30

Trp Asn Ala Leu Pro Pro Gln Pro Leu Ala Phe Ser Glu Val Glu Arg
                35                  40                  45

Ile Asn Lys Asn Ile Arg Thr Ser Ile Ile Asp Ala Val Glu Leu Ala
            50                  55                  60

Lys Asp His Ser Asp Leu Ser Arg Leu Thr Glu Leu Ser Leu Arg Arg
65                  70                  75                  80

Arg Gln Met Leu Leu Leu Glu Thr Leu Lys Val Lys Gln Thr Ile Leu
                85                  90                  95

Glu Pro Ile Pro Thr Ser Leu Lys Leu Pro Ile Ala Val Ser Cys Tyr
                100                 105                 110

Trp Leu Gln His Thr Glu Thr Lys Ala Lys Leu His His Leu Gln Ser
```

```
            115                 120                 125
Leu Leu Leu Thr Met Leu Val Gly Pro Leu Ile Ala Ile Ile Asn Ser
    130                 135                 140
Pro Gly Lys Glu Glu Leu Gln Glu Asp Gly Ala Lys Met Leu Tyr Ala
145                 150                 155                 160
Glu Phe Gln Arg Val Lys Ala Gln Thr Arg Leu Gly Thr Arg Leu Asp
                165                 170                 175
Leu Asp Thr Ala His Ile Phe Cys Gln Trp Gln Ser Cys Leu Gln Met
            180                 185                 190
Gly Met Tyr Leu Asn Gln Leu Leu Ser Thr Pro Leu Pro Glu Pro Asp
                195                 200                 205
Leu Thr Arg Leu Tyr Ser Gly Ser Leu Val His Gly Leu Cys Gln Gln
    210                 215                 220
Leu Leu Ala Ser Thr Ser Val Glu Ser Leu Leu Ser Ile Cys Pro Glu
225                 230                 235                 240
Ala Lys Gln Leu Tyr Glu Tyr Leu Phe Asn Ala Thr Arg Ser Tyr Ala
                245                 250                 255
Pro Ala Glu Ile Phe Leu Pro Lys Gly Arg Ser Asn Ser Lys Lys Lys
            260                 265                 270
Gly Arg Arg Asn Arg Ile Pro Ala Val Leu Arg Thr Glu Gly Glu Pro
    275                 280                 285
Leu His Thr Pro Ser Val Gly Met Arg Glu Thr Thr Gly Leu Gly Cys
290                 295                 300

<210> SEQ ID NO 3
<211> LENGTH: 282
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 3

Met Gln Arg Pro Asn Ala His Arg Ile Ser Gln Pro Ile Arg Gln Ile
1               5                   10                  15
Ile Tyr Gly Leu Leu Leu Asn Ala Ser Pro His Leu Asp Lys Thr Ser
                20                  25                  30
Trp Asn Ala Leu Pro Pro Gln Pro Leu Ala Phe Ser Glu Val Glu Arg
            35                  40                  45
Ile Asn Lys Asn Ile Arg Thr Ser Ile Ile Asp Ala Val Glu Leu Ala
        50                  55                  60
Lys Asp His Ser Asp Leu Ser Arg Leu Thr Glu Leu Ser Leu Arg Arg
65                  70                  75                  80
Arg Gln Met Leu Leu Glu Thr Leu Lys Val Lys Gln Thr Ile Leu
                85                  90                  95
Glu Pro Ile Pro Thr Ser Leu Lys Leu Pro Ile Ala Val Ser Cys Tyr
            100                 105                 110
Trp Leu Gln His Thr Glu Thr Lys Ala Lys Leu His His Leu Gln Ser
        115                 120                 125
Leu Leu Leu Thr Met Leu Val Gly Pro Leu Ile Ala Ile Ile Asn Ser
    130                 135                 140
Pro Gly Lys Glu Glu Leu Gln Glu Asp Gly Ala Lys Met Leu Tyr Ala
145                 150                 155                 160
Glu Phe Gln Arg Val Lys Ala Gln Thr Arg Leu Gly Thr Arg Leu Asp
                165                 170                 175
Leu Asp Thr Ala His Ile Phe Cys Gln Trp Gln Ser Cys Leu Gln Met
```

```
                      180                 185                 190

Gly Met Tyr Leu Asn Gln Leu Leu Ser Thr Pro Leu Pro Glu Pro Asp
                195                 200                 205

Leu Thr Arg Leu Tyr Ser Gly Ser Leu Val His Gly Leu Cys Gln Gln
            210                 215                 220

Leu Leu Ala Ser Thr Ser Val Glu Ser Leu Leu Ser Ile Cys Pro Glu
225                 230                 235                 240

Ala Lys Gln Leu Tyr Glu Tyr Leu Phe Asn Ala Thr Arg Ser Tyr Ala
                245                 250                 255

Pro Ala Glu Ile Phe Leu Pro Lys Gly Arg Ser Asn Ser Lys Lys Lys
            260                 265                 270

Lys Ala Glu Glu Thr Glu Tyr Gln Leu Phe
        275                 280

<210> SEQ ID NO 4
<211> LENGTH: 139
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 4

Met Gly His Pro Arg Ala Ile Gln Pro Ser Val Phe Phe Ser Pro Tyr
 1               5                  10                  15

Asp Val His Phe Leu Leu Tyr Pro Ile Arg Cys Pro Tyr Leu Lys Ile
                20                  25                  30

Gly Arg Phe His Ile Lys Leu Lys Gly Leu His Phe Leu Phe Ser Phe
            35                  40                  45

Leu Phe Phe Phe Glu Thr Gln Ser His Ser Val Thr Arg Leu Glu
 50                  55                  60

Cys Ser Gly Thr Ile Ser Ala His Cys Asn Leu Cys Leu Pro Gly Ser
65                  70                  75                  80

Ser Asn Ser Pro Ala Ser Ala Ser Arg Val Ala Gly Thr Ala Gly Thr
                85                  90                  95

Cys Arg Arg Ala Gln Leu Ile Phe Val Phe Leu Ala Glu Met Gly Phe
            100                 105                 110

His His Val Gly Arg Asp Gly Leu Asp Leu Asn Leu Val Ile His Pro
        115                 120                 125

Pro Arg Ser Pro Lys Ala Leu Gly Leu Gln Ala
    130                 135

<210> SEQ ID NO 5
<211> LENGTH: 101
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 5

Met Gly His Pro Arg Ala Ile Gln Pro Ser Val Phe Phe Ser Pro Tyr
 1               5                  10                  15

Asp Val His Phe Leu Leu Tyr Pro Ile Arg Cys Pro Tyr Leu Lys Ile
                20                  25                  30

Gly Arg Phe His Ile Lys Leu Lys Gly Leu His Phe Leu Phe Ser Phe
            35                  40                  45

Leu Phe Phe Phe Leu Arg His Ser Leu Thr Leu Ser Pro Gly Trp Ser
 50                  55                  60
```

```
Ala Val Ala Arg Ser Arg Leu Thr Ala Thr Ser Ala Ser Gln Val Gln
 65                  70                  75                  80

Val Ile Leu Leu Pro Gln Pro Pro Glu Trp Leu Gly Leu Gln Ala Arg
                 85                  90                  95

Ala Ala Ala Pro Ser
            100

<210> SEQ ID NO 6
<211> LENGTH: 53
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 6

Met Gly His Pro Arg Ala Ile Gln Pro Ser Val Phe Phe Ser Pro Tyr
  1               5                  10                  15

Asp Val His Phe Leu Leu Tyr Pro Ile Arg Cys Pro Tyr Leu Lys Ile
                 20                  25                  30

Gly Arg Phe His Ile Lys Leu Lys Gly Leu His Phe Leu Phe Ser Phe
             35                  40                  45

Leu Phe Phe Phe Phe
         50

<210> SEQ ID NO 7
<211> LENGTH: 209
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 7

Met Gln Arg Arg Leu Val Gln Gln Trp Ser Val Ala Val Phe Leu Leu
  1               5                  10                  15

Ser Tyr Ala Val Pro Ser Cys Gly Arg Ser Val Glu Gly Leu Ser Arg
                 20                  25                  30

Arg Leu Lys Arg Ala Val Ser Glu His Gln Leu Leu His Asp Lys Gly
             35                  40                  45

Lys Ser Ile Gln Asp Leu Arg Arg Phe Phe His His Leu Ile
 50                  55                  60

Ala Glu Ile His Thr Ala Glu Ile Arg Ala Thr Ser Glu Val Ser Pro
 65                  70                  75                  80

Asn Ser Lys Pro Ser Pro Asn Thr Lys Asn His Pro Val Arg Phe Gly
                 85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Gly
            115                 120                 125

Lys Pro Gly Lys Arg Lys Glu Gln Lys Lys Arg Arg Thr Arg
            130                 135                 140

Ser Ala Trp Leu Asp Ser Gly Val Thr Gly Ser Gly Leu Glu Gly Asp
145                 150                 155                 160

His Leu Ser Asp Thr Ser Thr Ser Leu Glu Leu Asp Ser Arg Thr
                165                 170                 175

Ala Leu Leu Trp Gly Leu Lys Lys Lys Glu Asn Asn Arg Arg Thr
            180                 185                 190
```

-continued

His His Met Gln Leu Met Ile Ser Leu Phe Lys Ser Pro Leu Leu Leu
        195                 200                 205

Leu

<210> SEQ ID NO 8
<211> LENGTH: 196
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 8

Met Gln Arg Arg Leu Val Gln Gln Trp Ser Val Ala Val Phe Leu Leu
 1               5                  10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Arg Arg Thr Arg
    130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Thr
                165                 170                 175

Ala Leu Leu Trp Gly Leu Lys Lys Lys Arg Lys Thr Thr Glu Glu His
            180                 185                 190

Ile Ile Cys Asn
        195

<210> SEQ ID NO 9
<211> LENGTH: 202
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 9

Met Gln Arg Arg Leu Val Gln Gln Trp Ser Val Ala Val Phe Leu Leu
 1               5                  10                  15

Ser Tyr Ala Val Pro Ser Cys Gly Arg Ser Val Glu Gly Leu Ser Arg
            20                  25                  30

Arg Leu Lys Arg Ala Val Ser Glu His Gln Leu Leu His Asp Lys Gly
        35                  40                  45

Lys Ser Ile Gln Asp Leu Arg Arg Arg Phe Phe Leu His His Leu Ile
    50                  55                  60

Ala Glu Ile His Thr Ala Glu Ile Arg Ala Thr Ser Glu Val Ser Pro
65                  70                  75                  80

```
Asn Ser Lys Pro Ser Pro Asn Thr Lys Asn His Pro Val Arg Phe Gly
                85                  90                  95

Ser Asp Asp Glu Gly Arg Tyr Leu Thr Gln Glu Thr Asn Lys Val Glu
            100                 105                 110

Thr Tyr Lys Glu Gln Pro Leu Lys Thr Pro Gly Lys Lys Lys Lys Gly
        115                 120                 125

Lys Pro Gly Lys Arg Lys Glu Gln Glu Lys Lys Arg Arg Thr Arg
130                 135                 140

Ser Ala Trp Leu Asp Ser Gly Val Thr Gly Ser Gly Leu Glu Gly Asp
145                 150                 155                 160

His Leu Ser Asp Thr Ser Thr Thr Ser Leu Glu Leu Asp Ser Arg Thr
                165                 170                 175

Ala Leu Leu Trp Gly Leu Lys Lys Lys Gly Lys Gln Gln Lys Asn
            180                 185                 190

Thr Ser Tyr Ala Thr Asn Asp Leu Ile Ile
        195                 200
```

<210> SEQ ID NO 10
<211> LENGTH: 567
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 10

```
Met Gly Arg Gly Leu Leu Arg Gly Leu Trp Pro Leu His Ile Val Leu
  1               5                  10                  15

Trp Thr Arg Ile Ala Ser Thr Ile Pro Pro His Val Gln Lys Ser Val
             20                  25                  30

Asn Asn Asp Met Ile Val Thr Asp Asn Asn Gly Ala Val Lys Phe Pro
         35                  40                  45

Gln Leu Cys Lys Phe Cys Asp Val Arg Phe Ser Thr Cys Asp Asn Gln
     50                  55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
            180                 185                 190

Arg Gln Gln Lys Leu Ser Ser Thr Trp Glu Thr Gly Lys Thr Arg Lys
        195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240
```

Leu Leu Pro Ile Glu Leu Asp Thr Leu Val Gly Lys Gly Arg Phe Ala
            245                 250                 255

Glu Val Tyr Lys Ala Lys Leu Lys Gln Asn Thr Ser Glu Gln Phe Glu
        260                 265                 270

Thr Val Ala Val Lys Ile Phe Pro Tyr Glu Tyr Ala Ser Trp Lys
        275                 280                 285

Thr Glu Lys Asp Ile Phe Ser Asp Ile Asn Leu Lys His Glu Asn Ile
        290                 295                 300

Leu Gln Phe Leu Thr Ala Glu Glu Arg Lys Thr Glu Leu Gly Lys Gln
305                 310                 315                 320

Tyr Trp Leu Ile Thr Ala Phe His Ala Lys Gly Asn Leu Gln Glu Tyr
                325                 330                 335

Leu Thr Arg His Val Ile Ser Trp Glu Asp Leu Arg Lys Leu Gly Ser
            340                 345                 350

Ser Leu Ala Arg Gly Ile Ala His Leu His Ser Asp His Thr Pro Cys
            355                 360                 365

Gly Arg Pro Lys Met Pro Ile Val His Arg Asp Leu Asn Ser Ser Asn
        370                 375                 380

Ile Leu Val Lys Asn Asp Leu Thr Cys Cys Leu Cys Asp Phe Gly Leu
385                 390                 395                 400

Ser Leu Arg Leu Asp Pro Thr Leu Ser Val Asp Asp Leu Ala Asn Ser
                405                 410                 415

Gly Gln Val Gly Thr Ala Arg Tyr Met Ala Pro Glu Val Leu Glu Ser
            420                 425                 430

Arg Met Asn Leu Glu Asn Ala Glu Ser Phe Lys Gln Thr Asp Val Tyr
        435                 440                 445

Ser Met Ala Leu Val Leu Trp Glu Met Thr Ser Arg Cys Asn Ala Val
        450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
            500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
        530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 11
<211> LENGTH: 161
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 11

Met Gly Arg Gly Leu Leu Arg Gly Leu Trp Pro Leu His Ile Val Leu
 1               5                  10                  15

Trp Thr Arg Ile Ala Ser Thr Ile Pro Pro His Val Gln Lys Ser Val
            20                  25                  30

```
Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
 50                  55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Ser
            115                 120                 125

Leu Val Arg Leu Ser Ser Cys Val Pro Val Ala Leu Met Ser Ala Met
130                 135                 140

Thr Thr Ser Ser Ser Gln Lys Asn Ile Thr Pro Ala Ile Leu Thr Cys
145                 150                 155                 160

Cys

<210> SEQ ID NO 12
<211> LENGTH: 130
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 12

Met Gly Arg Gly Leu Leu Arg Gly Leu Trp Pro Leu His Ile Val Leu
  1               5                  10                  15

Trp Thr Arg Ile Ala Ser Thr Ile Pro Pro His Val Gln Lys Ser Val
                 20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
 50                  55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys
            115                 120                 125

Ala Trp
    130

<210> SEQ ID NO 13
<211> LENGTH: 332
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 13

Met Gly Ala Gln Phe Ser Lys Thr Ala Ala Lys Gly Glu Ala Ala Ala
  1               5                  10                  15

Glu Arg Pro Gly Glu Ala Ala Val Ala Ser Ser Pro Ser Lys Ala Asn
```

```
                    20                  25                  30
Gly Gln Glu Asn Gly His Val Lys Val Asn Gly Asp Ala Ser Pro Ala
                35                  40                  45

Ala Ala Glu Ser Gly Ala Lys Glu Glu Leu Gln Ala Asn Gly Ser Ala
            50                  55                  60

Pro Ala Ala Asp Lys Glu Glu Pro Ala Ala Gly Ser Gly Ala Ala
 65                  70                  75                  80

Ser Pro Ser Ser Ala Glu Lys Gly Glu Pro Ala Ala Ala Ala Pro
                85                  90                  95

Glu Ala Gly Ala Ser Pro Val Glu Lys Glu Ala Pro Ala Glu Gly Glu
                100                 105                 110

Ala Ala Glu Pro Gly Ser Ala Thr Ala Ala Glu Gly Glu Ala Ala Ser
            115                 120                 125

Ala Ala Ser Ser Thr Ser Ser Pro Lys Ala Glu Asp Gly Ala Thr Pro
            130                 135                 140

Ser Pro Ser Asn Glu Thr Pro Lys Lys Lys Lys Arg Phe Ser Phe
145                 150                 155                 160

Lys Lys Ser Phe Lys Leu Ser Gly Phe Ser Phe Lys Lys Asn Lys Lys
                165                 170                 175

Glu Ala Gly Glu Gly Gly Glu Ala Glu Ala Pro Ala Ala Glu Gly Gly
                180                 185                 190

Lys Asp Glu Ala Ala Gly Gly Ala Ala Ala Ala Ala Glu Ala Gly
            195                 200                 205

Ala Ala Ser Gly Glu Gln Ala Ala Ala Pro Gly Glu Glu Ala Ala Ala
            210                 215                 220

Gly Glu Glu Gly Ala Ala Gly Gly Asp Pro Gln Glu Ala Lys Pro Gln
225                 230                 235                 240

Glu Ala Ala Val Ala Pro Glu Lys Pro Pro Ala Ser Asp Glu Thr Lys
                245                 250                 255

Ala Ala Glu Glu Pro Ser Lys Val Glu Glu Lys Lys Ala Glu Glu Ala
                260                 265                 270

Gly Ala Ser Ala Ala Ala Cys Glu Ala Pro Ser Ala Ala Gly Pro Gly
                275                 280                 285

Ala Pro Pro Glu Gln Glu Ala Ala Pro Ala Glu Glu Pro Ala Ala Ala
            290                 295                 300

Ala Ala Ser Ser Ala Cys Ala Ala Pro Ser Gln Ala Gln Pro Glu
305                 310                 315                 320

Cys Ser Pro Glu Ala Pro Pro Ala Glu Ala Ala Glu
                325                 330

<210> SEQ ID NO 14
<211> LENGTH: 165
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 14

Met Gly Ala Gln Phe Ser Lys Thr Ala Ala Lys Gly Glu Ala Ala Ala
 1               5                   10                  15

Glu Arg Pro Gly Glu Ala Ala Val Ala Ser Ser Pro Ser Lys Ala Asn
                20                  25                  30

Gly Gln Glu Asn Gly His Val Lys Val Asn Gly Asp Ala Ser Pro Ala
                35                  40                  45

Ala Ala Glu Ser Gly Ala Lys Glu Glu Leu Gln Ala Asn Gly Ser Ala
```

```
                50                  55                  60
Pro Ala Asp Lys Glu Glu Pro Ala Ala Gly Ser Gly Ala Ala
 65                  70                  75                  80

Ser Pro Ser Ser Ala Glu Lys Gly Glu Pro Ala Ala Ala Ala Pro
                 85                  90                  95

Glu Ala Gly Ala Ser Pro Val Glu Lys Glu Ala Pro Ala Glu Gly Glu
                100                 105                 110

Ala Ala Glu Pro Gly Ser Ala Thr Ala Ala Glu Gly Ala Ala Ser
                115                 120                 125

Ala Ala Ser Ser Thr Ser Ser Pro Lys Ala Glu Asp Gly Ala Thr Pro
            130                 135                 140

Ser Pro Ser Asn Glu Thr Pro Lys Lys Lys Arg Ser Ala Phe Pro Ser
145                 150                 155                 160

Arg Ser Leu Ser Ser
                165

<210> SEQ ID NO 15
<211> LENGTH: 182
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 15

Met Gly Ala Gln Phe Ser Lys Thr Ala Ala Lys Gly Glu Ala Ala Ala
  1               5                  10                  15

Glu Arg Pro Gly Glu Ala Ala Val Ala Ser Ser Pro Ser Lys Ala Asn
                 20                  25                  30

Gly Gln Glu Asn Gly His Val Lys Val Asn Gly Asp Ala Ser Pro Ala
             35                  40                  45

Ala Ala Glu Ser Gly Ala Lys Glu Glu Leu Gln Ala Asn Gly Ser Ala
         50                  55                  60

Pro Ala Ala Asp Lys Glu Glu Pro Ala Ala Gly Ser Gly Ala Ala
 65                  70                  75                  80

Ser Pro Ser Ser Ala Glu Lys Gly Glu Pro Ala Ala Ala Ala Pro
                 85                  90                  95

Glu Ala Gly Ala Ser Pro Val Glu Lys Glu Ala Pro Ala Glu Gly Glu
                100                 105                 110

Ala Ala Glu Pro Gly Ser Ala Thr Ala Ala Glu Gly Ala Ala Ser
                115                 120                 125

Ala Ala Ser Ser Thr Ser Ser Pro Lys Ala Glu Asp Gly Ala Thr Pro
            130                 135                 140

Ser Pro Ser Asn Glu Thr Pro Lys Lys Lys Glu Ala Leu Phe Leu
145                 150                 155                 160

Gln Glu Val Phe Gln Ala Glu Arg Leu Leu Leu Gln Glu Gln Glu
                165                 170                 175

Gly Gly Trp Arg Arg Arg
            180

<210> SEQ ID NO 16
<211> LENGTH: 596
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 16
```

```
Met Pro Gln Leu Asn Gly Gly Gly Asp Asp Leu Gly Ala Asn Asp
 1               5                  10                  15

Glu Leu Ile Ser Phe Lys Asp Glu Gly Glu Gln Glu Glu Lys Ser Ser
                 20                  25                  30

Glu Asn Ser Ser Ala Glu Arg Asp Leu Ala Asp Val Lys Ser Ser Leu
             35                  40                  45

Val Asn Glu Ser Glu Thr Asn Gln Asn Ser Ser Asp Ser Glu Ala
     50                  55                  60

Glu Arg Arg Pro Pro Arg Ser Glu Ser Phe Arg Asp Lys Ser Arg
 65              70                  75                  80

Glu Ser Leu Glu Glu Ala Ala Lys Arg Gln Asp Gly Gly Leu Phe Lys
                 85                  90                  95

Gly Pro Pro Tyr Pro Gly Tyr Pro Phe Ile Met Ile Pro Asp Leu Thr
             100                 105                 110

Ser Pro Tyr Leu Pro Asn Gly Ser Leu Ser Pro Thr Ala Arg Thr Tyr
             115                 120                 125

Leu Gln Met Lys Trp Pro Leu Leu Asp Val Gln Ala Gly Ser Leu Gln
     130                 135                 140

Ser Arg Gln Ala Leu Lys Asp Ala Arg Ser Pro Ser Pro Ala His Ile
145                 150                 155                 160

Val Ser Asn Lys Val Pro Val Val Gln His Pro His His Val His Pro
                 165                 170                 175

Leu Thr Pro Leu Ile Thr Tyr Ser Asn Glu His Phe Thr Pro Gly Asn
             180                 185                 190

Pro Pro Pro His Leu Pro Ala Asp Val Asp Pro Lys Thr Gly Ile Pro
     195                 200                 205

Arg Pro Pro His Pro Asp Ile Ser Pro Tyr Tyr Pro Leu Ser Pro
 210                 215                 220

Gly Thr Val Gly Gln Ile Pro His Pro Leu Gly Trp Leu Val Pro Gln
225                 230                 235                 240

Gln Gly Gln Pro Val Tyr Pro Ile Thr Thr Gly Gly Phe Arg His Pro
                 245                 250                 255

Tyr Pro Thr Ala Leu Thr Val Asn Ala Ser Val Ser Arg Phe Pro Pro
             260                 265                 270

His Met Val Pro Pro His His Thr Leu His Thr Thr Gly Ile Pro His
     275                 280                 285

Pro Ala Ile Val Thr Pro Thr Val Lys Gln Glu Ser Ser Gln Ser Asp
 290                 295                 300

Val Gly Ser Leu His Ser Ser Lys His Gln Asp Ser Lys Lys Glu Glu
305                 310                 315                 320

Glu Lys Lys Lys Pro His Ile Lys Lys Pro Leu Asn Ala Phe Met Leu
                 325                 330                 335

Tyr Met Lys Glu Met Arg Ala Lys Val Val Ala Glu Cys Thr Leu Lys
             340                 345                 350

Glu Ser Ala Ala Ile Asn Gln Ile Leu Gly Arg Arg Trp His Ala Leu
     355                 360                 365

Ser Arg Glu Glu Gln Ala Lys Tyr Tyr Glu Leu Ala Arg Lys Glu Arg
 370                 375                 380

Gln Leu His Met Gln Leu Tyr Pro Gly Trp Ser Ala Arg Asp Asn Tyr
385                 390                 395                 400

Gly Lys Lys Lys Arg Lys Arg Asp Lys Gln Pro Gly Glu Thr Asn
                 405                 410                 415

Glu His Ser Glu Cys Phe Leu Asn Pro Cys Leu Ser Leu Pro Pro Ile
```

```
                420             425             430
Thr Asp Leu Ser Ala Pro Lys Lys Cys Arg Ala Arg Phe Gly Leu Asp
            435                 440                 445

Gln Gln Asn Asn Trp Cys Gly Pro Cys Arg Arg Lys Lys Lys Cys Val
        450                 455                 460

Arg Tyr Ile Gln Gly Glu Gly Ser Cys Leu Ser Pro Ser Ser Asp
465                 470                 475                 480

Gly Ser Leu Leu Asp Ser Pro Pro Ser Pro Asn Leu Leu Gly Ser
                485                 490                 495

Pro Pro Arg Asp Ala Lys Ser Gln Thr Glu Gln Thr Gln Pro Leu Ser
            500                 505                 510

Leu Ser Leu Lys Pro Asp Pro Leu Ala His Leu Ser Met Met Pro Pro
        515                 520                 525

Pro Pro Ala Leu Leu Leu Ala Glu Ala Thr His Lys Ala Ser Ala Leu
        530                 535                 540

Cys Pro Asn Gly Ala Leu Asp Leu Pro Pro Ala Ala Leu Gln Pro Ala
545                 550                 555                 560

Ala Pro Ser Ser Ser Ile Ala Gln Pro Ser Thr Ser Trp Leu His Ser
                565                 570                 575

His Ser Ser Leu Ala Gly Thr Gln Pro Gln Pro Leu Ser Leu Val Thr
                580                 585                 590

Lys Ser Leu Glu
        595

<210> SEQ ID NO 17
<211> LENGTH: 483
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 17

Met Pro Gln Leu Asn Gly Gly Gly Gly Asp Asp Leu Gly Ala Asn Asp
  1               5                  10                  15

Glu Leu Ile Ser Phe Lys Asp Glu Gly Glu Gln Glu Glu Lys Ser Ser
             20                  25                  30

Glu Asn Ser Ser Ala Glu Arg Asp Leu Ala Asp Val Lys Ser Ser Leu
         35                  40                  45

Val Asn Glu Ser Glu Thr Asn Gln Asn Ser Ser Ser Asp Ser Glu Ala
     50                  55                  60

Glu Arg Arg Pro Pro Pro Arg Ser Glu Ser Phe Arg Asp Lys Ser Arg
 65                  70                  75                  80

Glu Ser Leu Glu Glu Ala Ala Lys Arg Gln Asp Gly Gly Leu Phe Lys
                 85                  90                  95

Gly Pro Pro Tyr Pro Gly Tyr Pro Phe Ile Met Ile Pro Asp Leu Thr
            100                 105                 110

Ser Pro Tyr Leu Pro Asn Gly Ser Leu Ser Pro Thr Ala Arg Thr Tyr
        115                 120                 125

Leu Gln Met Lys Trp Pro Leu Leu Asp Val Gln Ala Gly Ser Leu Gln
    130                 135                 140

Ser Arg Gln Ala Leu Lys Asp Ala Arg Ser Pro Ser Pro Ala His Ile
145                 150                 155                 160

Val Ser Asn Lys Val Pro Val Val Gln His Pro His His Val His Pro
                165                 170                 175

Leu Thr Pro Leu Ile Thr Tyr Ser Asn Glu His Phe Thr Pro Gly Asn
```

```
                    180                 185                 190
Pro Pro Pro His Leu Pro Ala Asp Val Asp Pro Lys Thr Gly Ile Pro
            195                 200                 205

Arg Pro His Pro Pro Asp Ile Ser Pro Tyr Tyr Pro Leu Ser Pro
    210                 215                 220

Gly Thr Val Gly Gln Ile Pro His Pro Leu Gly Trp Leu Val Pro Gln
225                 230                 235                 240

Gln Gly Gln Pro Val Tyr Pro Ile Thr Thr Gly Gly Phe Arg His Pro
                245                 250                 255

Tyr Pro Thr Ala Leu Thr Val Asn Ala Ser Val Ser Arg Phe Pro Pro
            260                 265                 270

His Met Val Pro Pro His His Thr Leu His Thr Thr Gly Ile Pro His
            275                 280                 285

Pro Ala Ile Val Thr Pro Thr Val Lys Gln Glu Ser Ser Gln Ser Asp
            290                 295                 300

Val Gly Ser Leu His Ser Ser Lys His Gln Asp Ser Lys Lys Glu Glu
305                 310                 315                 320

Glu Lys Lys Lys Pro His Ile Lys Lys Pro Leu Asn Ala Phe Met Leu
                325                 330                 335

Tyr Met Lys Glu Met Arg Ala Lys Val Val Ala Glu Cys Thr Leu Lys
                340                 345                 350

Glu Ser Ala Ala Ile Asn Gln Ile Leu Gly Arg Arg Trp His Ala Leu
            355                 360                 365

Ser Arg Glu Glu Gln Ala Lys Tyr Tyr Glu Leu Ala Arg Lys Glu Arg
    370                 375                 380

Gln Leu His Met Gln Leu Tyr Pro Gly Trp Ser Ala Arg Asp Asn Tyr
385                 390                 395                 400

Gly Lys Lys Lys Lys Arg Lys Arg Asp Lys Gln Pro Gly Glu Thr Asn
                405                 410                 415

Glu His Ser Glu Cys Phe Leu Asn Pro Cys Leu Ser Leu Pro Pro Ile
            420                 425                 430

Thr Asp Leu Ser Ala Pro Lys Lys Cys Arg Ala Arg Phe Gly Leu Asp
            435                 440                 445

Gln Gln Asn Asn Trp Cys Gly Pro Cys Arg Arg Lys Lys Ser Ala Phe
450                 455                 460

Ala Thr Tyr Lys Val Lys Ala Ala Ser Ala His Pro Leu Gln Met
465                 470                 475                 480

Glu Ala Tyr

<210> SEQ ID NO 18
<211> LENGTH: 469
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 18

Met Pro Gln Leu Asn Gly Gly Gly Gly Asp Asp Leu Gly Ala Asn Asp
1               5                   10                  15

Glu Leu Ile Ser Phe Lys Asp Glu Gly Glu Gln Glu Glu Lys Ser Ser
            20                  25                  30

Glu Asn Ser Ser Ala Glu Arg Asp Leu Ala Asp Val Lys Ser Ser Leu
        35                  40                  45

Val Asn Glu Ser Glu Thr Asn Gln Asn Ser Ser Ser Asp Ser Glu Ala
    50                  55                  60
```

```
Glu Arg Arg Pro Pro Arg Ser Glu Ser Phe Arg Asp Lys Ser Arg
 65                  70                  75                  80

Glu Ser Leu Glu Glu Ala Ala Lys Arg Gln Asp Gly Leu Phe Lys
             85                  90                  95

Gly Pro Pro Tyr Pro Gly Tyr Pro Phe Ile Met Ile Pro Asp Leu Thr
            100                 105                 110

Ser Pro Tyr Leu Pro Asn Gly Ser Leu Ser Pro Thr Ala Arg Thr Tyr
            115                 120                 125

Leu Gln Met Lys Trp Pro Leu Leu Asp Val Gln Ala Gly Ser Leu Gln
            130                 135                 140

Ser Arg Gln Ala Leu Lys Asp Ala Arg Ser Pro Ser Pro Ala His Ile
145                 150                 155                 160

Val Ser Asn Lys Val Pro Val Val Gln His Pro His His Val His Pro
                165                 170                 175

Leu Thr Pro Leu Ile Thr Tyr Ser Asn Glu His Phe Thr Pro Gly Asn
            180                 185                 190

Pro Pro Pro His Leu Pro Ala Asp Val Asp Pro Lys Thr Gly Ile Pro
            195                 200                 205

Arg Pro Pro His Pro Pro Asp Ile Ser Pro Tyr Tyr Pro Leu Ser Pro
210                 215                 220

Gly Thr Val Gly Gln Ile Pro His Pro Leu Gly Trp Leu Val Pro Gln
225                 230                 235                 240

Gln Gly Gln Pro Val Tyr Pro Ile Thr Thr Gly Gly Phe Arg His Pro
                245                 250                 255

Tyr Pro Thr Ala Leu Thr Val Asn Ala Ser Val Ser Arg Phe Pro Pro
            260                 265                 270

His Met Val Pro Pro His His Thr Leu His Thr Thr Gly Ile Pro His
            275                 280                 285

Pro Ala Ile Val Thr Pro Thr Val Lys Gln Glu Ser Ser Gln Ser Asp
290                 295                 300

Val Gly Ser Leu His Ser Ser Lys His Gln Asp Ser Lys Lys Glu Glu
305                 310                 315                 320

Glu Lys Lys Lys Pro His Ile Lys Lys Pro Leu Asn Ala Phe Met Leu
                325                 330                 335

Tyr Met Lys Glu Met Arg Ala Lys Val Val Ala Glu Cys Thr Leu Lys
            340                 345                 350

Glu Ser Ala Ala Ile Asn Gln Ile Leu Gly Arg Arg Trp His Ala Leu
            355                 360                 365

Ser Arg Glu Glu Gln Ala Lys Tyr Tyr Glu Leu Ala Arg Lys Glu Arg
            370                 375                 380

Gln Leu His Met Gln Leu Tyr Pro Gly Trp Ser Ala Arg Asp Asn Tyr
385                 390                 395                 400

Gly Lys Lys Lys Arg Lys Arg Asp Lys Gln Pro Gly Glu Thr Asn
                405                 410                 415

Glu His Ser Glu Cys Phe Leu Asn Pro Cys Leu Ser Leu Pro Pro Ile
            420                 425                 430

Thr Asp Leu Ser Ala Pro Lys Lys Cys Arg Ala Arg Phe Gly Leu Asp
            435                 440                 445

Gln Gln Asn Asn Trp Cys Gly Pro Cys Arg Arg Lys Lys Lys Val Arg
450                 455                 460

Ser Leu His Thr Arg
465
```

```
<210> SEQ ID NO 19
<211> LENGTH: 556
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 19

Ile Pro Ala Phe Pro Ala Gly Thr Val Leu Gln Pro Phe Pro Glu Ala
  1               5                  10                  15

Ala Leu Ala Thr Arg Val Thr Val Pro Ala Val Glu Ala Pro Ala Ala
             20                  25                  30

Pro Arg Leu Asp Leu Glu Glu Ser Glu Glu Phe Lys Glu Arg Cys Thr
         35                  40                  45

Gln Cys Ala Ala Val Ser Trp Gly Leu Thr Asp Glu Gly Lys Tyr Tyr
     50                  55                  60

Cys Thr Ser Cys His Asn Val Thr Glu Arg Tyr Gln Glu Val Thr Asn
 65                  70                  75                  80

Thr Asp Leu Ile Pro Asn Thr Gln Ile Lys Ala Leu Asn Arg Gly Leu
                 85                  90                  95

Lys Lys Lys Asn Asn Thr Glu Lys Gly Trp Asp Trp Tyr Val Cys Glu
            100                 105                 110

Gly Phe Gln Tyr Ile Leu Tyr Gln Gln Ala Glu Ala Leu Lys Asn Leu
        115                 120                 125

Gly Val Gly Pro Glu Leu Lys Asn Asp Val Leu His Asn Phe Trp Lys
    130                 135                 140

Arg Tyr Leu Gln Lys Ser Lys Gln Ala Tyr Cys Lys Asn Pro Val Tyr
145                 150                 155                 160

Thr Thr Gly Arg Lys Pro Thr Val Leu Glu Asp Asn Leu Ser His Ser
                165                 170                 175

Asp Trp Ala Ser Glu Pro Glu Leu Leu Ser Asp Val Ser Cys Pro Pro
            180                 185                 190

Phe Leu Glu Ser Gly Ala Glu Ser Gln Ser Asp Ile His Thr Arg Lys
        195                 200                 205

Pro Phe Pro Val Ser Lys Ala Ser Gln Ser Glu Thr Ser Val Cys Ser
    210                 215                 220

Gly Ser Leu Asp Gly Val Glu Tyr Ser Gln Arg Lys Glu Lys Gly Ile
225                 230                 235                 240

Val Lys Met Thr Met Pro Gln Thr Leu Ala Phe Cys Tyr Leu Ser Leu
                245                 250                 255

Leu Trp Gln Arg Glu Ala Ile Thr Leu Ser Asp Leu Leu Arg Phe Val
            260                 265                 270

Glu Glu Asp His Ile Pro Tyr Ile Asn Ala Phe Gln His Phe Pro Glu
        275                 280                 285

Gln Met Lys Leu Tyr Gly Arg Asp Arg Gly Ile Phe Gly Ile Glu Ser
    290                 295                 300

Trp Pro Asp Tyr Glu Asp Ile Tyr Lys Lys Thr Ile Glu Val Gly Thr
305                 310                 315                 320

Phe Leu Asp Leu Pro Arg Phe Pro Asp Ile Thr Glu Asp Cys Tyr Leu
                325                 330                 335

His Pro Asn Ile Leu Cys Met Lys Tyr Leu Met Glu Val Asn Leu Pro
            340                 345                 350

Asp Glu Met His Ser Leu Thr Cys His Val Val Lys Met Thr Gly Met
        355                 360                 365

Gly Glu Val Asp Phe Leu Thr Phe Asp Pro Ile Ala Lys Met Ala Lys
```

```
                    370                 375                 380
Ala Val Lys Tyr Asp Val Gln Ala Val Ala Ile Ile Val Val Val Leu
385                 390                 395                 400

Lys Leu Leu Phe Leu Met Asp Asp Ser Phe Glu Trp Ser Leu Ser Asn
                405                 410                 415

Leu Ala Glu Lys His Asn Glu Lys Asn Lys Lys Asp Lys Pro Trp Phe
            420                 425                 430

Asp Phe Arg Lys Trp Tyr Gln Ile Met Lys Lys Ala Phe Asp Glu Lys
            435                 440                 445

Lys Gln Lys Trp Glu Glu Ala Arg Ala Lys Tyr Leu Trp Lys Ser Glu
        450                 455                 460

Lys Pro Leu Tyr Tyr Ser Phe Val Asp Lys Pro Val Ala Tyr Lys Lys
465                 470                 475                 480

Arg Glu Met Val Val Asn Leu Gln Lys Gln Phe Ser Thr Leu Val Asp
                485                 490                 495

Ser Thr Ala Thr Ala Gly Lys Lys Ser Pro Ser Ser Phe Gln Phe Asn
                500                 505                 510

Trp Thr Glu Glu Asp Thr Asp Arg Thr Cys Phe His Gly His Ser Leu
                515                 520                 525

Gln Gly Val Leu Lys Glu Lys Gly Gln Ser Leu Leu Thr Lys Asn Ser
            530                 535                 540

Leu Tyr Trp Leu Ser Thr Gln Lys Phe Cys Arg Trp
545                 550                 555

<210> SEQ ID NO 20
<211> LENGTH: 124
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 20

Ile Pro Ala Phe Pro Ala Gly Thr Val Leu Gln Pro Phe Pro Glu Ala
  1               5                  10                  15

Ala Leu Ala Thr Arg Val Thr Val Pro Ala Val Glu Ala Pro Ala Ala
                 20                  25                  30

Pro Arg Leu Asp Leu Glu Glu Ser Glu Glu Phe Lys Glu Arg Cys Thr
             35                  40                  45

Gln Cys Ala Ala Val Ser Trp Gly Leu Thr Asp Glu Gly Lys Tyr Tyr
         50                  55                  60

Cys Thr Ser Cys His Asn Val Thr Glu Arg Tyr Gln Glu Val Thr Asn
 65                  70                  75                  80

Thr Asp Leu Ile Pro Asn Thr Gln Ile Lys Ala Leu Asn Arg Gly Leu
                 85                  90                  95

Lys Lys Lys Thr Ile Leu Lys Lys Ala Gly Ile Gly Met Cys Val Lys
            100                 105                 110

Val Ser Ser Ile Phe Phe Ile Asn Lys Gln Lys Pro
        115                 120

<210> SEQ ID NO 21
<211> LENGTH: 102
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 21
```

```
Ile Pro Ala Phe Pro Ala Gly Thr Val Leu Gln Phe Pro Glu Ala
1               5                   10                  15

Ala Leu Ala Thr Arg Val Thr Val Pro Ala Val Glu Ala Pro Ala Ala
                20                  25                  30

Pro Arg Leu Asp Leu Glu Glu Ser Glu Glu Phe Lys Glu Arg Cys Thr
            35                  40                  45

Gln Cys Ala Ala Val Ser Trp Gly Leu Thr Asp Glu Gly Lys Tyr Tyr
    50                  55                  60

Cys Thr Ser Cys His Asn Val Thr Glu Arg Tyr Gln Glu Val Thr Asn
65                  70                  75                  80

Thr Asp Leu Ile Pro Asn Thr Gln Ile Lys Ala Leu Asn Arg Gly Leu
                85                  90                  95

Lys Lys Lys Lys Gln Tyr
                100
```

<210> SEQ ID NO 22
<211> LENGTH: 93
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 22

```
Met Asp Thr Gln Lys Gln Ile His Lys Thr His Asn Ser Lys Asn Gln
1               5                   10                  15

Phe Phe Thr Ile Phe Phe Phe Leu Ser Val Gln Phe Gly Lys Glu Gly
                20                  25                  30

Thr Arg Lys Asn Phe Tyr Leu Leu Leu Ser Ile Gly His Tyr Gly Arg
            35                  40                  45

Lys Ser Arg Arg Ala Asp Leu Gly Thr Ala Asp Thr Ala Asp Lys Thr
    50                  55                  60

Glu Pro Glu Cys Phe Ala Ala Ser Trp Thr Phe Asp Pro Asn Pro Ser
65                  70                  75                  80

Val Thr Val Ser Gly Ala His Ser Thr Ala Val His Gln
                85                  90
```

<210> SEQ ID NO 23
<211> LENGTH: 80
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 23

```
Met Asp Thr Gln Lys Gln Ile His Lys Thr His Asn Ser Lys Asn Gln
1               5                   10                  15

Phe Phe Thr Ile Phe Phe Ser Cys Gln Leu Asn Leu Gly Arg Lys Glu
                20                  25                  30

His Ala Lys Ile Phe Thr Phe Phe Gln Leu Asp Thr Met Asp Gly
            35                  40                  45

Asn Pro Gly Glu Leu Thr Leu Glu Leu Gln Thr Leu Gln Ile Lys Gln
    50                  55                  60

Ser Gln Asn Ala Leu Leu Pro Ala Gly Pro Leu Thr Gln Thr Pro Val
65                  70                  75                  80
```

<210> SEQ ID NO 24
<211> LENGTH: 26

```
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 24

Met Asp Thr Gln Lys Gln Ile His Lys Thr His Asn Ser Lys Asn Gln
1               5                   10                  15

Phe Phe Thr Ile Phe Phe Phe Pro Val Ser
            20                  25

<210> SEQ ID NO 25
<211> LENGTH: 760
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 25

Met Ala Gly Gln Gln Phe Gln Tyr Asp Asp Ser Gly Asn Thr Phe Phe
1               5                   10                  15

Tyr Phe Leu Thr Ser Phe Val Gly Leu Ile Val Ile Pro Ala Thr Tyr
            20                  25                  30

Tyr Leu Trp Pro Arg Asp Gln Asn Ala Glu Gln Ile Arg Leu Lys Asn
        35                  40                  45

Ile Arg Lys Val Tyr Gly Arg Cys Met Trp Tyr Arg Leu Arg Leu Leu
    50                  55                  60

Lys Pro Gln Pro Asn Ile Ile Pro Thr Val Lys Lys Ile Val Leu Leu
65                  70                  75                  80

Ala Gly Trp Ala Leu Phe Leu Phe Leu Ala Tyr Lys Val Ser Lys Thr
                85                  90                  95

Asp Arg Glu Tyr Gln Glu Tyr Asn Pro Tyr Glu Val Leu Asn Leu Asp
            100                 105                 110

Pro Gly Ala Thr Val Ala Glu Ile Lys Lys Gln Tyr Arg Leu Leu Ser
        115                 120                 125

Leu Lys Tyr His Pro Asp Lys Gly Gly Asp Glu Val Met Phe Met Arg
    130                 135                 140

Ile Ala Lys Ala Tyr Ala Ala Leu Thr Asp Glu Glu Ser Arg Lys Asn
145                 150                 155                 160

Trp Glu Glu Phe Gly Asn Pro Asp Gly Pro Gln Ala Thr Ser Phe Gly
                165                 170                 175

Ile Ala Leu Pro Ala Trp Ile Val Asp Gln Lys Asn Ser Ile Leu Val
            180                 185                 190

Leu Leu Val Tyr Gly Leu Ala Phe Met Val Ile Leu Pro Val Val Val
        195                 200                 205

Gly Ser Trp Trp Tyr Arg Ser Ile Arg Tyr Ser Gly Asp Gln Ile Leu
    210                 215                 220

Ile Arg Thr Thr Gln Ile Tyr Thr Tyr Phe Val Tyr Lys Thr Arg Asn
225                 230                 235                 240

Met Asp Met Lys Arg Leu Ile Met Val Leu Ala Gly Ala Ser Glu Phe
                245                 250                 255

Asp Pro Gln Tyr Asn Lys Asp Ala Thr Ser Arg Pro Thr Asp Asn Ile
            260                 265                 270

Leu Ile Pro Gln Leu Ile Arg Glu Ile Gly Ser Ile Asn Leu Lys Lys
        275                 280                 285

Asn Glu Pro Pro Leu Thr Cys Pro Tyr Ser Leu Lys Ala Arg Val Leu
```

```
              290                 295                 300
Leu Leu Ser His Leu Ala Arg Met Lys Ile Pro Glu Thr Leu Glu Glu
305                 310                 315                 320

Asp Gln Gln Phe Met Leu Lys Lys Cys Pro Ala Leu Leu Gln Glu Met
                325                 330                 335

Val Asn Val Ile Cys Gln Leu Ile Val Met Ala Arg Asn Arg Glu Glu
                340                 345                 350

Arg Glu Phe Arg Ala Pro Thr Leu Ala Ser Leu Glu Asn Cys Met Lys
            355                 360                 365

Leu Ser Gln Met Ala Val Gln Gly Leu Gln Gln Phe Lys Ser Pro Leu
370                 375                 380

Leu Gln Leu Pro His Ile Glu Glu Asp Asn Leu Arg Arg Val Ser Asn
385                 390                 395                 400

His Lys Lys Tyr Lys Ile Lys Thr Ile Gln Asp Leu Val Ser Leu Lys
                405                 410                 415

Glu Ser Asp Arg His Thr Leu Leu His Phe Leu Glu Asp Glu Lys Tyr
            420                 425                 430

Glu Glu Val Met Ala Val Leu Gly Ser Phe Pro Tyr Val Thr Met Asp
                435                 440                 445

Ile Lys Ser Gln Val Leu Asp Asp Glu Asp Ser Asn Asn Ile Thr Val
450                 455                 460

Gly Ser Leu Val Thr Val Leu Val Lys Leu Thr Arg Gln Thr Met Ala
465                 470                 475                 480

Glu Val Phe Glu Lys Glu Gln Ser Ile Cys Ala Ala Glu Glu Gln Pro
                485                 490                 495

Ala Glu Asp Gly Gln Gly Glu Thr Asn Lys Asn Arg Thr Lys Gly Gly
            500                 505                 510

Trp Gln Gln Lys Ser Lys Gly Pro Lys Lys Thr Ala Lys Ser Lys Lys
        515                 520                 525

Lys Lys Pro Leu Lys Lys Pro Thr Pro Val Leu Leu Pro Gln Ser
530                 535                 540

Lys Gln Gln Lys Gln Lys Gln Ala Asn Gly Val Val Gly Asn Glu Ala
545                 550                 555                 560

Ala Val Lys Glu Asp Glu Glu Val Ser Asp Lys Gly Ser Asp Ser
                565                 570                 575

Glu Glu Glu Glu Thr Asn Arg Asp Ser Gln Ser Glu Lys Asp Asp Gly
                580                 585                 590

Ser Asp Arg Asp Ser Asp Arg Glu Gln Asp Glu Lys Gln Asn Lys Asp
            595                 600                 605

Asp Glu Ala Glu Trp Gln Glu Leu Gln Gln Ser Ile Gln Arg Lys Glu
610                 615                 620

Arg Ala Leu Leu Glu Thr Lys Ser Lys Ile Thr His Pro Val Tyr Ser
625                 630                 635                 640

Leu Tyr Phe Pro Glu Glu Lys Gln Glu Trp Trp Trp Leu Tyr Ile Ala
                645                 650                 655

Asp Arg Lys Glu Gln Thr Leu Ile Ser Met Pro Tyr His Val Cys Thr
            660                 665                 670

Leu Lys Asp Thr Glu Glu Val Glu Leu Lys Phe Pro Ala Pro Gly Lys
        675                 680                 685

Pro Gly Asn Tyr Gln Tyr Thr Val Phe Leu Arg Ser Asp Ser Tyr Met
    690                 695                 700

Gly Leu Asp Gln Ile Lys Pro Leu Lys Leu Glu Val His Glu Ala Lys
705                 710                 715                 720
```

```
Pro Val Pro Glu Asn His Pro Gln Trp Asp Thr Ala Ile Glu Gly Asp
            725                 730                 735

Glu Asp Gln Glu Asp Ser Glu Gly Phe Glu Asp Ser Phe Glu Glu Glu
            740                 745                 750

Glu Glu Glu Glu Glu Asp Asp Asp
        755                 760

<210> SEQ ID NO 26
<211> LENGTH: 531
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 26

Met Ala Gly Gln Gln Phe Gln Tyr Asp Asp Ser Gly Asn Thr Phe Phe
  1               5                  10                  15

Tyr Phe Leu Thr Ser Phe Val Gly Leu Ile Val Ile Pro Ala Thr Tyr
             20                  25                  30

Tyr Leu Trp Pro Arg Asp Gln Asn Ala Glu Gln Ile Arg Leu Lys Asn
         35                  40                  45

Ile Arg Lys Val Tyr Gly Arg Cys Met Trp Tyr Arg Leu Arg Leu Leu
     50                  55                  60

Lys Pro Gln Pro Asn Ile Ile Pro Thr Val Lys Lys Ile Val Leu Leu
 65                  70                  75                  80

Ala Gly Trp Ala Leu Phe Leu Phe Leu Ala Tyr Lys Val Ser Lys Thr
                 85                  90                  95

Asp Arg Glu Tyr Gln Glu Tyr Asn Pro Tyr Glu Val Leu Asn Leu Asp
            100                 105                 110

Pro Gly Ala Thr Val Ala Glu Ile Lys Lys Gln Tyr Arg Leu Leu Ser
        115                 120                 125

Leu Lys Tyr His Pro Asp Lys Gly Gly Asp Glu Val Met Phe Met Arg
    130                 135                 140

Ile Ala Lys Ala Tyr Ala Ala Leu Thr Asp Glu Glu Ser Arg Lys Asn
145                 150                 155                 160

Trp Glu Glu Phe Gly Asn Pro Asp Gly Pro Gln Ala Thr Ser Phe Gly
                165                 170                 175

Ile Ala Leu Pro Ala Trp Ile Val Asp Gln Lys Asn Ser Ile Leu Val
            180                 185                 190

Leu Leu Val Tyr Gly Leu Ala Phe Met Val Ile Leu Pro Val Val Val
        195                 200                 205

Gly Ser Trp Trp Tyr Arg Ser Ile Arg Tyr Ser Gly Asp Gln Ile Leu
    210                 215                 220

Ile Arg Thr Thr Gln Ile Tyr Thr Tyr Phe Val Tyr Lys Thr Arg Asn
225                 230                 235                 240

Met Asp Met Lys Arg Leu Ile Met Val Leu Ala Gly Ala Ser Glu Phe
                245                 250                 255

Asp Pro Gln Tyr Asn Lys Asp Ala Thr Ser Arg Pro Thr Asp Asn Ile
            260                 265                 270

Leu Ile Pro Gln Leu Ile Arg Glu Ile Gly Ser Ile Asn Leu Lys Lys
        275                 280                 285

Asn Glu Pro Pro Leu Thr Cys Pro Tyr Ser Leu Lys Ala Arg Val Leu
    290                 295                 300

Leu Leu Ser His Leu Ala Arg Met Lys Ile Pro Glu Thr Leu Glu Glu
305                 310                 315                 320
```

```
Asp Gln Gln Phe Met Leu Lys Lys Cys Pro Ala Leu Leu Gln Glu Met
                325                 330                 335

Val Asn Val Ile Cys Gln Leu Ile Val Met Ala Arg Asn Arg Glu Glu
            340                 345                 350

Arg Glu Phe Arg Ala Pro Thr Leu Ala Ser Leu Glu Asn Cys Met Lys
        355                 360                 365

Leu Ser Gln Met Ala Val Gln Gly Leu Gln Gln Phe Lys Ser Pro Leu
    370                 375                 380

Leu Gln Leu Pro His Ile Glu Glu Asp Asn Leu Arg Arg Val Ser Asn
385                 390                 395                 400

His Lys Lys Tyr Lys Ile Lys Thr Ile Gln Asp Leu Val Ser Leu Lys
            405                 410                 415

Glu Ser Asp Arg His Thr Leu Leu His Phe Leu Glu Asp Glu Lys Tyr
        420                 425                 430

Glu Glu Val Met Ala Val Leu Gly Ser Phe Pro Tyr Val Thr Met Asp
    435                 440                 445

Ile Lys Ser Gln Val Leu Asp Asp Glu Asp Ser Asn Asn Ile Thr Val
    450                 455                 460

Gly Ser Leu Val Thr Val Leu Val Lys Leu Thr Arg Gln Thr Met Ala
465                 470                 475                 480

Glu Val Phe Glu Lys Glu Gln Ser Ile Cys Ala Ala Glu Glu Gln Pro
            485                 490                 495

Ala Glu Asp Gly Gln Gly Glu Thr Asn Lys Asn Arg Thr Lys Gly Gly
        500                 505                 510

Trp Gln Gln Lys Ser Lys Gly Pro Lys Lys Thr Ala Lys Ser Lys Lys
    515                 520                 525

Arg Asn Leu
    530

<210> SEQ ID NO 27
<211> LENGTH: 558
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 27

Met Ala Gly Gln Gln Phe Gln Tyr Asp Asp Ser Gly Asn Thr Phe Phe
  1               5                  10                  15

Tyr Phe Leu Thr Ser Phe Val Gly Leu Ile Val Ile Pro Ala Thr Tyr
             20                  25                  30

Tyr Leu Trp Pro Arg Asp Gln Asn Ala Glu Gln Ile Arg Leu Lys Asn
         35                  40                  45

Ile Arg Lys Val Tyr Gly Arg Cys Met Trp Tyr Arg Leu Arg Leu Leu
     50                  55                  60

Lys Pro Gln Pro Asn Ile Ile Pro Thr Val Lys Lys Ile Val Leu Leu
 65                  70                  75                  80

Ala Gly Trp Ala Leu Phe Leu Phe Leu Ala Tyr Lys Val Ser Lys Thr
                 85                  90                  95

Asp Arg Glu Tyr Gln Glu Tyr Asn Pro Tyr Glu Val Leu Asn Leu Asp
            100                 105                 110

Pro Gly Ala Thr Val Ala Glu Ile Lys Lys Gln Tyr Arg Leu Leu Ser
        115                 120                 125

Leu Lys Tyr His Pro Asp Lys Gly Gly Asp Glu Val Met Phe Met Arg
    130                 135                 140
```

-continued

```
Ile Ala Lys Ala Tyr Ala Ala Leu Thr Asp Glu Glu Ser Arg Lys Asn
145                 150                 155                 160

Trp Glu Glu Phe Gly Asn Pro Asp Gly Pro Gln Ala Thr Ser Phe Gly
                165                 170                 175

Ile Ala Leu Pro Ala Trp Ile Val Asp Gln Lys Asn Ser Ile Leu Val
            180                 185                 190

Leu Leu Val Tyr Gly Leu Ala Phe Met Val Ile Leu Pro Val Val Val
        195                 200                 205

Gly Ser Trp Trp Tyr Arg Ser Ile Arg Tyr Ser Gly Asp Gln Ile Leu
    210                 215                 220

Ile Arg Thr Thr Gln Ile Tyr Thr Tyr Phe Val Tyr Lys Thr Arg Asn
225                 230                 235                 240

Met Asp Met Lys Arg Leu Ile Met Val Leu Ala Gly Ala Ser Glu Phe
                245                 250                 255

Asp Pro Gln Tyr Asn Lys Asp Ala Thr Ser Arg Pro Thr Asp Asn Ile
            260                 265                 270

Leu Ile Pro Gln Leu Ile Arg Glu Ile Gly Ser Ile Asn Leu Lys Lys
        275                 280                 285

Asn Glu Pro Pro Leu Thr Cys Pro Tyr Ser Leu Lys Ala Arg Val Leu
    290                 295                 300

Leu Leu Ser His Leu Ala Arg Met Lys Ile Pro Glu Thr Leu Glu Glu
305                 310                 315                 320

Asp Gln Gln Phe Met Leu Lys Lys Cys Pro Ala Leu Leu Gln Glu Met
                325                 330                 335

Val Asn Val Ile Cys Gln Leu Ile Val Met Ala Arg Asn Arg Glu Glu
            340                 345                 350

Arg Glu Phe Arg Ala Pro Thr Leu Ala Ser Leu Glu Asn Cys Met Lys
        355                 360                 365

Leu Ser Gln Met Ala Val Gln Gly Leu Gln Gln Phe Lys Ser Pro Leu
    370                 375                 380

Leu Gln Leu Pro His Ile Glu Glu Asp Asn Leu Arg Arg Val Ser Asn
385                 390                 395                 400

His Lys Lys Tyr Lys Ile Lys Thr Ile Gln Asp Leu Val Ser Leu Lys
                405                 410                 415

Glu Ser Asp Arg His Thr Leu Leu His Phe Leu Glu Asp Glu Lys Tyr
            420                 425                 430

Glu Glu Val Met Ala Val Leu Gly Ser Phe Pro Tyr Val Thr Met Asp
        435                 440                 445

Ile Lys Ser Gln Val Leu Asp Asp Glu Asp Ser Asn Asn Ile Thr Val
    450                 455                 460

Gly Ser Leu Val Thr Val Leu Val Lys Leu Thr Arg Gln Thr Met Ala
465                 470                 475                 480

Glu Val Phe Glu Lys Glu Gln Ser Ile Cys Ala Ala Glu Glu Gln Pro
                485                 490                 495

Ala Glu Asp Gly Gln Gly Glu Thr Asn Lys Asn Arg Thr Lys Gly Gly
            500                 505                 510

Trp Gln Gln Lys Ser Lys Gly Pro Lys Lys Thr Ala Lys Ser Lys Lys
        515                 520                 525

Lys Glu Thr Phe Lys Lys Thr Tyr Thr Cys Ala Ile Thr Thr Val
    530                 535                 540

Lys Ala Thr Glu Thr Lys Ala Gly Lys Trp Ser Arg Trp Glu
545                 550                 555
```

<210> SEQ ID NO 28

-continued

<211> LENGTH: 561
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 28

Met Ala Gly Gln Gln Phe Gln Tyr Asp Asp Ser Gly Asn Thr Phe Phe
 1               5                  10                  15

Tyr Phe Leu Thr Ser Phe Val Gly Leu Ile Val Ile Pro Ala Thr Tyr
            20                  25                  30

Tyr Leu Trp Pro Arg Asp Gln Asn Ala Glu Gln Ile Arg Leu Lys Asn
        35                  40                  45

Ile Arg Lys Val Tyr Gly Arg Cys Met Trp Tyr Arg Leu Arg Leu Leu
 50                  55                  60

Lys Pro Gln Pro Asn Ile Ile Pro Thr Val Lys Lys Ile Val Leu Leu
 65                  70                  75                  80

Ala Gly Trp Ala Leu Phe Leu Phe Leu Ala Tyr Lys Val Ser Lys Thr
                85                  90                  95

Asp Arg Glu Tyr Gln Glu Tyr Asn Pro Tyr Glu Val Leu Asn Leu Asp
            100                 105                 110

Pro Gly Ala Thr Val Ala Glu Ile Lys Lys Gln Tyr Arg Leu Leu Ser
        115                 120                 125

Leu Lys Tyr His Pro Asp Lys Gly Asp Glu Val Met Phe Met Arg
    130                 135                 140

Ile Ala Lys Ala Tyr Ala Ala Leu Thr Asp Glu Glu Ser Arg Lys Asn
145                 150                 155                 160

Trp Glu Glu Phe Gly Asn Pro Asp Gly Pro Gln Ala Thr Ser Phe Gly
                165                 170                 175

Ile Ala Leu Pro Ala Trp Ile Val Asp Gln Lys Asn Ser Ile Leu Val
            180                 185                 190

Leu Leu Val Tyr Gly Leu Ala Phe Met Val Ile Leu Pro Val Val Val
        195                 200                 205

Gly Ser Trp Trp Tyr Arg Ser Ile Arg Tyr Ser Gly Asp Gln Ile Leu
    210                 215                 220

Ile Arg Thr Thr Gln Ile Tyr Thr Tyr Phe Val Tyr Lys Thr Arg Asn
225                 230                 235                 240

Met Asp Met Lys Arg Leu Ile Met Val Leu Ala Gly Ala Ser Glu Phe
                245                 250                 255

Asp Pro Gln Tyr Asn Lys Asp Ala Thr Ser Arg Pro Thr Asp Asn Ile
            260                 265                 270

Leu Ile Pro Gln Leu Ile Arg Glu Ile Gly Ser Ile Asn Leu Lys Lys
        275                 280                 285

Asn Glu Pro Pro Leu Thr Cys Pro Tyr Ser Leu Lys Ala Arg Val Leu
    290                 295                 300

Leu Leu Ser His Leu Ala Arg Met Lys Ile Pro Glu Thr Leu Glu Glu
305                 310                 315                 320

Asp Gln Gln Phe Met Leu Lys Lys Cys Pro Ala Leu Leu Gln Glu Met
                325                 330                 335

Val Asn Val Ile Cys Gln Leu Ile Val Met Ala Arg Asn Arg Glu Glu
            340                 345                 350

Arg Glu Phe Arg Ala Pro Thr Leu Ala Ser Leu Glu Asn Cys Met Lys
        355                 360                 365

Leu Ser Gln Met Ala Val Gln Gly Leu Gln Gln Phe Lys Ser Pro Leu
    370                 375                 380

```
Leu Gln Leu Pro His Ile Glu Glu Asp Asn Leu Arg Arg Val Ser Asn
385                 390                 395                 400

His Lys Lys Tyr Lys Ile Lys Thr Ile Gln Asp Leu Val Ser Leu Lys
                405                 410                 415

Glu Ser Asp Arg His Thr Leu Leu His Phe Leu Glu Asp Glu Lys Tyr
            420                 425                 430

Glu Glu Val Met Ala Val Leu Gly Ser Phe Pro Tyr Val Thr Met Asp
        435                 440                 445

Ile Lys Ser Gln Val Leu Asp Asp Glu Asp Ser Asn Asn Ile Thr Val
    450                 455                 460

Gly Ser Leu Val Thr Val Leu Val Lys Leu Thr Arg Gln Thr Met Ala
465                 470                 475                 480

Glu Val Phe Glu Lys Glu Gln Ser Ile Cys Ala Ala Glu Glu Gln Pro
                485                 490                 495

Ala Glu Asp Gly Gln Gly Glu Thr Asn Lys Asn Arg Thr Lys Gly Gly
            500                 505                 510

Trp Gln Gln Lys Ser Lys Gly Pro Lys Thr Ala Lys Ser Lys Lys
        515                 520                 525

Lys Lys Pro Leu Lys Lys Asn Leu His Leu Cys Tyr Tyr His Ser Gln
530                 535                 540

Ser Asn Arg Asn Lys Ser Arg Gln Met Glu Ser Leu Gly Met Lys Leu
545                 550                 555                 560

Gln

<210> SEQ ID NO 29
<211> LENGTH: 558
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 29

Met Ala Gly Gln Gln Phe Gln Tyr Asp Asp Ser Gly Asn Thr Phe Phe
1               5                   10                  15

Tyr Phe Leu Thr Ser Phe Val Gly Leu Ile Val Ile Pro Ala Thr Tyr
                20                  25                  30

Tyr Leu Trp Pro Arg Asp Gln Asn Ala Glu Gln Ile Arg Leu Lys Asn
            35                  40                  45

Ile Arg Lys Val Tyr Gly Arg Cys Met Trp Tyr Arg Leu Arg Leu Leu
    50                  55                  60

Lys Pro Gln Pro Asn Ile Ile Pro Thr Val Lys Lys Ile Val Leu Leu
65                  70                  75                  80

Ala Gly Trp Ala Leu Phe Leu Phe Leu Ala Tyr Lys Val Ser Lys Thr
                85                  90                  95

Asp Arg Glu Tyr Gln Glu Tyr Asn Pro Tyr Glu Val Leu Asn Leu Asp
            100                 105                 110

Pro Gly Ala Thr Val Ala Glu Ile Lys Lys Gln Tyr Arg Leu Leu Ser
        115                 120                 125

Leu Lys Tyr His Pro Asp Lys Gly Gly Asp Glu Val Met Phe Met Arg
130                 135                 140

Ile Ala Lys Ala Tyr Ala Ala Leu Thr Asp Glu Ser Arg Lys Asn
145                 150                 155                 160

Trp Glu Glu Phe Gly Asn Pro Asp Gly Pro Gln Ala Thr Ser Phe Gly
                165                 170                 175
```

```
Ile Ala Leu Pro Ala Trp Ile Val Asp Gln Lys Asn Ser Ile Leu Val
            180                 185                 190

Leu Leu Val Tyr Gly Leu Ala Phe Met Val Ile Leu Pro Val Val Val
            195                 200                 205

Gly Ser Trp Trp Tyr Arg Ser Ile Arg Tyr Ser Gly Asp Gln Ile Leu
210                 215                 220

Ile Arg Thr Thr Gln Ile Tyr Thr Tyr Phe Val Tyr Lys Thr Arg Asn
225                 230                 235                 240

Met Asp Met Lys Arg Leu Ile Met Val Leu Ala Gly Ala Ser Glu Phe
                245                 250                 255

Asp Pro Gln Tyr Asn Lys Asp Ala Thr Ser Arg Pro Thr Asp Asn Ile
            260                 265                 270

Leu Ile Pro Gln Leu Ile Arg Glu Ile Gly Ser Ile Asn Leu Lys Lys
            275                 280                 285

Asn Glu Pro Pro Leu Thr Cys Pro Tyr Ser Leu Lys Ala Arg Val Leu
290                 295                 300

Leu Leu Ser His Leu Ala Arg Met Lys Ile Pro Glu Thr Leu Glu Glu
305                 310                 315                 320

Asp Gln Gln Phe Met Leu Lys Lys Cys Pro Ala Leu Leu Gln Glu Met
                325                 330                 335

Val Asn Val Ile Cys Gln Leu Ile Val Met Ala Arg Asn Arg Glu Glu
            340                 345                 350

Arg Glu Phe Arg Ala Pro Thr Leu Ala Ser Leu Glu Asn Cys Met Lys
                355                 360                 365

Leu Ser Gln Met Ala Val Gln Gly Leu Gln Gln Phe Lys Ser Pro Leu
370                 375                 380

Leu Gln Leu Pro His Ile Glu Glu Asp Asn Leu Arg Arg Val Ser Asn
385                 390                 395                 400

His Lys Lys Tyr Lys Ile Lys Thr Ile Gln Asp Leu Val Ser Leu Lys
                405                 410                 415

Glu Ser Asp Arg His Thr Leu Leu His Phe Leu Glu Asp Glu Lys Tyr
            420                 425                 430

Glu Glu Val Met Ala Val Leu Gly Ser Phe Pro Tyr Val Thr Met Asp
            435                 440                 445

Ile Lys Ser Gln Val Leu Asp Asp Glu Asp Ser Asn Asn Ile Thr Val
450                 455                 460

Gly Ser Leu Val Thr Val Leu Val Lys Leu Thr Arg Gln Thr Met Ala
465                 470                 475                 480

Glu Val Phe Glu Lys Glu Gln Ser Ile Cys Ala Ala Glu Glu Gln Pro
                485                 490                 495

Ala Glu Asp Gly Gln Gly Glu Thr Asn Lys Asn Arg Thr Lys Gly Gly
            500                 505                 510

Trp Gln Gln Lys Ser Lys Gly Pro Lys Lys Thr Ala Lys Ser Lys Lys
            515                 520                 525

Lys Lys Pro Leu Lys Lys Lys Thr Tyr Thr Cys Ala Ile Thr Thr Val
            530                 535                 540

Lys Ala Thr Glu Thr Lys Ala Gly Lys Trp Ser Arg Trp Glu
545                 550                 555
```

<210> SEQ ID NO 30
<211> LENGTH: 418
<212> TYPE: PRT
<213> ORGANISM: Artificial Sequence
<220> FEATURE:
<223> OTHER INFORMATION: Description of Artificial Sequence:
      polypeptides encoded by genes with coding microsatellites <400> SEQUENCE: 30

```
Met Phe Lys Gly Ile Leu Gln Ser Gly Leu Asp Asn Phe Val Ile Asn
  1               5                  10                  15
His Met Leu Lys Asn Asn Val Ala Gly Gln Thr Ser Ile Gln Thr Leu
             20                  25                  30
Val Pro Asn Thr Asp Gln Lys Ser Thr Ser Val Lys Lys Asp Asn His
         35                  40                  45
Lys Lys Lys Thr Val Lys Met Leu Glu Tyr Leu Gly Lys Asp Val Leu
     50                  55                  60
His Gly Val Phe Asn Tyr Leu Ala Lys His Asp Val Leu Thr Leu Lys
 65                  70                  75                  80
Glu Glu Glu Lys Lys Lys Tyr Tyr Asp Ala Lys Ile Glu Asp Lys Ala
                 85                  90                  95
Leu Ile Leu Val Asp Ser Leu Arg Lys Asn Arg Val Ala His Gln Met
            100                 105                 110
Phe Thr Gln Thr Leu Leu Asn Met Asp Gln Lys Ile Thr Ser Val Lys
        115                 120                 125
Pro Leu Leu Gln Ile Glu Ala Gly Pro Pro Glu Ser Ala Glu Ser Thr
130                 135                 140
Asn Ile Leu Lys Leu Cys Pro Arg Glu Glu Phe Leu Arg Leu Cys Lys
145                 150                 155                 160
Lys Asn His Asp Glu Ile Tyr Pro Ile Lys Lys Arg Glu Asp Arg Arg
                165                 170                 175
Arg Leu Ala Leu Ile Ile Cys Asn Thr Lys Phe Asp His Leu Pro Ala
            180                 185                 190
Arg Asn Gly Ala His Tyr Asp Ile Val Gly Met Lys Arg Leu Leu Gln
        195                 200                 205
Gly Leu Gly Tyr Thr Val Val Asp Glu Lys Asn Leu Thr Ala Arg Asp
    210                 215                 220
Met Glu Ser Val Leu Arg Ala Phe Ala Ala Arg Pro Glu His Lys Ser
225                 230                 235                 240
Ser Asp Ser Thr Phe Leu Val Leu Met Ser His Gly Ile Leu Glu Gly
                245                 250                 255
Ile Cys Gly Thr Ala His Lys Lys Lys Lys Pro Asp Val Leu Leu Tyr
            260                 265                 270
Asp Thr Ile Phe Gln Ile Phe Asn Asn Arg Asn Cys Leu Ser Leu Lys
        275                 280                 285
Asp Lys Pro Lys Val Ile Ile Val Gln Ala Cys Arg Gly Glu Lys His
    290                 295                 300
Gly Glu Leu Trp Val Arg Asp Ser Pro Ala Ser Leu Ala Val Ile Ser
305                 310                 315                 320
Ser Gln Ser Ser Glu Asn Leu Glu Ala Asp Ser Val Cys Lys Ile His
                325                 330                 335
Glu Glu Lys Asp Phe Ile Ala Phe Cys Ser Ser Thr Pro His Asn Val
            340                 345                 350
Ser Trp Arg Asp Arg Thr Arg Gly Ser Ile Phe Ile Thr Glu Leu Ile
        355                 360                 365
Thr Cys Phe Gln Lys Tyr Ser Cys Cys Cys His Leu Met Glu Ile Phe
    370                 375                 380
Arg Lys Val Gln Lys Ser Phe Glu Val Pro Gln Ala Lys Ala Gln Met
385                 390                 395                 400
Pro Thr Ile Glu Arg Ala Thr Leu Thr Arg Asp Phe Tyr Leu Phe Pro
                405                 410                 415
```

<210> SEQ ID NO 31
<211> LENGTH: 76
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 31

Met Phe Lys Gly Ile Leu Gln Ser Gly Leu Asp Asn Phe Val Ile Asn
 1               5                  10                  15

His Met Leu Lys Asn Asn Val Ala Gly Gln Thr Ser Ile Gln Thr Leu
            20                  25                  30

Val Pro Asn Thr Asp Gln Lys Ser Thr Ser Val Lys Lys Asp Asn His
        35                  40                  45

Lys Lys Lys Gln Leu Arg Cys Trp Asn Thr Trp Ala Lys Met Phe Phe
    50                  55                  60

Met Val Phe Leu Ile Ile Trp Gln Asn Thr Met Phe
65                  70                  75

<210> SEQ ID NO 32
<211> LENGTH: 53
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 32

Met Phe Lys Gly Ile Leu Gln Ser Gly Leu Asp Asn Phe Val Ile Asn
 1               5                  10                  15

His Met Leu Lys Asn Asn Val Ala Gly Gln Thr Ser Ile Gln Thr Leu
            20                  25                  30

Val Pro Asn Thr Asp Gln Lys Ser Thr Ser Val Lys Lys Asp Asn His
        35                  40                  45

Lys Lys Lys Asn Ser
    50

<210> SEQ ID NO 33
<211> LENGTH: 343
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 33

Met Glu Ser Lys Tyr Lys Glu Ile Leu Leu Leu Thr Gly Leu Asp Asn
 1               5                  10                  15

Ile Thr Asp Glu Glu Leu Asp Arg Phe Lys Phe Leu Ser Asp Glu
            20                  25                  30

Phe Asn Ile Ala Thr Gly Lys Leu His Thr Ala Asn Arg Ile Gln Val
        35                  40                  45

Ala Thr Leu Met Ile Gln Asn Ala Gly Ala Val Ser Ala Val Met Lys
    50                  55                  60

Thr Ile Arg Ile Phe Gln Lys Leu Asn Tyr Met Leu Leu Ala Lys Arg
65                  70                  75                  80

Leu Gln Glu Glu Lys Glu Lys Val Asp Lys Gln Tyr Lys Ser Val Thr
                85                  90                  95

```
Lys Pro Lys Pro Leu Ser Gln Ala Glu Met Ser Pro Ala Ala Ser Ala
            100                 105                 110

Ala Ile Arg Asn Asp Val Ala Lys Gln Arg Ala Ala Pro Lys Val Ser
            115                 120                 125

Pro His Val Lys Pro Glu Gln Lys Gln Met Val Ala Gln Gln Glu Ser
130                 135                 140

Ile Arg Glu Gly Phe Gln Lys Arg Cys Leu Pro Val Met Val Leu Lys
145                 150                 155                 160

Ala Lys Lys Pro Phe Thr Phe Glu Thr Gln Glu Gly Lys Gln Glu Met
                165                 170                 175

Phe His Ala Thr Val Ala Thr Glu Lys Glu Phe Phe Val Lys Val
                180                 185                 190

Phe Asn Thr Leu Leu Lys Asp Lys Phe Ile Pro Lys Arg Ile Ile Ile
                195                 200                 205

Ile Ala Arg Tyr Tyr Arg His Ser Gly Phe Leu Glu Val Asn Ser Ala
            210                 215                 220

Ser Arg Val Leu Asp Ala Glu Ser Asp Gln Lys Val Asn Val Pro Leu
225                 230                 235                 240

Asn Ile Ile Arg Lys Ala Gly Glu Thr Pro Lys Ile Asn Thr Leu Gln
                245                 250                 255

Thr Gln Pro Leu Gly Thr Ile Val Asn Gly Leu Phe Val Gln Lys
            260                 265                 270

Val Thr Glu Lys Lys Lys Asn Ile Leu Phe Asp Leu Ser Asp Asn Thr
            275                 280                 285

Gly Lys Met Glu Val Leu Gly Val Arg Asn Glu Asp Thr Met Lys Cys
        290                 295                 300

Lys Glu Gly Asp Lys Val Arg Leu Thr Phe Phe Thr Leu Ser Lys Asn
305                 310                 315                 320

Gly Glu Lys Leu Gln Leu Thr Ser Gly Val His Ser Thr Ile Lys Val
            325                 330                 335

Ile Lys Ala Lys Lys Lys Thr
            340

<210> SEQ ID NO 34
<211> LENGTH: 355
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 34

Met Glu Ser Lys Tyr Lys Glu Ile Leu Leu Thr Gly Leu Asp Asn
1               5                   10                  15

Ile Thr Asp Glu Glu Leu Asp Arg Phe Lys Phe Phe Leu Ser Asp Glu
            20                  25                  30

Phe Asn Ile Ala Thr Gly Lys Leu His Thr Ala Asn Arg Ile Gln Val
            35                  40                  45

Ala Thr Leu Met Ile Gln Asn Ala Gly Ala Val Ser Ala Val Met Lys
        50                  55                  60

Thr Ile Arg Ile Phe Gln Lys Leu Asn Tyr Met Leu Leu Ala Lys Arg
65                  70                  75                  80

Leu Gln Glu Glu Lys Glu Lys Val Asp Lys Gln Tyr Lys Ser Val Thr
                85                  90                  95

Lys Pro Lys Pro Leu Ser Gln Ala Glu Met Ser Pro Ala Ala Ser Ala
            100                 105                 110
```

```
Ala Ile Arg Asn Asp Val Ala Lys Gln Arg Ala Ala Pro Lys Val Ser
            115                 120                 125

Pro His Val Lys Pro Glu Gln Lys Gln Met Val Ala Gln Gln Glu Ser
        130                 135                 140

Ile Arg Glu Gly Phe Gln Lys Arg Cys Leu Pro Val Met Val Leu Lys
145                 150                 155                 160

Ala Lys Lys Pro Phe Thr Phe Glu Thr Gln Glu Gly Lys Gln Glu Met
                    165                 170                 175

Phe His Ala Thr Val Ala Thr Glu Lys Glu Phe Phe Val Lys Val
                180                 185                 190

Phe Asn Thr Leu Leu Lys Asp Lys Phe Ile Pro Lys Arg Ile Ile Ile
            195                 200                 205

Ile Ala Arg Tyr Tyr Arg His Ser Gly Phe Leu Glu Val Asn Ser Ala
        210                 215                 220

Ser Arg Val Leu Asp Ala Glu Ser Asp Gln Lys Val Asn Val Pro Leu
225                 230                 235                 240

Asn Ile Ile Arg Lys Ala Gly Glu Thr Pro Lys Ile Asn Thr Leu Gln
                    245                 250                 255

Thr Gln Pro Leu Gly Thr Ile Val Asn Gly Leu Phe Val Val Gln Lys
                260                 265                 270

Val Thr Glu Lys Lys Lys Asn Ile Leu Phe Asp Leu Ser Asp Asn Thr
            275                 280                 285

Gly Lys Met Glu Val Leu Gly Val Arg Asn Glu Asp Thr Met Lys Cys
        290                 295                 300

Lys Glu Gly Asp Lys Val Arg Leu Thr Phe Phe Thr Leu Ser Lys Asn
305                 310                 315                 320

Gly Glu Lys Leu Gln Leu Thr Ser Gly Val His Ser Thr Ile Lys Val
                    325                 330                 335

Ile Lys Ala Lys Lys Lys His Arg Glu Val Lys Arg Thr Asn Ser Ser
                340                 345                 350

Gln Leu Val
        355

<210> SEQ ID NO 35
<211> LENGTH: 346
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 35

Met Glu Ser Lys Tyr Lys Glu Ile Leu Leu Leu Thr Gly Leu Asp Asn
  1               5                  10                  15

Ile Thr Asp Glu Glu Leu Asp Arg Phe Lys Phe Phe Leu Ser Asp Glu
                 20                  25                  30

Phe Asn Ile Ala Thr Gly Lys Leu His Thr Ala Asn Arg Ile Gln Val
             35                  40                  45

Ala Thr Leu Met Ile Gln Asn Ala Gly Ala Val Ser Ala Val Met Lys
         50                  55                  60

Thr Ile Arg Ile Phe Gln Lys Leu Asn Tyr Met Leu Leu Ala Lys Arg
 65                  70                  75                  80

Leu Gln Glu Glu Lys Glu Lys Val Asp Lys Gln Tyr Lys Ser Val Thr
                     85                  90                  95

Lys Pro Lys Pro Leu Ser Gln Ala Glu Met Ser Pro Ala Ala Ser Ala
                100                 105                 110
```

```
Ala Ile Arg Asn Asp Val Ala Lys Gln Arg Ala Pro Lys Val Ser
            115                 120                 125

Pro His Val Lys Pro Glu Gln Lys Gln Met Val Ala Gln Gln Glu Ser
130                 135                 140

Ile Arg Glu Gly Phe Gln Lys Arg Cys Leu Pro Val Met Val Leu Lys
145                 150                 155                 160

Ala Lys Lys Pro Phe Thr Phe Glu Thr Gln Glu Gly Lys Gln Glu Met
                165                 170                 175

Phe His Ala Thr Val Ala Thr Glu Lys Glu Phe Phe Val Lys Val
            180                 185                 190

Phe Asn Thr Leu Leu Lys Asp Lys Phe Ile Pro Lys Arg Ile Ile Ile
                195                 200                 205

Ile Ala Arg Tyr Tyr Arg His Ser Gly Phe Leu Glu Val Asn Ser Ala
            210                 215                 220

Ser Arg Val Leu Asp Ala Glu Ser Asp Gln Lys Val Asn Val Pro Leu
225                 230                 235                 240

Asn Ile Ile Arg Lys Ala Gly Glu Thr Pro Lys Ile Asn Thr Leu Gln
                245                 250                 255

Thr Gln Pro Leu Gly Thr Ile Val Asn Gly Leu Phe Val Val Gln Lys
            260                 265                 270

Val Thr Glu Lys Lys Lys Asn Ile Leu Phe Asp Leu Ser Asp Asn Thr
275                 280                 285

Gly Lys Met Glu Val Leu Gly Val Arg Asn Glu Asp Thr Met Lys Cys
            290                 295                 300

Lys Glu Gly Asp Lys Val Arg Leu Thr Phe Phe Thr Leu Ser Lys Asn
305                 310                 315                 320

Gly Glu Lys Leu Gln Leu Thr Ser Gly Val His Ser Thr Ile Lys Val
                325                 330                 335

Ile Lys Ala Lys Lys Lys Asn Ile Glu Lys
            340                 345

<210> SEQ ID NO 36
<211> LENGTH: 650
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 36

Met Met Gly Ile Gly Lys Asn Thr Thr Ser Lys Ser Met Glu Ala Gly
1               5                   10                  15

Ser Ser Thr Glu Gly Lys Tyr Glu Asp Glu Ala Lys His Pro Ala Phe
                20                  25                  30

Phe Thr Leu Pro Val Val Ile Asn Gly Gly Ala Thr Ser Ser Gly Glu
            35                  40                  45

Gln Asp Asn Glu Asp Thr Glu Leu Met Ala Ile Tyr Thr Thr Glu Asn
        50                  55                  60

Gly Ile Ala Glu Lys Ser Ser Leu Ala Glu Thr Leu Asp Ser Thr Gly
65                  70                  75                  80

Ser Leu Asp Pro Gln Arg Ser Asp Met Ile Tyr Thr Ile Glu Asp Val
                85                  90                  95

Pro Pro Trp Tyr Leu Cys Ile Phe Leu Gly Leu Gln His Tyr Leu Thr
            100                 105                 110

Cys Phe Ser Gly Thr Ile Ala Val Pro Phe Leu Leu Ala Asp Ala Met
            115                 120                 125
```

```
Cys Val Gly Tyr Asp Gln Trp Ala Thr Ser Gln Leu Ile Gly Thr Ile
    130                 135                 140

Phe Phe Cys Val Gly Ile Thr Thr Leu Leu Gln Thr Thr Phe Gly Cys
145                 150                 155                 160

Arg Leu Pro Leu Phe Gln Thr Ser Ala Phe Ala Phe Leu Ala Pro Ala
                165                 170                 175

Arg Ala Ile Leu Ser Leu Asp Lys Trp Lys Cys Asn Thr Thr Asp Val
            180                 185                 190

Ser Val Ala Asn Gly Thr Ala Glu Leu Leu His Thr Glu His Ile Trp
        195                 200                 205

Tyr Pro Arg Ile Arg Glu Ile Gln Gly Ala Ile Ile Met Ser Ser Leu
    210                 215                 220

Ile Glu Val Val Ile Gly Leu Leu Gly Leu Pro Gly Ala Leu Leu Lys
225                 230                 235                 240

Tyr Ile Gly Pro Leu Thr Ile Thr Pro Thr Val Ala Leu Ile Gly Leu
                245                 250                 255

Ser Gly Phe Gln Ala Ala Gly Glu Arg Ala Gly Lys His Trp Gly Ile
            260                 265                 270

Ala Met Leu Thr Ile Phe Leu Val Leu Leu Phe Ser Gln Tyr Ala Arg
        275                 280                 285

Asn Val Lys Phe Pro Leu Pro Ile Tyr Lys Ser Lys Lys Gly Trp Thr
    290                 295                 300

Ala Tyr Lys Leu Gln Leu Phe Lys Met Phe Pro Ile Ile Leu Ala Ile
305                 310                 315                 320

Leu Val Ser Trp Leu Leu Cys Phe Ile Phe Thr Val Thr Asp Val Phe
                325                 330                 335

Pro Pro Asp Ser Thr Lys Tyr Gly Phe Tyr Ala Arg Thr Asp Ala Arg
            340                 345                 350

Gln Gly Val Leu Leu Val Ala Pro Trp Phe Lys Val Pro Tyr Pro Phe
        355                 360                 365

Gln Trp Gly Leu Pro Thr Val Ser Ala Ala Gly Val Ile Gly Met Leu
    370                 375                 380

Ser Ala Val Val Ala Ser Ile Ile Glu Ser Ile Gly Asp Tyr Tyr Ala
385                 390                 395                 400

Cys Ala Arg Leu Ser Cys Ala Pro Pro Pro Ile His Ala Ile Asn
                405                 410                 415

Arg Gly Ile Phe Val Glu Gly Leu Ser Cys Val Leu Asp Gly Ile Phe
            420                 425                 430

Gly Thr Gly Asn Gly Ser Thr Ser Ser Ser Pro Asn Ile Gly Val Leu
        435                 440                 445

Gly Ile Thr Lys Val Gly Ser Arg Arg Val Ile Gln Cys Gly Ala Ala
    450                 455                 460

Leu Met Leu Ala Leu Gly Met Ile Gly Lys Phe Ser Ala Leu Phe Ala
465                 470                 475                 480

Ser Leu Pro Asp Pro Val Leu Gly Ala Leu Phe Cys Thr Leu Phe Gly
                485                 490                 495

Met Ile Thr Ala Val Gly Leu Ser Asn Leu Gln Phe Ile Asp Leu Asn
            500                 505                 510

Ser Ser Arg Asn Leu Phe Val Leu Gly Phe Ser Ile Phe Phe Gly Leu
        515                 520                 525

Val Leu Pro Ser Tyr Leu Arg Gln Asn Pro Leu Val Thr Gly Ile Thr
    530                 535                 540

Gly Ile Asp Gln Val Leu Asn Val Leu Leu Thr Thr Ala Met Phe Val
```

```
                545                 550                 555                 560
Gly Gly Cys Val Ala Phe Ile Leu Asp Asn Thr Ile Pro Gly Thr Pro
                565                 570                 575

Glu Glu Arg Gly Ile Arg Lys Trp Lys Lys Gly Val Gly Lys Gly Asn
            580                 585                 590

Lys Ser Leu Asp Gly Met Glu Ser Tyr Asn Leu Pro Phe Gly Met Asn
            595                 600                 605

Ile Ile Lys Lys Tyr Arg Cys Phe Ser Tyr Leu Pro Ile Ser Pro Thr
            610                 615                 620

Phe Val Gly Tyr Thr Trp Lys Gly Leu Arg Lys Ser Asp Asn Ser Arg
625                 630                 635                 640

Ser Ser Asp Glu Asp Ser Gln Ala Thr Gly
            645                 650

<210> SEQ ID NO 37
<211> LENGTH: 414
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 37

Met Met Gly Ile Gly Lys Asn Thr Thr Ser Lys Ser Met Glu Ala Gly
1               5                   10                  15

Ser Ser Thr Glu Gly Lys Tyr Glu Asp Glu Ala Lys His Pro Ala Phe
            20                  25                  30

Phe Thr Leu Pro Val Val Ile Asn Gly Gly Ala Thr Ser Ser Gly Glu
        35                  40                  45

Gln Asp Asn Glu Asp Thr Glu Leu Met Ala Ile Tyr Thr Thr Glu Asn
    50                  55                  60

Gly Ile Ala Glu Lys Ser Ser Leu Ala Glu Thr Leu Asp Ser Thr Gly
65                  70                  75                  80

Ser Leu Asp Pro Gln Arg Ser Asp Met Ile Tyr Thr Ile Glu Asp Val
                85                  90                  95

Pro Pro Trp Tyr Leu Cys Ile Phe Leu Gly Leu Gln His Tyr Leu Thr
            100                 105                 110

Cys Phe Ser Gly Thr Ile Ala Val Pro Phe Leu Leu Ala Asp Ala Met
        115                 120                 125

Cys Val Gly Tyr Asp Gln Trp Ala Thr Ser Gln Leu Ile Gly Thr Ile
    130                 135                 140

Phe Phe Cys Val Gly Ile Thr Thr Leu Leu Gln Thr Thr Phe Gly Cys
145                 150                 155                 160

Arg Leu Pro Leu Phe Gln Thr Ser Ala Phe Ala Phe Leu Ala Pro Ala
                165                 170                 175

Arg Ala Ile Leu Ser Leu Asp Lys Trp Lys Cys Asn Thr Thr Asp Val
            180                 185                 190

Ser Val Ala Asn Gly Thr Ala Glu Leu Leu His Thr Glu His Ile Trp
        195                 200                 205

Tyr Pro Arg Ile Arg Glu Ile Gln Gly Ala Ile Ile Met Ser Ser Leu
    210                 215                 220

Ile Glu Val Val Ile Gly Leu Leu Gly Leu Pro Gly Ala Leu Leu Lys
225                 230                 235                 240

Tyr Ile Gly Pro Leu Thr Ile Thr Pro Thr Val Ala Leu Ile Gly Leu
                245                 250                 255

Ser Gly Phe Gln Ala Ala Gly Glu Arg Ala Gly Lys His Trp Gly Ile
```

```
                260                 265                 270
Ala Met Leu Thr Ile Phe Leu Val Leu Leu Phe Ser Gln Tyr Ala Arg
            275                 280                 285

Asn Val Lys Phe Pro Leu Pro Ile Tyr Lys Ser Lys Lys Gly Trp Thr
        290                 295                 300

Ala Tyr Lys Leu Gln Leu Phe Lys Met Phe Pro Ile Ile Leu Ala Ile
305                 310                 315                 320

Leu Val Ser Trp Leu Leu Cys Phe Ile Phe Thr Val Thr Asp Val Phe
                325                 330                 335

Pro Pro Asp Ser Thr Lys Tyr Gly Phe Tyr Ala Arg Thr Asp Ala Arg
            340                 345                 350

Gln Gly Val Leu Leu Val Ala Pro Trp Phe Lys Val Pro Tyr Pro Phe
        355                 360                 365

Gln Trp Gly Leu Pro Thr Val Ser Ala Ala Gly Val Ile Gly Met Leu
370                 375                 380

Ser Ala Val Val Ala Ser Ile Ile Glu Ser Ile Gly Asp Tyr Tyr Ala
385                 390                 395                 400

Cys Ala Arg Leu Ser Cys Ala Pro Pro Pro Ser Thr Gln
            405                 410

<210> SEQ ID NO 38
<211> LENGTH: 428
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 38

Met Met Gly Ile Gly Lys Asn Thr Thr Ser Lys Ser Met Glu Ala Gly
  1               5                  10                  15

Ser Ser Thr Glu Gly Lys Tyr Glu Asp Glu Ala Lys His Pro Ala Phe
             20                  25                  30

Phe Thr Leu Pro Val Val Ile Asn Gly Gly Ala Thr Ser Ser Gly Glu
         35                  40                  45

Gln Asp Asn Glu Asp Thr Glu Leu Met Ala Ile Tyr Thr Thr Glu Asn
  50                  55                  60

Gly Ile Ala Glu Lys Ser Ser Leu Ala Glu Thr Leu Asp Ser Thr Gly
 65                  70                  75                  80

Ser Leu Asp Pro Gln Arg Ser Asp Met Ile Tyr Thr Ile Glu Asp Val
                 85                  90                  95

Pro Pro Trp Tyr Leu Cys Ile Phe Leu Gly Leu Gln His Tyr Leu Thr
            100                 105                 110

Cys Phe Ser Gly Thr Ile Ala Val Pro Phe Leu Leu Ala Asp Ala Met
        115                 120                 125

Cys Val Gly Tyr Asp Gln Trp Ala Thr Ser Gln Leu Ile Gly Thr Ile
130                 135                 140

Phe Phe Cys Val Gly Ile Thr Thr Leu Leu Gln Thr Thr Phe Gly Cys
145                 150                 155                 160

Arg Leu Pro Leu Phe Gln Thr Ser Ala Phe Ala Phe Leu Ala Pro Ala
                165                 170                 175

Arg Ala Ile Leu Ser Leu Asp Lys Trp Lys Cys Asn Thr Thr Asp Val
            180                 185                 190

Ser Val Ala Asn Gly Thr Ala Glu Leu Leu His Thr Glu His Ile Trp
        195                 200                 205

Tyr Pro Arg Ile Arg Glu Ile Gln Gly Ala Ile Ile Met Ser Ser Leu
```

```
              210                 215                 220
Ile Glu Val Val Ile Gly Leu Gly Leu Pro Gly Ala Leu Leu Lys
225                 230                 235                 240

Tyr Ile Gly Pro Leu Thr Ile Thr Pro Thr Val Ala Leu Ile Gly Leu
                245                 250                 255

Ser Gly Phe Gln Ala Ala Gly Glu Arg Ala Gly Lys His Trp Gly Ile
                260                 265                 270

Ala Met Leu Thr Ile Phe Leu Val Leu Leu Phe Ser Gln Tyr Ala Arg
                275                 280                 285

Asn Val Lys Phe Pro Leu Pro Ile Tyr Lys Ser Lys Lys Gly Trp Thr
290                 295                 300

Ala Tyr Lys Leu Gln Leu Phe Lys Met Phe Pro Ile Ile Leu Ala Ile
305                 310                 315                 320

Leu Val Ser Trp Leu Leu Cys Phe Ile Phe Thr Val Thr Asp Val Phe
                325                 330                 335

Pro Pro Asp Ser Thr Lys Tyr Gly Phe Tyr Ala Arg Thr Asp Ala Arg
                340                 345                 350

Gln Gly Val Leu Leu Val Ala Pro Trp Phe Lys Val Pro Tyr Pro Phe
                355                 360                 365

Gln Trp Gly Leu Pro Thr Val Ser Ala Ala Gly Val Ile Gly Met Leu
370                 375                 380

Ser Ala Val Val Ala Ser Ile Ile Glu Ser Ile Gly Asp Tyr Tyr Ala
385                 390                 395                 400

Cys Ala Arg Leu Ser Cys Ala Pro Pro Pro His Pro Arg Asn Lys
                405                 410                 415

Gln Gly Asn Phe Arg Gly Arg Pro Leu Leu Cys Ser
                420                 425

<210> SEQ ID NO 39
<211> LENGTH: 807
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 39

Met Pro Lys Ala Pro Lys Gln Gln Pro Glu Pro Glu Trp Ile Gly
1               5                   10                  15

Asp Gly Glu Ser Thr Ser Pro Ser Asp Lys Val Val Lys Lys Gly Lys
                20                  25                  30

Lys Asp Lys Lys Ile Lys Lys Thr Phe Phe Glu Glu Leu Ala Val Glu
            35                  40                  45

Asp Lys Gln Ala Gly Glu Glu Lys Val Leu Lys Glu Lys Glu Gln
        50                  55                  60

Gln Gln Gln Gln Gln Gln Gln Gln Lys Lys Lys Arg Asp Thr Arg
65                  70                  75                  80

Lys Gly Arg Arg Lys Lys Asp Val Asp Asp Gly Glu Glu Lys Glu
                85                  90                  95

Leu Met Glu Arg Leu Lys Lys Leu Ser Val Pro Thr Ser Asp Glu Glu
                100                 105                 110

Asp Glu Val Pro Ala Pro Lys Pro Arg Gly Gly Lys Lys Thr Lys Gly
            115                 120                 125

Gly Asn Val Phe Ala Ala Leu Ile Gln Asp Gln Ser Glu Glu Glu
            130                 135                 140

Glu Glu Glu Lys His Pro Pro Lys Pro Ala Lys Pro Glu Lys Asn Arg
```

-continued

```
            145                 150                 155                 160
Ile Asn Lys Ala Val Ser Glu Glu Gln Gln Pro Ala Leu Lys Gly Lys
                165                 170                 175
Lys Gly Lys Glu Glu Lys Ser Lys Gly Lys Ala Lys Pro Gln Asn Lys
                180                 185                 190
Phe Ala Ala Leu Asp Asn Glu Glu Asp Lys Glu Glu Ile Ile
                195                 200                 205
Lys Glu Lys Glu Pro Pro Lys Gln Gly Lys Glu Lys Ala Lys Lys Ala
210                 215                 220
Glu Gln Met Glu Tyr Glu Arg Gln Val Ala Ser Leu Lys Ala Ala Asn
225                 230                 235                 240
Ala Ala Glu Asn Asp Phe Ser Val Ser Gln Ala Glu Met Ser Ser Arg
                245                 250                 255
Gln Ala Met Leu Glu Asn Ala Ser Asp Ile Lys Leu Glu Lys Phe Ser
                260                 265                 270
Ile Ser Ala His Gly Lys Glu Leu Phe Val Asn Ala Asp Leu Tyr Ile
                275                 280                 285
Val Ala Gly Arg Arg Tyr Gly Leu Val Gly Pro Asn Gly Lys Gly Lys
                290                 295                 300
Thr Thr Leu Leu Lys His Ile Ala Asn Arg Ala Leu Ser Ile Pro Pro
305                 310                 315                 320
Asn Ile Asp Val Leu Leu Cys Glu Gln Glu Val Val Ala Asp Glu Thr
                325                 330                 335
Pro Ala Val Gln Ala Val Leu Arg Ala Asp Thr Lys Arg Leu Lys Leu
                340                 345                 350
Leu Glu Glu Glu Arg Arg Leu Gln Gly Gln Leu Glu Gln Gly Asp Asp
                355                 360                 365
Thr Ala Ala Glu Arg Leu Glu Lys Val Tyr Glu Glu Leu Arg Ala Thr
                370                 375                 380
Gly Ala Ala Ala Glu Ala Lys Ala Arg Arg Ile Leu Ala Gly Leu
385                 390                 395                 400
Gly Phe Asp Pro Glu Met Gln Asn Arg Pro Thr Gln Lys Phe Ser Gly
                405                 410                 415
Gly Trp Arg Met Arg Val Ser Leu Ala Arg Ala Leu Phe Met Glu Pro
                420                 425                 430
Thr Leu Leu Met Leu Asp Glu Pro Thr Asn His Leu Asp Leu Asn Ala
                435                 440                 445
Val Ile Trp Leu Asn Asn Tyr Leu Gln Gly Trp Arg Lys Thr Leu Leu
                450                 455                 460
Ile Val Ser His Asp Gln Gly Phe Leu Asp Asp Val Cys Thr Asp Ile
465                 470                 475                 480
Ile His Leu Asp Ala Gln Arg Leu His Tyr Tyr Arg Gly Asn Tyr Met
                485                 490                 495
Thr Phe Lys Lys Met Tyr Gln Gln Lys Gln Lys Glu Leu Leu Lys Gln
                500                 505                 510
Tyr Glu Lys Gln Glu Lys Lys Leu Lys Glu Leu Lys Ala Gly Gly Lys
                515                 520                 525
Ser Thr Lys Gln Ala Glu Lys Gln Thr Lys Glu Ala Leu Thr Arg Lys
                530                 535                 540
Gln Gln Lys Cys Arg Arg Lys Asn Gln Asp Glu Ser Gln Glu Ala
545                 550                 555                 560
Pro Glu Leu Leu Lys Arg Pro Lys Glu Tyr Thr Val Arg Phe Thr Phe
                565                 570                 575
```

Pro Asp Pro Pro Leu Ser Pro Val Leu Gly Leu His Gly Val
        580                 585                 590

Thr Phe Gly Tyr Gln Gly Gln Lys Pro Leu Phe Lys Asn Leu Asp Phe
            595                 600                 605

Gly Ile Asp Met Asp Ser Arg Ile Cys Ile Val Gly Pro Asn Gly Val
610                 615                 620

Gly Lys Ser Thr Leu Leu Leu Leu Thr Gly Lys Leu Thr Pro Thr
625                 630                 635                 640

His Gly Glu Met Arg Lys Asn His Arg Leu Lys Ile Gly Phe Phe Asn
                645                 650                 655

Gln Gln Tyr Ala Glu Gln Leu Arg Met Glu Glu Thr Pro Thr Glu Tyr
            660                 665                 670

Leu Gln Arg Gly Phe Asn Leu Pro Tyr Gln Asp Ala Arg Lys Cys Leu
            675                 680                 685

Gly Arg Phe Gly Leu Glu Ser His Ala His Thr Ile Gln Ile Cys Lys
        690                 695                 700

Leu Ser Gly Gly Gln Lys Ala Arg Val Val Phe Ala Glu Leu Ala Cys
705                 710                 715                 720

Arg Glu Pro Asp Val Leu Ile Leu Asp Glu Pro Thr Asn Asn Leu Asp
                725                 730                 735

Ile Glu Ser Ile Asp Ala Leu Gly Glu Ala Ile Asn Glu Tyr Lys Gly
            740                 745                 750

Ala Val Ile Val Val Ser His Asp Ala Arg Leu Ile Thr Glu Thr Asn
            755                 760                 765

Cys Gln Leu Trp Val Val Glu Glu Gln Ser Val Ser Gln Ile Asp Gly
770                 775                 780

Asp Phe Glu Asp Tyr Lys Arg Glu Val Leu Glu Ala Leu Gly Glu Val
785                 790                 795                 800

Met Val Ser Arg Pro Arg Glu
                805

<210> SEQ ID NO 40
<211> LENGTH: 134
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 40

Met Pro Lys Ala Pro Lys Gln Gln Pro Glu Pro Glu Trp Ile Gly
 1               5                  10                  15

Asp Gly Glu Ser Thr Ser Pro Ser Asp Lys Val Val Lys Lys Gly Lys
            20                  25                  30

Lys Asp Lys Lys Ile Lys Lys Thr Phe Phe Glu Glu Leu Ala Val Glu
        35                  40                  45

Asp Lys Gln Ala Gly Glu Glu Lys Val Leu Lys Glu Lys Glu Gln
    50                  55                  60

Gln Gln Gln Gln Gln Gln Gln Gln Lys Lys Ser Glu Ile Pro Glu
65                  70                  75                  80

Lys Ala Gly Gly Arg Arg Met Trp Met Met Met Glu Lys Arg Lys Ser
                85                  90                  95

Ser Trp Ser Val Leu Arg Ser Ser Gln Cys Gln Pro Val Met Arg Arg
            100                 105                 110

Met Lys Tyr Pro Pro Gln Asn Pro Ala Glu Gly Arg Lys Pro Arg Val
        115                 120                 125

```
Val Met Phe Leu Gln Pro
    130

<210> SEQ ID NO 41
<211> LENGTH: 89
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 41

Met Pro Lys Ala Pro Lys Gln Gln Pro Pro Glu Pro Glu Trp Ile Gly
 1               5                  10                  15

Asp Gly Glu Ser Thr Ser Pro Ser Asp Lys Val Val Lys Lys Gly Lys
            20                  25                  30

Lys Asp Lys Lys Ile Lys Lys Thr Phe Phe Glu Glu Leu Ala Val Glu
        35                  40                  45

Asp Lys Gln Ala Gly Glu Glu Lys Val Leu Lys Glu Lys Glu Gln
    50                  55                  60

Gln Gln Gln Gln Gln Gln Gln Gln Lys Lys Lys Ala Arg Tyr Pro
65                  70                  75                  80

Lys Arg Gln Ala Glu Glu Gly Cys Gly
                85

<210> SEQ ID NO 42
<211> LENGTH: 286
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 42

Ser Pro Asp Tyr Phe Pro Gln Ile Ser Ser Gln Phe Gly Thr Val Glu
 1               5                  10                  15

Lys Met Glu Lys Ile Phe Ile Ser Ser Thr Lys Ala Glu Gly Lys
            20                  25                  30

Gly Ile Ser Pro Phe Glu Ala Pro Ile Asn Thr Gln Ala Pro Pro Glu
        35                  40                  45

Lys Gly Lys Glu Ala Val Val Gln Glu Pro Glu Arg Ser Trp Phe Gln
    50                  55                  60

Thr Lys Glu Glu Arg Lys Lys Glu Lys Ile Ala Lys Ala Leu Gln Glu
65                  70                  75                  80

Phe Asp Leu Ala Leu Arg Gly Lys Lys Arg Lys Lys Phe Met Lys
                85                  90                  95

Asp Ala Lys Lys Lys Gly Glu Met Thr Ala Glu Glu Arg Ser Gln Phe
            100                 105                 110

Glu Ile Leu Lys Ala Gln Met Phe Ala Glu Arg Leu Ala Lys Arg Asn
        115                 120                 125

Arg Arg Ala Lys Arg Ala Arg Ala Met Pro Glu Glu Glu Pro Val Arg
    130                 135                 140

Gly Pro Ala Lys Lys Gln Lys Gln Gly Lys Lys Ser Val Phe Asp Glu
145                 150                 155                 160

Glu Leu Thr Asn Thr Ser Lys Lys Ala Leu Lys Gln Tyr Arg Ala Gly
                165                 170                 175

Pro Ser Phe Glu Glu Arg Lys Gln Leu Gly Leu Pro His Gln Arg Arg
            180                 185                 190

Gly Gly Asn Phe Lys Ser Asn Pro Asp Thr Arg Gly Gly Ser Ser Cys
```

```
                 195                 200                 205

Arg Gly Leu Lys Lys Phe Met Gly Ala Ala Leu Lys Ser Leu Pro Cys
    210                 215                 220

Gly Lys Ser Ser Trp Leu Val Cys Leu Phe Ser Ile Cys Leu Lys Lys
225                 230                 235                 240

Lys Gln Lys Gln Lys Thr Thr Leu Trp Cys Gly Gly Met Val Arg Ser
                245                 250                 255

Tyr Phe Pro Lys His Val Cys Gln Ser Pro Phe Leu Leu Ile Ser Phe
            260                 265                 270

His Met Thr Ile Leu Asn Gly Ser Ile Phe Gly Lys Arg Glu
        275                 280                 285

<210> SEQ ID NO 43
<211> LENGTH: 251
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 43

Met Glu Lys Ile Phe Ile Ser Ser Ser Thr Lys Ala Glu Gly Lys Gly
1               5                   10                  15

Ile Ser Pro Phe Glu Ala Pro Ile Asn Thr Gln Ala Pro Pro Glu Lys
            20                  25                  30

Gly Lys Glu Ala Val Val Gln Glu Pro Glu Arg Ser Trp Phe Gln Thr
        35                  40                  45

Lys Glu Glu Arg Lys Lys Glu Lys Ile Ala Lys Ala Leu Gln Glu Phe
    50                  55                  60

Asp Leu Ala Leu Arg Gly Lys Lys Lys Arg Lys Lys Phe Met Lys Asp
65                  70                  75                  80

Ala Lys Lys Lys Gly Glu Met Thr Ala Glu Glu Arg Ser Gln Phe Glu
                85                  90                  95

Ile Leu Lys Ala Gln Met Phe Ala Glu Arg Leu Ala Lys Arg Asn Arg
            100                 105                 110

Arg Ala Lys Arg Ala Arg Ala Met Pro Glu Glu Glu Pro Val Arg Gly
        115                 120                 125

Pro Ala Lys Lys Gln Lys Gln Gly Lys Lys Ser Val Phe Asp Glu Glu
    130                 135                 140

Leu Thr Asn Thr Ser Lys Lys Ala Leu Lys Gln Tyr Arg Ala Gly Pro
145                 150                 155                 160

Ser Phe Glu Glu Arg Lys Gln Leu Gly Leu Pro His Gln Arg Arg Gly
                165                 170                 175

Gly Asn Phe Lys Ser Asn Pro Asp Thr Arg Gly Gly Ser Ser Cys Arg
            180                 185                 190

Gly Leu Lys Lys Phe Met Gly Ala Ala Leu Lys Ser Leu Pro Cys Gly
        195                 200                 205

Lys Ser Ser Trp Leu Val Cys Leu Phe Ser Ile Cys Leu Lys Lys Asn
    210                 215                 220

Lys Asn Lys Lys Gln His Phe Gly Val Val Val Trp Tyr Val Ala Ile
225                 230                 235                 240

Phe Leu Ser Met Ser Val Asn Leu Pro Ser Cys
                245                 250

<210> SEQ ID NO 44
<211> LENGTH: 238
<212> TYPE: PRT
```

```
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 44

Met Glu Lys Ile Phe Ile Ser Ser Thr Lys Ala Glu Gly Lys Gly
 1               5                  10                  15

Ile Ser Pro Phe Glu Ala Pro Ile Asn Thr Gln Ala Pro Glu Lys
                20                  25                  30

Gly Lys Glu Ala Val Val Gln Glu Pro Glu Arg Ser Trp Phe Gln Thr
            35                  40                  45

Lys Glu Glu Arg Lys Lys Glu Lys Ile Ala Lys Ala Leu Gln Glu Phe
         50                  55                  60

Asp Leu Ala Leu Arg Gly Lys Lys Arg Lys Lys Phe Met Lys Asp
65                  70                  75                  80

Ala Lys Lys Lys Gly Glu Met Thr Ala Glu Glu Arg Ser Gln Phe Glu
                85                  90                  95

Ile Leu Lys Ala Gln Met Phe Ala Glu Arg Leu Ala Lys Arg Asn Arg
                100                 105                 110

Arg Ala Lys Arg Ala Arg Ala Met Pro Glu Glu Pro Val Arg Gly
                115                 120                 125

Pro Ala Lys Lys Gln Lys Gln Gly Lys Lys Ser Val Phe Asp Glu Glu
        130                 135                 140

Leu Thr Asn Thr Ser Lys Lys Ala Leu Lys Gln Tyr Arg Ala Gly Pro
145                 150                 155                 160

Ser Phe Glu Glu Arg Lys Gln Leu Gly Leu Pro His Gln Arg Arg Gly
                165                 170                 175

Gly Asn Phe Lys Ser Asn Pro Asp Thr Arg Gly Gly Ser Ser Cys Arg
                180                 185                 190

Gly Leu Lys Lys Phe Met Gly Ala Ala Leu Lys Ser Leu Pro Cys Gly
                195                 200                 205

Lys Ser Ser Trp Leu Val Cys Leu Phe Ser Ile Cys Leu Lys Lys Lys
        210                 215                 220

Thr Lys Thr Lys Asn Asn Thr Leu Val Trp Trp Tyr Gly Thr
225                 230                 235

<210> SEQ ID NO 45
<211> LENGTH: 192
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 45

Met Asp Gly Ser Gly Glu Gln Pro Arg Gly Gly Pro Thr Ser Ser
 1               5                  10                  15

Glu Gln Ile Met Lys Thr Gly Ala Leu Leu Leu Gln Gly Phe Ile Gln
                20                  25                  30

Asp Arg Ala Gly Arg Met Gly Gly Glu Ala Pro Glu Leu Ala Leu Asp
            35                  40                  45

Pro Val Pro Gln Asp Ala Ser Thr Lys Lys Leu Ser Glu Cys Leu Lys
         50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95
```

-continued

```
Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
130                 135                 140

Arg Glu Arg Leu Leu Gly Trp Ile Gln Asp Gln Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 46
<211> LENGTH: 58
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 46

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Arg His Pro Ser Trp Pro Trp Thr
        35                  40                  45

Arg Cys Leu Arg Met Arg Pro Pro Arg Ser
    50                  55

<210> SEQ ID NO 47
<211> LENGTH: 72
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 47

Met Asp Gly Ser Gly Glu Gln Pro Arg Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Gly Gly Thr Arg Ala Gly Pro Gly
        35                  40                  45

Pro Gly Ala Ser Gly Cys Val His Gln Glu Ala Glu Arg Val Ser Gln
    50                  55                  60

Ala His Arg Gly Arg Thr Gly Gln
65                  70

<210> SEQ ID NO 48
<211> LENGTH: 246
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 48

Met Ala Phe Leu Arg Ser Met Trp Gly Val Leu Ser Ala Leu Gly Arg
```

```
                1               5                  10                 15
            Ser Gly Ala Glu Leu Cys Thr Gly Cys Gly Ser Arg Leu Arg Ser Pro
                            20                  25                  30

Phe Ser Phe Val Tyr Leu Pro Arg Trp Phe Ser Ser Val Leu Ala Ser
                        35                  40                  45

Cys Pro Lys Lys Pro Val Ser Ser Tyr Leu Arg Phe Ser Lys Glu Gln
                    50                  55                  60

Leu Pro Ile Phe Lys Ala Gln Asn Pro Asp Ala Lys Thr Thr Glu Leu
             65                  70                  75                  80

Ile Arg Arg Ile Ala Gln Arg Trp Arg Glu Leu Pro Asp Ser Lys Lys
                            85                  90                  95

Lys Ile Tyr Gln Asp Ala Tyr Arg Ala Glu Trp Gln Val Tyr Lys Glu
                        100                 105                 110

Glu Ile Ser Arg Phe Lys Glu Gln Leu Thr Pro Ser Gln Ile Met Ser
                        115                 120                 125

Leu Glu Lys Glu Ile Met Asp Lys His Leu Lys Arg Lys Ala Met Thr
                        130                 135                 140

Lys Lys Lys Glu Leu Thr Leu Leu Gly Lys Pro Lys Arg Pro Arg Ser
            145                 150                 155                 160

Ala Tyr Asn Val Tyr Val Ala Glu Arg Phe Gln Glu Ala Lys Gly Asp
                            165                 170                 175

Ser Pro Gln Glu Lys Leu Lys Thr Val Lys Glu Asn Trp Lys Asn Leu
                        180                 185                 190

Ser Asp Ser Glu Lys Glu Leu Tyr Ile Gln His Ala Lys Glu Asp Glu
                        195                 200                 205

Thr Arg Tyr His Asn Glu Met Lys Ser Trp Glu Glu Gln Met Ile Glu
                        210                 215                 220

Val Gly Arg Lys Asp Leu Leu Arg Arg Thr Ile Lys Lys Gln Arg Lys
            225                 230                 235                 240

Tyr Gly Ala Glu Glu Cys
                        245

<210> SEQ ID NO 49
<211> LENGTH: 148
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 49

Met Ala Phe Leu Arg Ser Met Trp Gly Val Leu Ser Ala Leu Gly Arg
 1               5                  10                  15

Ser Gly Ala Glu Leu Cys Thr Gly Cys Gly Ser Arg Leu Arg Ser Pro
            20                  25                  30

Phe Ser Phe Val Tyr Leu Pro Arg Trp Phe Ser Ser Val Leu Ala Ser
        35                  40                  45

Cys Pro Lys Lys Pro Val Ser Ser Tyr Leu Arg Phe Ser Lys Glu Gln
    50                  55                  60

Leu Pro Ile Phe Lys Ala Gln Asn Pro Asp Ala Lys Thr Thr Glu Leu
 65                  70                  75                  80

Ile Arg Arg Ile Ala Gln Arg Trp Arg Glu Leu Pro Asp Ser Lys Lys
                85                  90                  95

Lys Ile Tyr Gln Asp Ala Tyr Arg Ala Glu Trp Gln Val Tyr Lys Glu
            100                 105                 110

Glu Ile Ser Arg Phe Lys Glu Gln Leu Thr Pro Ser Gln Ile Met Ser
```

```
            115                 120                 125

Leu Glu Lys Glu Ile Met Asp Lys His Leu Lys Arg Lys Ala Met Thr
130                 135                 140

Lys Lys Lys Ser
145

<210> SEQ ID NO 50
<211> LENGTH: 162
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 50

Met Ala Phe Leu Arg Ser Met Trp Gly Val Leu Ser Ala Leu Gly Arg
1               5                   10                  15

Ser Gly Ala Glu Leu Cys Thr Gly Cys Gly Ser Arg Leu Arg Ser Pro
            20                  25                  30

Phe Ser Phe Val Tyr Leu Pro Arg Trp Phe Ser Ser Val Leu Ala Ser
        35                  40                  45

Cys Pro Lys Lys Pro Val Ser Ser Tyr Leu Arg Phe Ser Lys Glu Gln
    50                  55                  60

Leu Pro Ile Phe Lys Ala Gln Asn Pro Asp Ala Lys Thr Thr Glu Leu
65                  70                  75                  80

Ile Arg Arg Ile Ala Gln Arg Trp Arg Glu Leu Pro Asp Ser Lys Lys
                85                  90                  95

Lys Ile Tyr Gln Asp Ala Tyr Arg Ala Glu Trp Gln Val Tyr Lys Glu
            100                 105                 110

Glu Ile Ser Arg Phe Lys Glu Gln Leu Thr Pro Ser Gln Ile Met Ser
        115                 120                 125

Leu Glu Lys Glu Ile Met Asp Lys His Leu Lys Arg Lys Ala Met Thr
130                 135                 140

Lys Lys Lys Arg Val Asn Thr Ala Trp Lys Thr Lys Lys Thr Ser Phe
145                 150                 155                 160

Ser Leu

<210> SEQ ID NO 51
<211> LENGTH: 235
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 51

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
        35                  40                  45

Ser Asp Tyr Leu Leu Gln Asp Tyr Pro Val Thr Val Ala Ser Asn Leu
    50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95
```

```
Leu Leu Glu Arg Val Asn Thr Glu Ile His Phe Val Thr Lys Cys Ala
                100                 105                 110

Phe Gln Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Trp Ser Pro Arg Pro Leu Glu Ala
                165                 170                 175

Thr Ala Pro Thr Ala Pro Gln Pro Leu Leu Leu Leu Leu Leu
            180                 185                 190

Pro Val Gly Leu Leu Leu Ala Ala Ala Trp Cys Leu His Trp Gln
            195                 200                 205

Arg Thr Arg Arg Arg Thr Pro Arg Pro Gly Glu Gln Val Pro Pro Val
            210                 215                 220

Pro Ser Pro Gln Asp Leu Leu Val Glu His
225                 230                 235
```

<210> SEQ ID NO 52
<211> LENGTH: 140
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 52

```
Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
                20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
        50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
                100                 105                 110

Phe Gln Pro Pro Pro Ala Val Phe Ala Ser Ser Arg Pro Thr Ser Pro
            115                 120                 125

Ala Ser Cys Arg Arg Pro Pro Ser Ser Trp Trp Arg
130                 135                 140
```

<210> SEQ ID NO 53
<211> LENGTH: 161
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 53

```
Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
```

```
                    20                  25                  30
Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
        50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
                85                  90                  95

Leu Leu Glu Arg Val Asn Thr Glu Ile His Phe Val Thr Lys Cys Ala
            100                 105                 110

Phe Gln Pro Pro Pro Gln Leu Ser Ser Leu Arg Pro Asp Gln His Leu
        115                 120                 125

Pro Pro Pro Ala Gly Asp Leu Arg Ala Ala Gly Gly Ala Glu Ala Leu
130                 135                 140

Asp His Ser Pro Glu Leu Leu Pro Val Pro Gly Ala Ala Val Ser Ala
145                 150                 155                 160

Arg

<210> SEQ ID NO 54
<211> LENGTH: 920
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 54

Met Leu Gln Gly His Phe Trp Leu Val Arg Glu Gly Ile Met Ile Ser
1               5                   10                  15

Pro Ser Ser Pro Pro Pro Asn Leu Phe Phe Pro Leu Gln Ile
                20                  25                  30

Phe Pro Phe Pro Phe Thr Ser Phe Pro Ser His Leu Ser Leu Thr
            35                  40                  45

Pro Pro Lys Ala Cys Tyr Leu Lys Ala Ile Glu Thr Gln Pro Asn Phe
    50                  55                  60

Ala Val Ala Trp Ser Asn Leu Gly Cys Val Phe Asn Ala Gln Gly Glu
65                  70                  75                  80

Ile Trp Leu Ala Ile His His Phe Glu Lys Ala Val Thr Leu Asp Pro
                85                  90                  95

Asn Phe Leu Asp Ala Tyr Ile Asn Leu Gly Asn Val Leu Lys Glu Ala
            100                 105                 110

Arg Ile Phe Asp Arg Ala Val Ala Ala Tyr Leu Arg Ala Leu Ser Leu
        115                 120                 125

Ser Pro Asn His Ala Val Val His Gly Asn Leu Ala Cys Val Tyr Tyr
130                 135                 140

Glu Gln Gly Leu Ile Asp Leu Ala Ile Asp Thr Tyr Arg Arg Ala Ile
145                 150                 155                 160

Glu Leu Gln Pro His Phe Pro Asp Ala Tyr Cys Asn Leu Ala Asn Ala
                165                 170                 175

Leu Lys Glu Lys Gly Ser Val Ala Glu Ala Glu Asp Cys Tyr Asn Thr
            180                 185                 190

Ala Leu Arg Leu Cys Pro Thr His Ala Asp Ser Leu Asn Asn Leu Ala
        195                 200                 205

Asn Ile Lys Arg Glu Gln Gly Asn Ile Glu Glu Ala Val Arg Leu Tyr
210                 215                 220
```

-continued

Arg Lys Ala Leu Glu Val Phe Pro Glu Phe Ala Ala His Ser Asn
225                 230                 235                 240

Leu Ala Ser Val Leu Gln Gln Gly Lys Leu Gln Glu Ala Leu Met
            245                 250                 255

His Tyr Lys Glu Ala Ile Arg Ile Ser Pro Thr Phe Ala Asp Ala Tyr
        260                 265                 270

Ser Asn Met Gly Asn Thr Leu Lys Glu Met Gln Asp Val Gln Gly Ala
    275                 280                 285

Leu Gln Cys Tyr Thr Arg Ala Ile Gln Ile Asn Pro Ala Phe Ala Asp
    290                 295                 300

Ala His Ser Asn Leu Ala Ser Ile His Lys Asp Ser Gly Asn Ile Pro
305                 310                 315                 320

Glu Ala Ile Ala Ser Tyr Arg Thr Ala Leu Lys Leu Lys Pro Asp Phe
            325                 330                 335

Pro Asp Ala Tyr Cys Asn Leu Ala His Cys Leu Gln Ile Val Cys Asp
            340                 345                 350

Trp Thr Asp Tyr Asp Glu Arg Met Lys Lys Leu Val Ser Ile Val Ala
    355                 360                 365

Asp Gln Leu Glu Lys Asn Arg Leu Pro Ser Val His Pro His His Ser
    370                 375                 380

Met Leu Tyr Pro Leu Ser His Gly Phe Arg Lys Ala Ile Ala Glu Arg
385                 390                 395                 400

His Gly Asn Leu Cys Leu Asp Lys Ile Asn Val Leu His Lys Pro Pro
            405                 410                 415

Tyr Glu His Pro Lys Asp Leu Lys Leu Ser Asp Gly Arg Leu Arg Val
            420                 425                 430

Gly Tyr Val Ser Ser Asp Phe Gly Asn His Pro Thr Ser His Leu Met
    435                 440                 445

Gln Ser Ile Pro Gly Met His Asn Pro Asp Lys Phe Glu Val Phe Cys
    450                 455                 460

Tyr Ala Leu Ser Pro Asp Asp Gly Thr Asn Phe Arg Val Lys Val Met
465                 470                 475                 480

Ala Glu Ala Asn His Phe Ile Asp Leu Ser Gln Ile Pro Cys Asn Gly
            485                 490                 495

Lys Ala Ala Asp Arg Ile His Gln Asp Gly Ile His Ile Leu Val Asn
            500                 505                 510

Met Asn Gly Tyr Thr Lys Gly Ala Arg Asn Glu Leu Phe Ala Leu Arg
    515                 520                 525

Pro Ala Pro Ile Gln Ala Met Trp Leu Gly Tyr Pro Gly Thr Ser Gly
    530                 535                 540

Ala Leu Phe Met Asp Tyr Ile Ile Thr Asp Gln Glu Thr Ser Pro Ala
545                 550                 555                 560

Glu Val Ala Glu Gln Tyr Ser Glu Lys Leu Ala Tyr Met Pro His Thr
            565                 570                 575

Phe Phe Ile Gly Asp His Ala Asn Met Phe Pro His Leu Lys Lys Lys
            580                 585                 590

Ala Val Ile Asp Phe Lys Ser Asn Gly His Ile Tyr Asp Asn Arg Ile
            595                 600                 605

Val Leu Asn Gly Ile Asp Leu Lys Ala Phe Leu Asp Ser Leu Pro Asp
    610                 615                 620

Val Lys Ile Val Lys Met Lys Cys Pro Asp Gly Gly Asp Asn Ala Asp
625                 630                 635                 640

Ser Ser Asn Thr Ala Leu Asn Met Pro Val Ile Pro Met Asn Thr Ile

```
                    645                 650                 655
Ala Glu Ala Val Ile Glu Met Ile Asn Arg Gly Gln Ile Gln Ile Thr
                660                 665                 670

Ile Asn Gly Phe Ser Ile Ser Asn Gly Leu Ala Thr Thr Gln Ile Asn
            675                 680                 685

Asn Lys Ala Ala Thr Gly Glu Val Pro Arg Thr Ile Ile Val Thr
        690                 695                 700

Thr Arg Ser Gln Tyr Gly Leu Pro Glu Asp Ala Ile Val Tyr Cys Asn
705                 710                 715                 720

Phe Asn Gln Leu Tyr Lys Ile Asp Pro Ser Thr Leu Gln Met Trp Ala
                725                 730                 735

Asn Ile Leu Lys Arg Val Pro Asn Ser Val Leu Trp Leu Leu Arg Phe
            740                 745                 750

Pro Ala Val Gly Glu Pro Asn Ile Gln Gln Tyr Ala Gln Asn Met Gly
        755                 760                 765

Leu Pro Gln Asn Arg Ile Ile Phe Ser Pro Val Ala Pro Lys Glu Glu
770                 775                 780

His Val Arg Arg Gly Gln Leu Ala Asp Val Cys Leu Asp Thr Pro Leu
785                 790                 795                 800

Cys Asn Gly His Thr Thr Gly Met Asp Val Leu Trp Ala Gly Thr Pro
                805                 810                 815

Met Val Thr Met Pro Gly Glu Thr Leu Ala Ser Arg Val Ala Ala Ser
            820                 825                 830

Gln Leu Thr Cys Leu Gly Cys Leu Glu Leu Ile Ala Lys Asn Arg Gln
        835                 840                 845

Glu Tyr Glu Asp Ile Ala Val Lys Leu Gly Thr Asp Leu Glu Tyr Leu
850                 855                 860

Lys Lys Val Arg Gly Lys Val Trp Lys Gln Arg Ile Ser Ser Pro Leu
865                 870                 875                 880

Phe Asn Thr Lys Gln Tyr Thr Met Glu Leu Arg Leu Tyr Leu Gln
                885                 890                 895

Met Trp Glu His Tyr Ala Ala Gly Asn Lys Pro Asp His Met Ile Lys
            900                 905                 910

Pro Val Glu Val Thr Glu Ser Ala
        915                 920

<210> SEQ ID NO 55
<211> LENGTH: 46
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 55

Met Leu Gln Gly His Phe Trp Leu Val Arg Glu Gly Ile Met Ile Ser
 1               5                  10                  15

Pro Ser Pro Pro Pro Pro Asn Leu Phe Phe Ser Leu Tyr Lys Phe
                20                  25                  30

Ser Pro Phe Pro Leu Pro Pro Phe Pro Ile Phe Phe His
            35                  40                  45

<210> SEQ ID NO 56
<211> LENGTH: 50
<212> TYPE: PRT
<213> ORGANISM: Artificial Sequence
<220> FEATURE:
<223> OTHER INFORMATION: Description of Artificial Sequence:
``` polypeptides encoded by genes with coding microsatellites

<400> SEQUENCE: 56

```
Met Leu Gln Gly His Phe Trp Leu Val Arg Glu Gly Ile Met Ile Ser
 1               5                  10                  15

Pro Ser Ser Pro Pro Pro Asn Leu Phe Phe Phe Pro Phe Thr Asn
            20                  25                  30

Phe Pro Leu Ser Leu Tyr Leu Leu Ser Leu Pro Ser Ser Phe Ile Asn
        35                  40                  45

Pro Ser
    50
```

<210> SEQ ID NO 57
<211> LENGTH: 350
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 57

```
Met Glu Ser Gln Val Gly Gly Gly Pro Ala Gly Arg Pro Ala Gln Arg
 1               5                  10                  15

Pro Leu Leu Gly Thr Asn Gly Ala Thr Asp Asp Ser Lys Thr Asn Leu
            20                  25                  30

Ile Val Asn Tyr Leu Pro Gln Asn Met Thr Gln Asp Glu Phe Lys Ser
        35                  40                  45

Leu Phe Gly Ser Ile Gly Asp Ile Glu Ser Cys Lys Leu Val Arg Asp
 50                  55                  60

Lys Ile Thr Gly Gln Ser Leu Gly Tyr Gly Phe Val Asn Tyr Ser Asp
 65                  70                  75                  80

Pro Asn Asp Ala Asp Lys Ala Ile Asn Thr Leu Asn Gly Leu Lys Leu
                85                  90                  95

Gln Thr Lys Thr Ile Lys Val Ser Tyr Ala Arg Pro Ser Ser Ala Ser
            100                 105                 110

Ile Arg Asp Ala Asn Leu Tyr Val Ser Gly Leu Pro Lys Thr Met Ser
        115                 120                 125

Gln Lys Glu Met Glu Gln Leu Phe Ser Gln Tyr Gly Arg Ile Ile Thr
130                 135                 140

Ser Arg Ile Leu Val Asp Gln Val Thr Gly Val Ser Arg Gly Val Gly
145                 150                 155                 160

Phe Ile Arg Phe Asp Lys Arg Ile Glu Ala Glu Ala Ile Lys Gly
                165                 170                 175

Leu Asn Gly Gln Lys Pro Leu Gly Ala Arg Glu Pro Ile Thr Val Lys
            180                 185                 190

Phe Ala Asn Asn Pro Ser Gln Lys Thr Gly Gln Ala Leu Leu Thr His
        195                 200                 205

Leu Tyr Gln Ser Ser Ala Arg Arg Tyr Ala Gly Pro Leu His His Gln
    210                 215                 220

Thr Gln Arg Phe Arg Leu Asp Asn Leu Leu Asn Met Ala Tyr Ala Val
225                 230                 235                 240

Lys Arg Phe Ser Pro Ile Ala Ile Asp Gly Met Ser Gly Leu Ala Gly
                245                 250                 255

Val Gly Leu Ser Gly Gly Ala Ala Gly Gly Trp Cys Ile Phe Val Tyr
            260                 265                 270

Asn Leu Ser Pro Glu Pro Asp Gln Ser Val Leu Trp Gln Leu Phe Gly
        275                 280                 285
```

```
Pro Phe Gly Ala Val Thr Asn Val Lys Val Ile Arg Asp Phe Thr Thr
    290                 295                 300

Asn Lys Cys Lys Gly Phe Gly Phe Met Thr Met Thr Asn Tyr Asp Glu
305                 310                 315                 320

Ala Ala Met Ala Ile Ala Ser Leu Asn Gly Tyr Arg Leu Gly Gln Arg
                325                 330                 335

Val Leu Gln Val Ser Phe Lys Thr Ser Lys Gln His Lys Ala
            340                 345                 350

<210> SEQ ID NO 58
<211> LENGTH: 40
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 58

Met Glu Ser Gln Val Gly Gly Ala Arg Pro Ala Gly Leu Pro Asn Gly
1               5                   10                  15

His Ser Leu Val Gln Met Glu Pro Leu Thr Thr Ala Arg Pro Thr Ser
            20                  25                  30

Ser Ser Thr Thr Cys Pro Arg Thr
        35                  40

<210> SEQ ID NO 59
<211> LENGTH: 25
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 59

Met Glu Ser Gln Val Gly Gly Gly Pro Gly Arg Pro Ala Cys Pro Thr
1               5                   10                  15

Ala Thr Pro Trp Tyr Lys Trp Ser His
            20                  25

<210> SEQ ID NO 60
<211> LENGTH: 189
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 60

Leu Phe Ser His Gln Arg Val Gln Ala Gln Pro Thr Asp Tyr Gly Gly
1               5                   10                  15

Ser Phe Thr Arg Arg Cys Val Glu Trp Leu Leu Gly Leu Tyr Phe Leu
            20                  25                  30

Ser His Ile Pro Ile Thr Leu Phe Met Asp Leu Gln Ala Val Val Pro
        35                  40                  45

Arg Glu Leu Tyr Pro Val Glu Phe Arg Asn Leu Leu Lys Trp Tyr Ala
    50                  55                  60

Lys Glu Phe Lys Asp Pro Leu Leu Gln Glu Pro Pro Ala Trp Phe Lys
65                  70                  75                  80

Ser Phe Leu Phe Cys Glu Leu Val Phe Gln Leu Pro Phe Phe Pro Ile
                85                  90                  95

Ala Thr Tyr Ala Phe Leu Lys Gly Ser Cys Lys Trp Ile Arg Thr Pro
```

-continued

```
                100                 105                 110
Ala Ile Ile Tyr Ser Val His Thr Met Thr Thr Leu Ile Leu Ile Leu
            115                 120                 125

Ser Thr Phe Leu Phe Glu Asp Phe Ser Lys Ala Ser Gly Phe Lys Gly
130                 135                 140

Gln Arg Pro Glu Thr Leu His Glu Arg Leu Thr Leu Val Ser Val Tyr
145                 150                 155                 160

Ala Pro Tyr Leu Leu Ile Pro Phe Ile Leu Leu Ile Phe Met Leu Arg
                165                 170                 175

Ser Pro Tyr Tyr Lys Tyr Glu Glu Lys Arg Lys Lys Lys
            180                 185

<210> SEQ ID NO 61
<211> LENGTH: 251
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 61

Leu Phe Ser His Gln Arg Val Gln Ala Gln Pro Thr Asp Tyr Gly Gly
1               5                   10                  15

Ser Phe Thr Arg Arg Cys Val Glu Trp Leu Leu Gly Leu Tyr Phe Leu
            20                  25                  30

Ser His Ile Pro Ile Thr Leu Phe Met Asp Leu Gln Ala Val Val Pro
        35                  40                  45

Arg Glu Leu Tyr Pro Val Glu Phe Arg Asn Leu Leu Lys Trp Tyr Ala
    50                  55                  60

Lys Glu Phe Lys Asp Pro Leu Leu Gln Glu Pro Pro Ala Trp Phe Lys
65                  70                  75                  80

Ser Phe Leu Phe Cys Glu Leu Val Phe Gln Leu Pro Phe Phe Pro Ile
                85                  90                  95

Ala Thr Tyr Ala Phe Leu Lys Gly Ser Cys Lys Trp Ile Arg Thr Pro
            100                 105                 110

Ala Ile Ile Tyr Ser Val His Thr Met Thr Thr Leu Ile Leu Ile Leu
        115                 120                 125

Ser Thr Phe Leu Phe Glu Asp Phe Ser Lys Ala Ser Gly Phe Lys Gly
    130                 135                 140

Gln Arg Pro Glu Thr Leu His Glu Arg Leu Thr Leu Val Ser Val Tyr
145                 150                 155                 160

Ala Pro Tyr Leu Leu Ile Pro Phe Ile Leu Leu Ile Phe Met Leu Arg
                165                 170                 175

Ser Pro Tyr Tyr Lys Tyr Glu Glu Lys Arg Lys Lys Asn Glu Gly Asn
            180                 185                 190

Asn His Trp Pro Arg Val Glu Met Pro Thr Gly Trp Leu Leu Val Gly
        195                 200                 205

Tyr Ile Gln Glu His Cys Ser Glu Pro Thr Ser Ser Ala Ala Phe Glu
    210                 215                 220

Thr Leu Ala Ala Met His Lys Ser Lys Met Val Ser Gly Thr Met Ser
225                 230                 235                 240

Asn Pro His Leu Leu Pro Phe Phe Phe Phe
                245                 250

<210> SEQ ID NO 62
<211> LENGTH: 198
<212> TYPE: PRT
```

-continued

```
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 62

Leu Phe Ser His Gln Arg Val Gln Ala Gln Pro Thr Asp Tyr Gly Gly
 1               5                  10                  15

Ser Phe Thr Arg Arg Cys Val Glu Trp Leu Leu Gly Leu Tyr Phe Leu
            20                  25                  30

Ser His Ile Pro Ile Thr Leu Phe Met Asp Leu Gln Ala Val Val Pro
        35                  40                  45

Arg Glu Leu Tyr Pro Val Glu Phe Arg Asn Leu Leu Lys Trp Tyr Ala
    50                  55                  60

Lys Glu Phe Lys Asp Pro Leu Leu Gln Glu Pro Pro Ala Trp Phe Lys
65                  70                  75                  80

Ser Phe Leu Phe Cys Glu Leu Val Phe Gln Leu Pro Phe Phe Pro Ile
                85                  90                  95

Ala Thr Tyr Ala Phe Leu Lys Gly Ser Cys Lys Trp Ile Arg Thr Pro
            100                 105                 110

Ala Ile Ile Tyr Ser Val His Thr Met Thr Thr Leu Ile Leu Ile Leu
        115                 120                 125

Ser Thr Phe Leu Phe Glu Asp Phe Ser Lys Ala Ser Gly Phe Lys Gly
    130                 135                 140

Gln Arg Pro Glu Thr Leu His Glu Arg Leu Thr Leu Val Ser Val Tyr
145                 150                 155                 160

Ala Pro Tyr Leu Leu Ile Pro Phe Ile Leu Leu Ile Phe Met Leu Arg
                165                 170                 175

Ser Pro Tyr Tyr Lys Tyr Glu Glu Lys Arg Lys Lys Met Lys Glu
            180                 185                 190

Thr Thr Thr Gly Pro Gly
        195

<210> SEQ ID NO 63
<211> LENGTH: 1232
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 63

Met Ala Asn Gly Val Ile Pro Pro Pro Gly Gly Ala Ser Pro Leu Pro
 1               5                  10                  15

Gln Val Arg Val Pro Leu Glu Glu Pro Pro Leu Ser Pro Asp Val Glu
            20                  25                  30

Glu Glu Asp Asp Asp Leu Gly Lys Thr Leu Ala Val Ser Arg Phe Gly
        35                  40                  45

Asp Leu Ile Ser Lys Pro Pro Ala Trp Asp Pro Glu Lys Pro Ser Arg
    50                  55                  60

Ser Tyr Ser Glu Arg Asp Phe Glu Phe His Arg His Thr Ser His His
65                  70                  75                  80

Thr His His Pro Leu Ser Ala Arg Leu Pro Pro His Lys Leu Arg
                85                  90                  95

Arg Leu Pro Pro Thr Ser Ala Arg His Thr Arg Arg Lys Arg Lys Lys
            100                 105                 110

Glu Lys Thr Ser Ala Pro Pro Ser Glu Gly Thr Pro Pro Ile Gln Glu
        115                 120                 125
```

```
Glu Gly Gly Ala Gly Val Asp Glu Glu Glu Glu Glu Glu Glu
        130                 135                 140

Glu Gly Glu Ser Glu Ala Glu Pro Val Glu Pro Pro Ser Gly Thr
145                 150                 155                 160

Pro Gln Lys Ala Lys Phe Ser Ile Gly Ser Asp Glu Asp Ser Pro
                165                 170                 175

Gly Leu Pro Gly Arg Ala Ala Val Thr Lys Pro Leu Pro Ser Val Gly
                180                 185                 190

Pro His Thr Asp Lys Ser Pro Gln His Ser Ser Ser Pro Ser Pro
                195                 200                 205

Arg Ala Arg Ala Ser Arg Leu Ala Gly Glu Lys Ser Arg Pro Trp Ser
210                 215                 220

Pro Ser Ala Ser Tyr Asp Leu Arg Glu Arg Leu Cys Pro Gly Ser Ala
225                 230                 235                 240

Leu Gly Asn Pro Gly Pro Glu Gln Gln Val Pro Thr Asp Glu Ala
                245                 250                 255

Glu Ala Gln Met Leu Gly Ser Ala Asp Leu Asp Asp Met Lys Ser His
                260                 265                 270

Arg Leu Glu Asp Asn Pro Gly Val Arg Arg His Leu Val Lys Lys Pro
                275                 280                 285

Ser Arg Thr Gln Gly Gly Arg Gly Ser Pro Ser Gly Leu Ala Pro Ile
290                 295                 300

Leu Arg Arg Lys Lys Lys Lys Lys Leu Asp Arg Arg Pro His Glu
305                 310                 315                 320

Val Phe Val Glu Leu Asn Glu Leu Met Leu Asp Arg Ser Gln Glu Pro
                325                 330                 335

His Trp Arg Glu Thr Ala Arg Trp Ile Lys Phe Glu Glu Asp Val Glu
                340                 345                 350

Glu Glu Thr Glu Arg Trp Gly Lys Pro His Val Ala Ser Leu Ser Phe
                355                 360                 365

Arg Ser Leu Leu Glu Leu Arg Arg Thr Ile Ala His Gly Ala Ala Leu
370                 375                 380

Leu Asp Leu Glu Gln Thr Thr Leu Pro Gly Ile Ala His Leu Val Val
385                 390                 395                 400

Glu Thr Met Ile Val Ser Asp Gln Ile Arg Pro Glu Asp Arg Ala Ser
                405                 410                 415

Val Leu Arg Thr Leu Leu Leu Lys His Ser His Pro Asn Asp Asp Lys
                420                 425                 430

Asp Ser Gly Phe Phe Pro Arg Asn Pro Ser Ser Ser Met Asn Ser
        435                 440                 445

Val Leu Gly Asn His His Pro Thr Pro Ser His Gly Pro Asp Gly Ala
                450                 455                 460

Val Pro Thr Met Ala Asp Asp Leu Gly Glu Pro Ala Pro Leu Trp Pro
465                 470                 475                 480

His Asp Pro Asp Ala Lys Glu Lys Pro Leu His Met Pro Gly Gly Asp
                485                 490                 495

Gly His Arg Gly Lys Ser Leu Lys Leu Leu Glu Lys Ile Pro Glu Asp
                500                 505                 510

Ala Glu Ala Thr Val Val Leu Val Gly Cys Val Pro Phe Leu Glu Gln
                515                 520                 525

Pro Ala Ala Ala Phe Val Arg Leu Asn Glu Ala Val Leu Leu Glu Ser
530                 535                 540

Val Leu Glu Val Pro Val Pro Val Arg Phe Leu Phe Val Met Leu Gly
```

```
            545                 550                 555                 560
    Pro Ser His Thr Ser Thr Asp Tyr His Glu Leu Gly Arg Ser Ile Ala
                    565                 570                 575

Thr Leu Met Ser Asp Lys Leu Phe His Glu Ala Ala Tyr Gln Ala Asp
                    580                 585                 590

Asp Arg Gln Asp Leu Leu Ser Ala Ile Ser Glu Phe Leu Asp Gly Ser
                    595                 600                 605

Ile Val Ile Pro Pro Ser Glu Val Glu Gly Arg Asp Leu Leu Arg Ser
                610                 615                 620

Val Ala Ala Phe Gln Arg Glu Leu Leu Arg Lys Arg Arg Glu Arg Glu
    625                 630                 635                 640

Gln Thr Lys Val Glu Met Thr Thr Arg Gly Gly Tyr Thr Ala Pro Gly
                    645                 650                 655

Lys Glu Leu Ser Leu Glu Leu Gly Gly Ser Glu Ala Thr Pro Glu Asp
                    660                 665                 670

Asp Pro Leu Leu Arg Thr Gly Ser Val Phe Gly Leu Val Arg Asp
                    675                 680                 685

Val Arg Arg Arg Tyr Pro His Tyr Pro Ser Asp Leu Arg Asp Ala Leu
                690                 695                 700

His Ser Gln Cys Val Ala Ala Val Leu Phe Ile Tyr Phe Ala Ala Leu
    705                 710                 715                 720

Ser Pro Ala Ile Thr Phe Gly Gly Leu Leu Gly Glu Lys Thr Glu Gly
                    725                 730                 735

Leu Met Gly Val Ser Glu Leu Ile Val Ser Thr Ala Val Leu Gly Val
                    740                 745                 750

Leu Phe Ser Leu Leu Gly Ala Gln Pro Leu Leu Val Val Gly Phe Ser
                    755                 760                 765

Gly Pro Leu Leu Val Phe Glu Glu Ala Phe Phe Lys Phe Cys Arg Ala
                770                 775                 780

Gln Asp Leu Glu Tyr Leu Thr Gly Arg Val Trp Val Gly Leu Trp Leu
    785                 790                 795                 800

Val Val Phe Val Leu Ala Leu Val Ala Ala Glu Gly Ser Phe Leu Val
                    805                 810                 815

Arg Tyr Ile Ser Pro Phe Thr Gln Glu Ile Phe Ala Phe Leu Ile Ser
                    820                 825                 830

Leu Ile Phe Ile Tyr Glu Thr Phe Tyr Lys Leu Tyr Lys Val Phe Thr
                    835                 840                 845

Glu His Pro Leu Leu Pro Phe Tyr Pro Pro Glu Gly Ala Leu Glu Gly
                    850                 855                 860

Ser Leu Ala Ala Gly Leu Glu Pro Asn Gly Ser Ala Leu Pro Pro Thr
    865                 870                 875                 880

Glu Gly Pro Pro Ser Pro Arg Asn Gln Pro Asn Thr Ala Leu Leu Ser
                    885                 890                 895

Leu Ile Leu Met Leu Gly Thr Phe Phe Ile Ala Phe Leu Arg Lys
                    900                 905                 910

Phe Arg Asn Ser Arg Phe Leu Gly Gly Lys Ala Arg Arg Ile Ile Gly
                    915                 920                 925

Asp Phe Gly Ile Pro Ile Ser Ile Leu Val Met Val Leu Val Asp Tyr
                930                 935                 940

Ser Ile Thr Asp Thr Tyr Thr Gln Lys Leu Thr Val Pro Thr Gly Leu
    945                 950                 955                 960

Ser Val Thr Ser Pro Asp Lys Arg Ser Trp Phe Ile Pro Pro Leu Gly
                    965                 970                 975
```

-continued

```
Ser Ala Arg Pro Phe Pro Pro Trp Met Met Val Ala Ala Ala Val Pro
            980                 985                 990

Ala Leu Leu Val Leu Ile Leu Ile Phe Met Glu Thr Gln Ile Thr Ala
            995                 1000                1005

Leu Ile Val Ser Gln Lys Ala Arg Arg Leu Leu Lys Gly Ser Gly Phe
            1010                1015                1020

His Leu Asp Leu Leu Ile Gly Ser Leu Gly Gly Leu Cys Gly Leu
    1025                1030                1035            1040

Phe Gly Leu Pro Trp Leu Thr Ala Ala Thr Val Arg Ser Val Thr His
                1045                1050                1055

Val Asn Ala Leu Thr Val Met Arg Thr Ala Ile Ala Pro Gly Asp Lys
                1060                1065                1070

Pro Gln Ile Gln Glu Val Arg Glu Gln Arg Val Thr Gly Val Leu Ile
                1075                1080                1085

Ala Ser Leu Val Gly Leu Ser Ile Val Met Gly Ala Val Leu Arg Arg
                1090                1095                1100

Ile Pro Leu Ala Val Leu Phe Gly Ile Phe Leu Tyr Met Gly Val Thr
1105                1110                1115                1120

Ser Leu Ser Gly Ile Gln Leu Ser Gln Arg Leu Leu Leu Ile Leu Met
                1125                1130                1135

Pro Ala Lys His His Pro Glu Gln Pro Tyr Val Thr Lys Val Lys Thr
                1140                1145                1150

Trp Arg Met His Leu Phe Thr Cys Ile Gln Leu Gly Cys Ile Ala Leu
                1155                1160                1165

Leu Trp Val Val Lys Ser Thr Ala Ala Ser Leu Ala Phe Pro Phe Leu
                1170                1175                1180

Leu Leu Leu Thr Val Pro Leu Arg His Cys Leu Leu Pro Arg Leu Phe
1185                1190                1195                1200

Gln Asp Arg Glu Leu Gln Ala Leu Asp Ser Glu Asp Ala Glu Pro Asn
                1205                1210                1215

Phe Asp Glu Asp Gly Gln Asp Glu Tyr Asn Glu Leu His Met Pro Val
                1220                1225                1230

<210> SEQ ID NO 64
<211> LENGTH: 268
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 64

Met Ala Asn Gly Val Ile Pro Pro Gly Gly Ala Ser Pro Leu Pro
1               5                   10                  15

Gln Val Arg Val Pro Leu Glu Glu Pro Pro Leu Ser Pro Asp Val Glu
                20                  25                  30

Glu Glu Asp Asp Asp Leu Gly Lys Thr Leu Ala Val Ser Arg Phe Gly
            35                  40                  45

Asp Leu Ile Ser Lys Pro Pro Ala Trp Asp Pro Glu Lys Pro Ser Arg
        50                  55                  60

Ser Tyr Ser Glu Arg Asp Phe Glu Phe His Arg His Thr Ser His His
65                  70                  75                  80

Thr His His Pro Leu Ser Ala Arg Leu Pro Pro His Lys Leu Arg
                    85                  90                  95

Arg Leu Pro Pro Thr Ser Ala Arg His Thr Arg Arg Lys Arg Lys Lys
                100                 105                 110
```

```
Glu Lys Thr Ser Ala Pro Pro Ser Glu Gly Thr Pro Ile Gln Glu
            115                 120                 125

Glu Gly Gly Ala Gly Val Asp Glu Glu Glu Glu Glu Glu Glu Glu
        130                 135                 140

Glu Gly Glu Ser Glu Ala Glu Pro Val Glu Pro Pro Gln Gly Pro
145                 150                 155                 160

His Arg Arg Gln Ser Ser Pro Leu Glu Val Thr Arg Met Thr Val Gln
                165                 170                 175

Ala Ser Leu Gly Gly Leu Leu Ser Pro Ser Pro Cys Pro Arg Trp Ala
            180                 185                 190

His Thr Leu Thr Arg Ala Pro Ser Thr Pro Ala Ala Pro Pro Ala Pro
            195                 200                 205

Gly Pro Gly Pro Pro Asp Ser Leu Gly Arg Lys Ala Gly Pro Gly Ala
    210                 215                 220

His Arg Pro Val Met Thr Cys Gly Ser Asp Cys Ala Gln Ala Val Pro
225                 230                 235                 240

Trp Ala Thr Gln Val Gln Ser Ser Arg Cys Pro Gln Met Arg Arg
                245                 250                 255

Arg Pro Arg Cys Trp Val Leu Gln Thr Trp Thr Thr
            260                 265

<210> SEQ ID NO 65
<211> LENGTH: 170
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 65

Met Ala Asn Gly Val Ile Pro Pro Gly Gly Ala Ser Pro Leu Pro
  1               5                  10                  15

Gln Val Arg Val Pro Leu Glu Glu Pro Leu Ser Pro Asp Val Glu
                 20                  25                  30

Glu Glu Asp Asp Asp Leu Gly Lys Thr Leu Ala Val Ser Arg Phe Gly
            35                  40                  45

Asp Leu Ile Ser Lys Pro Pro Ala Trp Asp Pro Glu Lys Pro Ser Arg
    50                  55                  60

Ser Tyr Ser Glu Arg Asp Phe Glu Phe His Arg His Thr Ser His His
 65                  70                  75                  80

Thr His His Pro Leu Ser Ala Arg Leu Pro Pro His Lys Leu Arg
                 85                  90                  95

Arg Leu Pro Pro Thr Ser Ala Arg His Thr Arg Arg Lys Arg Lys Lys
            100                 105                 110

Glu Lys Thr Ser Ala Pro Pro Ser Glu Gly Thr Pro Ile Gln Glu
            115                 120                 125

Glu Gly Gly Ala Gly Val Asp Glu Glu Glu Glu Glu Glu Glu Glu
        130                 135                 140

Glu Gly Glu Ser Glu Ala Glu Pro Val Glu Pro Pro Leu Arg Asp
145                 150                 155                 160

Pro Thr Glu Gly Lys Val Leu His Trp Lys
                165                 170

<210> SEQ ID NO 66
<211> LENGTH: 686
<212> TYPE: PRT
<213> ORGANISM: Artificial Sequence
<220> FEATURE:
```

<223> OTHER INFORMATION: Description of Artificial Sequence:
polypeptides encoded by genes with coding microsatellites

<400> SEQUENCE: 66

```
Met Ala Gly Ser Gly Ala Gly Val Arg Cys Ser Leu Leu Arg Leu Gln
  1               5                  10                  15

Glu Thr Leu Ser Ala Ala Asp Arg Cys Gly Ala Ala Leu Ala Gly His
             20                  25                  30

Gln Leu Ile Arg Gly Leu Gly Gln Glu Cys Val Leu Ser Ser Ser Pro
         35                  40                  45

Ala Val Leu Ala Leu Gln Thr Ser Leu Val Phe Ser Arg Asp Phe Gly
     50                  55                  60

Leu Leu Val Phe Val Arg Lys Ser Leu Asn Ser Ile Glu Phe Arg Glu
 65                  70                  75                  80

Cys Arg Glu Glu Ile Leu Lys Phe Leu Cys Ile Phe Leu Glu Lys Met
                 85                  90                  95

Gly Gln Lys Ile Ala Pro Tyr Ser Val Glu Ile Lys Asn Thr Cys Thr
            100                 105                 110

Ser Val Tyr Thr Lys Asp Arg Ala Ala Lys Cys Lys Ile Pro Ala Leu
        115                 120                 125

Asp Leu Leu Ile Lys Leu Leu Gln Thr Phe Arg Ser Ser Arg Leu Met
130                 135                 140

Asp Glu Phe Lys Ile Gly Glu Leu Phe Ser Lys Phe Tyr Gly Glu Leu
145                 150                 155                 160

Ala Leu Lys Lys Lys Ile Pro Asp Thr Val Leu Glu Lys Val Tyr Glu
                165                 170                 175

Leu Leu Gly Leu Leu Gly Glu Val His Pro Ser Glu Met Ile Asn Asn
            180                 185                 190

Ala Glu Asn Leu Phe Arg Ala Phe Leu Gly Glu Leu Lys Thr Gln Met
        195                 200                 205

Thr Ser Ala Val Arg Glu Pro Lys Leu Pro Val Leu Ala Gly Cys Leu
    210                 215                 220

Lys Gly Leu Ser Ser Leu Leu Cys Asn Phe Thr Lys Ser Met Glu Glu
225                 230                 235                 240

Asp Pro Gln Thr Ser Arg Glu Ile Phe Asn Phe Val Leu Lys Ala Ile
                245                 250                 255

Arg Pro Gln Ile Asp Leu Lys Arg Tyr Ala Val Pro Ser Ala Gly Leu
            260                 265                 270

Arg Leu Phe Ala Leu His Ala Ser Gln Phe Ser Thr Cys Leu Leu Asp
        275                 280                 285

Asn Tyr Val Ser Leu Phe Glu Val Leu Leu Lys Trp Cys Ala His Thr
    290                 295                 300

Asn Val Glu Leu Lys Lys Ala Ala Leu Ser Ala Leu Glu Ser Phe Leu
305                 310                 315                 320

Lys Gln Val Ser Asn Met Val Ala Lys Asn Ala Glu Met His Lys Asn
                325                 330                 335

Lys Leu Gln Tyr Phe Met Glu Gln Phe Tyr Gly Ile Ile Arg Asn Val
            340                 345                 350

Asp Ser Asn Asn Lys Glu Leu Ser Ile Ala Ile Arg Gly Tyr Gly Leu
        355                 360                 365

Phe Ala Gly Pro Cys Lys Val Ile Asn Ala Lys Asp Val Asp Phe Met
    370                 375                 380

Tyr Val Glu Leu Ile Gln Arg Cys Lys Gln Met Phe Leu Thr Gln Thr
385                 390                 395                 400
```

```
Asp Thr Gly Asp Asp Arg Val Tyr Gln Met Pro Ser Phe Leu Gln Ser
                405                 410                 415

Val Ala Ser Val Leu Leu Tyr Leu Asp Thr Val Pro Glu Val Tyr Thr
            420                 425                 430

Pro Val Leu Glu His Leu Val Val Met Gln Ile Asp Ser Phe Pro Gln
        435                 440                 445

Tyr Ser Pro Lys Met Gln Leu Val Cys Cys Arg Ala Ile Val Lys Val
    450                 455                 460

Phe Leu Ala Leu Ala Ala Lys Gly Pro Val Leu Arg Asn Cys Ile Ser
465                 470                 475                 480

Thr Val Val His Gln Gly Leu Ile Arg Ile Cys Ser Lys Pro Val Val
                485                 490                 495

Leu Pro Lys Gly Pro Glu Ser Glu Ser Glu Asp His Arg Ala Ser Gly
            500                 505                 510

Glu Val Arg Thr Gly Lys Trp Lys Val Pro Thr Tyr Lys Asp Tyr Val
        515                 520                 525

Asp Leu Phe Arg His Leu Leu Ser Ser Asp Gln Met Met Asp Ser Ile
    530                 535                 540

Leu Ala Asp Glu Ala Phe Phe Ser Val Asn Ser Ser Glu Ser Leu
545                 550                 555                 560

Asn His Leu Leu Tyr Asp Glu Phe Val Lys Ser Val Leu Lys Ile Val
                565                 570                 575

Glu Lys Leu Asp Leu Thr Leu Glu Ile Gln Thr Val Gly Glu Gln Glu
            580                 585                 590

Asn Gly Asp Glu Ala Pro Gly Val Trp Met Ile Pro Thr Ser Asp Pro
        595                 600                 605

Ala Ala Asn Leu His Pro Ala Lys Pro Lys Asp Phe Ser Ala Phe Ile
    610                 615                 620

Asn Leu Val Glu Phe Cys Arg Glu Ile Leu Pro Glu Lys Gln Ala Glu
625                 630                 635                 640

Phe Phe Glu Pro Trp Val Tyr Ser Phe Ser Tyr Glu Leu Ile Leu Gln
                645                 650                 655

Ser Thr Arg Leu Pro Leu Ile Ser Gly Phe Tyr Lys Leu Leu Ser Ile
            660                 665                 670

Thr Val Arg Asn Ala Lys Lys Ile Lys Tyr Phe Glu Gly Ser
        675                 680                 685

<210> SEQ ID NO 67
<211> LENGTH: 170
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 67

Met Ala Gly Ser Gly Ala Gly Val Arg Cys Ser Leu Leu Arg Leu Gln
1               5                   10                  15

Glu Thr Leu Ser Ala Ala Asp Arg Cys Gly Ala Ala Leu Ala Gly His
            20                  25                  30

Gln Leu Ile Arg Gly Leu Gly Gln Glu Cys Val Leu Ser Ser Ser Pro
        35                  40                  45

Ala Val Leu Ala Leu Gln Thr Ser Leu Val Phe Ser Arg Asp Phe Gly
    50                  55                  60

Leu Leu Val Phe Val Arg Lys Ser Leu Asn Ser Ile Glu Phe Arg Glu
65                  70                  75                  80
```

```
Cys Arg Glu Glu Ile Leu Lys Phe Leu Cys Ile Phe Leu Glu Lys Met
            85                  90                  95

Gly Gln Lys Ile Ala Pro Tyr Ser Val Glu Ile Lys Asn Thr Cys Thr
            100                 105                 110

Ser Val Tyr Thr Lys Asp Arg Ala Ala Lys Cys Lys Ile Pro Ala Leu
            115                 120                 125

Asp Leu Leu Ile Lys Leu Leu Gln Thr Phe Arg Ser Ser Arg Leu Met
            130                 135                 140

Asp Glu Phe Lys Ile Gly Glu Leu Phe Ser Lys Phe Tyr Gly Glu Leu
145                 150                 155                 160

Ala Leu Lys Lys Lys Tyr Gln Ile Gln Phe
            165                 170

<210> SEQ ID NO 68
<211> LENGTH: 175
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 68

Met Ala Gly Ser Gly Ala Gly Val Arg Cys Ser Leu Leu Arg Leu Gln
1               5                   10                  15

Glu Thr Leu Ser Ala Ala Asp Arg Cys Gly Ala Ala Leu Ala Gly His
            20                  25                  30

Gln Leu Ile Arg Gly Leu Gly Gln Glu Cys Val Leu Ser Ser Ser Pro
        35                  40                  45

Ala Val Leu Ala Leu Gln Thr Ser Leu Val Phe Ser Arg Asp Phe Gly
    50                  55                  60

Leu Leu Val Phe Val Arg Lys Ser Leu Asn Ser Ile Glu Phe Arg Glu
65                  70                  75                  80

Cys Arg Glu Glu Ile Leu Lys Phe Leu Cys Ile Phe Leu Glu Lys Met
            85                  90                  95

Gly Gln Lys Ile Ala Pro Tyr Ser Val Glu Ile Lys Asn Thr Cys Thr
            100                 105                 110

Ser Val Tyr Thr Lys Asp Arg Ala Ala Lys Cys Lys Ile Pro Ala Leu
            115                 120                 125

Asp Leu Leu Ile Lys Leu Leu Gln Thr Phe Arg Ser Ser Arg Leu Met
            130                 135                 140

Asp Glu Phe Lys Ile Gly Glu Leu Phe Ser Lys Phe Tyr Gly Glu Leu
145                 150                 155                 160

Ala Leu Lys Lys Lys Asn Thr Arg Tyr Ser Phe Arg Lys Ser Ile
            165                 170                 175

<210> SEQ ID NO 69
<211> LENGTH: 648
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 69

Met Ser Ala Ser Ala Ser Val Gly Gly Pro Val Pro Gln Pro Pro Pro
1               5                   10                  15

Gly Pro Ala Ala Ala Leu Pro Pro Gly Ser Ala Ala Arg Ala Leu His
            20                  25                  30

Val Glu Leu Pro Ser Gln Gln Arg Arg Leu Arg His Leu Arg Asn Ile
```

-continued

```
            35                  40                  45
Ala Ala Arg Asn Ile Val Asn Arg Asn Gly His Gln Leu Leu Asp Thr
         50                  55                  60
Tyr Phe Thr Leu His Leu Cys Ser Thr Glu Lys Ile Tyr Lys Glu Phe
 65                  70                  75                  80
Tyr Arg Ser Glu Val Ile Lys Asn Ser Leu Asn Pro Thr Trp Arg Ser
                 85                  90                  95
Leu Asp Phe Gly Ile Met Pro Asp Arg Leu Asp Thr Ser Val Ser Cys
            100                 105                 110
Phe Val Val Lys Ile Trp Gly Gly Lys Glu Asn Ile Tyr Gln Leu Leu
            115                 120                 125
Ile Glu Trp Lys Val Cys Leu Asp Gly Leu Lys Tyr Leu Gly Gln Gln
            130                 135                 140
Ile His Ala Arg Asn Gln Asn Glu Ile Ile Phe Gly Leu Asn Asp Gly
145                 150                 155                 160
Tyr Tyr Gly Ala Pro Phe Glu His Lys Gly Tyr Ser Asn Ala Gln Lys
                165                 170                 175
Thr Ile Leu Leu Gln Val Asp Gln Asn Cys Val Arg Asn Ser Tyr Asp
            180                 185                 190
Val Phe Ser Leu Leu Arg Leu His Arg Ala Gln Cys Ala Ile Lys Gln
            195                 200                 205
Thr Gln Val Thr Val Gln Lys Ile Gly Lys Glu Ile Glu Glu Lys Leu
            210                 215                 220
Arg Leu Thr Ser Thr Ser Asn Glu Leu Lys Lys Ser Glu Cys Leu
225                 230                 235                 240
Gln Leu Lys Ile Leu Val Leu Gln Asn Glu Leu Glu Arg Gln Lys Lys
            245                 250                 255
Ala Leu Gly Arg Glu Val Ala Leu Leu His Lys Gln Ile Ala Leu
            260                 265                 270
Gln Asp Lys Gly Ser Ala Phe Ser Ala Glu His Leu Lys Leu Gln Leu
            275                 280                 285
Gln Lys Glu Ser Leu Asn Glu Leu Arg Lys Glu Cys Thr Ala Lys Arg
            290                 295                 300
Glu Leu Phe Leu Lys Thr Asn Ala Gln Leu Thr Ile Arg Cys Arg Gln
305                 310                 315                 320
Leu Leu Ser Glu Leu Ser Tyr Ile Tyr Pro Ile Asp Leu Asn Glu His
                325                 330                 335
Lys Asp Tyr Phe Val Cys Gly Val Lys Leu Pro Asn Ser Glu Asp Phe
            340                 345                 350
Gln Ala Lys Asp Asp Gly Ser Ile Ala Val Ala Leu Gly Tyr Thr Ala
            355                 360                 365
His Leu Val Ser Met Ile Ser Phe Phe Leu Gln Val Pro Leu Arg Tyr
            370                 375                 380
Pro Ile Ile His Lys Gly Ser Arg Ser Thr Ile Lys Asp Asn Ile Asn
385                 390                 395                 400
Asp Lys Leu Thr Glu Lys Glu Arg Glu Phe Pro Leu Tyr Pro Lys Gly
            405                 410                 415
Gly Glu Lys Leu Gln Phe Asp Tyr Gly Val Tyr Leu Leu Asn Lys Asn
            420                 425                 430
Ile Ala Gln Leu Arg Tyr Gln His Gly Leu Gly Thr Pro Asp Leu Arg
            435                 440                 445
Gln Thr Leu Pro Asn Leu Lys Asn Phe Met Glu His Gly Leu Met Val
            450                 455                 460
```

```
Arg Cys Asp Arg His His Thr Ser Ser Ala Ile Pro Val Pro Lys Arg
465                 470                 475                 480

Gln Ser Ser Ile Phe Gly Gly Ala Asp Val Gly Phe Ser Gly Gly Ile
                485                 490                 495

Pro Ser Pro Asp Lys Gly His Arg Lys Arg Ala Ser Ser Glu Asn Glu
            500                 505                 510

Arg Leu Gln Tyr Lys Thr Pro Pro Ser Tyr Asn Ser Ala Leu Ala
        515                 520                 525

Gln Pro Val Thr Thr Val Pro Ser Met Gly Glu Thr Glu Arg Lys Ile
        530                 535                 540

Thr Ser Leu Ser Ser Ser Leu Asp Thr Ser Leu Asp Phe Ser Lys Glu
545                 550                 555                 560

Asn Lys Lys Lys Gly Glu Asp Leu Val Gly Ser Leu Asn Gly Gly His
                565                 570                 575

Ala Asn Val His Pro Ser Gln Glu Gln Gly Glu Ala Leu Ser Gly His
                580                 585                 590

Arg Ala Thr Val Asn Gly Thr Leu Leu Pro Ser Glu Gln Ala Gly Ser
                595                 600                 605

Ala Ser Val Gln Leu Pro Gly Glu Phe His Pro Val Ser Glu Ala Glu
                610                 615                 620

Leu Cys Cys Thr Val Glu Gln Ala Glu Glu Ile Ile Gly Leu Glu Ala
625                 630                 635                 640

Gln Val Ser Pro Gln Val Ile Ser
                645

<210> SEQ ID NO 70
<211> LENGTH: 241
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 70

Met Ser Ala Ser Ala Ser Val Gly Gly Pro Val Pro Gln Pro Pro Pro
1               5                   10                  15

Gly Pro Ala Ala Ala Leu Pro Pro Gly Ser Ala Ala Arg Ala Leu His
                20                  25                  30

Val Glu Leu Pro Ser Gln Gln Arg Leu Arg His Leu Arg Asn Ile
            35                  40                  45

Ala Ala Arg Asn Ile Val Asn Arg Asn Gly His Gln Leu Leu Asp Thr
    50                  55                  60

Tyr Phe Thr Leu His Leu Cys Ser Thr Glu Lys Ile Tyr Lys Glu Phe
65                  70                  75                  80

Tyr Arg Ser Glu Val Ile Lys Asn Ser Leu Asn Pro Thr Trp Arg Ser
                85                  90                  95

Leu Asp Phe Gly Ile Met Pro Arg Leu Asp Thr Ser Val Ser Cys
                100                 105                 110

Phe Val Val Lys Ile Trp Gly Gly Lys Glu Asn Ile Tyr Gln Leu Leu
            115                 120                 125

Ile Glu Trp Lys Val Cys Leu Asp Gly Leu Lys Tyr Leu Gly Gln Gln
130                 135                 140

Ile His Ala Arg Asn Gln Asn Glu Ile Ile Phe Gly Leu Asn Asp Gly
145                 150                 155                 160

Tyr Tyr Gly Ala Pro Phe Glu His Lys Gly Tyr Ser Asn Ala Gln Lys
                165                 170                 175
```

```
Thr Ile Leu Leu Gln Val Asp Gln Asn Cys Val Arg Asn Ser Tyr Asp
            180                 185                 190

Val Phe Ser Leu Leu Arg Leu His Arg Ala Gln Cys Ala Ile Lys Gln
            195                 200                 205

Thr Gln Val Thr Val Gln Lys Ile Gly Lys Glu Ile Glu Glu Lys Leu
    210                 215                 220

Arg Leu Thr Ser Thr Ser Asn Glu Leu Lys Lys Lys Val Asn Ala Cys
225                 230                 235                 240

Ser

<210> SEQ ID NO 71
<211> LENGTH: 237
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 71

Met Ser Ala Ser Ala Ser Val Gly Gly Pro Val Pro Gln Pro Pro Pro
  1               5                  10                  15

Gly Pro Ala Ala Ala Leu Pro Pro Gly Ser Ala Ala Arg Ala Leu His
             20                  25                  30

Val Glu Leu Pro Ser Gln Gln Arg Arg Leu Arg His Leu Arg Asn Ile
         35                  40                  45

Ala Ala Arg Asn Ile Val Asn Arg Asn Gly His Gln Leu Leu Asp Thr
     50                  55                  60

Tyr Phe Thr Leu His Leu Cys Ser Thr Glu Lys Ile Tyr Lys Glu Phe
 65                  70                  75                  80

Tyr Arg Ser Glu Val Ile Lys Asn Ser Leu Asn Pro Thr Trp Arg Ser
                 85                  90                  95

Leu Asp Phe Gly Ile Met Pro Asp Arg Leu Asp Thr Ser Val Ser Cys
            100                 105                 110

Phe Val Val Lys Ile Trp Gly Gly Lys Glu Asn Ile Tyr Gln Leu Leu
        115                 120                 125

Ile Glu Trp Lys Val Cys Leu Asp Gly Leu Lys Tyr Leu Gly Gln Gln
    130                 135                 140

Ile His Ala Arg Asn Gln Asn Glu Ile Ile Phe Gly Leu Asn Asp Gly
145                 150                 155                 160

Tyr Tyr Gly Ala Pro Phe Glu His Lys Gly Tyr Ser Asn Ala Gln Lys
                165                 170                 175

Thr Ile Leu Leu Gln Val Asp Gln Asn Cys Val Arg Asn Ser Tyr Asp
            180                 185                 190

Val Phe Ser Leu Leu Arg Leu His Arg Ala Gln Cys Ala Ile Lys Gln
        195                 200                 205

Thr Gln Val Thr Val Gln Lys Ile Gly Lys Glu Ile Glu Glu Lys Leu
    210                 215                 220

Arg Leu Thr Ser Thr Ser Asn Glu Leu Lys Lys Lys
225                 230                 235

<210> SEQ ID NO 72
<211> LENGTH: 1137
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 72
```

```
Met Ser Arg Arg Lys Pro Ala Ser Gly Gly Leu Ala Ala Ser Ser Ser
 1               5                  10                  15

Ala Pro Ala Arg Gln Ala Val Leu Ser Arg Phe Phe Gln Ser Thr Gly
                20                  25                  30

Ser Leu Lys Ser Thr Ser Ser Thr Gly Ala Ala Asp Gln Val Asp
            35                  40                  45

Pro Gly Ala Ala Ala Ala Ala Ala Ala Ala Ala Ala Ala Pro Pro
         50                  55                  60

Ala Pro Pro Ala Pro Ala Phe Pro Pro Gln Leu Pro Pro His Val Ala
 65              70                  75                  80

Thr Glu Ile Asp Arg Arg Lys Lys Arg Pro Leu Glu Asn Asp Gly Pro
                85                  90                  95

Val Lys Lys Lys Val Lys Lys Val Gln Gln Lys Glu Gly Gly Ser Asp
            100                 105                 110

Leu Gly Met Ser Gly Asn Ser Glu Pro Lys Lys Cys Leu Arg Thr Arg
            115                 120                 125

Asn Val Ser Lys Ser Leu Glu Lys Leu Lys Glu Phe Cys Cys Asp Ser
            130                 135                 140

Ala Leu Pro Gln Ser Arg Val Gln Thr Glu Ser Leu Gln Glu Arg Phe
145                 150                 155                 160

Ala Val Leu Pro Lys Cys Thr Asp Phe Asp Asp Ile Ser Leu Leu His
                165                 170                 175

Ala Lys Asn Ala Val Ser Ser Glu Asp Ser Lys Arg Gln Ile Asn Gln
                180                 185                 190

Lys Asp Thr Thr Leu Phe Asp Leu Ser Gln Phe Gly Ser Ser Asn Thr
            195                 200                 205

Ser His Glu Asn Leu Gln Lys Thr Ala Ser Lys Ser Ala Asn Lys Arg
            210                 215                 220

Ser Lys Ser Ile Tyr Thr Pro Leu Glu Leu Gln Tyr Ile Glu Met Lys
225                 230                 235                 240

Gln Gln His Lys Asp Ala Val Leu Cys Val Glu Cys Gly Tyr Lys Tyr
                245                 250                 255

Arg Phe Phe Gly Glu Asp Ala Glu Ile Ala Ala Arg Glu Leu Asn Ile
                260                 265                 270

Tyr Cys His Leu Asp His Asn Phe Met Thr Ala Ser Ile Pro Thr His
                275                 280                 285

Arg Leu Phe Val His Val Arg Arg Leu Val Ala Lys Gly Tyr Lys Val
            290                 295                 300

Gly Val Val Lys Gln Thr Glu Thr Ala Ala Leu Lys Ala Ile Gly Asp
305                 310                 315                 320

Asn Arg Ser Ser Leu Phe Ser Arg Lys Leu Thr Ala Leu Tyr Thr Lys
                325                 330                 335

Ser Thr Leu Ile Gly Glu Asp Val Asn Pro Leu Ile Lys Leu Asp Asp
            340                 345                 350

Ala Val Asn Val Asp Glu Ile Met Thr Asp Thr Ser Thr Ser Tyr Leu
            355                 360                 365

Leu Cys Ile Ser Glu Asn Lys Glu Asn Val Arg Asp Lys Lys Lys Gly
            370                 375                 380

Asn Ile Phe Ile Gly Ile Val Gly Val Gln Pro Ala Thr Gly Glu Val
385                 390                 395                 400

Val Phe Asp Ser Phe Gln Asp Ser Ala Ser Arg Ser Glu Leu Glu Thr
                405                 410                 415

Arg Met Ser Ser Leu Gln Pro Val Glu Leu Leu Leu Pro Ser Ala Leu
```

```
                    420                 425                 430
Ser Glu Gln Thr Glu Ala Leu Ile His Arg Ala Thr Ser Val Ser Val
            435                 440                 445
Gln Asp Asp Arg Ile Arg Val Glu Arg Met Asp Asn Ile Tyr Phe Glu
            450                 455                 460
Tyr Ser His Ala Phe Gln Ala Val Thr Glu Phe Tyr Ala Lys Asp Thr
465                 470                 475                 480
Val Asp Ile Lys Gly Ser Gln Ile Ile Ser Gly Ile Val Asn Leu Glu
                485                 490                 495
Lys Pro Val Ile Cys Ser Leu Ala Ala Ile Ile Lys Tyr Leu Lys Glu
                500                 505                 510
Phe Asn Leu Glu Lys Met Leu Ser Lys Pro Glu Asn Phe Lys Gln Leu
            515                 520                 525
Ser Ser Lys Met Glu Phe Met Thr Ile Asn Gly Thr Thr Leu Arg Asn
            530                 535                 540
Leu Glu Ile Leu Gln Asn Gln Thr Asp Met Lys Thr Lys Gly Ser Leu
545                 550                 555                 560
Leu Trp Val Leu Asp His Thr Lys Thr Ser Phe Gly Arg Arg Lys Leu
                565                 570                 575
Lys Lys Trp Val Thr Gln Pro Leu Leu Lys Leu Arg Glu Ile Asn Ala
                580                 585                 590
Arg Leu Asp Ala Val Ser Glu Val Leu His Ser Glu Ser Ser Val Phe
            595                 600                 605
Gly Gln Ile Glu Asn His Leu Arg Lys Leu Pro Asp Ile Gly Arg Gly
            610                 615                 620
Leu Cys Ser Ile Tyr His Lys Lys Cys Ser Thr Gln Glu Phe Phe Leu
625                 630                 635                 640
Ile Val Lys Thr Leu Tyr His Leu Lys Ser Glu Phe Gln Ala Ile Ile
                645                 650                 655
Pro Ala Val Asn Ser His Ile Gln Ser Asp Leu Leu Arg Thr Val Ile
                660                 665                 670
Leu Glu Ile Pro Glu Leu Leu Ser Pro Val Glu His Tyr Leu Lys Ile
            675                 680                 685
Leu Asn Glu Gln Ala Ala Lys Val Gly Asp Lys Thr Glu Leu Phe Lys
            690                 695                 700
Asp Leu Ser Asp Phe Pro Leu Ile Lys Lys Arg Lys Asp Glu Ile Gln
705                 710                 715                 720
Gly Val Ile Asp Glu Ile Arg Met His Leu Gln Glu Ile Arg Lys Ile
                725                 730                 735
Leu Lys Asn Pro Ser Ala Gln Tyr Val Thr Val Ser Gly Gln Glu Phe
                740                 745                 750
Met Ile Glu Ile Lys Asn Ser Ala Val Ser Cys Ile Pro Thr Asp Trp
            755                 760                 765
Val Lys Val Gly Ser Thr Lys Ala Val Ser Arg Phe His Ser Pro Phe
            770                 775                 780
Ile Val Glu Asn Tyr Arg His Leu Asn Gln Leu Arg Glu Gln Leu Val
785                 790                 795                 800
Leu Asp Cys Ser Ala Glu Trp Leu Asp Phe Leu Glu Lys Phe Ser Glu
                805                 810                 815
His Tyr His Ser Leu Cys Lys Ala Val His His Leu Ala Thr Val Asp
                820                 825                 830
Cys Ile Phe Ser Leu Ala Lys Val Ala Lys Gln Gly Asp Tyr Cys Arg
            835                 840                 845
```

-continued

```
Pro Thr Val Gln Glu Glu Arg Lys Ile Val Ile Lys Asn Gly Arg His
    850                 855                 860

Pro Val Ile Asp Val Leu Leu Gly Glu Gln Asp Gln Tyr Val Pro Asn
865                 870                 875                 880

Asn Thr Asp Leu Ser Glu Asp Ser Glu Arg Val Met Ile Ile Thr Gly
                885                 890                 895

Pro Asn Met Gly Gly Lys Ser Ser Tyr Ile Lys Gln Val Ala Leu Ile
            900                 905                 910

Thr Ile Met Ala Gln Ile Gly Ser Tyr Val Pro Ala Glu Glu Ala Thr
        915                 920                 925

Ile Gly Ile Val Asp Gly Ile Phe Thr Arg Met Gly Ala Ala Asp Asn
    930                 935                 940

Ile Tyr Lys Gly Arg Ser Thr Phe Met Glu Glu Leu Thr Asp Thr Ala
945                 950                 955                 960

Glu Ile Ile Arg Lys Ala Thr Ser Gln Ser Leu Val Ile Leu Asp Glu
                965                 970                 975

Leu Gly Arg Gly Thr Ser Thr His Asp Gly Ile Ala Ile Ala Tyr Ala
            980                 985                 990

Thr Leu Glu Tyr Phe Ile Arg Asp Val Lys Ser Leu Thr Leu Phe Val
        995                 1000                1005

Thr His Tyr Pro Pro Val Cys Glu Leu Glu Lys Asn Tyr Ser His Gln
    1010                1015                1020

Val Gly Asn Tyr His Met Gly Phe Leu Val Ser Glu Asp Glu Ser Lys
1025                1030                1035                1040

Leu Asp Pro Gly Thr Ala Glu Gln Val Pro Asp Phe Val Thr Phe Leu
                1045                1050                1055

Tyr Gln Ile Thr Arg Gly Ile Ala Ala Arg Ser Tyr Gly Leu Asn Val
            1060                1065                1070

Ala Lys Leu Ala Asp Val Pro Gly Glu Ile Leu Lys Lys Ala Ala His
        1075                1080                1085

Lys Ser Lys Glu Leu Glu Gly Leu Ile Asn Thr Lys Arg Lys Arg Leu
    1090                1095                1100

Lys Tyr Phe Ala Lys Leu Trp Thr Met His Asn Ala Gln Asp Leu Gln
1105                1110                1115                1120

Lys Trp Thr Glu Glu Phe Asn Met Glu Glu Thr Gln Thr Ser Leu Leu
                1125                1130                1135

His
```

<210> SEQ ID NO 73
<211> LENGTH: 413
<212> TYPE: PRT
<213> ORGANISM: Artificial Sequence
<220> FEATURE:
<223> OTHER INFORMATION: Description of Artificial Sequence:
    polypeptides encoded by genes with coding microsatellites

<400> SEQUENCE: 73

```
Met Ser Arg Arg Lys Pro Ala Ser Gly Gly Leu Ala Ala Ser Ser Ser
1               5                   10                  15

Ala Pro Ala Arg Gln Ala Val Leu Ser Arg Phe Phe Gln Ser Thr Gly
            20                  25                  30

Ser Leu Lys Ser Thr Ser Ser Thr Gly Ala Ala Asp Gln Val Asp
        35                  40                  45

Pro Gly Ala Ala Ala Ala Ala Ala Ala Ala Ala Ala Ala Pro Pro
    50                  55                  60

Ala Pro Pro Ala Pro Ala Phe Pro Pro Gln Leu Pro Pro His Val Ala
```

```
            65                  70                  75                  80
Thr Glu Ile Asp Arg Arg Lys Lys Arg Pro Leu Glu Asn Asp Gly Pro
                    85                  90                  95
Val Lys Lys Lys Val Lys Lys Val Gln Gln Lys Glu Gly Gly Ser Asp
                    100                 105                 110
Leu Gly Met Ser Gly Asn Ser Glu Pro Lys Lys Cys Leu Arg Thr Arg
                    115                 120                 125
Asn Val Ser Lys Ser Leu Glu Lys Leu Glu Phe Cys Cys Asp Ser
                    130                 135                 140
Ala Leu Pro Gln Ser Arg Val Gln Thr Glu Ser Leu Gln Glu Arg Phe
145                 150                 155                 160
Ala Val Leu Pro Lys Cys Thr Asp Phe Asp Asp Ile Ser Leu Leu His
                    165                 170                 175
Ala Lys Asn Ala Val Ser Ser Glu Asp Ser Lys Arg Gln Ile Asn Gln
                    180                 185                 190
Lys Asp Thr Thr Leu Phe Asp Leu Ser Gln Phe Gly Ser Ser Asn Thr
                    195                 200                 205
Ser His Glu Asn Leu Gln Lys Thr Ala Ser Lys Ser Ala Asn Lys Arg
                    210                 215                 220
Ser Lys Ser Ile Tyr Thr Pro Leu Glu Leu Gln Tyr Ile Glu Met Lys
225                 230                 235                 240
Gln Gln His Lys Asp Ala Val Leu Cys Val Cys Gly Tyr Lys Tyr
                    245                 250                 255
Arg Phe Phe Gly Glu Asp Ala Glu Ile Ala Ala Arg Glu Leu Asn Ile
                    260                 265                 270
Tyr Cys His Leu Asp His Asn Phe Met Thr Ala Ser Ile Pro Thr His
                    275                 280                 285
Arg Leu Phe Val His Val Arg Arg Leu Val Ala Lys Gly Tyr Lys Val
                    290                 295                 300
Gly Val Val Lys Gln Thr Glu Thr Ala Ala Leu Lys Ala Ile Gly Asp
305                 310                 315                 320
Asn Arg Ser Ser Leu Phe Ser Arg Lys Leu Thr Ala Leu Tyr Thr Lys
                    325                 330                 335
Ser Thr Leu Ile Gly Glu Asp Val Asn Pro Leu Ile Lys Leu Asp Asp
                    340                 345                 350
Ala Val Asn Val Asp Glu Ile Met Thr Asp Thr Ser Thr Ser Tyr Leu
                    355                 360                 365
Leu Cys Ile Ser Glu Asn Lys Glu Asn Val Arg Asp Lys Lys Arg Ala
                    370                 375                 380
Thr Phe Leu Leu Ala Leu Trp Glu Cys Ser Leu Pro Gln Ala Arg Leu
385                 390                 395                 400
Cys Leu Ile Val Ser Arg Thr Leu Leu Leu Val Gln Ser
                    405                 410

<210> SEQ ID NO 74
<211> LENGTH: 402
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 74

Met Ser Arg Arg Lys Pro Ala Ser Gly Gly Leu Ala Ala Ser Ser Ser
1               5                   10                  15

Ala Pro Ala Arg Gln Ala Val Leu Ser Arg Phe Phe Gln Ser Thr Gly
```

```
                    20                  25                  30
Ser Leu Lys Ser Thr Ser Ser Thr Gly Ala Ala Asp Gln Val Asp
            35                  40                  45

Pro Gly Ala Ala Ala Ala Ala Ala Ala Ala Ala Ala Ala Pro Pro
    50                  55                  60

Ala Pro Pro Ala Pro Ala Phe Pro Pro Gln Leu Pro Pro His Val Ala
65                  70                  75                  80

Thr Glu Ile Asp Arg Arg Lys Lys Arg Pro Leu Glu Asn Asp Gly Pro
                85                  90                  95

Val Lys Lys Lys Val Lys Lys Val Gln Gln Lys Glu Gly Gly Ser Asp
            100                 105                 110

Leu Gly Met Ser Gly Asn Ser Glu Pro Lys Lys Cys Leu Arg Thr Arg
            115                 120                 125

Asn Val Ser Lys Ser Leu Glu Lys Leu Lys Glu Phe Cys Cys Asp Ser
            130                 135                 140

Ala Leu Pro Gln Ser Arg Val Gln Thr Glu Ser Leu Gln Glu Arg Phe
145                 150                 155                 160

Ala Val Leu Pro Lys Cys Thr Asp Phe Asp Asp Ile Ser Leu Leu His
                165                 170                 175

Ala Lys Asn Ala Val Ser Ser Glu Asp Ser Lys Arg Gln Ile Asn Gln
            180                 185                 190

Lys Asp Thr Thr Leu Phe Asp Leu Ser Gln Phe Gly Ser Ser Asn Thr
            195                 200                 205

Ser His Glu Asn Leu Gln Lys Thr Ala Ser Lys Ser Ala Asn Lys Arg
            210                 215                 220

Ser Lys Ser Ile Tyr Thr Pro Leu Glu Leu Gln Tyr Ile Glu Met Lys
225                 230                 235                 240

Gln Gln His Lys Asp Ala Val Leu Cys Val Glu Cys Gly Tyr Lys Tyr
                245                 250                 255

Arg Phe Phe Gly Glu Asp Ala Glu Ile Ala Ala Arg Glu Leu Asn Ile
            260                 265                 270

Tyr Cys His Leu Asp His Asn Phe Met Thr Ala Ser Ile Pro Thr His
            275                 280                 285

Arg Leu Phe Val His Val Arg Arg Leu Val Ala Lys Gly Tyr Lys Val
            290                 295                 300

Gly Val Val Lys Gln Thr Glu Thr Ala Ala Leu Lys Ala Ile Gly Asp
305                 310                 315                 320

Asn Arg Ser Ser Leu Phe Ser Arg Lys Leu Thr Ala Leu Tyr Thr Lys
                325                 330                 335

Ser Thr Leu Ile Gly Glu Asp Val Asn Pro Leu Ile Lys Leu Asp Asp
            340                 345                 350

Ala Val Asn Val Asp Glu Ile Met Thr Asp Thr Ser Thr Ser Tyr Leu
            355                 360                 365

Leu Cys Ile Ser Glu Asn Lys Asn Val Arg Asp Lys Lys Lys Gly
            370                 375                 380

Gln His Phe Tyr Trp His Cys Gly Ser Ala Ala Cys His Arg Arg Gly
385                 390                 395                 400

Cys Val

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Frameshift
```

```
                              Peptide

<400> SEQUENCE: 75

Ser Leu Val Arg Leu Ser Ser Cys Val
  1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 76

Arg Leu Ser Ser Cys Val Pro Val Ala
  1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 77

Cys Val Pro Val Ala Leu Met Ser Ala
  1               5

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 78

Leu Leu His Ser Ala Pro Thr Pro Ser Leu
  1               5                  10

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 79

Phe Leu Ser Ala Ser His Phe Leu Leu
  1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 80

Arg Val Phe Phe Phe Tyr Gln His Leu
  1               5

<210> SEQ ID NO 81
<211> LENGTH: 10
```

```
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 81

Ser Leu Tyr Lys Phe Ser Pro Phe Pro Leu
 1               5                  10

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 82

Lys Ile Phe Thr Phe Phe Phe Gln Leu
 1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 83

Ala Leu Leu Pro Ala Gly Pro Leu Thr
 1               5

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 84

Leu Leu Pro Ala Gly Pro Leu Thr Gln Thr
 1               5                  10

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 85

Thr Leu Ser Pro Gly Trp Ser Ala Val
 1               5

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 86

Ile Leu Leu Pro Gln Pro Pro Glu Trp Leu
 1               5                  10
```

```
<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 87

Arg Gln Met Glu Ser Leu Gly Met Lys Leu
 1               5                  10

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 88

Val Glu Met Pro Thr Gly Trp Leu Leu
 1               5

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 89

Val Glu Met Pro Thr Gly Trp Leu Leu Val
 1               5                  10

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 90

Phe Gln Pro Pro Pro Ala Val Phe Ala
 1               5

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 91

Ala Leu Trp Glu Cys Ser Leu Pro Gln Ala
 1               5                  10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide
```

```
<400> SEQUENCE: 92

Phe Leu Leu Ala Leu Trp Glu Cys Ser Leu
 1               5                  10

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 93

Leu Leu Ala Leu Trp Glu Cys Ser Leu
 1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 94

Ser Leu Pro Gln Ala Arg Leu Cys Leu
 1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 95

Leu Ile Val Ser Arg Thr Leu Leu Leu
 1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 96

Cys Leu Ile Val Ser Arg Thr Leu Leu
 1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 97

Ile Val Ser Arg Thr Leu Leu Leu Val
 1               5

<210> SEQ ID NO 98
<211> LENGTH: 9
<212> TYPE: PRT
<213> ORGANISM: Artificial Sequence
```

```
<220> FEATURE:
<223> OTHER INFORMATION: Description of Artificial Sequence: Frameshift
      Peptide

<400> SEQUENCE: 98

Lys Arg Ala Thr Phe Leu Leu Ala Leu
 1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 99

Lys Met Phe Phe Met Val Phe Leu Ile
 1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 100

Phe Leu Ile Ile Trp Gln Asn Thr Met
 1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 101

Gly Met Cys Val Lys Val Ser Ser Ile
 1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 102

Val Leu Arg Thr Glu Gly Glu Pro Leu
 1               5

<210> SEQ ID NO 103
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 103

Leu Ile Val Ser Arg Thr Leu Leu Leu Val
 1               5                   10
```

```
<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 104

Ser Leu Pro Gln Ala Arg Leu Cys Leu Ile
 1               5                  10

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 105

Cys Leu Ile Val Ser Arg Thr Leu Leu Leu
 1               5                  10

<210> SEQ ID NO 106
<211> LENGTH: 10
<212> TYPE: PRT
<213> ORGANISM: Artificial Sequence
<220> FEATURE:
<223> OTHER INFORMATION: Description of Artificial Sequence: Frameshift
      Peptide

<400> SEQUENCE: 106

Arg Leu Cys Leu Ile Val Ser Arg Thr Leu
 1               5                  10

<210> SEQ ID NO 107
<211> LENGTH: 513
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 107

Met Gly Ala Ala Ala Lys Leu Ala Phe Ala Val Phe Leu Ile Ser Cys
 1               5                  10                  15

Ser Ser Gly Ala Ile Leu Gly Arg Ser Glu Thr Gln Glu Cys Leu Phe
             20                  25                  30

Phe Asn Ala Asn Trp Glu Lys Asp Arg Thr Asn Gln Thr Gly Val Glu
         35                  40                  45

Pro Cys Tyr Gly Asp Lys Asp Lys Arg Arg His Cys Phe Ala Thr Trp
     50                  55                  60

Lys Asn Ile Ser Gly Ser Ile Glu Ile Val Lys Gln Gly Cys Trp Leu
 65                  70                  75                  80

Asp Asp Ile Asn Cys Tyr Asp Arg Thr Asp Cys Val Glu Lys Lys Asp
                 85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
```

```
            145                 150                 155                 160
Tyr Arg His His Lys Met Ala Tyr Pro Pro Val Leu Val Pro Thr Gln
                165                 170                 175
Asp Pro Gly Pro Pro Pro Ser Pro Leu Leu Gly Leu Lys Pro Leu
            180                 185                 190
Gln Leu Leu Glu Val Lys Ala Arg Gly Arg Phe Gly Cys Val Trp Lys
            195                 200                 205
Ala Gln Leu Leu Asn Glu Tyr Val Ala Val Lys Ile Phe Pro Ile Gln
            210                 215                 220
Asp Lys Gln Ser Trp Gln Asn Glu Tyr Glu Val Tyr Ser Leu Pro Gly
225                 230                 235                 240
Met Lys His Glu Asn Ile Leu Gln Phe Ile Gly Ala Glu Lys Arg Gly
                245                 250                 255
Thr Ser Val Asp Val Asp Leu Trp Leu Ile Thr Ala Phe His Glu Lys
                260                 265                 270
Gly Ser Leu Ser Asp Phe Leu Lys Ala Asn Val Val Ser Trp Asn Glu
                275                 280                 285
Leu Cys His Ile Ala Glu Thr Met Ala Arg Gly Leu Ala Tyr Leu His
            290                 295                 300
Glu Asp Ile Pro Gly Leu Lys Asp Gly His Lys Pro Ala Ile Ser His
305                 310                 315                 320
Arg Asp Ile Lys Ser Lys Asn Val Leu Leu Lys Asn Asn Leu Thr Ala
                325                 330                 335
Cys Ile Ala Asp Phe Gly Leu Ala Leu Lys Phe Glu Ala Gly Lys Ser
                340                 345                 350
Ala Gly Asp Thr His Gly Gln Val Gly Thr Arg Arg Tyr Met Ala Pro
            355                 360                 365
Glu Val Leu Glu Gly Ala Ile Asn Phe Gln Arg Asp Ala Phe Leu Arg
            370                 375                 380
Ile Asp Met Tyr Ala Met Gly Leu Val Leu Trp Glu Leu Ala Ser Arg
385                 390                 395                 400
Cys Thr Ala Ala Asp Gly Pro Val Asp Glu Tyr Met Leu Pro Phe Glu
                405                 410                 415
Glu Glu Ile Gly Gln His Pro Ser Leu Glu Asp Met Gln Glu Val Val
            420                 425                 430
Val His Lys Lys Lys Arg Pro Val Leu Arg Asp Tyr Trp Gln Lys His
            435                 440                 445
Ala Gly Met Ala Met Leu Cys Glu Thr Ile Glu Glu Cys Trp Asp His
            450                 455                 460
Asp Ala Glu Ala Arg Leu Ser Ala Gly Cys Val Gly Glu Arg Ile Thr
465                 470                 475                 480
Gln Met Gln Arg Leu Thr Asn Ile Ile Thr Thr Glu Asp Ile Val Thr
                485                 490                 495
Val Val Thr Met Val Thr Asn Val Asp Phe Pro Pro Lys Glu Ser Ser
                500                 505                 510
Leu

<210> SEQ ID NO 108
<211> LENGTH: 148
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 108
```

```
Met Gly Ala Ala Ala Lys Leu Ala Phe Ala Val Phe Leu Ile Ser Cys
 1               5                  10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Thr
                85                  90                  95

Ala Leu Lys Tyr Ile Phe Val Ala Val Arg Ala Ile Cys Val Met Lys
                100                 105                 110

Ser Phe Leu Ile Phe Arg Arg Trp Lys Ser His Ser Pro Leu Gln Ile
            115                 120                 125

Gln Leu His Leu Ser Pro Ile Thr Thr Ser Cys Ser Ile Pro Trp
130                 135                 140

Cys His Leu Cys
145

<210> SEQ ID NO 109
<211> LENGTH: 440
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 109

Met Gly Ala Ala Ala Lys Leu Ala Phe Ala Val Phe Leu Ile Ser Cys
 1               5                  10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
            35                  40                  45

Pro Cys Tyr Gly Asp Lys Asp Lys Arg Arg His Cys Phe Ala Thr Trp
50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
                100                 105                 110

Lys Phe Ser Tyr Phe Pro Glu Met Glu Val Thr Gln Pro Thr Ser Asn
            115                 120                 125

Pro Val Thr Pro Lys Pro Pro Tyr Tyr Asn Ile Leu Leu Tyr Ser Leu
130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
            195                 200                 205
```

```
Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335

Cys Ile Ala Asp Phe Gly Leu Ala Leu Lys Phe Glu Ala Gly Lys Ser
            340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
    370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
            420                 425                 430

Val His Lys Lys Arg Gly Leu Phe
        435                 440

<210> SEQ ID NO 110
<211> LENGTH: 630
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 110

Met Val Leu Arg Lys Leu Ser Lys Lys Asp Val Thr Thr Lys Leu Lys
1               5                   10                  15

Ala Met Gln Glu Phe Gly Thr Met Cys Thr Glu Arg Asp Thr Glu Thr
            20                  25                  30

Val Lys Gly Val Leu Pro Tyr Trp Pro Arg Ile Phe Cys Lys Ile Ser
        35                  40                  45

Leu Asp His Asp Arg Arg Val Arg Glu Ala Thr Gln Gln Ala Phe Glu
    50                  55                  60

Lys Leu Thr Leu Lys Val Lys Lys Gln Leu Ala Pro Tyr Leu Lys Ser
65                  70                  75                  80

Leu Met Gly Tyr Trp Leu Met Ala Gln Cys Asp Thr Tyr Thr Pro Ala
                85                  90                  95

Ala Phe Ala Ala Lys Asp Ala Phe Glu Ala Phe Pro Pro Ser Lys
            100                 105                 110

Gln Pro Glu Ala Ile Ala Phe Cys Lys Asp Glu Ile Thr Ser Val Leu
    115                 120                 125
```

```
Gln Asp His Leu Ile Lys Glu Thr Pro Asp Thr Leu Ser Asp Pro Gln
    130                 135                 140

Thr Val Pro Glu Glu Glu Arg Glu Ala Lys Phe Tyr Arg Val Val Thr
145                 150                 155                 160

Cys Ser Leu Leu Ala Leu Lys Arg Leu Cys Leu Leu Pro Asp Asn
                165                 170                 175

Glu Leu Asp Ser Leu Glu Glu Lys Phe Lys Ser Leu Leu Ser Gln Asn
            180                 185                 190

Lys Phe Trp Lys Tyr Gly Lys His Ser Val Pro Gln Ile Arg Ser Ala
        195                 200                 205

Tyr Phe Glu Leu Val Ser Ala Leu Cys Gln Arg Ile Pro Gln Leu Met
    210                 215                 220

Lys Glu Glu Ala Ser Lys Val Ser Pro Ser Val Leu Leu Ser Ile Asp
225                 230                 235                 240

Asp Ser Asp Pro Ile Val Cys Pro Ala Leu Trp Glu Ala Val Leu Tyr
                245                 250                 255

Thr Leu Thr Thr Ile Glu Asp Cys Trp Leu His Val Asn Ala Lys Lys
            260                 265                 270

Ser Val Phe Pro Lys Leu Ser Thr Val Ile Arg Glu Gly Gly Arg Gly
        275                 280                 285

Leu Ala Thr Val Ile Tyr Pro Tyr Leu Leu Pro Phe Ile Ser Lys Leu
    290                 295                 300

Pro His Ser Ile Thr Asn Pro Lys Leu Asp Phe Phe Lys Asn Phe Leu
305                 310                 315                 320

Thr Ser Leu Val Ala Gly Leu Ser Thr Glu Arg Thr Lys Thr Ser Ser
                325                 330                 335

Ser Glu Ser Ser Ala Val Ile Ser Ala Phe Tyr Glu Cys Leu Arg Phe
            340                 345                 350

Ile Met Gln Gln Asn Leu Gly Glu Glu Ile Glu Gln Met Leu Val
        355                 360                 365

Asn Asp Gln Leu Ile Pro Phe Ile Asp Ala Val Leu Lys Asp Pro Gly
    370                 375                 380

Leu Gln His Gly Gln Leu Phe Asn His Leu Ala Glu Thr Leu Ser Ser
385                 390                 395                 400

Trp Glu Ala Lys Ala Asp Thr Glu Lys Asp Glu Lys Thr Ala His Asn
                405                 410                 415

Leu Glu Asn Val Leu Ile His Phe Trp Glu Arg Leu Ser Glu Ile Cys
            420                 425                 430

Val Ala Lys Ile Ser Glu Pro Glu Ala Asp Val Glu Ser Val Leu Gly
        435                 440                 445

Val Ser Asn Leu Leu Gln Val Leu Gln Lys Pro Lys Ser Ser Leu Lys
    450                 455                 460

Ser Ser Lys Lys Lys Asn Gly Lys Val Arg Phe Ala Asp Glu Ile Leu
465                 470                 475                 480

Glu Ser Asn Lys Glu Asn Glu Lys Cys Val Ser Ser Glu Gly Glu Lys
                485                 490                 495

Ile Glu Gly Trp Glu Leu Thr Thr Glu Pro Ser Leu Thr His Asn Ser
            500                 505                 510

Ser Gly Leu Leu Ser Pro Leu Arg Lys Lys Pro Leu Glu Asp Leu Val
        515                 520                 525

Cys Lys Leu Ala Asp Ile Ser Ile Asn Tyr Val Asn Glu Arg Lys Ser
530                 535                 540

Glu Gln His Leu Arg Phe Leu Ser Thr Leu Leu Asp Ser Phe Ser Ser
```

```
                545                 550                 555                 560

Ser Arg Val Phe Lys Met Leu Leu Gly Asp Glu Lys Gln Ser Ile Val
                    565                 570                 575

Gln Ala Lys Pro Leu Glu Ile Ala Lys Leu Val Gln Lys Asn Pro Ala
                580                 585                 590

Val Gln Phe Leu Tyr Gln Lys Leu Ile Gly Trp Leu Asn Glu Asp Gln
            595                 600                 605

Arg Lys Asp Phe Gly Phe Leu Val Asp Ile Leu Tyr Ser Ala Leu Arg
        610                 615                 620

Cys Cys Asp Asn Asp Met
625                 630

<210> SEQ ID NO 111
<211> LENGTH: 501
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 111

Met Val Leu Arg Lys Leu Ser Lys Lys Asp Val Thr Thr Lys Leu Lys
1               5                   10                  15

Ala Met Gln Glu Phe Gly Thr Met Cys Thr Glu Arg Asp Thr Glu Thr
            20                  25                  30

Val Lys Gly Val Leu Pro Tyr Trp Pro Arg Ile Phe Cys Lys Ile Ser
        35                  40                  45

Leu Asp His Asp Arg Arg Val Arg Glu Ala Thr Gln Gln Ala Phe Glu
    50                  55                  60

Lys Leu Thr Leu Lys Val Lys Lys Gln Leu Ala Pro Tyr Leu Lys Ser
65                  70                  75                  80

Leu Met Gly Tyr Trp Leu Met Ala Gln Cys Asp Thr Tyr Thr Pro Ala
                85                  90                  95

Ala Phe Ala Ala Lys Asp Ala Phe Glu Ala Ala Phe Pro Pro Ser Lys
            100                 105                 110

Gln Pro Glu Ala Ile Ala Phe Cys Lys Asp Glu Ile Thr Ser Val Leu
        115                 120                 125

Gln Asp His Leu Ile Lys Glu Thr Pro Asp Thr Leu Ser Asp Pro Gln
    130                 135                 140

Thr Val Pro Glu Glu Glu Arg Glu Ala Lys Phe Tyr Arg Val Val Thr
145                 150                 155                 160

Cys Ser Leu Leu Ala Leu Lys Arg Leu Leu Cys Leu Leu Pro Asp Asn
                165                 170                 175

Glu Leu Asp Ser Leu Glu Glu Lys Phe Lys Ser Leu Leu Ser Gln Asn
            180                 185                 190

Lys Phe Trp Lys Tyr Gly Lys His Ser Val Pro Gln Ile Arg Ser Ala
        195                 200                 205

Tyr Phe Glu Leu Val Ser Ala Leu Cys Gln Arg Ile Pro Gln Leu Met
    210                 215                 220

Lys Glu Glu Ala Ser Lys Val Ser Pro Ser Val Leu Leu Ser Ile Asp
225                 230                 235                 240

Asp Ser Asp Pro Ile Val Cys Pro Ala Leu Trp Glu Ala Val Leu Tyr
                245                 250                 255

Thr Leu Thr Thr Ile Glu Asp Cys Trp Leu His Val Asn Ala Lys Lys
            260                 265                 270

Ser Val Phe Pro Lys Leu Ser Thr Val Ile Arg Glu Gly Gly Arg Gly
```

```
                    275                 280                 285
Leu Ala Thr Val Ile Tyr Pro Tyr Leu Leu Pro Phe Ile Ser Lys Leu
    290                 295                 300
Pro His Ser Ile Thr Asn Pro Lys Leu Asp Phe Phe Lys Asn Phe Leu
305                 310                 315                 320
Thr Ser Leu Val Ala Gly Leu Ser Thr Glu Arg Thr Lys Thr Ser Ser
                325                 330                 335
Ser Glu Ser Ser Ala Val Ile Ser Ala Phe Tyr Glu Cys Leu Arg Phe
                340                 345                 350
Ile Met Gln Gln Asn Leu Gly Glu Glu Ile Glu Gln Met Leu Val
                355                 360                 365
Asn Asp Gln Leu Ile Pro Phe Ile Asp Ala Val Leu Lys Asp Pro Gly
    370                 375                 380
Leu Gln His Gly Gln Leu Phe Asn His Leu Ala Glu Thr Leu Ser Ser
385                 390                 395                 400
Trp Glu Ala Lys Ala Asp Thr Glu Lys Asp Glu Lys Thr Ala His Asn
                405                 410                 415
Leu Glu Asn Val Leu Ile His Phe Trp Glu Arg Leu Ser Glu Ile Cys
                420                 425                 430
Val Ala Lys Ile Ser Glu Pro Glu Ala Asp Val Glu Ser Val Leu Gly
                435                 440                 445
Val Ser Asn Leu Leu Gln Val Leu Gln Lys Pro Lys Ser Ser Leu Lys
    450                 455                 460
Ser Ser Lys Lys Lys Met Val Arg Leu Asp Leu Leu Met Arg Tyr Leu
465                 470                 475                 480
Lys Ala Ile Lys Arg Met Lys Asn Val Tyr Leu Gln Lys Glu Arg Arg
                485                 490                 495
Leu Lys Ala Gly Asn
            500

<210> SEQ ID NO 112
<211> LENGTH: 470
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 112

Met Val Leu Arg Lys Leu Ser Lys Lys Asp Val Thr Thr Lys Leu Lys
1               5                   10                  15
Ala Met Gln Glu Phe Gly Thr Met Cys Thr Glu Arg Asp Thr Glu Thr
                20                  25                  30
Val Lys Gly Val Leu Pro Tyr Trp Pro Arg Ile Phe Cys Lys Ile Ser
            35                  40                  45
Leu Asp His Asp Arg Arg Val Arg Glu Ala Thr Gln Gln Ala Phe Glu
        50                  55                  60
Lys Leu Thr Leu Lys Val Lys Lys Gln Leu Ala Pro Tyr Leu Lys Ser
65                  70                  75                  80
Leu Met Gly Tyr Trp Leu Met Ala Gln Cys Asp Thr Tyr Thr Pro Ala
                85                  90                  95
Ala Phe Ala Ala Lys Asp Ala Phe Glu Ala Ala Phe Pro Pro Ser Lys
                100                 105                 110
Gln Pro Glu Ala Ile Ala Phe Cys Lys Asp Glu Ile Thr Ser Val Leu
            115                 120                 125
Gln Asp His Leu Ile Lys Glu Thr Pro Asp Thr Leu Ser Asp Pro Gln
```

|     |     |     |     |     |     |     |     |     |     |     |     |
|-----|-----|-----|-----|-----|-----|-----|-----|-----|-----|-----|-----|
|     |     | 130 |     |     |     | 135 |     |     |     | 140 |     |
| Thr | Val | Pro | Glu | Glu | Arg | Glu | Ala | Lys | Phe | Tyr | Arg | Val | Val | Thr |
| 145 |     |     |     |     | 150 |     |     |     |     | 155 |     |     |     | 160 |
| Cys | Ser | Leu | Leu | Ala | Leu | Lys | Arg | Leu | Leu | Cys | Leu | Leu | Pro | Asp | Asn |
|     |     |     |     | 165 |     |     |     |     | 170 |     |     |     |     | 175 |
| Glu | Leu | Asp | Ser | Leu | Glu | Glu | Lys | Phe | Lys | Ser | Leu | Leu | Ser | Gln | Asn |
|     |     |     | 180 |     |     |     |     | 185 |     |     |     |     | 190 |
| Lys | Phe | Trp | Lys | Tyr | Gly | Lys | His | Ser | Val | Pro | Gln | Ile | Arg | Ser | Ala |
|     |     | 195 |     |     |     |     | 200 |     |     |     |     | 205 |
| Tyr | Phe | Glu | Leu | Val | Ser | Ala | Leu | Cys | Gln | Arg | Ile | Pro | Gln | Leu | Met |
|     | 210 |     |     |     |     | 215 |     |     |     |     | 220 |
| Lys | Glu | Glu | Ala | Ser | Lys | Val | Ser | Pro | Ser | Val | Leu | Leu | Ser | Ile | Asp |
| 225 |     |     |     |     | 230 |     |     |     |     | 235 |     |     |     | 240 |
| Asp | Ser | Asp | Pro | Ile | Val | Cys | Pro | Ala | Leu | Trp | Glu | Ala | Val | Leu | Tyr |
|     |     |     |     | 245 |     |     |     |     | 250 |     |     |     |     | 255 |
| Thr | Leu | Thr | Thr | Ile | Glu | Asp | Cys | Trp | Leu | His | Val | Asn | Ala | Lys | Lys |
|     |     |     | 260 |     |     |     |     | 265 |     |     |     |     | 270 |
| Ser | Val | Phe | Pro | Lys | Leu | Ser | Thr | Val | Ile | Arg | Glu | Gly | Gly | Arg | Gly |
|     |     | 275 |     |     |     |     | 280 |     |     |     |     | 285 |
| Leu | Ala | Thr | Val | Ile | Tyr | Pro | Tyr | Leu | Leu | Pro | Phe | Ile | Ser | Lys | Leu |
|     | 290 |     |     |     |     | 295 |     |     |     |     | 300 |
| Pro | His | Ser | Ile | Thr | Asn | Pro | Lys | Leu | Asp | Phe | Phe | Lys | Asn | Phe | Leu |
| 305 |     |     |     |     | 310 |     |     |     |     | 315 |     |     |     | 320 |
| Thr | Ser | Leu | Val | Ala | Gly | Leu | Ser | Thr | Glu | Arg | Thr | Lys | Thr | Ser | Ser |
|     |     |     |     | 325 |     |     |     |     | 330 |     |     |     |     | 335 |
| Ser | Glu | Ser | Ser | Ala | Val | Ile | Ser | Ala | Phe | Tyr | Glu | Cys | Leu | Arg | Phe |
|     |     |     | 340 |     |     |     |     | 345 |     |     |     |     | 350 |
| Ile | Met | Gln | Gln | Asn | Leu | Gly | Glu | Glu | Ile | Glu | Gln | Met | Leu | Val |
|     |     | 355 |     |     |     |     | 360 |     |     |     |     | 365 |
| Asn | Asp | Gln | Leu | Ile | Pro | Phe | Ile | Asp | Ala | Val | Leu | Lys | Asp | Pro | Gly |
|     | 370 |     |     |     |     | 375 |     |     |     |     | 380 |
| Leu | Gln | His | Gly | Gln | Leu | Phe | Asn | His | Leu | Ala | Glu | Thr | Leu | Ser | Ser |
| 385 |     |     |     |     | 390 |     |     |     |     | 395 |     |     |     | 400 |
| Trp | Glu | Ala | Lys | Ala | Asp | Thr | Glu | Lys | Asp | Glu | Lys | Thr | Ala | His | Asn |
|     |     |     |     | 405 |     |     |     |     | 410 |     |     |     |     | 415 |
| Leu | Glu | Asn | Val | Leu | Ile | His | Phe | Trp | Glu | Arg | Leu | Ser | Glu | Ile | Cys |
|     |     |     | 420 |     |     |     |     | 425 |     |     |     |     | 430 |
| Val | Ala | Lys | Ile | Ser | Glu | Pro | Gly | Ala | Asp | Val | Glu | Ser | Val | Leu | Gly |
|     |     |     | 435 |     |     |     |     | 440 |     |     |     |     | 445 |
| Val | Ser | Asn | Leu | Leu | Gln | Val | Leu | Gln | Lys | Pro | Lys | Ser | Ser | Leu | Lys |
| 450 |     |     |     |     | 455 |     |     |     |     | 460 |
| Ser | Ser | Lys | Lys | Lys | Trp |
| 465 |     |     |     |     | 470 |

```
<210> SEQ ID NO 113
<211> LENGTH: 471
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 113
```

|     |     |     |     |     |     |     |     |     |     |     |     |     |     |     |
|-----|-----|-----|-----|-----|-----|-----|-----|-----|-----|-----|-----|-----|-----|-----|
| Met | Val | Leu | Arg | Lys | Leu | Ser | Lys | Lys | Asp | Val | Thr | Thr | Lys | Leu | Lys |
| 1   |     |     |     | 5   |     |     |     |     | 10  |     |     |     |     | 15  |
| Ala | Met | Gln | Glu | Phe | Gly | Thr | Met | Cys | Thr | Glu | Arg | Asp | Thr | Glu | Thr |

-continued

```
                20                  25                  30
Val Lys Gly Val Leu Pro Tyr Trp Pro Arg Ile Phe Cys Lys Ile Ser
             35                  40                  45

Leu Asp His Asp Arg Arg Val Arg Glu Ala Thr Gln Gln Ala Phe Glu
 50                  55                  60

Lys Leu Thr Leu Lys Val Lys Lys Gln Leu Ala Pro Tyr Leu Lys Ser
 65                  70                  75                  80

Leu Met Gly Tyr Trp Leu Met Ala Gln Cys Asp Thr Tyr Thr Pro Ala
                 85                  90                  95

Ala Phe Ala Ala Lys Asp Ala Phe Glu Ala Ala Phe Pro Pro Ser Lys
                100                 105                 110

Gln Pro Glu Ala Ile Ala Phe Cys Lys Asp Glu Ile Thr Ser Val Leu
            115                 120                 125

Gln Asp His Leu Ile Lys Glu Thr Pro Asp Thr Leu Ser Asp Pro Gln
            130                 135                 140

Thr Val Pro Glu Glu Arg Glu Ala Lys Phe Tyr Arg Val Val Thr
145                 150                 155                 160

Cys Ser Leu Leu Ala Leu Lys Arg Leu Leu Cys Leu Leu Pro Asp Asn
                165                 170                 175

Glu Leu Asp Ser Leu Glu Glu Lys Phe Lys Ser Leu Leu Ser Gln Asn
                180                 185                 190

Lys Phe Trp Lys Tyr Gly Lys His Ser Val Pro Gln Ile Arg Ser Ala
            195                 200                 205

Tyr Phe Glu Leu Val Ser Ala Leu Cys Gln Arg Ile Pro Gln Leu Met
            210                 215                 220

Lys Glu Glu Ala Ser Lys Val Ser Pro Ser Val Leu Leu Ser Ile Asp
225                 230                 235                 240

Asp Ser Asp Pro Ile Val Cys Pro Ala Leu Trp Glu Ala Val Leu Tyr
                245                 250                 255

Thr Leu Thr Thr Ile Glu Asp Cys Trp Leu His Val Asn Ala Lys Lys
                260                 265                 270

Ser Val Phe Pro Lys Leu Ser Thr Val Ile Arg Glu Gly Gly Arg Gly
            275                 280                 285

Leu Ala Thr Val Ile Tyr Pro Tyr Leu Leu Pro Phe Ile Ser Lys Leu
            290                 295                 300

Pro His Ser Ile Thr Asn Pro Lys Leu Asp Phe Lys Asn Phe Leu
305                 310                 315                 320

Thr Ser Leu Val Ala Gly Leu Ser Thr Glu Arg Thr Lys Thr Ser Ser
                325                 330                 335

Ser Glu Ser Ser Ala Val Ile Ser Ala Phe Tyr Glu Cys Leu Arg Phe
                340                 345                 350

Ile Met Gln Gln Asn Leu Gly Glu Glu Ile Glu Gln Met Leu Val
            355                 360                 365

Asn Asp Gln Leu Ile Pro Phe Ile Asp Ala Val Leu Lys Asp Pro Gly
            370                 375                 380

Leu Gln His Gly Gln Leu Phe Asn His Leu Ala Glu Thr Leu Ser Ser
385                 390                 395                 400

Trp Glu Ala Lys Ala Asp Thr Glu Lys Asp Glu Lys Thr Ala His Asn
                405                 410                 415

Leu Glu Asn Val Leu Ile His Phe Trp Glu Arg Leu Ser Glu Ile Cys
                420                 425                 430

Val Ala Lys Ile Ser Glu Pro Glu Ala Asp Val Glu Ser Val Leu Gly
            435                 440                 445
```

```
Val Ser Asn Leu Leu Gln Val Leu Gln Lys Pro Lys Ser Ser Leu Lys
450                 455                 460

Ser Ser Lys Lys Lys Lys Trp
465                 470

<210> SEQ ID NO 114
<211> LENGTH: 1455
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 114

Met Ala Gly Arg Pro Leu Arg Ile Gly Asp Gln Leu Val Leu Glu Glu
1               5                   10                  15

Asp Tyr Asp Glu Thr Tyr Ile Pro Ser Glu Gln Glu Ile Leu Glu Phe
                20                  25                  30

Ala Arg Glu Ile Gly Ile Asp Pro Ile Lys Glu Pro Gly Leu Met Trp
            35                  40                  45

Leu Ala Arg Glu Gly Ile Val Ala Pro Leu Pro Gly Glu Trp Lys Pro
        50                  55                  60

Cys Gln Asp Ile Thr Gly Asp Ile Tyr Tyr Phe Asn Phe Ala Asn Gly
65                  70                  75                  80

Gln Ser Met Trp Asp His Pro Cys Asp Glu His Tyr Arg Ser Leu Val
                85                  90                  95

Ile Gln Glu Arg Ala Lys Leu Ser Thr Ser Gly Ala Ile Lys Lys Lys
            100                 105                 110

Lys Lys Lys Lys Glu Lys Lys Asp Lys Lys Asp Arg Asp Pro Pro Lys
        115                 120                 125

Ser Ser Leu Ala Leu Gly Ser Ser Leu Ala Pro Val His Val Pro Leu
130                 135                 140

Gly Gly Leu Ala Pro Leu Arg Gly Leu Val Asp Thr Pro Pro Ser Ala
145                 150                 155                 160

Leu Arg Gly Ser Gln Ser Val Ser Leu Gly Ser Ser Val Glu Ser Gly
                165                 170                 175

Arg Gln Leu Gly Glu Leu Met Leu Pro Ser Gln Gly Leu Lys Thr Ser
            180                 185                 190

Ala Tyr Thr Lys Gly Leu Leu Gly Ser Ile Tyr Glu Asp Lys Thr Ala
        195                 200                 205

Leu Ser Leu Leu Gly Leu Gly Glu Glu Thr Asn Glu Glu Asp Glu Glu
210                 215                 220

Glu Ser Asp Asn Gln Ser Val His Ser Ser Glu Pro Leu Arg Asn
225                 230                 235                 240

Leu His Leu Asp Ile Gly Ala Leu Gly Gly Asp Phe Glu Tyr Glu Glu
                245                 250                 255

Ser Leu Arg Thr Ser Gln Pro Glu Glu Lys Lys Asp Val Ser Leu Asp
            260                 265                 270

Ser Asp Ala Ala Gly Pro Pro Thr Pro Cys Lys Pro Ser Ser Pro Gly
        275                 280                 285

Ala Asp Ser Ser Leu Ser Ser Ala Val Gly Lys Gly Arg Gln Gly Ser
290                 295                 300

Gly Ala Arg Pro Gly Leu Pro Glu Lys Glu Glu Asn Glu Lys Ser Glu
305                 310                 315                 320

Pro Lys Ile Cys Arg Asn Leu Val Thr Pro Lys Ala Asp Pro Thr Gly
                325                 330                 335
```

```
Ser Glu Pro Ala Lys Ala Ser Glu Lys Glu Ala Pro Glu Asp Thr Val
            340                 345                 350

Asp Ala Gly Glu Gly Ser Arg Glu Glu Ala Ala Lys Glu Pro
            355                 360                 365

Lys Lys Lys Ala Ser Ala Leu Glu Glu Gly Ser Ser Asp Ala Ser Gln
370                 375                 380

Glu Leu Glu Ile Ser Glu His Met Lys Glu Pro Gln Leu Ser Asp Ser
385                 390                 395                 400

Ile Ala Ser Asp Pro Lys Ser Phe His Gly Leu Asp Phe Gly Phe Arg
                405                 410                 415

Ser Arg Ile Ser Glu His Leu Leu Asp Val Asp Val Leu Ser Pro Val
            420                 425                 430

Leu Gly Gly Ala Cys Arg Gln Ala Gln Gln Pro Leu Gly Ile Glu Asp
            435                 440                 445

Lys Asp Asp Ser Gln Ser Ser Gln Asp Glu Leu Gln Ser Lys Gln Ser
    450                 455                 460

Lys Gly Leu Glu Glu Arg Tyr His Arg Leu Ser Pro Pro Leu Pro His
465                 470                 475                 480

Glu Glu Arg Ala Gln Ser Pro Pro Arg Ser Leu Ala Thr Glu Glu
                485                 490                 495

Pro Pro Gln Gly Pro Glu Gly Gln Pro Glu Trp Lys Glu Ala Glu Glu
            500                 505                 510

Leu Gly Glu Asp Ser Ala Ala Ser Leu Ser Leu Gln Leu Ser Leu Gln
            515                 520                 525

Arg Glu Gln Ala Pro Ser Pro Ala Ala Cys Glu Lys Gly Lys Glu
            530                 535                 540

Gln His Ser Gln Ala Glu Glu Leu Gly Pro Gly Gln Glu Glu Ala Glu
545                 550                 555                 560

Asp Pro Glu Glu Lys Val Ala Val Ser Pro Thr Pro Val Ser Pro
                565                 570                 575

Glu Val Arg Ser Thr Glu Pro Val Ala Pro Pro Glu Gln Leu Ser Glu
            580                 585                 590

Ala Ala Leu Lys Ala Met Glu Glu Ala Val Ala Gln Val Leu Glu Gln
            595                 600                 605

Asp Gln Arg His Leu Leu Glu Ser Lys Gln Glu Lys Met Gln Gln Leu
    610                 615                 620

Arg Glu Lys Leu Cys Gln Glu Glu Glu Glu Ile Leu Arg Leu His His
625                 630                 635                 640

Gln Gln Lys Glu Gln Ser Leu Ser Ser Leu Arg Glu Arg Leu Gln Lys
                645                 650                 655

Ala Ile Glu Glu Glu Ala Arg Met Arg Glu Glu Ser Gln Arg
            660                 665                 670

Leu Ser Trp Leu Arg Ala Gln Val Gln Ser Ser Thr Gln Ala Asp Glu
    675                 680                 685

Asp Gln Ile Arg Ala Glu Gln Glu Ala Ser Leu Gln Lys Leu Arg Glu
    690                 695                 700

Glu Leu Glu Ser Gln Gln Lys Ala Glu Arg Ala Ser Leu Glu Gln Lys
705                 710                 715                 720

Asn Arg Gln Met Leu Glu Gln Leu Lys Glu Glu Ile Glu Ala Ser Glu
                725                 730                 735

Lys Ser Glu Gln Ala Ala Leu Asn Ala Ala Lys Glu Lys Ala Leu Gln
    740                 745                 750

Gln Leu Arg Glu Gln Leu Glu Gly Glu Arg Lys Glu Ala Val Ala Thr
            755                 760                 765
```

```
Leu Glu Lys Glu His Ser Ala Glu Leu Glu Arg Leu Cys Ser Ser Leu
    770                 775                 780

Glu Ala Lys His Arg Glu Val Val Ser Ser Leu Gln Lys Lys Ile Gln
785                 790                 795                 800

Glu Ala Gln Gln Lys Glu Ala Gln Leu Gln Lys Cys Leu Gly Gln
                    805                 810                 815

Val Glu His Arg Val His Gln Lys Ser Tyr His Val Ala Gly Tyr Glu
            820                 825                 830

His Glu Leu Ser Ser Leu Leu Arg Glu Lys Arg Gln Glu Val Glu Gly
                835                 840                 845

Glu His Glu Arg Arg Leu Asp Lys Met Lys Glu Glu His Gln Gln Val
    850                 855                 860

Met Ala Lys Ala Arg Glu Gln Tyr Glu Ala Glu Glu Arg Lys Gln Arg
865                 870                 875                 880

Ala Glu Leu Leu Gly His Leu Thr Gly Glu Leu Glu Arg Leu Gln Arg
                    885                 890                 895

Ala His Glu Arg Glu Leu Glu Thr Val Arg Gln Glu Gln His Lys Arg
                900                 905                 910

Leu Glu Asp Leu Arg Arg Arg His Arg Glu Gln Glu Arg Lys Leu Gln
                    915                 920                 925

Asp Leu Glu Leu Asp Leu Glu Thr Arg Ala Lys Asp Val Lys Ala Arg
930                 935                 940

Leu Ala Leu Leu Glu Val Gln Glu Glu Thr Ala Arg Arg Glu Lys Gln
945                 950                 955                 960

Gln Leu Leu Asp Val Gln Arg Gln Val Ala Leu Lys Ser Glu Glu Ala
                    965                 970                 975

Thr Ala Thr His Gln Gln Leu Glu Ala Gln Lys Glu His Thr His
                980                 985                 990

Leu Leu Gln Ser Asn Gln Gln Leu Arg Glu Ile Leu Asp Glu Leu Gln
                    995                 1000                1005

Ala Arg Lys Leu Lys Leu Glu Ser Gln Val Asp Leu Leu Gln Ala
    1010                1015                1020

Gln Ser Gln Gln Leu Gln Lys His Phe Ser Ser Leu Glu Ala Glu
    1025                1030                1035

Ala Gln Lys Lys Gln His Leu Leu Arg Glu Val Thr Val Glu Glu
    1040                1045                1050

Asn Asn Ala Ser Pro His Phe Glu Pro Asp Leu His Ile Glu Asp
    1055                1060                1065

Leu Arg Lys Ser Leu Gly Thr Asn Gln Thr Lys Glu Val Ser Ser
    1070                1075                1080

Ser Leu Ser Gln Ser Lys Glu Asp Leu Tyr Leu Asp Ser Leu Ser
    1085                1090                1095

Ser His Asn Val Trp His Leu Leu Ser Ala Glu Gly Val Ala Leu
    1100                1105                1110

Arg Ser Ala Lys Glu Phe Leu Val Gln Gln Thr Arg Ser Met Arg
    1115                1120                1125

Arg Arg Gln Thr Ala Leu Lys Ala Ala Gln Gln His Trp Arg His
    1130                1135                1140

Glu Leu Ala Ser Ala Gln Glu Val Ala Lys Asp Pro Pro Gly Ile
    1145                1150                1155

Lys Ala Leu Glu Asp Met Arg Lys Asn Leu Glu Lys Glu Thr Arg
    1160                1165                1170

His Leu Asp Glu Met Lys Ser Ala Met Arg Lys Gly His Asn Leu
```

-continued

```
                1175                1180                1185

Leu Lys Lys Lys Glu Glu Lys Leu Asn Gln Leu Glu Ser Ser Leu
        1190                1195                1200

Trp Glu Glu Ala Ser Asp Glu Gly Thr Leu Gly Gly Ser Pro Thr
        1205                1210                1215

Lys Lys Ala Val Thr Phe Asp Leu Ser Asp Met Asp Ser Leu Ser
        1220                1225                1230

Ser Glu Ser Ser Glu Ser Phe Ser Pro Pro His Leu Asp Ser Thr
        1235                1240                1245

Pro Ser Leu Thr Ser Arg Lys Ile His Gly Leu Ser His Ser Leu
        1250                1255                1260

Arg Gln Ile Ser Ser Gln Leu Ser Ser Val Leu Ser Ile Leu Asp
        1265                1270                1275

Ser Leu Asn Pro Gln Ser Pro Pro Leu Leu Ala Ser Met Pro
        1280                1285                1290

Ala Gln Leu Pro Pro Arg Asp Pro Lys Ser Thr Pro Thr Pro Thr
        1295                1300                1305

Tyr Tyr Gly Ser Leu Ala Arg Phe Ser Ala Leu Ser Ser Ala Thr
        1310                1315                1320

Pro Thr Ser Thr Gln Trp Ala Trp Asp Ser Gly Gln Gly Pro Arg
        1325                1330                1335

Leu Pro Ser Ser Val Ala Gln Thr Val Asp Asp Phe Leu Leu Glu
        1340                1345                1350

Lys Trp Arg Lys Tyr Phe Pro Ser Gly Ile Pro Leu Leu Ser Asn
        1355                1360                1365

Ser Pro Thr Pro Leu Glu Ser Arg Leu Gly Tyr Met Ser Ala Ser
        1370                1375                1380

Glu Gln Leu Arg Leu Leu Gln His Ser His Ser Gln Val Pro Glu
        1385                1390                1395

Ala Gly Ser Thr Thr Phe Gln Gly Ile Ile Glu Ala Asn Arg Arg
        1400                1405                1410

Trp Leu Glu Arg Val Lys Asn Asp Pro Arg Leu Pro Leu Phe Ser
        1415                1420                1425

Ser Thr Pro Lys Pro Lys Ala Thr Leu Ser Leu Leu Gln Leu Gly
        1430                1435                1440

Leu Asp Glu His Asn Arg Val Lys Val Tyr Arg Phe
        1445                1450                1455

<210> SEQ ID NO 115
<211> LENGTH: 136
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 115

Met Ala Gly Arg Pro Leu Arg Ile Gly Asp Gln Leu Val Leu Glu Glu
  1               5                  10                  15

Asp Tyr Asp Glu Thr Tyr Ile Pro Ser Glu Gln Glu Ile Leu Glu Phe
                 20                  25                  30

Ala Arg Glu Ile Gly Ile Asp Pro Ile Lys Glu Pro Glu Leu Met Trp
             35                  40                  45

Leu Ala Arg Glu Gly Ile Val Ala Pro Leu Pro Gly Glu Trp Lys Pro
         50                  55                  60

Cys Gln Asp Ile Thr Gly Asp Ile Tyr Tyr Phe Asn Phe Ala Asn Gly
```

```
                65                  70                  75                  80
Gln Ser Met Trp Asp His Pro Cys Asp Glu His Tyr Arg Ser Leu Val
                    85                  90                  95

Ile Gln Glu Arg Ala Lys Leu Ser Thr Ser Gly Ala Ile Lys Lys Lys
                    100                 105                 110

Lys Lys Lys Arg Lys Arg Lys Thr Arg Arg Thr Glu Thr Pro Pro Lys
                    115                 120                 125

Val Arg Trp Pro Trp Val Pro His
        130                 135

<210> SEQ ID NO 116
<211> LENGTH: 202
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 116

Met Ala Gly Arg Pro Leu Arg Ile Gly Asp Gln Leu Val Leu Glu Glu
 1               5                  10                  15

Asp Tyr Asp Glu Thr Tyr Ile Pro Ser Glu Gln Glu Ile Leu Glu Phe
                    20                  25                  30

Ala Arg Glu Ile Gly Ile Asp Pro Ile Lys Glu Pro Glu Leu Met Trp
                35                  40                  45

Leu Ala Arg Glu Gly Ile Val Ala Pro Leu Pro Gly Glu Trp Lys Pro
        50                  55                  60

Cys Gln Asp Ile Thr Gly Asp Ile Tyr Tyr Phe Asn Phe Ala Asn Gly
65                  70                  75                  80

Gln Ser Met Trp Asp His Pro Cys Asp Glu His Tyr Arg Ser Leu Val
                    85                  90                  95

Ile Gln Glu Arg Ala Lys Leu Ser Thr Ser Gly Ala Ile Lys Lys Lys
                    100                 105                 110

Lys Lys Lys Gly Lys Glu Arg Gln Glu Gly Gln Arg Pro Pro Gln Lys
                    115                 120                 125

Phe Ala Gly Leu Gly Phe Leu Ile Ser Pro Ser Ser Cys Ser Ser Trp
        130                 135                 140

Gly Pro Gly Ser Phe Thr Arg Ser Cys Gly Tyr Pro Thr Leu Cys Ser
145                 150                 155                 160

Ser Trp Ile Ser Lys Arg Glu Pro Gly Glu Leu Ser Gly Val Trp Thr
                    165                 170                 175

Ser Ala Trp Arg Thr His Ala Ala Phe Thr Gly Ser Gln Asp Leu Cys
                    180                 185                 190

Leu Tyr Lys Gly Ser Leu Gly Leu His Ile
                    195                 200

<210> SEQ ID NO 117
<211> LENGTH: 203
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 86

Met Ala Gly Arg Pro Leu Arg Ile Gly Asp Gln Leu Val Leu Glu Glu
 1               5                  10                  15

Asp Tyr Asp Glu Thr Tyr Ile Pro Ser Glu Gln Glu Ile Leu Glu Phe
                    20                  25                  30
```

```
Ala Arg Glu Ile Gly Ile Asp Pro Ile Lys Glu Pro Glu Leu Met Trp
            35                  40                  45

Leu Ala Arg Glu Gly Ile Val Ala Pro Leu Pro Gly Glu Trp Lys Pro
 50                  55                  60

Cys Gln Asp Ile Thr Gly Asp Ile Tyr Tyr Phe Asn Phe Ala Asn Gly
 65                  70                  75                  80

Gln Ser Met Trp Asp His Pro Cys Asp Glu His Tyr Arg Ser Leu Val
                85                  90                  95

Ile Gln Glu Arg Ala Lys Leu Ser Thr Ser Gly Ala Ile Lys Lys Lys
            100                 105                 110

Lys Lys Lys Lys Gly Lys Glu Arg Gln Glu Gly Gln Arg Pro Pro Gln
        115                 120                 125

Lys Phe Ala Gly Leu Gly Phe Leu Ile Ser Pro Ser Cys Ser Ser
    130                 135                 140

Trp Gly Pro Gly Ser Phe Thr Arg Ser Cys Gly Tyr Pro Thr Leu Cys
145                 150                 155                 160

Ser Ser Trp Ile Ser Lys Arg Glu Pro Gly Glu Leu Ser Gly Val Trp
                165                 170                 175

Thr Ser Ala Trp Arg Thr His Ala Ala Phe Thr Gly Ser Gln Asp Leu
            180                 185                 190

Cys Leu Tyr Lys Gly Ser Leu Gly Leu His Ile
        195                 200

<210> SEQ ID NO 118
<211> LENGTH: 281
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 118

Met Gln Arg Pro Asn Ala His Arg Ile Ser Gln Pro Ile Arg Gln Ile
 1               5                  10                  15

Ile Tyr Gly Leu Leu Leu Asn Ala Ser Pro His Leu Asp Lys Thr Ser
            20                  25                  30

Trp Asn Ala Leu Pro Pro Gln Pro Leu Ala Phe Ser Glu Val Glu Arg
         35                  40                  45

Ile Asn Lys Asn Ile Arg Thr Ser Ile Ile Asp Ala Val Glu Leu Ala
 50                  55                  60

Lys Asp His Ser Asp Leu Ser Arg Leu Thr Glu Leu Ser Leu Arg Arg
 65                  70                  75                  80

Arg Gln Met Leu Leu Leu Glu Thr Leu Lys Val Lys Gln Thr Ile Leu
                85                  90                  95

Glu Pro Ile Pro Thr Ser Leu Lys Leu Pro Ile Ala Val Ser Cys Tyr
            100                 105                 110

Trp Leu Gln His Thr Glu Thr Lys Ala Lys Leu His His Leu Gln Ser
        115                 120                 125

Leu Leu Leu Thr Met Leu Val Gly Pro Leu Ile Ala Ile Ile Asn Ser
    130                 135                 140

Pro Gly Lys Glu Glu Leu Gln Glu Asp Gly Ala Lys Met Leu Tyr Ala
145                 150                 155                 160

Glu Phe Gln Arg Val Lys Ala Gln Thr Arg Leu Gly Thr Arg Leu Asp
                165                 170                 175

Leu Asp Thr Ala His Ile Phe Cys Gln Trp Gln Ser Cys Leu Gln Met
            180                 185                 190
```

```
Gly Met Tyr Leu Asn Gln Leu Leu Ser Thr Pro Leu Pro Glu Pro Asp
            195                 200                 205

Leu Thr Arg Leu Tyr Ser Gly Ser Leu Val His Gly Leu Cys Gln Gln
        210                 215                 220

Leu Leu Ala Ser Thr Ser Val Glu Ser Leu Leu Ser Ile Cys Pro Glu
225                 230                 235                 240

Ala Lys Gln Leu Tyr Glu Tyr Leu Phe Asn Ala Thr Arg Ser Tyr Ala
                245                 250                 255

Pro Ala Glu Ile Phe Leu Pro Lys Gly Arg Ser Asn Ser Lys Lys Lys
            260                 265                 270

Ala Glu Glu Thr Glu Tyr Gln Leu Phe
        275                 280

<210> SEQ ID NO 119
<211> LENGTH: 129
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 119

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Ala
        115                 120                 125

Trp

<210> SEQ ID NO 120
<211> LENGTH: 101
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 120

Ile Pro Ala Phe Pro Ala Gly Thr Val Leu Gln Pro Phe Pro Glu Ala
1               5                   10                  15

Ala Leu Ala Thr Arg Val Thr Val Pro Ala Val Glu Ala Pro Ala Ala
            20                  25                  30

Pro Arg Leu Asp Leu Glu Glu Ser Glu Glu Phe Lys Glu Arg Cys Thr
        35                  40                  45

Gln Cys Ala Ala Val Ser Trp Gly Leu Thr Asp Glu Gly Lys Tyr Tyr
    50                  55                  60

Cys Thr Ser Cys His Asn Val Thr Glu Arg Tyr Gln Glu Val Thr Asn
```

```
                65                  70                  75                  80
Thr Asp Leu Ile Pro Asn Thr Gln Ile Lys Ala Leu Asn Arg Gly Leu
                    85                  90                  95
Lys Lys Lys Gln Tyr
            100

<210> SEQ ID NO 121
<211> LENGTH: 32
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 121

Gly Arg Arg Asn Arg Ile Pro Ala Val Leu Arg Thr Glu Gly Glu Pro
1               5                   10                  15
Leu His Thr Pro Ser Val Gly Met Arg Glu Thr Thr Gly Leu Gly Cys
            20                  25                  30

<210> SEQ ID NO 122
<211> LENGTH: 10
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 122

Lys Ala Glu Glu Thr Glu Tyr Gln Leu Phe
1               5                   10

<210> SEQ ID NO 123
<211> LENGTH: 25
<212> TYPE: PRT
<213> ORGANISM: Artificial Sequence
<220> FEATURE:
<223> OTHER INFORMATION: Description of Artificial Sequence:
      polypeptides encoded by genes with coding microsatellites

<400> SEQUENCE: 123

Thr Ile Leu Lys Lys Ala Gly Ile Gly Met Cys Val Lys Val Ser Ser
1               5                   10                  15
Ile Phe Phe Ile Asn Lys Gln Lys Pro
            20                  25

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence:
      polypeptide encoded by genes with coding microsatellites

<400> SEQUENCE: 124

Ala Glu Glu Thr Glu Tyr Gln Leu Phe
1               5
```

NEOPEPTIDES AND METHODS USEFUL FOR DETECTION AND TREATMENT OF CANCER

This application is a National Stage of International Application PCT/EP03/04083, filed Apr. 17, 2003, published Oct. 23, 2003, under PCT Article 21(2) in English; which claims the priority of EP 02008773.0, filed Apr. 18, 2002, EP 02008771.4, filed Apr. 18, 2002, and EP 02008774.8, filed Apr. 18, 2002.

The present invention relates to compounds and methods useful for the detection and treatment of disorders associated with frameshift mutations in coding microsatellite regions. The compounds and methods are applicable in cancers, especially of DNA mismatch repair deficient (MMR) sporadic tumours and HNPCC associated tumours. The compounds disclosed in the invention are useful for detection of disorders and in therapy such as e.g. immuno-therapy. The diagnostic methods relate to diagnosis and prognostic assessment of disorders associated with frameshift polypeptides originating from frameshift mutations in coding microsatellite regions of genes based on the detection of immunological entities directed against said frameshift polypeptides in body fluids. With respect to the treatment of cancer, especially of DNA mismatch repair deficient (MMR) sporadic tumours and HNPCC associated tumours, the invention pertains to methods which use immuno therapy with combinatorial mixtures of tumour specific frameshift peptides to elicit a cytotoxic T-cell response specifically directed against tumour cells for use in prevention as well as in curative treatment of cancers and precancers.

Tumour cells accumulate mutations in components of cellular pathways, that are essential for the maintenance of normal growth and differentiation. In human epithelial tumours, 2 types of genetic instability have been identified: chromosomal instability (CIN), which marks structural and numerical chromosomal aberration in aneuploid neoplastic cells, and microsatellite instability (MSI), which reflects length variations at repetitive DNA sequences in diploid tumour cells. The type and spectrum of mutated genes markedly differs among CIN and MSI tumours, suggesting distinct but not mutually exclusive pathways of carcinogenesis. MSI occurs in about 90% of hereditary nonpolyposis colorectal cancers (HNPCC) as well as in about 15% of sporadic tumours of the colon and other organs, and is caused by mutational inactivation of different DNA mismatch repair genes.

The mutations lead especially in the case of frameshift mutations in coding microsatellite regions to the expression of new peptide sequences in the affected cells, that do not occur in wild-type cells. The altered peptides may be used as detection markers for disorders associated with frameshift mutations in coding microsatellite regions such as degenerative disorders or cancers (e.g. gastrointestinal cancers).

The accumulation of genetic alterations and resulting mutant proteins represent a major obstacle for tumour cells to escape immune surveillance. The mutant proteins or peptides encoded by expressed mutant genes may elicit a specific cellular immune response and thus may be recognized by CTL. This is especially true concerning mutations resulting from chromosomal instabilities, but also pertains to more subtle genetic alterations, such as small deletions and insertions in microsatellites.

This situation can be used for prevention and therapies in cancers. The cancer cells are characterized by the expression of neo-peptides, which arouse from the genetic alterations. These proteins are not present in normal, non cancerous tissues. Thus, the neo-peptides may be used to distinguish on a molecular level between tumours and normal tissues. As tools suitable for the molecular discrimination antigen specific molecules or cells may be used. Thus it is possible to elicit an immune response against frameshift peptides, as might arise from MSI mutations, specific for tumours. Using cytotoxic T lymphocytes or FS8-specific antibodies it is thus possible to specifically attack and eliminate tumour cells in organisms and tissues.

A large number of genes containing coding microsatellites have been identified. Various of these genes show mutations within the microsatellites with certain frequencies in sporadic tumours. For few of these genes it could be shown, that they are involved in the majority of cases of particular tumours. For example the $(A)_{10}$ tract within the TGFβRII gene and the $(G)_8$ tract within the BAX gene are commonly mutated in gastrointestinal cancers such as colon cancer or gastric cancer.

The T-cell mediated immune response on the other hand provides a strong and specific selection pressure for the rapidly growing tumour cells. (Tomlinson I, et al., Nat. Med. 1999; 5: 11-2) Thus tumour evolution is forced to circumvent the immune surveillance by the cellular immune response. As a consequence of this selection pressure, mutations in genes of the antigen processing or presenting machinery arise in MMR-deficient tumour cells. In fact evasion of the immune surveillance by acquiring β2-microglobulin mutations has been observed at high frequency in MSI$^+$ tumour cells (Bicknell D C, et al., Curr. Biol 1996; 6: 1695-7). Other targets of specific mutation or down-regulation of expression are TAP1/TAP2 or HLA alleles. Direct down-regulation of expression of immunogenic epitopes is also a possible mechanism of immune escape as has been shown for melanoma-associated antigens in vivo (Jager E, et al., Int. J. Cancer 1997; 71: 142-7). Due to this fact the relevant epitopes may not be detectable by the immune system.

As a consequence the promising therapies based on immune response directed against frameshift peptides in tumour tissues may fail in a not yet determined number of cases of tumours. So the approaches for the use of the vaccination therapy of cancer mediated by frameshift peptides might be limited by the fact, that the potential immunogenic frameshift peptides are not always detectable by the immune system due to mutations in the antigen presenting and processing properties of the cancer cells.

Even supposed, that during specific stages of tumour development cells express the aberrant proteins and thus are vulnerable to the immune surveillance, there potentially remains a population of tumour cells, that is not eliminated by the therapy. This state is quite undesirable for any therapy of cancers, for the remaining cells may continue growing and thus the tumour is not eliminated from the organism.

Similarly methods for detection of molecular markers suitable for diagnosis of disorders associated with frameshift mutations in coding microsatellite regions and for assessment of prognosis for said disorders are prone to overlook especially markers originating from small populations of affected cells as they may occur particularly in early stages of the disorder. This may in part be overcome by an elevated effort in the preparation of testing samples to raise the probability of the detection of disorders. However especially concerning disorders located in body regions, that are merely inaccessible, or accessible only under circumstances, that are quite consuming or discomfortable to patients alternative methods for reliable detection of molecular markers associated with disorders are desirable.

It is known in the art, that the mutant proteins or peptides derived from aberrantly expressed proteins may elicit a specific cellular immune response and thus may be recognized by cytotoxic T lymphocytes (CTL). This is especially true concerning mutations resulting from chromosomal instabilities, but pertains also to the more subtle genetic alterations, such as small deletions and insertions in microsatellites.

The T-cell mediated immune response on the other hand provides a strong and specific selection pressure for the rapidly growing tumour cells (Tomlinson I, et al., Nat. Med. 1999; 5: 11-2). Thus tumour evolution is forced to circumvent the immune surveillance by the cellular immune response. As a consequence of this selection pressure, mutations in genes of the antigen processing or presenting machinery arise in DNA mismatch repair (MMR)-deficient tumour cells. In fact evasion of the immune surveillance by acquiring $\beta$2-microglobulin mutations has been observed at high frequency in MSI$^+$ tumour cells (Bicknell D C, et al., Curr. Biol 1996; 6: 1695-7). Other targets of specific mutation or down-regulation of expression are TAP1/TAP2 or HLA alleles. Direct down-regulation of expression of immunogenic epitopes is also a possible mechanism of immune escape as has been shown for melanoma-associated antigens in vivo (Jager E, et al., Int. J. Cancer 1997; 71: 142-7). Due to this fact the relevant epitopes may not be detectable by the immune system. Thus it was suspected, that components of the immune system directed against novel peptides, characteristic for e.g. tumour cells, are not suitable for the detection of the disorders especially in the case of frameshift mutation peptides. This is due to the fact, that MSI disorders are frequently associated with DNA mismatch repair deficiency and thus are especially prone to mutations. This makes the affected cells especially apt to escape mutations in response to the attack by the immune system.

The inventors have now surprisingly found, that specific antibodies or antigen recognizing cells directed against a particular new frameshift peptide are in detectable levels present within the body fluids of individuals harbouring MSI associated disorders. This is especially due to the fact, that during specific stages of tumour development cells express the aberrant proteins. During these stages the peptides may be accessible to the immune surveillance, and thus an immune response may be elicited. Even though cell populations affected by respective disorders such as tumours may be eliminated from the organism, or may be mutated, such, that no further presentation of immunogenic epitopes may occur, there remains an immunological memory of the presence of the respective peptides at a certain time. Such the evolution of a cell population affected by a disorder associated with the expression of new frameshift peptides leaves immunological traces of its existence consisting e.g. of antibodies and specific T-lymphocytes directed against the particular peptides. Hence the presence of specific immune response elements directed against a particular frameshift peptide is indicative of the presence of a population of (tumour) cells, that expresses or has expressed at a certain time the respective peptide.

To further enhance the fidelity of the detection of the presence or absence of a disorder a set of peptides frequently occurring in disorders such as tumours may be applied in the detection reaction.

The present invention thus provides a method for the detection of disorders associated with frameshift peptides arising from mutations in coding microsatellite regions based on the detection of specific immunological entities directed against said frameshift peptides present in the body fluids of affected individuals directed against said frameshift peptides. The method is suited for primary detection of disorders such as tumours, for the early detection of disorders or of precursory stages of disorders, and for the assessment of prognosis in said disorders.

One further aspect of the invention is based on the inventors findings, that a mixture of frameshift peptides chosen according to combinatorial parameters minimizes the escape of particular populations of tumour cells from immunogenic elimination and may be used as a vaccine against a wide variety of DNA mismatch repair deficient tumours. The invention is based on the fact, that the immune escape of tumour cells is directed towards single immunogenic epitopes (frameshift peptides) in a potentially restricted subpopulation of the tumour cells. In the vast majority of MSI+ tumours various mutations may be found within the genome of the affected cells. So a combinatorial vaccination approach including several antigenic peptides could overcome this obstacle.

It is one aspect of the present invention to provide nucleic acid sequences of the genes TAF1B, MACS, UVRAG, ELAVL3, TCF6L1, ABCF1, AIM2, CHD2 and HT001, that have frameshift mutations within their coding regions.

A second aspect of the present invention is to provide new frameshift peptides, that occur in a wide range of different MSI$^+$ tumours.

A third aspect of the present invention is a method for detection of MSI$^+$ tumours using said frameshift peptides as molecular markers.

A fourth aspect of the present invention is a method for treatment of MSI$^+$ tumours using said frameshift peptides for therapeutic purposes.

In a fifth aspect the present invention provides sets of frameshift peptides, that occur in a wide range of different MSI$^+$ tumours and that diminish the probability of escape of tumours to be attacked by the immuno-therapy.

A sixth aspect of the present invention is a method for vaccination against MSI$^+$ tumours using said set of frameshift peptides.

A seventh aspect of the present invention is a method for treatment of MSI$^+$ tumours using a set of frameshift peptides, that elicit an immune response directed against a wide range of tumours.

An eighth aspect of the invention relates to the detection of disorders associated with frameshift mutations in coding microsatellite regions comprising the detection of immunological entities directed against frameshift peptides in body fluids of individuals.

The present invention thus provides compounds and methods for the therapy and detection of disorders associated with frameshift peptides arising from mutations in coding microsatellite regions. The diagnostic and therapeutic methods are suited for application in disorders such as tumours or in precursory stages of disorders.

Within the context of the present invention disorders associated with frameshift mutations comprises for example degenerative diseases, such as neurodegenerative diseases, vascular disorders, disorders caused by stress, such as oxidative stress, chemically induced stress, irradiation induced stress, etc. and cancers including all sporadic cancers as well as HNPCC associated cancers. Cancers as used herein may comprise e.g. colorectal cancer, small cell lung cancer, liver cancer (primary and secondary), renal cancer, melanoma, cancer of the brain, head and neck cancer, gastrointestinal cancers, leukemias, lymphomas, prostate cancer, breast cancer, ovary cancer, endometrial cancer, lung cancer, bladder cancer etc.

The method according to the present invention may be applied to any eucaryotic organisms. In one aspect the eucaryotic organisms are those exhibiting an immunologic defense system. The eucaryotic organisms are for example mammalian animals and especially animals of agricultural value such as pigs, cows, sheep, etc., companion animals, such as cats, dogs, horses etc., animals employed in research purposes such as mice, rats, rabbits, hamsters etc. or humans.

Nucleic acid molecules according to the present invention may comprise polynucleotides or fragments thereof. Preferred polynucleotides may comprise at least 20 consecutive nucleotides, preferably at least 30 consecutive nucleotides and more preferably at least 45 consecutive nucleotides of the sequences. The nucleic acids according to the present invention may also be complementary or reverse complementary to any of said polynucleotides. Polynucleotides may for example include single-stranded (sense or antisense) or double-stranded molecules, and may be DNA (genomic, cDNA or synthetic) or RNA. RNA molecules comprise as well hnRNA (containing introns) as mRNA (not containing introns). According to the present invention the polynucleotides may also be linked to any other molecules, such as support materials or detection marker molecules, and may, but need not, contain additional coding or non-coding sequences.

Mutation as used in the context of the present invention may comprise insertions or deletions of one or several nucleotides (or nucleotide repeats) within the specified microsatellite sequences. In a preferred embodiment of the present invention the number of nucleotides to be inserted or deleted is not 3 or must not be divisible by 3, such that the mutation leads to a frameshift with respect to the translational reading frame of the downstream nucleic acid sequence. Thus the nucleic acid sequence downstream of the mutation point will render a polypeptide-sequence different from the native sequence encoded by the respective gene. The mutation in these cases leads to a novel peptide sequence (a neo-peptide). Commonly the new peptide sequence is short due to the fact, that novel stop codons arise from the shift in the reading frame.

Frameshift mutations in microsatellites are usually due to DNA polymerase slippage and may be characterized by the type of the repeat. Thus in mono nucleotides repeats this type of mutation renders 1 nt insertion or deletion. In dinucleotide repeats and tetranucleotide repeats mutations are insertions or deletions of 2 or 4 nt respectively. For example commonly (−1) mutations occur in mononucleotide repeats (MNRs). In these mutations one nucleotide is deleted such that the reading frame is shifted by one nucleotide toward the 5' end of the gene compared to the original reading frame. This type of mutation renders a reading frame identical to that produced by (+2) mutations, which arise from two nucleotide insertions in the respective microsatellites. The respective (−1) or (+2) polypeptides might differ by one amino acid. The other frameshift mutation variant leading to frameshift mutations differing from (−1) mutations concerning the resulting reading frame is the (+1) mutation, arising from one nucleotide insertion, thus rendering a reading frame one nucleotide toward the 3' end of the gene compared to the original reading frame. This mutation type gives a reading frame identical to that of (−2) mutations, wherein the encoded polypeptides differ by one amino acid. (−3) and (+3) mutations are irrelevant according to the present invention, for they do not give rise to frameshift polypeptides.

Frameshift polypeptides as used herein shall comprise any polypeptides or fragments thereof, that arise by a frameshift mutation within a coding microsatellite sequence of a gene. A gene may harbour one or more coding microsatellite regions, that may give rise to frameshift peptides. The coding microsatellites according to the present invention comprise mononucleotide repeats, dinucleotide repeats, trinucleotide repeats, tetranucleotide repeats and pentanucleotide repeats of any length. According to present invention coding microsatellites contain preferably at least 3 and more preferably at least 5 repeats of the respective nucleotide pattern (1-5 nucleotides, which are repeated).

The frameshift polypeptides as used according to the present invention comprise at least 1, more preferred at least 2 and even more preferred at least 3 amino acids of the mutated part of the polypeptide. Additionally, the frameshift polypeptides may comprise fragments of the originally non-mutated proteins and/or may be fused to any other polypeptide sequences suitable for the purposes of the present invention. Examples of such polypeptide sequences are linker sequences, or structural peptide sequences, such as beta barrels, loop sequences etc. that facilitate the immunogenicity of the frameshift sequences according to the present invention within the fusion polypeptide.

In certain embodiments of the invention the frameshift polypeptides suitable for the methods disclosed herein are immunogenic polypeptides. This requires, that the polypeptides may stimulate immune responses in host organisms either in the form the polypeptides adopt in their natural environment and/or especially in the form the polypeptides adopt after processing by the cellular antigen processing and presenting machinery.

According to the present invention the frameshift polypeptides may also be represented by nucleic acids coding for said polypeptides. These nucleic acids may for example be used for the in situ expression of the respective polypeptides. For the purpose of expression of nucleic acids, the particular nucleic acids may be joined with suitable other nucleic acid sequences, that enable for the cloning and expression of said nucleic acids encoding the frameshift polypeptides.

In certain embodiments of the present invention frameshift polypeptides may comprise fusion or chimeric polypeptides containing sequences disclosed herein. Fusion proteins comprise the frameshift polypeptide according to the present invention together with any second and further polypeptides, such as e.g. one more frameshift polypeptide of the same sequence or of another sequence. Heterologous polypeptides may comprise enzymes, receptor molecules, antigens, antigenic or immunogenic epitopes or fragments, antibodies or fragments thereof, signalling polypeptides or signal transducing polypeptides, labelled polypeptides etc. In one embodiment of the invention the fusion peptides may be constructed for enhanced detection or purification of the frameshift polypeptides, or of complexes of the frameshift polypeptides with the respective immunological entities according to the present invention. For the purpose of purification tags, such as e.g. his-tags, myc-tags etc. may be added to the polypeptides. For the purpose of detection antigenic portions, enzymes, chromogenic sequences etc. may be fused to the polypeptides. The fusion proteins of the present invention may (but need not) include a linker peptide between the first and second polypeptides.

A nucleic acid sequence encoding a fusion protein of the present invention is constructed using known recombinant DNA techniques to assemble separate nucleic acid sequences encoding the first and second polypeptides into an appropriate expression vector. The 3' end of a nucleic acid sequence encoding the first polypeptide is ligated, with or without a peptide linker, to the 5' end of a nucleic acid sequence encoding the second polypeptide ensuring the appropriate reading frames of the sequences to permit mRNA translation of the two nucleic acid sequences into a single fusion protein that retains the biological activity (antigenicity) of both the first and the second polypeptides.

A peptide linker sequence may be employed to separate the first and the second polypeptides by a distance sufficient to ensure, that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

In certain embodiments of the present invention, especially for the detection of specific antibodies directed against frameshift polypeptides, the frameshift polypeptides themselves may be employed. Immunogenic portions as used herein is a portion of a protein, that is recognized by a B-cell and/or T-cell surface antigen receptor. The immunogenic portions comprise at least 5 amino acid residues, more preferably at least 10 amino acid residues and most preferably at least 15 amino acid residues of the frameshift polypeptides according to the present invention.

Immunogenic portions useful for the detection of specific antibodies may be provided as oligopeptides or as part of larger proteins. This is dependent on the embodiment of the invention. Where antibodies are to be detected, the antigenic epitopes may either be primary structures of polypeptides or the epitopes may be built by complex arrangements of tertiary structures of polypeptides. Concerning cells directed against specific frameshift peptides the relevant immunogenic portions are merely short fragments of peptides with a length of about 10-20 amino acids. Thus depending on the particular detection method the immunogenic portions have to be chosen.

In one embodiment of the invention a set of frameshift polypeptides is used for the detection of antibodies. The set may be a combination of the relevant peptides in solution, in cases, where information about the presence of immunological entities in general is sought. In contrast, when information about the presence or absence of particular frameshift peptides within a set of peptides is sought, the frameshift peptides may for example be tested each as a single, simultaneously in multiple testing reactions. Such experiments may for example be carried out in form of multi-well tests or using peptide arrays etc.

In order to address a representative choice of mutations potentially characterizing a disorder a set of frameshift polypeptides used according to the method disclosed herein comprises for example 5-20, in a preferred embodiment 10-30, in another preferred embodiment 20-50, in a more preferred embodiment 50-100, in an even more preferred embodiment 100-500 and in the most preferred embodiment more than 500 different frameshift polypeptides originating from frameshift mutations in coding microsatellite regions. The frameshift polypeptides to be used as a set according to the present invention are selected with respect to a number of parameters characterizing said polypeptides. A nucleic acid sequence encoding a fusion protein of the present invention is constructed using known recombinant DNA techniques to assemble separate nucleic acid sequences encoding the first and second polypeptides into an appropriate expression vector. The 3' end of a nucleic acid sequence encoding the first polypeptide is ligated, with or without a peptide linker, to the 5' end of a nucleic acid sequence encoding the second polypeptide ensuring the appropriate reading frames of the sequences to permit mRNA translation of the two nucleic acid sequences into a single fusion protein that retains the biological activity (antigenicity) of both the first and the second polypeptides.

Generally using an immense or unlimited number of occurring frameshift peptides it would be possible to address any potential number of disorder, that is associated with frameshift mutations. Due to practical and immunological concerns the number of peptides, that are included in a vaccine must be limited. To ensure a broad range of impact for any diagnostic or therapeutic method employing a set of frameshift polypeptides, the selection of particular peptides has to be based on rationale considerations.

A set of frameshift polypeptides used according to the method disclosed herein comprises at least 3, 4, 5, 6 or even 7 and in certain embodiments 8, 9 or 10 frameshift polypeptides. Due to immunological as well as practical concerns The set of frameshift peptides used as a vaccine may not include an unlimited number of frameshift peptides. Preferably the set of frameshift peptides comprises at maximum 15, in a more preferred embodiment at maximum 20 and in the most preferred embodiment of the invention at maximum 30 frameshift polypeptides. In order to ensure a maximum range of disorders to be addressed by the selected set of frameshift polypeptides the members of the set have to be selected by reasonable considerations. The frameshift polypeptides to be used as a set according to the present invention are selected with respect to a number of parameters characterizing said polypeptides.

In one embodiment the members of the set are chosen, so that only three different peptides may be used to cover a wide range of tumours for as well therapeutic as well as diagnostic approaches. Using larger panels of frameshift peptides the stringency to the choice of individual peptides is lowered. In especially small sets all parameters influencing the efficacy of addressing a wide range of tumours need to be optimally met. In larger panels even peptides occurring with lower frequencies or allowing for efficient immune-escape may be included.

One crucial aspect influencing the selection of the frameshift peptides is the mutation frequency of the relevant microsatellite region and thus the frequency of a particular expressed frameshift polypeptide. Mutation frequency as used in the context of the present invention pertains to the percentage of samples within a defined range of total samples, which show a particular mutation. Any method suitable for the determination of the percentage of individuals in a range of samples displaying the existence of a particular genotype or phenotype (with respect to the expression of polypeptides) may be employed for the determination of the frequency according to the present invention. The frequencies may be determined e.g. as described below in example 1.

The frequency may be the frequency of frameshift mutation within a coding microsatellite region or a frequency of expression of a frameshift polypeptide. Furthermore the frequency may be e.g. a frequency over a total of different tumour entities, the frequency with respect to a particular tumour entity, a frequency over several tumours entities restricted to particular stages of tumourigenesis or a frequency with respect to a particular tumour entity restricted to particular stages of tumourigenesis.

The frequency according to the present invention has to be determined taking into account a range of samples sufficient to render significant data. For example preferably at least 50 to 100 tumours may be included in the range of samples analysed. In case, that a smaller number of samples has been taken into account for determination of the frequency, a variation of the determined frequency may take place, if the range of samples is broadened.

Generally any frequency as determined may be used as a tool for the choice of a set of frameshift polypeptides according to the present invention. To ensure best results for the method according to the present invention a largest possible number of samples has to be taken into account. Yet if there are only rare data, a frequency may also be determined with respect to a restricted number of samples. This may especially be true, if the data for the restricted population of samples indicates a quite high frequency of a particular peptide, and thus implies a high therapeutic value for the respective peptide. Especially in cases, where a frequency is to be determined related to a particular tumour entity or related to particular stages of the tumorigenesis, the population of samples may be restricted.

The mutation may occur at any time during the tumour evolution and may be persistent or may be eliminated from the genome. Thus the frequency may comprise the frequency of the expression of a peptide at a particular stage of tumourigenesis or the occurrence of a genetic mutation at a particular defined stage of tumorigenesis. In one embodiment of the invention the frequency for the mutation is determined taking into account the widest possible range of samples. In this embodiment the method disclosed herein may be especially useful for the preventive vaccination of tumours. In another embodiment of the present invention the frequencies of mutation are related to specified tumour entities. In this embodiment the method according to the present invention may e.g. especially be useful for immuno-therapeutic approaches in treatment of tumours or in the preventive vaccination of particular subpopulations with an elevated risk for the occurrence of particular tumours. In a third embodiment of the present invention the frequency may be related to particular stages in tumourigenesis of particular tumours. This embodiment may be e.g. especially useful for the treatment of diagnostically defined tumours or for adjuvant treatment of tumours simultaneously or following primary treatment of tumours.

Using frameshift polypeptides, that occur with a high frequency, the probability, that a particular tumour expresses the peptide and may thus be recognized by antibodies or antigen-recognizing cells, increases. By combination of multiple such polypeptides, the probability to address particular tumour cells further is raised. Preferred frameshift polypeptides according to the present invention occur in at least 25%, more preferred frameshift polypeptides in at least 30% and most preferred frameshift polypeptides in at least 33% of the cases of the particular condition to be treated by the method according to the present invention.

According to the present invention the polypeptides are chosen to be expressed with a high frequency, thus the set of polypeptides may be limited to a number of members and nonetheless may cover a range of occurring diseases as wide as possible. For example a set of 10 polypeptides, each occurring with a frequency of more than 30 percent will statistically cover a range of more than 95% of the potentially existing disorders, as far as they have been included in the studies leading to the respective frequencies. Using 7 polypeptides requires the application of polypeptides with higher frequencies in order to cover a range of about 95% of potentially existing tumours. Using a set of polypeptides derived from enormously frequent mutated microsatellite regions may also allow for the employment of a set of only five different polypeptides without lowering the range of potentially addressed tumours. Thus the set of polypeptides comprises in a preferred embodiment at least 5, in a more preferred embodiment at least 7 and in the most preferred embodiment at least 10 different frameshift polypeptides.

A second aspect influencing the choice of a suitable set of frameshift polypeptides concerns the type of mutation found in the microsatellite region. Frameshift mutations microsatellites are usually due to DNA polymerase slippage and may be characterized by the type of the repeat. Thus in mono nucleotides repeats this type of mutation renders 1 nt insertion or deletion. In dinucleotide repeats and tetranucleotide repeats mutations are insertions or deletions of 2 or 4 nt respectively. (Polypeptides encoded by genes with coding microsatellites and the respective polypeptides encoded by genes with frameshift mutations are given in FIG. 5) For example commonly (−1) mutations occur in mononucleotide repeats (MNRs). In these mutations one nucleotide is deleted such that the reading frame is shifted by one nucleotide toward the 5' end of the gene compared to the original reading frame. This type of mutation renders a reading frame identical to that produced by (+2) mutations, which arise from two nucleotide insertions in the respective microsatellites. The respective (−1) or (+2) polypeptides might differ by one amino acid. The other frameshift mutation variant leading to frameshift mutations differing from (−1) mutations concerning the resulting reading frame is the (+1) mutation, arising from one nucleotide insertion, thus rendering a reading frame shifted one nucleotide toward the 3' end of the gene compared to the original reading frame. This mutation type gives a reading frame identical to that of (−2) mutations, wherein the encoded polypeptides differ by one amino acid. (−3) and (+3) mutations are irrelevant according to the present invention, for they do not give rise to frameshift polypeptides. According to the present invention the polypeptides included within the set shall be selected as to cover the widest possible range of tumours. Thus a set comprises for example (−1) frameshift polypeptides and additionally (+1) frameshift polypeptides. Using more than one possible novel reading frame of the particular gene broadens the spectrum of target cells and thus may prevent escape of particular cells from being eliminated according to the present invention.

A further aspect influencing the choice of the member polypeptides included in a set of frameshift polypeptides according to the present invention is the involvement of the gene encoded for by the coding sequence containing the respective microsatellite in particular biochemical pathways. The term biochemical pathway is used with a rather broad meaning herein. Biochemical pathways as used within this document shall for example include signal transduction pathways, enzymatic pathways, metabolic pathways, the apoptosis pathway, DNA repair or polymerization pathways, the pathway of meiosis etc. To broaden the spectrum of tumours to be addressed by the set of frameshift polypeptides, members of different pathways are included in the set. In a preferred embodiment at least 5 different pathways, in a more preferred embodiment at least 4 different pathways and in the most preferred embodiment at least 3 different pathways are represented by the frameshift polypeptides in a set according to the present invention. For example the TGFβRII as a member of a signal transduction pathway may be used in combination with the BAX gene as a member of the apoptosis pathway with additional other polypeptides associated with other pathways.

A final aspect influencing the choice of suitable frameshift polypeptides to be included in the set according to the present invention is the length of the novel (poly)peptide sequence arising from the mutation. The shift of the reading frame leads to novel stop codons. Thus the new peptides are not of the same length as the polypeptides naturally encoded by the particular gene. In most cases the new peptides are shorter or even significantly shorter than the original wild-type polypeptide. Frequently rather oligopeptides arise from the frameshift mutations. The fidelity of the immune system in recognizing "foreign" molecules reaches thus far, to identify even polypeptides, that differ from "own" polypeptides in only one single amino-acid mutation. The fragments, bound by the antigen presenting HLA molecules comprise about 12 amino acid residues. To enhance the fidelity of recognition of new polypeptides more than one single amino-acid difference should be present. A polypeptide comprising 3 consecutive amino acids differing from the wild-type amino acid sequence is reliably recognized as foreign by the immune system. This may be due to the increased probability of new amino acid combinations being present in different fragments produced by the antigen presenting machinery. Thus the frameshift polypeptides according to the present invention contain at least one new amino acid, not present in the wild-type polypeptide, in a more preferred embodiment at least 2 new amino acids and in the most preferred embodiment at least 3 new amino acids.

According to the named parameters a basic set of frameshift polypeptides may be tailored, that is suitable to address a large variety of tumours and minimizes the danger of escape of single tumour cells from the therapy. Thus the probability of survival of tumour cells in an organism following immuno-therapy can be minimized and the rate of recurrence of the cancer can be reduced.

A basic set of frameshift polypeptides includes frameshift polypeptides, that do occur with a high mutation frequency in associated disorders. Additionally the polypeptides within the set are chosen to be involved in different biochemical pathways. The mutation types are chosen, that polypeptides of a minimal length of 3 amino acid residues is expressed from the mutated nucleic acid sequence. Furthermore different mutation types of one single microsatellite may be included in the set if applicable.

Examples of basic sets of frameshift polypeptides for use in therapeutic as well as diagnostic methods of the present invention include:

| Set1: | HT001 | U79260 | MACS | | |
| Set2: | HT001 | TAF1B | MACS | | |
| Set3: | HT001 | TGFB2R | MACS | | |
| Set4: | HT001 | U79260 | TGFB2R | | |
| Set5: | HT001 | U79260 | TAF1B | | |
| Set6: | HT001 | TGFB2R | TAF1B | | |
| Set7: | HT001 | U79260 | TGFB2R | MACS | |
| Set8: | HT001 | U79260 | TGFB2R | AC1 | |
| Set9: | HT001 | U79260 | TGFB2R | TAF1B | |
| Set10: | HT001 | TGFB2R | MACS | CASP5 | |
| Set11: | HT001 | U79260 | MACS | CASP5 | |
| Set12: | HT001 | U79260 | MACS | AC1 | |
| Set13: | HT001 | TGFB2R | TAF1B | CASP5 | |
| Set14: | HT001 | U79260 | MACS | OGT | |
| Set15: | U79260 | TGFB2R | AC1 | CASP5 | |
| Set16: | HT001 | U79260 | TGFB2R | MACS | AC1 |
| Set17: | HT001 | U79260 | TGFB2R | TAF1B | MACS |
| Set18: | HT001 | U79260 | TGFB2R | TAF1B | AC1 |
| Set19: | HT001 | U79260 | TGFB2R | MACS | AIM2 |
| Set20: | HT001 | U79260 | TGFB2R | TAF1B | AIM2 |
| Set21: | U79260 | TGFB2R | TAF1B | AC1 | CASP5 |
| Set1: | HT001 | U79260 | TGFB2R | AC1 | CASP5 |
| Set22: | U79260 | TGFB2R | MACS | AC1 | CASP5 |
| Set23: | HT001 | U79260 | TAF1B | MACS | AC1 |
| Set24: | HT001 | U79260 | TAF1B | MACS | CASP5 |
| Set1: | HT001 | U79260 | MACS | AC1 | OGT |
| Set25: | HT001 | U79260 | MACS | MSH3 | OGT |
| Set26: | HT001 | U79260 | TGFB2R | MACS | OGT |
| Set27: | HT001 | TGFB2R | TAF1B | AC1 | CASP5 |
| Set28: | HT001 | U79260 | TGFB2R | AC1 | AIM2 |

Additional to the parameters given above, data concerning the particular disorder in focus are taken into account for the design of particular sets of frameshift peptides according to the present invention. Thus individual mutation frequencies, typical mutation types, relevant biochemical pathways or special immunological characteristics may contribute to a set to be used in particular cases. Furthermore in particular cases based on results of examination of particular samples of individuals vaccines may be tailored as to optimally fit the therapy of the respective disorder. In one embodiment of the present invention individual tumour vaccine compositions may be set up according to molecular profiling of individual tumours Choosing suitable combinations of the peptides within the mixture of frameshift peptides thus enables for generation of therapeutic or diagnostic preparations with a wide range of applicability. E.g. vaccines that elicit immune response specifically for tumours of particular organs. On the other hand it is possible to design sets of frameshift polypeptides that cover a wide range of degenerative disorders or cancers in individuals. The first possibility may e.g. be especially useful for the design of curative treatment, whereas the second variant of sets may be of special interest for the design of preventive vaccines.

The compositions and methods according to the present invention may be applied to any eukaryotic organisms exhibiting an immunologic defense system. The eukaryotic organisms are for example animals of agricultural value such as pigs, cows, sheep, etc., companion animals, such as cats, dogs, horses etc., animals employed in research purposes such as mice, rats, rabbits, hamsters etc. or humans.

Therapeutic methods for use in the present invention comprise immunogenic treatment such as vaccination therapy or generally immuno-therapy. The vaccines for use in the present invention comprise for example one or more sets of frameshift polypeptides.

According to the present invention frameshift polypeptides that comprise an immunogenic portion may be used for immuno-therapy for the treatment of cancer. Immunotherapy may be broadly classified into either active or passive immunotherapy. In active immunotherapy, treatment relies on the in vivo stimulation of the endogenous host immune system to react against tumours with the administration of immune response-modifying agents (for example, tumour vaccines, bacterial adjuvants, and/or cytokines). A patient may be afflicted with disease, or may be free of detectable disease. Accordingly, the compounds disclosed herein may be used to treat cancer or to inhibit the development of cancer. The compounds are preferably administered either prior to or following primary treatment of tumours such as surgical removal of the tumours, treatment by administration of radiotherapy and/or conventional chemotherapeutic drugs or any other mode of treatment of the respective cancer or its precursors.

In passive immunotherapy, treatment involves the delivery of biologic reagents with established tumour-immune reactivity (such as effector cells or antibodies) that can directly or indirectly mediate antitumour effects and does not necessarily depend on an intact host immune system. Examples of effector cells include T lymphocytes (for example, CD8+ cytotoxic T-lymphocytes, CD4+ T-helper, tumour-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive transfer immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T-cell cultures in order to generate sufficient number of cells for immunotherapy. In particular, antigen-presenting cells, such as dendritic-, macrophage- or B-cells, may be pulsed with immunoreactive polypeptides or transfected with a nucleic acid sequence(s), using standard techniques well known in the art. For example, antigen presenting cells may be transfected with a nucleic acid sequence, wherein said sequence contains a promoter region appropriate for increasing expression, and can be expressed as part of a recombinant virus or other expression system. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T-Cells: Principles Revisited," Immunological Reviews, 157: 177, 1997).

According to the present invention sets of frameshift polypeptides may be employed to generate and/or isolate tumour-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL or CD4+ T-helper cells clones may be isolated from the patient, expanded using standard tissue culture techniques, and returned to the patient.

Alternatively, peptides corresponding to immunogenic portions of the polypeptides of the invention may be employed to generate tumour reactive T-cell subsets by selective in vitro stimulation and expansion of autologous T-cells to provide antigen-specific T-cells which may be subsequently transferred to the patient as described, for example, by Chang et al. (Crit. Rev. Oncol. Hematol., 22(3), 213, 1996). Cells of the immune system, such as T-cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T-cells. The population of tumour antigen-specific T-cells is then expanded using standard techniques and the cells are administered back to the patient.

In another embodiment, T-cell receptors and/or antibodies specific for the polypeptides can be cloned, expanded, and transferred into other vectors or effector cells for use in adoptive immunotherapy.

In a further embodiment, syngeneic or autologous dendritic cells may be pulsed with peptides corresponding to at least an immunogenic portion of a polypeptide disclosed herein. The resulting antigen-expressing and/or presenting dendritic cells may either be transferred into a patient, or employed to stimulate T-cells to provide antigen-specific T-cells which may, in turn, be administered to a patient. The use of peptide-pulsed dendritic cells to generate antigen-specific T-cells and the subsequent use of such antigen-specific T-cells to eradicate tumours in a murine model has been demonstrated by Cheever et al, (Immunological Reviews, 157:177, 1997).

Monoclonal antibodies directed against frameshift peptides presented on cellular membranes may according to the present invention also be used as therapeutic compounds in order to diminish or eliminate tumours. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include 90Y, 123I, 125I, 131I, 186Re, 188Re, 211At, and 212Bi. Preferred drugs include methotrexate, and pyrimidine and purine analogues. Preferred differentiation inducers include phorbol esters and butyric acid. Preferred toxins include ricin, abrin, diphtheria toxin, cholera toxin, gelonin, Pseudomonas exotoxin, Shigella toxin, and pokeweed antiviral protein.

Pharmaceutical compositions useful in immuno-therapy according to the present invention may comprise a set of at least 3, 4, 5, 6, 7, 8, 9 or 10 frameshift polypeptides (or variants thereof). Moreover sets of frameshift polypeptides may comprise 5 to 20, 7 to 30 or even ore than 15, 20 or 30 frameshift peptides (or variants thereof). (or variants thereof), In certain embodiments the pharmaceutical compositions comprise the frameshift polypeptides and a physiologically acceptable carrier. The vaccines may additionally comprise a non-specific immune-response enhancer, wherein the non-specific immune response enhancer is capable of eliciting or enhancing an immune response to an exogenous antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of tumour antigens, either incorporated into a fusion protein or present within a separate polypeptide.

Alternatively, a pharmaceutical composition or vaccine suitable for immunotherapy according to the present invention may contain nucleic acids, that code for one or more frameshift polypeptides according to the present invention. Nucleic acids may for example include single-stranded (sense or antisense) or double-stranded molecules, and may be DNA (genomic, cDNA or synthetic) or RNA. RNA molecules comprise as well HnRNA (containing introns) as mRNA (not containing introns). According to the present invention the polynucleotides may also be linked to any other molecules, such as support materials or detection marker molecules, and may, but need not, contain additional coding or non-coding sequences. The nucleic acid may be administered in a way that allows the polypeptides to be generated in situ. Suitable expression systems are known to those skilled in the art. The expression of the polypeptides may for example be persistent or transient. In pharmaceutical compositions and/or vaccines, providing for in-situ expression of polypeptides, the nucleic acids may be present within any suitable delivery system known to those of ordinary skill in the art, including nucleic acid expression systems, bacteria and viral expression systems.

Appropriate nucleic acid expression systems comprise the necessary regulatory nucleic acid sequences for expression in the patient, such as suitable promoters, terminators etc. Bacterial delivery systems may for example employ the administration of a bacterium that expresses an epitope of a cell antigen on its cell surface. In a preferred embodiment, the nucleic acid may be introduced using a viral expression system such as e.g., vaccinia virus, retrovirus, or adenovirus, which may involve the use of a non-pathogenic, replication competent virus. Suitable systems are known to those of ordinary skill in the art and are disclosed, for example, in Fisher-Hoch et al., PNAS 86:317-321, 1989; Flexner et al., Ann. N.Y. Acad Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., PNAS 91:215-219, 1994; Kass-Eisler et al., PNAS 90:11498-11502, 1993; Guzman et al., Circulation 88:2838-2848, 1993; and Guzman et al., Cir. Res. 73:1202-1207, 1993.

In another embodiment transgenic mammalian cells may be used for delivery and/or expression of the nucleic acids. The methods for producing nucleic acid constructs suitable for in-situ expression of polypeptides are known to those of skill in the art.

Furthermore the nucleic acid may be administered as naked nucleic acids. In this case appropriate physical delivery systems, which enhance the uptake of nucleic acid may be employed, such as coating the nucleic acid onto biodegradable beads, which are efficiently transported into the cells. Administration of naked nucleic acids may for example be useful for the purpose of transient expression within a host or host cell.

The pharmaceutical compositions used for immunotherapy according to the present invention may be administered by any suitable way known to those of skill in the art. The administration may for example comprise injection, such as e.g., intra-cutaneous, intramuscular, intravenous or subcutaneous injection, intranasal administration for example by aspiration or oral administration. A suitable dosage to ensure the pharmaceutical benefit of the treatment should be chosen according to the parameters, such as age, sex, body weight etc. of the patient, known to those of skill in the art.

The type of carrier to be employed in the pharmaceutical compositions of this invention, will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109. Any of a variety of immune-response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, Bordetella pertussis or Mycobacterium tuberculosis. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

The pharmaceutical compositions or immuno-therapeutic methods according to the present invention may be used for the treatment of degenerative disorders or cancers. For example the compositions and methods may be employed in the therapy of diagnosed cancers in order to eliminate the tumour cells from the affected organism. As well primary tumours as metastases or disseminated tumour cells within an organism may be targets to the therapeutic compounds and methods disclosed herein.

Furthermore the compositions and methods of the invention may be employed in the treatment of pre-neoplastic conditions. In this case the pre-neoplastic cells or tissues may be directly addressed by the immuno-therapeutic compositions or methods, or may be hindered from evolving into neoplastic or dysplastic conditions. For example in this case the pre-neoplastic condition may be treated preventively. By the vaccination the immune response may be elicited, so that emerging neoplasms may be destroyed.

The methods and compositions according to the present invention may also be used for the prevention of degenerative disorders or cancers associated with frameshift mutations in coding microsatellites. For this purpose a vaccination of a population of organisms or of subgroups of said population may be performed. The subgroups may be built by suitable parameters such as hereditary predisposition for the emergence of degenerative disorders, exposure to factors, that increase the risk of being affected by said disorders etc.

In one embodiment of the present invention the peptides disclosed herein may be used for the diagnosis of disorders associated with frameshift mutations in coding microsatellite regions.

Diagnosis as used in the context of the present invention may comprise determining the presence or absence and/or the level of frameshift peptides or of specific immunological entities directed against particular frameshift peptides in a sample, and assessing diagnosis from said presence or absence and/or level of frameshift peptides and/or immunological entities specifically directed against said frameshift polypeptides.

Based upon the determined presence or absence and/or the levels of frameshift peptides or of immunological entities specifically directed against particular frameshift peptides in the samples individuals can be subdivided into subgroups. The subgroups may be created according to scientific or clinical data, such as e.g. survival, recurrence of disease, frequency of metastases etc., related to the presence or absence and/or levels of frameshift peptides or of particular frameshift peptides in samples of tissues affected with a particular disorder, of tissues being in question of being affected with a particular disorder or of tissues at risk of being affected with a particular disorder.

Based upon these subgroups an assessment of prognosis may be done. According to the subgroups the therapy of the individuals affected by the disorders (e.g. tumours) may be tailored.

Monitoring may comprise detecting the presence or absence or level of frameshift peptides or of immunologic entities specifically directed against frameshift polypeptides in samples taken at different points in time and determining the changes in said levels or presences or absences. According to said changes the course of the disease can be followed. E.g. the occurrence of frameshift peptides or of immunologic entities directed against frameshift peptides, that have not been present at an earlier time-point may be indicative of the progression of evolution of the affected tissue. The course of the disease may be used to select therapy strategies for the particular individual.

Another aspect of diagnosis and monitoring of the disease course according to the present invention may comprise the detection of minimal residual disease. This may comprise for example the detection of presence and/or level of frameshift peptides or of immunologic entities specifically directed against said frameshift polypeptides, that have not been present in earlier examinations in one or more body samples following initial therapy of an individual once or at several timepoints. According to the presence and/or level of frameshift peptides or of immunologic entities specifically directed against new frameshift polypeptides detected in the samples one may select a suitable therapy for the particular individual.

Furthermore the diagnostic method may be carried out to detect disseminated tumor cells in biological samples as MRD diagnosis of minimal residual disease. For this purpose the detection of the level of immunological entities or the presence of frameshift peptides or of immunological entities, specific for particular frameshift peptides, that have not been detected in prior examinations, may be performed.

Immunological entities as used in the context of the present invention shall comprise any components of the mammalian immune system, that are able to specifically react with an antigenic epitope. Such immunlogical entities may comprise for example antibodies, all immunoglobulins, such as e.g. IgG, IgM, IgA, IgE, IgD, specific CD8+ T-cells or specific T-helper cells.

A sample according to the method of the present invention may comprise any sample comprising frameshift peptides or immunological entities as defined above. Samples may comprise samples of clinical relevance, such as e.g. secretions, smears, body fluids, urine, semen, stool, bile, biopsies, cell- and tissue-samples. Biopsies as used in the context of the present invention may comprise e.g. resection samples of tumors, tissue samples prepared by endoscopic means or needle biopsies of organs.

Such samples may comprise for example intact cells, lysed cells or any liquids containing polypeptides, antibodies, immunoglobulins or cells specifically directed against frameshift peptides. Even solids, to which peptides, cells, cell fragments or antigen binding polypeptides, such as antibodies or immunoglobulins may adhere, or may be fixed to, may be samples according to the method disclosed herein. The method for detection of the level of the frameshift peptides or of the immunological entities according to the present invention is any method, which is suited to detect very small amounts of specific frameshift peptides or of specific immunological entities in biological samples. The detection reaction according to the present invention is a detection either on the level of polypeptides, nucleic acids, antibodies or on the level of cells specific for particular antigens.

For diagnostic purposes detection procedures related to one single frameshift polypeptides or to immunological entities specifically recognizing said frameshift peptides may be performed. Furthermore detection procedures may be performed that are tailored to display the presence or absence or the level of one or more sets of polypeptides or immunological entities directed against these polypeptides, wherein the sets have been put together according to rational combinatorial parameters as they are given below.

The detection may be carried out in solution or using reagents fixed to a solid phase. Solid phases may comprise beads of a variety of materials, such as e.g. agarose, dextrane polymers, polystyrene, silica, etc. or surfaces of suitable materials such as e.g. polystyrene, glass, agarose, protein, dextran etc. coated surfaces etc. The detection of one or more immunological entities, such as immunoglobulins or cells carrying specific antigen recognizing epitopes, with different antigen binding specificities may be performed in a single reaction mixture or in two or more separate reaction mixtures. Alternatively the detection reactions for several immunological entities may for example be performed simultaneously in multi-well reaction vessels.

Applicable formats for the detection reaction according to the present invention may be, (reverse) blotting techniques, such as Western-Blot. The blotting techniques are known to those of ordinary skill in the art and may be performed for example as electro-blots, semidry-blots, vacuum-blots or dot-blots. Furthermore immunological methods for detection of molecules may be applied, such as for example immunoprecipitation or immunological assays, such as ELISA, RIA, Elispot assay, lateral flow assays, immuno-cytochemical methods etc.

The immunological entities specifically recognizing particular frameshift peptides may be detected using reagents that specifically recognise these immunological entities alone or in complex with their respective antigen (e.g. antibodies), or reagents, that are specifically recognized by the immunological entities themselves (e.g. the antigen). In one embodiment the antigen may be fused to another polypeptide, so as to allow binding of the antigen by the immunological entity in question and simultaneously binding of the second part of the fusion protein by another (labelled) antibody for the detection. The detection reaction for the immunological entities may comprise one or more reactions with detecting agents either recognizing the initial entities or recognizing the prior molecules used to recognize the immunological entities.

The detection reaction further may comprise a reporter reaction indicating the presence or absence and/or the level of the immunological entities. The reporter reaction may be for example a reaction producing a coloured compound, a bioluminescence reaction, a chemiluminescent reaction, a fluorescence reaction, generally a radiation emitting reaction etc. The detection reactions may for example employ antibodies or binding reagents that are detectably labelled.

Furthermore the binding of detection molecules to the entities in question may be detected by any measurable changes in physical or physical-chemical properties, such as changes in spectroscopic properties, in magnetic resonance properties etc. Different immunological entities or immunological entities of different specificities may be recognized by different methods or agents. This may be due to difficulties in detection of several entities, or entities with particular specificities by a particular method. An advantage of the use of different detection techniques for different immunological entities or for immunological entities with different specificities may for example be, that the different reporter signals referring to different immunological entities could be distinguished.

Generally in a method according to the present invention the detection of different immunological entities such as the detection of immunoglobulins and the detection of immunocompetent cells may be performed simultaneously.

For all detection purposes optionally the original sample may be concentrated by any suitable means known to those of ordinary skill in the art. Furthermore steps may be involved to selectively extract immunological entities from the sample mixture such as affinity based purification techniques either employing specific antibodies or the respective antigen recognized by the entities in question.

In one preferred embodiment of the invention the detection of the level of immunological entities specific for frameshift peptides is carried out on the level of antibodies. This may be e.g. performed using the specific interaction between the respective frameshift peptides with the antibodies. The determination of the presence or absence and/or the level of the antibodies may for example be carried out with recombinantly produces frameshift peptides. The peptides can be used in many different detection techniques for example in western-blot, ELISA or immuno-precipitation. In one embodiment the detection of antibodies is carryout as antibody capture assay (Antibodies A laboratory Manual, Harlow, Ed. et al., Cold Spring Harbor Laboratory 1988).

In another embodiment of the invention the detection of the specific antibodies is carried out using monoclonal or polyclonal antibodies specifically recognizing the antigen binding epitope of the first antibodies. For this purpose the above mentioned immunological detection procedures may be applied. In a further embodiment chimeric antigens may be employed in the detection reaction. Such chimeric antigens may for example comprise fusion proteins combining the antigenic epitope of a frameshift polypeptide, recognized by the antibody in question, fused to another antigen, that may be recognized by a detection antibody. The particular antigens within the chimeric polypeptide may be separated by a linker or spacer region.

Any other method for determining the amount of particular antibodies or immunoglobulins in biological samples can be used according to the present invention.

Generally the detection of the antibodies according to the present invention may be performed as well in vitro as directly in situ for example in the course of an immuno-histochemical or immuno-cytochemical staining reaction.

Cells exhibiting specificity for a particular antigen may be detected by any methods suitable for that purpose known to those of ordinary skill in the art. Methods may for example comprise proliferation-assays, cytokine-ELISAs, ELISpot assays, intracellular FACS-staining, PCR-mediated identification of peptide-specific cytokine (or similar)—expressing cells, tetramer-staining, cytotoxicity assays and DTH—(delayed type hypersensitivity) reactions.

In case of proliferation-assays induction of peptide-specific T-cell proliferation may be measured by methods known to those of skill in the art. This can be achieved by simply counting of cells, by measuring incorporation of labelled nucleotides into cellular DNA or by measuring level and/or activity of cellular protein(s). Cytokine-ELISA may comprise identification of peptide-specific cytokine-secreting cells by measuring cytokine levels in supernatant. In the course of an ELISpot assay the number of peptide-specific cytokine (i.e. IFN-g)—secreting cells in a sample is determined. Similarly the Intracellular FACS-staining identifies cytokine-expressing cells on the protein level. In contrast (real-time) PCR may be used for identification of peptide-specific cytokine (or similar)—expressing cells on the transcript level. In the course of a tetramer-staining assay the label is a tetramer-molecule of recombinant MHC-class I molecules, loaded with specific peptide and coupled to a dye. The tetramer binds to the T-cell receptor. Cytotoxicity assays are a method for identification of cells, that can recognize and kill target cells in a peptide-specific manner. DTH—(delayed type hypersensitivity) reaction is based on the measuring of skin-reaction of vaccinated persons after intradermal (or similar) application of peptide(s).

In a preferred embodiment of the invention the detection of the immunological entities directed against particular frameshift polypeptides is carried out on the level of antibodies. In this embodiment the binding agent may be for example a frameshift polypeptide or a fragment thereof, recognized by the respective antibody, or a fusion polypeptide comprising said frameshift polypeptide or a fragment thereof. Furthermore the binding agent may comprise an antibody or a fragment thereof specific for the antibody in question, for the complex of the antibody with the respective frameshift polypeptide or for an antigenic epitope fused to the frameshift polypeptide.

In another embodiment of the test kit the detection of the immunological entities is carried out on the level of cells specifically recognizing frameshift polypeptides. In this embodiment the reagent for the detection of the invention may be for example a frameshift polypeptide or a fragment thereof, recognized by the respective antibody or T-cell receptor, or a fusion polypeptide comprising said frameshift polypeptide or a fragment thereof. Furthermore the binding agent may comprise an antibody or a fragment thereof specific for the antibody in question, for the complex of the antibody with the respective frameshift polypeptide or for an antigenic epitope fused to the frameshift polypeptide.

The method for detection of the level of the frameshift polypeptides according to the present invention is any method, which is suited to detect very small amounts of specific biologically active molecules in biological samples. The detection reaction according to the present invention is a detection either on the level of nucleic acids or on the level of polypeptides.

The detection may be carried out in solution or using reagents fixed to a solid phase. The detection of one or more molecular markers, such as polypeptides or nucleic acids, may be performed in a single reaction mixture or in two or separate reaction mixtures. Alternatively the detection reactions for several marker molecules may for example be performed simultaneously in multi-well reaction vessels. The markers characteristic for the frameshift polypeptides may be detected using reagents that specifically recognise these molecules. The detection reaction for the marker molecules may comprise one or more reactions with detecting agents either recognizing the initial marker molecules or recognizing the prior molecules used to recognize other molecules.

In one preferred embodiment of the invention the detection of the level of frameshift polypeptides is carried out by detection of the level of nucleic acids coding for the frameshift polypeptides or fragments thereof present in the sample. The means for detection of nucleic acid molecules are known to those skilled in the art. The procedure for the detection of nucleic acids can for example be carried out by a binding reaction of the molecule to be detected to complementary nucleic acid probes, proteins with binding specificity for the nucleic acids or any other entities specifically recognizing and binding to said nucleic acids. This method can be performed as well in vitro as directly in situ for example in the course of a detecting staining reaction. The use of this detection procedure is restricted to cases, where hybridisation properties of the respective frameshift mutations are significantly altered in comparison to the respective wild-type nucleic acids. Another way of detecting the frameshift polypeptides in a sample on the level of nucleic acids performed in the method according to the present invention may comprise an amplification reaction of nucleic acids. In these cases a subsequent reaction displaying the presence or absence of a frameshift mutation within the coding microsatellite region is necessary.

In another preferred embodiment of the invention the detection of the level of frameshift polypeptides is carried out by determining the level of expression of a protein. The determination of the frameshift polypeptides on the protein level can for example be carried out in a reaction comprising an antibody specific for the detection of the frameshift polypeptides. The antibodies can be used in many different detection techniques for example in western-blot, ELISA or immunoprecipitation. Generally antibody based detection can be carried out as well in vitro as directly in situ for example in the course of an immuno-histochemical staining reaction. Any other method for determining the amount of particular polypeptides in biological samples can be used according to the present invention.

Furthermore according to the present invention diagnosis may comprise detection of immunological entities specifically recognizing particular frameshift peptides using reagents that specifically recognise these immunological entities alone or in complex with their respective antigen (e.g. antibodies), or reagents, that are specifically recognized by the immunological entities themselves (e.g. the antigen). In one embodiment the antigen may be fused to another polypeptide, so as to allow binding of the antigen by the immunological entity in question and simultaneously binding of the second part of the fusion protein by another (labelled) antibody for the detection. The detection reaction for the immunological entities may comprise one or more reactions with detecting agents either recognizing the initial entities or recognizing the prior molecules used to recognize the immunological entities.

The detection reaction further may comprise a reporter reaction indicating the presence or absence and/or the level of the frameshift polypeptides or of the immunological entities. The reporter reaction may be for example a reaction producing a coloured compound, a bioluminescence reaction, a chemiluminescent reaction, a fluorescence reaction, generally a radiation emitting reaction etc. The detection reactions may for example employ antibodies or binding reagents that are detectably labelled.

Furthermore the binding of detection molecules to the peptides or immunological entities in question may be detected by any measurable changes in physical or physical-chemical properties, such as changes in spectroscopic properties, in magnetic resonance properties etc. Different polypeptides or immunological entities or immunological entities of different specificities may be recognized by different methods or agents. This may be due to difficulties in detection of several entities, or entities with particular specificities by a particular method. An advantage of the use of different detection techniques for different polypeptides and/or immunological entities or for immunological entities with different specificities may for example be, that the different reporter signals referring to different immunological entities could be distinguished.

Generally in a method according to the present invention the detection of different polypeptides, of different immunological entities such as the detection of immunoglobulins and the detection of immunocompetent cells may be performed simultaneously.

For all detection purposes optionally the original sample may be concentrated by any suitable means known to those of ordinary skill in the art. Furthermore steps may be involved to selectively extract polypeptides and/or immunological entities from the sample mixture such as affinity based purification techniques either employing specific antibodies or the respective antigen recognized by the entities in question.

Another aspect of the present invention is a testing kit for performing the method according to the present invention. The kit may be for example a diagnostic kit or a research kit.

A kit according to the present invention comprises at least an agent suitable for detecting the immunological entities according to the method disclosed herein. Furthermore a kit according to present invention may comprise:
a) reagents for the detection of the antibodies or cells specifically recognizing antigens.
b) reagents and buffers commonly used for carrying out the detection reactions as described herein, such as buffers, detection-markers, carrier substances and others
c) a sample for carrying out a positive control reaction, that may comprise an antigen or a set of antigens, to which all members of a target population of individuals have antibodies.

The reagent for the detection of the antibodies or cells specifically recognizing antigens may include any agent capable of binding to the antibodies or cells specifically recognizing antigens. Such reagents may include proteins, polypeptides, nucleic acids, peptide nucleic acids, glycoproteins, proteoglycans, polysaccharides or lipids.

The sample for carrying out a positive control may comprise for example an antigenic peptide or a set of antigenic peptides. Suitable antigens may include antigens, against which a wide percentage of the population has antibodies. Examples of such antigens may for example comprise antigens present in lysed *E. coli* cells, tetanus antigen, the viral capsid antigen of the Epstein-Barr virus, antigens derived from matrix proteins of *Haemophilus influenzae*. The antigens may for example be used as a mixture to ensure, that a particular individual actually displays a positive reaction.

The present invention provides compositions and methods for enhanced immunotherapy of disorders associated with MSI$^+$ related occurrence of frameshift peptides. The invention provides sets for the immuno-therapy of said disorders, that address a wide range of different types of disorders in an organism and may thus be employed as a preventive vaccine against said disorders. Furthermore the invention also provides sets of polypeptides useful for the treatment of particular types of disorders. The use of sets of frameshift polypeptides for the immuno-therapy according to the present invention provides the means for a reliable treatment of degenerative disorders and cancers associated with frameshift mutations in coding microsatellites reducing the risk of escape of several tumour cells or of a population of tumour cells from being addressed by the therapy. Thus the method of the invention reduces the risk of recurrence of tumours after immuno-therapy employing CTLs, T-helper cells and possibly specific antibody producing B-cells raised against frameshift polypeptides characteristic for tumour cells. The present invention furthermore provides compositions and methods for enhanced diagnosis and therapy of disorders associated with MSI$^+$ related occurrence of frameshift peptides. The invention provides new frameshift polypeptides for diagnosis therapy of said disorders, that may be used each alone or in combinations tailored, to address a wide range of different types of disorders in an organism and may thus be employed as a preventive vaccine against said disorders.

BRIEF DESCRIPTION OF THE DRAWINGS

FIG. 1: ELISpot-analysis of FSP T-cell lines. Titrated amounts of T-cells were incubated overnight with 3.5×10$^4$ peptide loaded T2 cells per well. The number of IFN-γ-releasing activated T-cells (spots) among the total number of cells analyzed (10$^6$) is depicted for each frameshift peptide. Reactivity against peptide YLLPAIVHI from the nuclear protein P68 served as a negative control and is indicated (open bars).

FIG. 2: Listing of sequences of polypeptides encoded by genes with coding microsatellites; the sequences of polypeptides arising from different possible frameshift mutations are depicted. For each polypeptide the sequence expressed from the wild type open reading frames is given (wtORF); Furthermore the sequences expressed from (−1) mutations and from (−2/+1) mutation are given.

Figure 3:
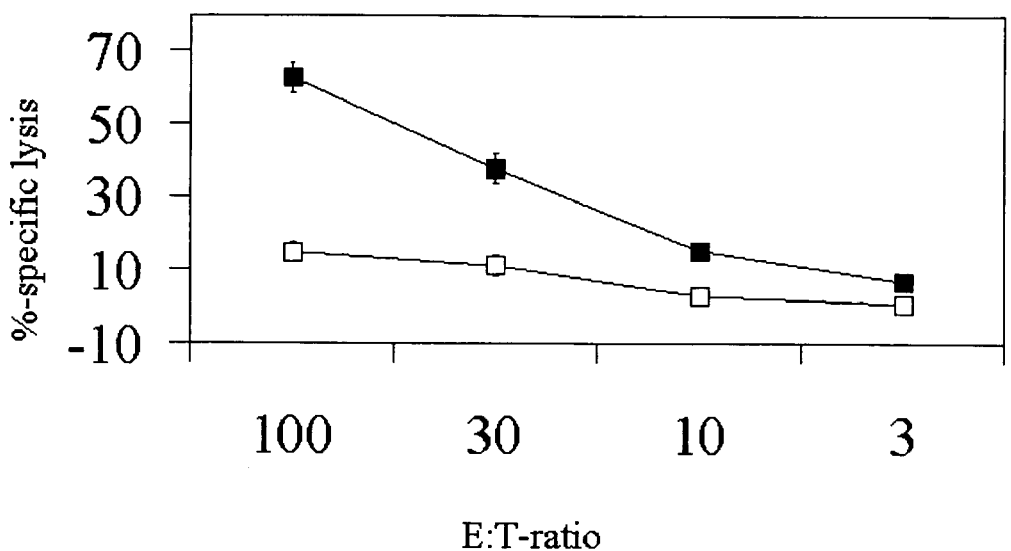
FIG. 3: Frameshift peptide specific and HLA-A2-restricted lysis of target cells. (FSP02); The antigen specificity of the FSP02 CTL line was tested in the presence of unlabeled cold targets, T2 cells pulsed with FSP02 (open squares) at an inhibitor:target ratio of 50:1. Lysis without cold targets is shown as a control (closed squares). All data are shown as the mean and standard deviation from 3 replicate wells. For experimental details see example 6.

The following examples are given for illustration of the invention only and are not intended to limit the scope of the invention.

EXAMPLE 1

Analysis of the Mutation Frequency of Genes Harbouring Repeat Tracts

Investigations were performed regarding the mutation frequencies of unpublished coding microsatellite regions. Nine novel coding microsatellites residing in genes not yet analyzed for frameshift mutations in MSI colorectal, endometrial or gastric tumours have been examined in the course of the studies leading to the present invention. They include three genes containing A11 repeats (TAF1B, MACS, HT001), five genes with A10 repeats (CHD2, UVRAG, TCF6L1, ABCF1, AIM2) and one gene harboring a G9 repeat (ELAVL3). The MSI status of these specimen was determined using the NCI ICG-HNPCC microsatellite reference marker panel (8). PCR reactions were performed as follows:

Genomic DNA was isolated from 5-8 haematoxylin and eosin stained 5 μm sections after microdissection, using the Qiamp Tissue Kit (Qiagen, Hilden, Germany). Preparation of DNA from cell lines was performed according to standard protocols. PCR primers were designed to closely flank the target sequence, yielding short amplimeres of about 100 base pairs thus allowing precise fragment sizing and robust amplification from archival tissues (Table 1). PCR reactions were performed in a total volume of 25 μl containing 50 ng genomic DNA, 2.5 μl 10× reaction buffer (Life Technologies, Karlsruhe, Germany), 1.5 mM MgCl$_2$, 200 μM dNTPs, 0.3 μM of each primer, and 0.5 U Taq DNA polymerase (Life Technologies) and using the following conditions: initial denaturation at 94° C. for 4 min, followed by 35 cycles of denaturation at 94° C. for 30 s, annealing at 58° C. for 45 s, and primer extension at 72° C. for 30 s. The final extension step was carried out at 72° C. for 6 min. PCR fragments were analyzed on an ALF DNA sequencing device (Amersham Pharmacia Biotech, Freiburg, Germany) using 6.6% polyacrylamide/7 M urea gels. Size, height and profile of microsatellite peaks were analyzed using the AlleleLinks software (Amersham Pharmacia Biotech). Coding microsatellite instability was scored, if smaller or larger-sized amplimeres were detected in tumour DNA compared to DNA from non-neoplastic cells. Allele intensities were determined and ratios of wild-type and novel alleles in normal and tumour tissues were calculated, defining a two-fold difference as threshold for allelic shifts. Similarly, unstable alleles in tumour cell lines were identified by comparison to 36 unmatched normal mucosae. In order to determine the predicted repeat type and length amplified coding microsatellites were subjected to Big Dye terminator cycle sequencing (Perkin Elmer, Darmstadt, Germany) and subsequent analysis on an ABI 310 sequencing device.

The frequencies of mutations in a particular microsatellite region examined herein are given in FIG. 1/2. The mutation rates are calculated with respect to the total number of samples included in the study.

TABLE 1

Coding microsatellite genes investigated in MSI-H colorectal cancer.

| gene | acc. no. | repeat | n | mut. | % |
|---|---|---|---|---|---|
| HPDMPK | Y10936 | T14 | 21 | 20 | 95% |
| HT001 | AF113539 | A11 | 20 | 17 | 85% |
| TGFbIIR | D50683 | A10 | 735 | 602 | 82% |
| U79260 | U79260 | T14 | 21 | 17 | 81% |
| PTHL3 | M24350 | A11 | 21 | 17 | 81% |
| MACS | D10522 | A11 | 19 | 14 | 74% |
| TAF1B | L39061 | A11 | 19 | 13 | 68% |
| AC1 | D82070 | T10 | 21 | 14 | 67% |
| AIM2 | AF024714 | A10 | 19 | 10 | 53% |
| BAX | L22473 | G8 | 538 | 235 | 44% |
| SLC23A1 | AF058319 | C9 | 21 | 9 | 43% |
| ABCF1 | AF027302 | A10 | 19 | 8 | 42% |
| TCF-4 | Y11306 | A9 | 248 | 98 | 40% |
| Caspase 5 | U28015 | A10 | 120 | 47 | 39% |
| TCF6L1 | M85079 | A10 | 18 | 7 | 39% |
| FLT3LG | U29874 | C9 | 21 | 8 | 38% |
| MSH3 | J04810 | A8 | 596 | 223 | 37% |
| ELAVL3 | D26158 | G9 | 19 | 7 | 37% |
| MAC30X | L19183 | A10 | 21 | 7 | 33% |
| UVRAG | X99050 | A10 | 18 | 6 | 33% |
| SLC4A3 | U05596 | C9 | 21 | 7 | 33% |
| GRB-14 | L76687 | A9 | 57 | 18 | 32% |
| RIZ | U17838 | A9 | 83 | 23 | 28% |
| MBD4/MED1 | AF072250 | A10 | 83 | 22 | 27% |
| RAD50 | U63139 | A9 | 109 | 28 | 26% |
| MSH6 | U54777 | C8 | 684 | 169 | 25% |
| IGFIIR | Y00285 | G8 | 423 | 90 | 21% |
| Axin2 | AF205888 | G7 | 45 | 9 | 20% |
| GART | X54199 | A10 | 21 | 4 | 19% |
| Bcl-10 | AF082283 | A8 | 32 | 6 | 19% |
| RHAMM | U29343 | A9 | 57 | 9 | 16% |
| PTEN | U92436 | A6 | 32 | 5 | 16% |
| OGT | U77413 | T10 | 78 | 10 | 13% |
| BLM | U39817 | A9 | 170 | 19 | 11% |
| Fas | X63717 | T7 | 30 | 3 | 10% |
| Apaf-1 | AF013263 | A8 | 43 | 4 | 9% |
| MLH3 | AF195657 | A9 | 99 | 9 | 9% |
| CBF | M37197 | A9 | 57 | 5 | 9% |
| HTP1 | AB024582 | A9 | 57 | 5 | 9% |

TABLE 1-continued

Coding microsatellite genes investigated in MSI-H colorectal cancer.

| gene | acc. no. | repeat | n | mut. | % |
|---|---|---|---|---|---|
| RECQL | L36140 | A9 | 68 | 5 | 7% |
| RBBP8 | U72066 | A9 | 70 | 5 | 7% |
| MLH3 | AF195657 | A8 | 123 | 7 | 6% |
| PTEN | U92436 | A6 | 32 | 2 | 6% |
| CHD2 | AF006514 | A10 | 19 | 1 | 5% |
| ATRmRNA | U76308 | A10 | 77 | 4 | 5% |
| INPPL1/DRP | L24444 | C7 | 82 | 4 | 5% |
| CHK1 | AF016582 | A9 | 21 | 1 | 5% |
| SYCP1 | X95654 | A10 | 71 | 3 | 4% |
| RIZ | U17838 | A8 | 83 | 3 | 4% |
| ANG2 | AF004327 | A9 | 57 | 2 | 4% |
| KKIAMRE/CDKL2 | U35146 | A9 | 57 | 2 | 4% |
| ATM | U82828 | T7 | 39 | 1 | 3% |
| CDX2 | Y13709 | G7 | 45 | 1 | 2% |
| Axin2 | AF205888 | A6 | 45 | 1 | 2% |
| BRCA1 | U14680 | A8 | 92 | 2 | 2% |
| Doc-1 | U53445 | A9 | 57 | 1 | 2% |
| BRCA2 | U43746 | A8 | 119 | 2 | 2% |
| RFC3 | L07541 | A10 | 76 | 1 | 1% |
| Casp8AP2/FLASH | AF154415 | A9 | 13 | 0 | 0% |
| ERCC5/XPG | D16305 | A9 | 13 | 0 | 0% |
| HUMGPRKLG | L03718 | A9 | 57 | 0 | 0% |
| DP2 | U18422 | A9 | 57 | 0 | 0% |
| PMS2 | U14658 | A8 | 133 | 0 | 0% |
| Caspase 1/ICE | M87507 | A8 | 42 | 0 | 0% |
| WRN | L76937 | A8 | 11 | 0 | 0% |
| POLA | X06745 | A8 | 83 | 0 | 0% |
| NSEP | M85234 | C8 | 132 | 0 | 0% |
| SHC1 | U73377 | G8 | 11 | 0 | 0% |
| NBS1 | AF058696 | A7 | 39 | 0 | 0% |
| BRCA2 | X95152 | T6 | 31 | 0 | 0% |

Repeat: type of nucleotide and length of repeat tract,
n: number of samples investigated,
mut.: number of samples mutated,
%: percentage of mutated samples,

TABLE 2

Coding microsatellite genes investigated in MSI-H gastric cancer.

| gene | acc. no. | repeat | n | mut. | % |
|---|---|---|---|---|---|
| HPDMPK | Y10936 | T14 | 15 | 15 | 100% |
| TAF1B | L39061 | A11 | 15 | 13 | 87% |
| PTHL3 | M24350 | A11 | 15 | 11 | 73% |
| MACS | D10522 | A11 | 15 | 9 | 60% |
| TGFbIIR | M85079 | A10 | 227 | 122 | 54% |
| HT001 | AF113539 | A11 | 15 | 8 | 53% |
| MBD4/MED1 | AF072250 | A10 | 15 | 7 | 47% |
| RIZ | U17838 | A9 | 51 | 23 | 45% |
| Caspase 5 | U28015 | A10 | 25 | 11 | 44% |
| AIM2 | AF024714 | A10 | 15 | 6 | 40% |
| OGT | U77413 | T10 | 15 | 6 | 40% |
| SLC23A1 | AF058319 | C9 | 15 | 6 | 40% |
| BAX | L22473 | A8 | 208 | 72 | 35% |
| MSH6 | U54777 | C8 | 224 | 76 | 34% |
| ABCF1 | AF027302 | A10 | 15 | 5 | 33% |
| FLT3LG | U29874 | C9 | 15 | 5 | 33% |
| MSH3 | J04810 | A8 | 202 | 65 | 32% |
| RAD50 | Z75311 | A9 | 36 | 10 | 28% |
| PRKDC | U63630 | A10 | 30 | 8 | 27% |
| SLC4A3 | U05596 | C9 | 15 | 4 | 27% |
| BLM | U39817 | A9 | 36 | 9 | 25% |
| ATRmRNA | U76308 | A10 | 18 | 4 | 22% |
| B2M | AB021288 | A5 | 28 | 6 | 21% |
| MAC30X | L19183 | A10 | 15 | 3 | 20% |
| RFC3 | L07541 | A10 | 15 | 3 | 20% |
| UVRAG | X99050 | A10 | 15 | 3 | 20% |
| AC1 | D82070 | T10 | 15 | 3 | 20% |
| IGFIIR | Y00285 | G8 | 202 | 36 | 18% |
| Apaf-1 | AF013263 | A8 | 20 | 3 | 15% |
| TCF-4 | Y11306 | A9 | 23 | 3 | 13% |

TABLE 2-continued

Coding microsatellite genes investigated in MSI-H gastric cancer.

| gene | acc. no. | repeat | n | mut. | % |
|---|---|---|---|---|---|
| SYCP1 | X95654 | A10 | 40 | 4 | 10% |
| Bcl-10 | AF082283 | A8 | 20 | 2 | 10% |
| Fas | X63717 | T7 | 20 | 2 | 10% |
| U79260 | U79260 | T14 | 15 | 1 | 7% |
| GART | X54199 | A10 | 15 | 1 | 7% |
| TCF6L1 | M85079 | A10 | 15 | 1 | 7% |
| ELAVL3 | D26158 | G9 | 15 | 1 | 7% |
| ATM | U82828 | T7 | 36 | 2 | 6% |
| BRCA1 | U14680 | A8 | 64 | 3 | 5% |
| INPPL1/DRP | L24444 | C7 | 25 | 1 | 4% |
| RIZ | U17838 | A8 | 51 | 1 | 2% |
| CHD2 | AF006514 | A10 | 15 | 0 | 0% |
| CHK1 | AF016582 | A9 | 15 | 0 | 0% |
| BRCA2 | U43746 | A8 | 68 | 0 | 0% |
| PMS2 | U14658 | A8 | 30 | 0 | 0% |
| NSEP | M85234 | C8 | 50 | 0 | 0% |
| NBS1 | AF058696 | A7 | 36 | 0 | 0% |

Repeat: type of nucleotide and length of repeat tract,
n: number of samples investigated,
mut.: number of samples mutated,
%: percentage of mutated samples The results presented in Tables 1 and 2 show, that the tested microsatellite regions are frequently mutated in tumour samples.

EXAMPLE 2

Detection of the Expression of Frameshift Mutated mRNA from Genes Harbouring Coding Microsatellite Regions Using PCR Samples of colon, gastric and endometrial carcinomas are used to determine the expression of mRNA showing frameshift mutations in coding microsatellite regions using PCR and subsequent sequencing of the amplified nucleic acid products.

Tumours are collected, snap frozen, and stored at −80° C. They are verified to be composed predominantly of neoplastic cells by histopathological analysis. mRNA is isolated from tumours using Qiagen reagents (Qiagen, Hilden, Germany), and single-stranded cDNA is synthesized using Superscript II (Life Technologies, Inc.).

PCR reactions were performed in a total volume of 25 μl containing 50 ng cDNA, 2.5 μl 10× reaction buffer (Life Technologies, Karlsruhe, Germany), 1.5 mM $MgCl_2$, 200 μM dNTPs, 0.3 μM of each primer, and 0.5 U Taq DNA polymerase (Life Technologies) and using the following conditions: initial denaturation at 94° C. for 4 min, followed by 35 cycles of denaturation at 94° C. for 30 s, annealing at 58° C. for 45 s, and primer extension at 72° C. for 30 s. The final extension step was carried out at 72° C. for 6 min. PCR fragments were analyzed on an ALF DNA sequencing device (Amersham Pharmacia Biotech, Freiburg, Germany) using 6.6% polyacrylamide/7 M urea gels.

The experiments described show, that in the cases of the tested genes CHD2, UVRAG, ELAVL3, TCF6L1, ABCF1, AIM2, TAF1B, MACS and HT001 mutated coding microsatellite regions are transcribed into mRNA.

These results indicate, that the cells harbouring mutations in coding microsatellite regions of the nine genes tested express neo-polypeptides derived from these frameshift mutations.

EXAMPLE 3

Stimulation of Cellular Immune Response by Frameshift Peptides

The present experiments were performed in order to determine, whether the frameshift peptides arising from mutations in coding microsatellite regions according to the present invention are suited to stimulate a cellular immune response. The experiments were performed as follows:

Peptides displaying HLA-A2.1-binding motifs were selected by taking advantage of specific computer programs [(Parker, Bednarek, & Coligan 1994); http://bimas.dcrt.nih.gov/molbio/hla_bind/ and (Rammensee et al. 1999); http://134.2.96.221/scripts/MHCServer.dll/home.htm].

TABLE 3

Frameshift Peptides analysed for in vitro stimulation of a cellular immune response; All analysed peptides are derived from (−1) mutations in microsatellites of the cognate proteins; The protein or nucleotide accession numbers are indicated within the table; the position of the start amino acid in the protein is indicated in the tables; the predicted binding scores to HLA-A2.1 using computer assisted analysis;

|  |  |  |  |  | Theoretical Scores | |
|---|---|---|---|---|---|---|
| Protein | Accession Number | Name | SEQ ID NO | Peptide | Ken Parker | SYFPEITHI |
| TGF-betaRII (−1) | AAA61164 | FSP01 | 75 | $^{128}$-SLVRLSSCV | 70 | 23 |
| TGF-betaRII (−1) | AAA61164 | FSP02 | 76 | $^{131}$-RLSSCVPVA | 5 | 19 |
| TGF-betaRII (−1) | AAA61164 | FSP03 | 77 | $^{135}$-CVPVALMSA | 1 | 14 |
| HPDMPK (−1) | CAA71862 | FSP04 | 78 | $^{136}$-LLHSAPTPSL | 36 | 25 |
| HPDMPK (−1) | CAA71862 | FSP05 | 79 | $^{129}$-FLSASHFLL | 570 | 21 |
| HPDMPK (−1) | CAA71862 | FSP07 | 80 | $^{125}$-RVFFFYQHL | 39 | 15 |
| OGT (−1) | AAB63466 | FSP06 | 81 | $^{128}$-SLYKFSPFPL | 397 | 23 |
| D070 (−1) | BAA11534 | FSP08 | 82 | $^{35}$-KIFTFFFQL | 1593 | 21 |
| D070 (−1) | BAA11534 | FSP09 | 83 | $^{68}$-ALLPAGPLT | 28 | 21 |
| D070 (−1) | BAA11534 | FSP10 | 84 | $^{69}$-LLPAGPLTQT | 29 | 20 |
| U79260 (−1) | AAB50206 | FSP11 | 85 | $^{59}$-TLSPGWSAV | 118 | 25 |
| U79260 (−1) | AAB50206 | FSP12 | 86 | $^{83}$-ILLPQPPEWL | 362 | 26 |
| Sec63 (−1) | AAC83375 | FSP13 | 87 | $^{551}$-RQMESLGMKL | 33 | 15 |
| MAC30X (−1) | AAA16188 | FSP14 | 88 | $^{198}$-VEMPTGWLL | 20 | 14 |
| MAC30X (−1) | AAA16188 | FSP15 | 89 | $^{198}$-VEMPTGWLLV | 14 | 15 |
| FLT3L (−1) | U29874 | FSP16 | 90 | $^{113}$-FQPPPAVFA | 13 | 10 |
| MSH-3 (−1) | AAB47281 | FSP17 | 91 | $^{389}$-ALWECSLPQA | 389 | 24 |
| MSH-3 (−1) | AAB47281 | FSP18 | 92 | $^{386}$-FLLALWECSL | 364 | 25 |
| MSH-3 (−1) | AAB47281 | FSP19 | 93 | $^{387}$-LLALWECSL | 36 | 26 |
| MSH-3 (−1) | AAB47281 | FSP20 | 94 | $^{394}$-SLPQARLCL | 21 | 23 |
| MSH-3 (−1) | AAB47281 | FSP21 | 95 | $^{402}$-LIVSRTLLL | 5 | 23 |
| MSH-3 (−1) | AAB47281 | FSP22 | 96 | $^{401}$-CLIVSRTLL | 21 | 22 |
| MSH-3 (−1) | AAB47281 | FSP23 | 97 | $^{403}$-IVSRTLLLV | 24 | 21 |
| MSH-3 (−1) | AAB47281 | FSP24 | 98 | $^{382}$-KRATFLLAL | 0.1 | 20 |
| Caspase-5 (−1) | U28015 | FSP25 | 99 | $^{61}$-KMFFMVFLI | 1301 | 20 |
| Caspase-5 (−1) | U28015 | FSP26 | 100 | $^{67}$-FLIIWQNTM | 22.85 | 21 |
| TAF-1b (−1) | L39061 | FSP27 | 101 | $^{108}$-GMCVKVSSI | 17 | 24 |
| HT001 (−1) | NP 054784 | FSP30 | 102 | $^{281}$-VLRTEGEPL | n.d. | 21 |
| MSH-3 (−1) | AAB47281 | FSP31 | 103 | $^{402}$-LIVSRTLLLV | 37 | 25 |
| MSH-3 (−1) | AAB47281 | FSP32 | 104 | $^{394}$-SLPQARLCLI | 24 | 24 |
| MSH-3 (−1) | AAB47281 | FSP33 | 105 | $^{401}$-CLIVSRTLLL | 21 | 23 |
| MSH-3 (−1) | AAB47281 | FSP34 | 106 | $^{399}$-RLCLIVSRTL | 4 | 22 |

Peptides were purchased from the peptide synthesis unit of the DKFZ. Stock solutions (10 mg/ml in DMSO) were stored at −70° C. and diluted to 1 mg/ml in PBS before use. T2 cells were pulsed with 50 μg/ml peptide and 5 μg/ml β2-microglobulin (Sigma; Deisenhofen, Germany) overnight at 37° C. The expression of HLA-A2.1 was then analysed by flow cytometry using mAb BB7.2 followed by incubation with FITC-conjugated (ab')2 goat anti-mouse Ig (Vonderheide et al. 1999).

Peripheral blood was obtained from a healthy HLA-A2.1+ donor and collected in heparinized tubes. PBMNC were isolated by Ficoll-density gradient centrifugation. Whole CD3+ T-cells were isolated from PBMNC by magnetic depletion of non-T-cells using the MACS Pan T-cell Isolation Kit (Miltenyi; Bergisch Gladbach, Germany) according to manufacturer's instructions. Preparations contained at least 97% of CD3+ cells as assessed by immunophenotypic analysis.

HLA-A2.1-restricted peptides were FSP27 and FSP29 from a (−1) in the TAF1B-gene; FSP30 was derived from a (−1) mutation in the HT001 gene.

CD40 Bs of a HLA-A2.1+ donor were incubated with peptide (10 μg/ml) and human β2-microglobulin (3 μg/ml; Sigma) in serum-free Iscov's DMEM medium for one hour at room temperature, washed twice to remove excess of peptide, were irradiated (30 Gy) and added to purified CD3+ autologous T-cells (>97% CD3+) at a ratio of 4:1 (T:CD40 Bs) in Iscov's MEM containing 10% human AB-serum, supplements (1:100) and hIL-7 (10 ng/ml, R&D). Cells were plated at a density of 2×106 T-cells/well in 1 ml of medium. After three days in culture they were fed with 1 ml complete medium. For restimulation of T-cells, this was repeated weekly. IL-2 was first given at day 21 (10 IU/ml, R&D), also at day 24 and from day 28 on only hIL-2 was used instead of hIL7.

ELISpot assays were performed as described elsewhere (Meyer et al. 1998). Briefly, nitrocellulose-96-well plates (Multiscreen; Millipore, Bedford, USA) were covered with mouse anti-human IFN-g monoclonal antibody (Mabtech, Sweden) and blocked with serum containing medium. Varying numbers of effector cells were plated in triplicates with 3.5×104 peptide-loaded T2 cells per well as targets. After incubation for 18 h, plates were washed, incubated with biotinylated rabbit anti-human IFN-g second antibody, washed again, incubated with streptavidin coupled alkaline phosphatase, followed by a final wash. Spots were detected by incubation with NBT/BCIP (Sigma) for 45 min, reaction was stopped with water, after drying spots were counted using the KS-ELISpot reader (Zeiss Kontron; Göttingen, Germany).

The analysis shows, that the used peptides are suited to raise an immune response. Peptides arising from frameshift mutations thus may be used to raise immune response for example in the course of vaccinations according to the present invention.

EXAMPLE 4

Screening for Antibodies Directed against Frameshift Peptides in Patient Samples Serum of 25 patients with diagnosed colorectal carcinomas was tested for the presence of antibodies to a set of frameshift peptides arising from frameshift mutations in coding microsatellite regions of the following genes: CHD2, UVRAG, ELAVL3, TCF6L1, ABCF1, AIM2, TAF1B, MACS and HT001. As a control the serum of 50 normal individuals was tested.

For the test synthetic peptides representing immunogenic portions of all relevant frameshift peptides (see FIG. 2) arising from the respective genes were spotted onto nylon membranes. The nylon membranes were subsequently incubated for one hour in phosphate-buffered saline (PBS) with 5% milk powder for blocking unspecific membrane binding. After washing the membranes 3× with PBS, the membranes were incubated with the test and control sera. The sera were diluted 1:1.000 in PBS/0.5% milk powder and incubated overnight with gentle shaking. Subsequently the sera were removed, and membranes were washed three times in PBS before they were incubated with a polyclonal alkaline phosphatase conjugated goat anti-human IgG antibody for one hour. Thereafter, the membranes were washed repeatedly with PBS/0.05% TWEEN20 before staining reaction was developed using nitroblue tetrazolium chloride and bromochoro-indoyl-phosphate (SigmaAldrich) in Tris-buffered saline (TBS). Binding of human antibodies specific for individual frameshift polypeptides thus was made visible by color-deposit on the respective membrane.

The results show, that in all samples of tumour patients antibodies directed against at least one peptide arising from frameshift mutations were present.

This illustrates, that the method according to the present invention may be used for diagnosis of diseases associated with frameshift mutations in coding regions of genes.

EXAMPLE 5

In Vitro Stimulation of Cellular Immune Response by Frameshift Peptides

The present experiments were performed in order to determine, whether the frameshift peptides arising from mutations in coding microsatellite regions according to the present invention are suited to stimulate a cellular immune response. The experiments were performed as follows:

Peptides displaying HLA-A2.1-binding motifs were selected by taking advantage of specific computer programs [(Parker, Bednarek, & Coligan 1994); http://bimas.dcrt.nih.gov/molbio/hla_bind/ and (Rammensee et al. 1999); http://134.2.96.221/scripts/MHCServer.dll/home.htm]. Peptides were purchased from the peptide synthesis unit of the DKFZ. Stock solutions (10 mg/ml in DMSO) were stored at −70° C. and diluted to 1 mg/ml in PBS before use. T2 cells were pulsed with 50 µg/ml peptide and 5 µg/ml β2-microglobulin (Sigma; Deisenhofen, Germany) overnight at 37° C. The expression of HLA-A2.1 was then analysed by flow cytometry using mAb BB7.2 followed by incubation with FITC-conjugated (ab')2 goat anti-mouse Ig (Vonderheide et al. 1999).

Peripheral blood was obtained from a healthy HLA-A2.1+ donor and collected in heparinized tubes. PBMNC were isolated by Ficoll-density gradient centrifugation. Whole CD3+ T-cells were isolated from PBMNC by magnetic depletion of non-T-cells using the MACS Pan T-Cell Isolation Kit (Miltenyi; Bergisch Gladbach, Germany) according to manufacturer's instructions. Preparations contained at least 97% of CD3+ cells as assessed by immunophenotypic analysis.

CD40 Bs of a HLA-A2.1+ donor were incubated with peptide (10 µg/ml) and human β2-microglobulin (3 µg/ml; Sigma) in serum-free Iscov's DMEM medium for one hour at room temperature, washed twice to remove excess of peptide, were irradiated (30 Gy) and added to purified CD3+ autologous T-cells (>97% CD3+) at a ratio of 4:1 (T:CD40 Bs) in Iscov's MEM containing 10% human AB-serum, supplements (1:100) and hIL-7 (10 ng/ml, R&D). Cells were plated at a density of 2×10⁶ T-cells/well in 1 ml of medium. After three days in culture they were fed with 1 ml complete medium. For restimulation of T-cells, this was repeated weekly. IL-2 was first given at day 21 (10 IU/ml, R&D), also at day 24 and from day 28 on only hIL-2 was used instead of hIL7.

ELISpot assays were performed as described elsewhere (Meyer et al. 1998). Briefly, nitrocellulose-96-well plates (Multiscreen; Millipore, Bedford, USA) were covered with mouse anti-human IFN-g monoclonal antibody (Mabtech, Sweden) and blocked with serum containing medium. Varying numbers of effector cells were plated in triplicates with 3.5×10⁴ peptide-loaded T2 cells per well as targets. After incubation for 18 h, plates were washed, incubated with biotinylated rabbit anti-human IFN-g second antibody, washed again, incubated with streptavidin coupled alkaline phosphatase, followed by a final wash. Spots were detected by incubation with NBT/BCIP (Sigma) for 45 min, reaction was stopped with water, after drying spots were counted using the KS-ELISpot reader (Zeiss Kontron; Göttingen, Germany).

These procedures were performed for peptides derived from mutations in the coding regions of the following genes: TGFβRII, OGT, U79260, CASP 5, MSH 3, HPDMPK, HT001, TAF1B, D070, MAC30X, FLT3L and SEC63. Peptides are listed in FIG. 1. Results for ELIspot analysis is shown in FIG. 2.

The analysis shows, that the used peptides are suited to raise an immune response. Peptides arising from frameshift mutations thus may be used to raise immune response for example in the course of vaccinations according to the present invention.

EXAMPLE 6

Cytotoxicity Assay Directed against Cells Displaying Frameshift Peptides

CTL bulk cultures and/or CTL clones obtained according to the method described in Example 1 were tested for their cytotoxicity as follows:

Due to the limited amount of cell material clones were in some experiments pooled for the determination of the cytotoxicity.

To obtain cells presenting frameshift peptides on the one hand different MSI+ cell lines endogenously expressing mutated mRNA of the respective frameshift peptides of TGF-βRII, OGT, U79260, CASP 5, MSH 3, HPDMPK, HT001, TAF1B, D070, MAC30X, FLT3L and SEC63 either expressed HLA-A2.1 endogenously or were stably transfected with HLA-A2.1 on the other hand several MSI– cell lines expressing HLA-A2.1 were transfected with the mutated full-length cDNA of the respective frameshift peptides (of TGFβRII, OGT, U79260, CASP 5, MSH 3, HPDMPK, HT001, TAF1B, D070, MAC30X, FLT3L and SEC63). After selection and expansion of the transfected cell lines for each respective frameshift peptide at least two stably transfected sub-cell lines were available. These cell lines were used in cytotoxicity assays, wherein negative controls were the respective untransfected MSI+ HLA-A2.1 negative and/or the MSI–, HLA-A2.1 positive cell lines.

It could be shown, that the transfected cell lines were lysed by the bulk cultures and/or pooled clones of CTLs. The reactivity was tested at different target cell to effector cell ratios. In average around 20%-30% of the target cells were lysed in the assays. The control cells were always lysed at a significantly lower percentage.

Figure 4:
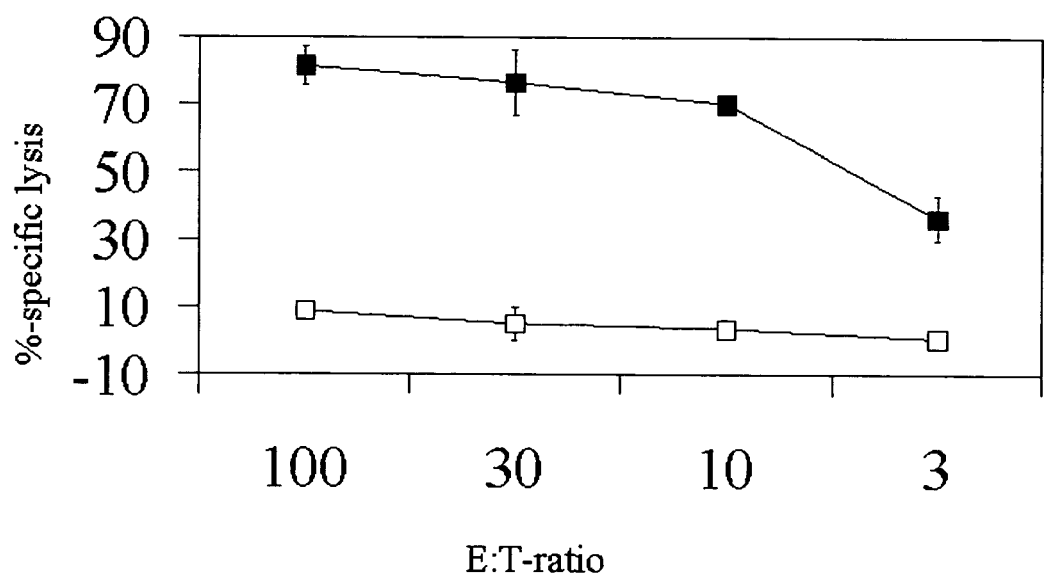
FIG. 4: Frameshift peptide specific and HLA-A2-restricted lysis of target cells. (FSP06); The antigen specificity of the FSP06 CTL line was tested in the presence of unlabeled cold targets, T2 cells pulsed either with FSP06 (open squares) at an inhibitor:target ratio of 50:1. Lysis without cold targets is shown as a control (closed squares). All data are shown as the mean and standard deviation from 3 replicate wells. For experimental details see example 6.

In FIGS. 3 and 4 results for the frameshift peptides FSP02 (TGFβRII(–1)) and FSP06 (OGT(–1)) respectively are shown. These results shall be representative for the results related to the other frameshift peptides, which rendered similar rates of lysis.

The experiments show, that frameshift peptides may generate immune response. The frameshift peptides may furthermore be applied for the detection of the presence of cytotoxic T-cells directed against a particular frameshift peptide.

EXAMPLE 7

Screening for Antibodies Directed against Frameshift Peptides in Patient Samples Serum of 25 patients with diagnosed colorectal carcinomas was tested for the presence of antibodies to a set of frameshift peptides arising from frameshift mutations in coding microsatellite regions of the following genes: TGFβRII, U79260, CASP 5, HT001, PTHL3, MACS, TCF4, TAF1B, AC1, AIM2, SLC23A1, ABCF1, HSPC259, BAX, TCF6L1, FTL3L, OGT, ELAVL3, MAC30X, MAC30X, SLC4A3, PRKDC, UVRAG, MSH3 and SEC63. As a control the serum of 50 normal individuals was tested.

For the test synthetic peptides (20 to 40 mers, partly overlapping) representing immunogenic portions of all relevant frameshift peptides (see FIG. 5) arising from the respective genes were spotted onto nylon membranes. The nylon membranes were subsequently incubated for one hour in phosphate-buffered saline (PBS) with 5% milk powder for blocking unspecific membrane binding. After washing the membranes 3× with PBS, the membranes were incubated with the test and control sera. The sera were diluted 1:1.000 in PBS/0.5% milk powder and incubated overnight with gentle shaking. Subsequently the sera were removed, and membranes were washed three times in PBS before they were incubated with a polyclonal alkaline phosphatase conjugated goat anti-human IgG antibody for one hour. Thereafter, the membranes were washed repeatedly with PBS/0.05% TWEEN20 before staining reaction was developed using nitroblue tetrazolium chloride and bromochoro-indoyl-phosphate (SigmaAldrich) in Tris-buffered saline (TBS). Binding of human antibodies specific for individual frameshift polypeptides thus was made visible by color-deposit on the respective membrane.

The results show, that in all samples of tumour patients antibodies directed against at least one peptide arising from frameshift mutations were present.

This illustrates, that the method according to the present invention may be used for diagnosis of diseases associated with frameshift mutations in coding regions of genes.

We claim:

1. An isolated fragment peptide consisting of a fragment of a frameshift polypeptide selected from the group consisting of TAF1b (−1) ORF, SEQ ID NO: 20; TAF1b (+1) ORF, SEQ ID NO: 21; HT001 (−1) ORF, SEQ ID NO: 2; HT001 (+1) ORF, SEQ ID NO: 3; and HT001 (−2) ORF, SEQ ID NO: 118; wherein said fragment peptide comprises at least 3 amino acids of a mutated part of the frameshift polypeptide and has a length of at least 15 amino acids, wherein the mutated part of SEQ ID NO: 20 is SEQ ID NO: 123, the mutated part of SEQ ID NO:21 is KQY, the mutated part of SEQ ID NO: 2 is SEQ ID NO: 121, the mutated part of SEQ ID NO: 3 is SEQ ID NO: 122, and the mutated part of SEQ ID NO: 118 is SEQ ID NO: 124.

2. The fragment peptide according to claim 1, wherein said fragment peptide has an immunogenic portion with a length of about 10-20 amino acids.

3. The fragment peptide according to claim 1, wherein the frameshift polypeptide has the amino acid sequence of SEQ ID NO: 20 and the three amino acids are TIL.

4. The fragment peptide according to claim 1, wherein the frameshift polypeptide has the amino acid sequence of SEQ ID NO: 21.

5. The fragment peptide according to claim 1, wherein the frameshift polypeptide has the amino acid sequence of SEQ ID NO: 2 and the three amino acids are GRR.

6. The fragment peptide according to claim 1, wherein the frameshift polypeptide has the amino acid sequence of SEQ ID NO: 3 and the three amino acids are KAE.

7. A pharmaceutical composition comprising the fragment peptide according to claim 1 and a physiologically acceptable carrier.

8. A pharmaceutical composition comprising the fragment peptide according to claim 3 and a physiologically acceptable carrier.

9. A pharmaceutical composition comprising the fragment peptide according to claim 4 and a physiologically acceptable carrier.

10. A pharmaceutical composition comprising the fragment peptide according to claim 5 and a physiologically acceptable carrier.

11. A pharmaceutical composition comprising the fragment peptide according to claim 6 and a physiologically acceptable carrier.

12. A diagnostic kit comprising the fragment peptide according to claim 1 as a reagent for detecting antibodies or cells specifically recognizing the fragment peptide, and additional reagents and buffers for carrying out the detection reactions.

13. A diagnostic kit comprising the fragment peptide according to claim 3 as a reagent for detecting antibodies or cells specifically recognizing the fragment peptide, and additional reagents and buffers for carrying out the detection reactions.

14. A diagnostic kit comprising the fragment peptide according to claim 4 as a reagent for detecting antibodies or cells specifically recognizing the fragment peptide, and additional reagents and buffers for carrying out the detection reactions.

15. A diagnostic kit comprising the fragment peptide according to claim 5 as a reagent for detecting antibodies or cells specifically recognizing the fragment peptide, and additional reagents and buffers for carrying out the detection reactions.

16. A diagnostic kit comprising the fragment peptide according to claim 6 as a reagent for detecting antibodies or cells specifically recognizing the fragment peptide, and additional reagents and buffers for carrying out the detection reactions.

17. The fragment peptide according to claim 1, wherein the frameshift polypeptide has the amino acid sequence of SEQ ID NO: 118 and the three amino acids are AEE.

18. A pharmaceutical composition comprising the fragment peptide according to claim 17 and a physiologically acceptable carrier.

19. A diagnostic kit comprising the fragment peptide according to claim 17 as a reagent for detecting antibodies or cells specifically recognizing the fragment peptide, and additional reagents and buffers for carrying out the detection reactions.

* * * * *